US008080578B2

(12) United States Patent
Liggett et al.

(10) Patent No.: US 8,080,578 B2
(45) Date of Patent: *Dec. 20, 2011

(54) METHODS FOR TREATMENT WITH BUCINDOLOL BASED ON GENETIC TARGETING

(75) Inventors: Stephen B. Liggett, Clarksville, MD (US); Michael Bristow, Englewood, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 280 days.

This patent is subject to a terminal disclaimer.

(21) Appl. No.: 11/838,131

(22) Filed: Aug. 13, 2007

(65) Prior Publication Data

US 2008/0096982 A1 Apr. 24, 2008

Related U.S. Application Data

(62) Division of application No. 11/226,908, filed on Sep. 14, 2005.

(60) Provisional application No. 60/609,689, filed on Sep. 14, 2004, provisional application No. 60/610,706, filed on Sep. 17, 2004.

(51) Int. Cl.
*A61K 31/405* (2006.01)
*A61K 47/00* (2006.01)
*A61P 43/00* (2006.01)
*C12Q 1/68* (2006.01)
*C07H 21/02* (2006.01)
*C07H 21/04* (2006.01)
*G01N 33/53* (2006.01)

(52) U.S. Cl. ........ 514/415; 514/789; 435/6.1; 435/6.11; 435/6.17; 435/7.1; 536/23.5; 536/24.31; 530/350

(58) Field of Classification Search ........................ None
See application file for complete search history.

(56) References Cited

U.S. PATENT DOCUMENTS

| | | | |
|---|---|---|---|
| 4,234,595 A | 11/1980 | Kreighbaum et al. | 424/274 |
| 4,873,191 A | 10/1989 | Wagner et al. | 435/172.3 |
| 4,965,188 A | 10/1990 | Mullis et al. | 435/6 |
| 5,002,867 A | 3/1991 | Macevicz | 435/6 |
| 5,130,238 A | 7/1992 | Malek et al. | 435/91 |
| 5,169,766 A | 12/1992 | Schuster et al. | 435/91 |
| 5,202,231 A | 4/1993 | Drmanac et al. | 435/6 |
| 5,302,509 A | 4/1994 | Cheeseman | 435/6 |
| 5,595,880 A | 1/1997 | Weinshank et al. | 435/7.21 |
| 5,648,482 A | 7/1997 | Meyer | 536/24.33 |
| 5,679,524 A | 10/1997 | Nikiforov et al. | 435/6 |
| 5,766,851 A | 6/1998 | Shuldiner et al. | 435/6 |
| 5,846,710 A | 12/1998 | Bajaj | 435/6 |
| 5,856,092 A | 1/1999 | Dale et al. | 435/6 |
| 5,888,819 A | 3/1999 | Goelet et al. | 435/5 |
| 5,981,174 A | 11/1999 | Wolf et al. | 435/6 |
| 5,998,458 A | 12/1999 | Bristow | 514/392 |
| 6,004,744 A | 12/1999 | Goelet et al. | 435/5 |
| 6,013,431 A | 1/2000 | Söderlund et al. | 435/5 |
| 6,156,503 A | 12/2000 | Drazen et al. | 435/6 |
| 6,221,851 B1 | 4/2001 | Feldman | 514/46 |
| 6,316,188 B1 | 11/2001 | Yan et al. | 435/6 |
| 6,365,618 B1 | 4/2002 | Swartz | 514/411 |
| 6,498,009 B1 | 12/2002 | Liggett | 435/6 |
| 6,566,101 B1 | 5/2003 | Shuber et al. | 435/91.2 |
| 6,586,183 B2 | 7/2003 | Drysdale et al. | 435/6 |
| 6,784,177 B2 | 8/2004 | Cohn et al. | 514/248 |
| 6,797,472 B1 | 9/2004 | Liggett | 435/6 |
| 6,821,724 B1 | 11/2004 | Mittman et al. | 435/6 |
| 6,861,217 B1 | 3/2005 | Liggett | 435/6 |
| 7,041,810 B2 | 5/2006 | Small et al. | 435/6 |
| 7,195,873 B2 | 3/2007 | Fligheddu et al. | 435/6 |
| 7,211,386 B2 | 5/2007 | Small et al. | 435/6 |
| 7,229,756 B1 | 6/2007 | Small et al. | 435/6 |
| 7,449,292 B2 | 11/2008 | Liggett et al. | 435/6 |
| 7,572,603 B2 | 8/2009 | Small et al. | 435/91.2 |
| 7,642,052 B2 | 1/2010 | Small et al. | 435/6 |
| 7,678,824 B2 * | 3/2010 | Liggett et al. | 514/415 |
| 2001/0016338 A1 | 8/2001 | Snapir et al. | 435/69.1 |
| 2001/0051712 A1 | 12/2001 | Drysdale et al. | 536/23.5 |
| 2002/0187491 A1 | 12/2002 | Johnson | 435/6 |
| 2003/0039979 A1 | 2/2003 | Liggett et al. | 435/6 |
| 2003/0091998 A1 | 5/2003 | Drysdale et al. | 435/6 |
| 2003/0113725 A1 | 6/2003 | Small et al. | 536/23.1 |
| 2003/0124636 A1 | 7/2003 | Leyland-Jones | 435/7.92 |
| 2003/0143608 A1 | 7/2003 | Filigheddu et al. | 435/6 |
| 2003/0233118 A1 | 12/2003 | Hui | 606/201 |
| 2004/0023967 A1 | 2/2004 | Cohn et al. | 514/248 |
| 2004/0033524 A1 | 2/2004 | Johnson | 435/6 |

(Continued)

FOREIGN PATENT DOCUMENTS

EP 0329822 6/1994

(Continued)

OTHER PUBLICATIONS

Borjesson et al., "A novel polymorphism in the gene coding for the beta 1-adrenergic receptor associated with survival in patients with heart failure," *Eur Heart J.*, 21:1853-1858, 2000.

Bouzamondo et al., "Beta-blocker treatment in heart failure," *Fundamental & Clinical Pharmacology*, 15:95-109, 2001.

Bristow et al. "Selective versus nonselective beta-blockade for heart failure therapy: are there lessons to be learned from the COMET trial?" *J Card Fail.* 9:444-53, 2003.

Bristow et al., "Effect of baseline or changes in adrenergic activity on clinical outcomes in the beta-blocker evaluation of survival trial," *Circulation.* 110:1437-42, 2004.

Bristow et al., "The role of third-generation beta-blocking agents in chronic heart failure," *Clinical Cardiology*, 21(Suppl I):I-3-I-13, 1998.

(Continued)

*Primary Examiner* — Carla Myers
(74) *Attorney, Agent, or Firm* — Fulbright & Jaworski L.L.P.

(57) ABSTRACT

The present invention concerns the use of methods for evaluating bucindolol treatment for a patient, particularly one with heart failure. It concerns methods for determining whether to administer or prescribe bucindolol to a patient based on whether the patient is homozygous for the Arg 389 polymorphism in the β1-adrenergic receptor (AR).

28 Claims, 29 Drawing Sheets

U.S. PATENT DOCUMENTS

| | | | |
|---|---|---|---|
| 2004/0106954 A1 | 6/2004 | Whitehurst et al. | 607/3 |
| 2004/0192625 A1 | 9/2004 | Liggett | 514/44 |
| 2006/0073508 A1* | 4/2006 | Small et al. | 435/6 |
| 2008/0269346 A1 | 10/2008 | Johnson et al. | 514/651 |
| 2009/0092964 A1 | 4/2009 | Liggett | 435/5 |
| 2009/0228995 A1 | 9/2009 | Liggett et al. | 800/13 |

FOREIGN PATENT DOCUMENTS

| | | |
|---|---|---|
| EP | 0874048 | 10/1998 |
| JP | 06-121686 | 5/1994 |
| WO | WO 88/10315 | 12/1988 |
| WO | WO 89/06700 | 7/1989 |
| WO | WO 89/10414 | 11/1989 |
| WO | WO 90/01069 | 2/1990 |
| WO | WO 90/09455 | 8/1990 |
| WO | WO 91/02087 | 2/1991 |
| WO | WO 92/15712 | 9/1992 |
| WO | WO 94/03630 | 2/1994 |
| WO | WO 95/17676 | 6/1995 |
| WO | WO 95/33048 | 12/1995 |
| WO | WO 97/11698 | 4/1997 |
| WO | WO 99/13721 | 3/1999 |
| WO | WO 99/19512 | 4/1999 |
| WO | WO 00/20450 | 4/2000 |
| WO | WO 00/22166 | 4/2000 |
| WO | WO 00/31307 | 6/2000 |
| WO | WO 01/11039 | 2/2001 |
| WO | WO 01/29082 | 4/2001 |
| WO | WO 01/79561 | 10/2001 |
| WO | WO 02/09760 | 2/2002 |
| WO | WO 02/071070 | 9/2002 |
| WO | WO 03/057920 | 7/2003 |
| WO | WO 03/088978 | 10/2003 |
| WO | WO 2004/011018 | 2/2004 |
| WO | WO 2004/023101 | 3/2004 |
| WO | WO 2005/025409 | 3/2005 |

OTHER PUBLICATIONS

Bristow et al., "$\alpha_{2c}$-adrenergic receptor 322-325 Del polymorphism enhance the sympatholytic effect of bucindolol, and adversely affected clinical outcomes in the BEST trial," Circulation 112:II-351, 2005.

Bristow, "Antiadrenergic therapy of chronic heart failure: surprises and new opportunities," Circulation, 107:1100-2, 2003.

Bristow, "Beta-adrenergic receptor blockade in chronic heart failure," Circulation, 101:558-69, 2000.

Brodde and Stein, "The gly389arg $\beta_1$—adrenergic receptor polymorphism: a predictor of response to β-blocker treatment?" Clinical Pharmacology and Therapeutics, 74:299-302, 2003.

Domanski et al., "A comparative analysis of the results from 4 trials of beta-blocker therapy for heart failure: BEST, CIBIS-II, MERIT-HF, and COPERNICUS," Journal of Cardiac Failure, 9(5):354-63, 2003.

Domanski et al., "The effect of diabetes on outcomes of patients with advanced heart failure in the BEST trial," J Am Coll Cardiol. 42:914-22, 2003.

Eichhorn and Bristow "Practical guidelines for initiation of beta-adrenergic blockade in patients with chronic heart failure," Am J Cardiol, 79:794-8, 1997.

Eichhorn et al., "A trial of the beta-blocker bucindolol in patients with advanced chronic heart failure," N Engl J Med, 344:1659-67, 2001.

Fagerberg et al., "Effect of metoprolol CR/XL in chronic heart failure: Metoprolol CR/XL randomised intervention trial in congestive heart failure (MERIT-HF)" The Lancet, 353:2001-2007, 1999.

Filigheddu et al., "Genetic polymorphisms of the beta-adrenergic system: association with essential hypertension and response to beta-blockade," The Pharmacogenomics Journal, 4:154-160, 2004.

Flather et al., "FASTTRACK randomized trial to determine the effect of nebivolol on mortality and cardiovascular hospital admission in elderly patients with heart failure (SENIORS)," The European Heart Journal, 26:215-225, 2005.

Forleo et al., "Association of beta-adrenergic receptor polymorphisms and progression to heart failure in patients with idiopathic dilated cardiomyopathy," Am J Med., 117:451-8, 2004.

Gene Card for ADRA2C/α2c-AR available via url: <genecards.org/cgi-bin/carddisp.pl?gene=Adra2c>, Feb. 6, 2008.

Gene Card for ADRBI/β1-AR available via url: <genecards.org/cgi-bin/carddisp.pl?gene=ADRBI>, Feb. 6, 2008.

Goldstein et al., "Metoprolol controlled release/extended release in patients with severe heart failure," J of Am College of Cardiology, 38:932-8, 2001.

Goldstein, "Beta blocker therapy in African American patients with heart failure," Heart Fail Rev., 9:161-7, 2004.

Hein et al., "Two functionally distinct $a_2$-adrenergic receptors regulate sympathetic neurotransmission," Nature, 402:181-184, 1999.

Humma and Terra, "Pharmacogenetics and cardiovascular disease: impact on drug response and applications to disease management," Am J Health-Syst Pharm, 59:1241-1252, 2002.

Iwai et al., "Arg389Gly polymorphism of the human beta1-adrenergic receptor in patients with nonfatal acute myocardial infarction," Am. Heart J., 146:106-109, 2003.

Johnson and Terra., "β-adrenergic receptor polymorphisms: cardiovascular disease associations and pharmacogenetics," Pharmaceutical Research, 19:1779-1787, 2002.

Johnson et al., "$\beta_1$-adrenergic receptor polymorphisms and antihypertensive response to metoprolol," Clin Pharmacol Ther., 74:44-52, 2003.

Joseph et al., "Markedly reduced effects of (−)-isoprenaline but not of (−)-CGP12177 and unchanged affinity of beta-blockers at Gyl389-$\beta_{1-}$ adrenoceptors compared to Arg389- $\beta_{1-}$ adrenoceptors," British J of Pharmacology, 142:51-56, 2004.

Karlsson et al., "Beta1-adrenergic receptor gene polymorphisms and response to beta1-adrenergic receptor blockade in patients with essential hypertension," Clin Cardiol., 27(6):347-50, 2004.

Kaye et al., "Interaction between cardiac sympathetic drive and heart rate in heart failure: modulation by adrenergic receptor genotype," J Am Coll Cardiol., 44:2008-15, 2004.

La Rosee, "The Arg389Gly beta1-adrenoceptor gene polymorphism determines contractile response to catecholamines," Pharmacogenetics, 14:711-716, 2004.

Lechat et al., "The cardiac insufficiency bisoprolol study II (CIBIS-II): a randomised trial," The Lancet, 353:9-13, 1999.

Leineweber, "Beta-adrenergic receptor polymorphism in human cardiovascular disease," Ann Med, 36(suppl 1):64-69, 2004.

Liggett et al. "A polymorphism within a conserved $\beta_1$-adrenergic receptor motif alters cardiac function and β-blocker response in human heart failure." (Under review at PNAS.).

Liggett, "Genetically modified mouse models for pharmacogenomic research," Nat Rev Genet, 5:657-663, 2004.

Liggett, "Polymorphisms of adrenergic receptors: variations on a theme," Assay Drug Dev Technol, 1(2):317-26, 2003.

Liu et al., "Gly389Arg polymorphism of beta-adrenergic receptor is associated with the cardiovascular response to metoprolol," Clinical Pharmacology and Therapeutics, 74(4):372-379, 2003.

Lohse, "Beta-adrenoceptor polymorphisms and heart failure," Trends Mol. Med., 10(2):55-8, 2004.

Mann et al., "Mechanisms and models in heart failure: the biomechanical model and beyond," Circulation, 111:2837-49 2005.

Maqbool et al., "Common polymorphisms of $\beta_1$-adrenoceptor: identification and rapid screening assay," The Lancet, 353:897, 1999.

Mason et al., "A gain-of-function polymorphism in a G-protein coupling domain of the human beta1-adrenergic receptor," The Journal of Biological Chemistry, 274:12670-4, 1999.

McNamara et al., "Clinical importance of beta-adrenoceptor polymorphisms in cardiovascular disease," Am J Pharmacogenomics, 2(2):73-8, 2002.

Muszkat et al., "Pharmacogenetics and response to beta-adrenergic receptor antagonists in heart failure," Clin Pharmacol Ther, 77:123-6, 2005.

O'Shaughnessy et al., "The gain-of-function G389R variant of the beta1-adrenoceptor does not influence blood pressure or heart rate response to beta blockade in hypertensive subjects," Clin Sci, 99(3):233-8, 2000.

Packer et al., "Effect of carvedilol on survival in severe chronic heart failure," The New English Journal of Medicine, 344(22):1651-1658, 2001.

Packer et al., "Effect of carvedilol on the morbidity of patients with severe chronic heart failure," *Circulation*, 106:2194-2199, 2002.

Packer et al., "The effect of carvedilol on morbidity and mortality in patients with chronic heart failure," *N Engl J Med*, 334:1349-55, 1996.

Perez et al., "Beta 1-adrenergic receptor polymorphisms confer differential function and predisposition to heart failure," *Nat Med*, 9(10):1300-5, 2003.

Poole-Wilson et al., "Comparison of carvedilol and metoprolol on clinical outcomes in patients with chronic heart failure in the Carvedilol or Metoprolol European Trial (COMET): randomised controlled trial," *Lancet*, 362:7-13 2003.

Port and Bristow., "β-adrenergic receptors, transgenic mice, and pharmacological model systems," *Molecular Pharmacology*, 60(4):629-631, 2001.

Rathz et al., "Hierarchy of polymorphic variation and desensitization permutations relative to beta 1 and beta 2-adrenergic receptor signaling," *J Biol Chem*, 278:10784-10789, 2003.

Robinson and Bristow, "Beta blockers," Chapter 5 in: *The Pharmacologic Management of Chronic Heart Failure*, The University of Colorado Cardiovascular Institute, pp. 57-81, 2005.

Sallach and Goldstein, "Use of beta-blockers in congestive heart failure," *Ann Med.*, 35:259-266, 2003.

Schwartz and Turner, "Pharmacogenetics of antihypertensive drug responses," *Am J Pharmacogenomics*, 4:151-60, 2004.

Small et al., "A four amino acid deletion polymorphism in the third intracellular loop of the human $a_{2c}$ —adrenergic receptor confers impaired coupling to multiple effectors," *The Journal of Biological Chemistry*, 275(30):23059-23064, 2000.

Small et al., "Pharmacology and physiology of human adrenergic receptor polymorphisms," *Annu Rev Pharmacol Toxicol*, 43:381-411, 2003.

Small et al., "Polymorphisms of cardiac presynaptic $\alpha_{2c}$ adrenergic receptors: diverse intragenic variability with haplotype-specific functional effects," *PNAS*, 101:13020-13025, 2004.

Small et al., "Synergistic polymorphisms of beta1- and alpha2C-adrenergic receptors and the risk of congestive heart failure," *N Engl J Med*, 347:1135-42, 2002.

Sofowora et al., "A common beta 1-adrenergic receptor polymorphism (Arg389Gly) affects blood pressure to beta-blockade," *Clin Pharmacol Ther*, 73:366-71, 2003.

Terra et al., "beta-Adrenergic receptor polymorphisms and responses during titration of metoprolol controlled release/extended release in heart failure," *Clin Pharmacol Ther*, 77:127-37, 2005.

The BEST Steering Committee, "Design of the beta-blocker evaluation survival trial (BEST)," *Am J Cardiol.* 75:1220-3, 1995.

Torp-Pedersen et al., "The incomplete bucindolol evaluation in acute myocardial infarction trial (BEAT)," *The European Journal of Heart Failure*, 4:495-499, 2002.

Wedel et al., "Challenges of subgroup anaylses in multinational clinical trials: experiences from MERIT-HF trial," *Am Heart J*, 142:502-511, 2001.

White et al., "An evaluation of the beta-1 adrenergic receptor Arg389Gly polymorphism in individuals with heart failure: a MERIT-HF sub-study," *Eur J Heart Fail.*, 5:463-8, 2003.

Wollert and Drexler, "Carvedilol prospective randomized cumulative survival (COPERNICUS) trial," *Circulation*, 106:2164-2166, 2002.

Bettoni and Zimmermann, "Autonomic tone variations before the onset of paroxysmal atrial fibrillation," *Circulation*, 105:2753-2759, 2002.

Blumenfeld et al., "Beta-adrenergic receptor blockade as a therapeutic approach for suppressing the renin-angiotensin-aldosterone system in normotensive and hypertensive subjects," *Am J Hypertens*, 12(5):451-459, 1999.

Chen et al., "Initiation of atrial fibrillation by ectopic beats originating from the pulmonary veins: electrophysiological characteristics, pharmacological responses, and effects of radiofrequency ablation," *Circulation*, 100:1879-1886, 1999.

Flaa et al., "Sympathetic activity and cardiovascular risk factors in young men in the low, normal, and high blood pressure ranges," *Hypertension*, 47:396-402, 2006.

Julius and Majahalme, "The changing face of sympathetic overactivity in hypertension," *Ann. Med.*, 32:365-370, 2000.

Kannell et al., "Prevalence, incidence, prognosis, and predisposing conditions for atrial fibrillation: population-based estimates," *Am. J. Cardiol.*, 82(8A):2N-9N, 1998.

McLeod et al., "Differentiation of hemodynamic, humoral and metabolic responses to beta 1- and beta 2-adrenergic stimulation in man using atenolol and propranolol," *Circulation*, 67:1076-1084, 1983.

Office Communication, issued in European Patent Application No. 05814066.6, mail date Oct. 24, 2007.

Office Communication, issued in Russian Patent Application No. 2007114060/13, mail date Mar. 27, 2009.

Office Communication, issued in U.S. Appl. No. 11/226,908, mail date Apr. 28, 2009.

Office Communication, issued in U.S. Appl. No. 11/226,908, mail date Apr. 8, 2009.

Office Communication, issued in U.S. Appl. No. 11/226,908, mail date Nov. 21, 2008.

Office Communication, issued in U.S. Appl. No. 11/226,908, mail date May 20, 2008.

Office Communication, issued in U.S. Appl. No. 11/226,908, mail date Feb. 15, 2008.

Office Communication, issued in U.S. Appl. No. 11/226,908, mail date Aug. 6, 2007.

Office Communication, issued in U.S. Appl. No. 11/838,142, mail date Apr. 3, 2009.

PCT International Preliminary Report on Patentability, issued in International application No. PCT/US2005/032901, mail date Mar. 29, 2007.

PCT International Search Report and Written Opinion, issued in International application No. PCT/US2005/032901, mail date Sep. 26, 2005.

SEC Filing: Registration Statement on Form S-4, dated Oct. 30, 2008.

SEC Filing: Amendment No. 1 to Registration Statement on Form S-4, dated Nov. 21, 2008.

The Beta-Blocker Evaluation of Survival Trial Investigators, "A trial of the beta-blocker bucindolol in patients with advanced chronic heart failure," *N. Engl. J. Med.*, 344(22):1659-1667, 2001.

Workman et al., "Chronic beta-adrenoceptor blockade and human atrial cell electrophysiology: evidence of pharmacological remodelling," *Cardiovascular Research*, 58:518-525, 2003.

Office Communication, issued in Australian Patent Application No. 2005284822, dated Mar. 1, 2010.

"Introduction to α-adrenoreceptors," located online at http://www.adrenoceptor.com/alphaintro.htm, printed on Apr. 7, 2010.

Adolfsson et al., "Characterization of $\alpha_2$-adrenoceptor subtypes in pregnant human myometrium," *Gynecol. Obstet. Invest.*, 45:145-150, 1998.

Arner, "Adrenergic receptor function in fat cells," *Am. J. Clin. Nutr.*, 55:228S-236S, 1992.

Baldwin et al., "Identification of a polymorphic glutamic acid stretch in the $\alpha_{2B}$-adrenergic receptor and lack of linkage with essential hypertension ," *Journal of the American Society of Hypertension*, 12:853-857, 1999.

Barany, "Genetic disease detection and DNA amplification using cloned thermostable ligase," *Proc. Natl. Acad. Sci. USA*, 88:189-193, 1991.

Bengtsson, "Polymorphism in the B1-adrenergic receptor gene and hypertension," *Circulation*, 104(2):187-190, 2001.

Berrettini and Hoehe, "A polymorphism of the $beta_1$ adrenergic receptor gene (BADR) detected with Bgl I," *Nucleic Acids Res.*, 16:7754, 1988.

Björklund et al., "$\alpha_{2C}$-adrenoceptor-overexpressing mice are impaired in executing nonspatial and spatial escape strategies," *Mol. Pharmacol.*, 54:569-576, 1998.

Blum et al., "Molecular mechanism of slow acetylation of drugs and carcinogens in humans," *Proc. Natl. Acad. Sci. USA*, 88:5237-5241, 1991.

Böhm et al., "Desensitization of adenylate cyclase and increase of $G_{i\alpha}$ in cardiac hypertrophy due to acquired hypertension," *Hypertension*, 20(1):103-112, 1992.

Böhm et al., "Increase of $G_{i\alpha}$ in human hearts with dilated but not ischemic cardiomyopathy," *Circulation*, 82:1249-1265, 1990.

Bristow et al., "Decreased catecholamine sensitivity and β-adrenergic-receptor density in failing human hearts," *N. Engl. J. Med.*, 307(4):205-211, 1982.

Bristow et al., "$β_1$- and $β_2$-adrenergic receptor-mediated adenylate cyclase stimulation in nonfailing and failing human ventricular myocardium," *Mol. Pharmacol.*, 35:295-303, 1988.

Bristow et al., "$β_1$- and $β_2$-adrenergic-receptor subpopulations in nonfailing and failing human ventricular myocardium: coupling of both receptor subtypes to muscle contraction and selective $β_1$-receptor down-regulation in heart failure," *Circ. Res.*, 59(3):297-309, 1986.

Brodde et al., "Regional distribution of β-adrenoceptors in the human heart: coexistence of functional $β_1$- and $β_2$-adrenoceptors in both atria and ventricles in severe congestive cardiomyopathy," *J. Cardiovasc. Pharmacol.*, 8:1235-1242, 1986.

Carstairs et al., "Autoradiographic visualization of beta-adrenoceptor subtypes in human lung," *Am. Rev. Respir. Dis.*, 132:541-547, 1985.

Comings et al., "Additive effect of three noradrenergic genes (ADRA2A, ADRA2C, DBH) on attention-deficit hyperactivity disorder and learning disabilities in Tourette syndrome subjects," *Clinical Genetics*, 55(3):160-172, 1999.

Cooper et al., "Epidemiology of a polymorphism of the β-2 adrenergic receptor gene in asthma," *Am. J. Respir. Crit. Care Med.*, Abstract, 153:A254, 1996.

D'Angelo et al., "Transgenic Gαq overexpression induces cardiac contractile failure in mice," *Proc. Natl. Acad. Sci. U.S.A.*, 94:8121-8126, 1997.

de Boer et al., "Polypharmacy in chronic heart failure: practical issues regarding the use of angiotensin-converting enzyme inhibitors, beta-blockers and other drugs," *European Society of Cardiology*, 4(Suppl. D):D111-D116, 2002.

Dewar et al., "The glutamine 27 $β_2$-adrenoceptor polymorphism is associated with elevated IgE levels in asthmatic families," *J. Allergy Clin. Immunol.*, 100:261-265, 1997.

Dohlman et al., "Model systems for the study of seven-transmembrane-segment receptors," *Annu. Rev. Biochem.*, 60:653-688, 1991.

Dorn II et al., "Mechanisms of impaired β-adrenergic receptor signaling in $G_{αq}$-mediated cardiac hypertrophy and ventricular dysfunction," *Molecular Pharmacology*, 57:278-287, 2000.

Dorn II et al., "$α_{2A}$-adrenergic receptor stimulated calcium release is transduced by $G_i$-associated $G_{αγ}$-mediated activation of phospholipase C," *Biochem.*, 36:6415-6423, 1997.

Dunigan et al., "Complexity of agonist- and cyclic AMP-mediated downregulation of the human $β_1$-adrenergic receptor: role of internalization, degradation, and mRNA destabilization," *Biochemistry*, 41:8019-8030, 2002.

Eason and Liggett, "Human $α_2$-adrenergic receptor subtype distribution: widespread and subtype-selective expression of $α_2$C10, $α_2$C4, and $α_2$C2 mRNA in multiple tissues," *Mol. Pharmacol.*, 44:70-75, 1993.

Eason and Liggett, "Subtype-selective desensitization of $α_2$-adrenergic receptors. Different mechanisms control short and long term agonist-promoted desensitization of $α_2$C10, $α_2$C4, and $α_2$C2," *J. Biol. Chem.*, 267:25473-25479, 1992.

Eason et al., "Simultaneous coupling of $α_2$-adrenergic receptors to two G-proteins with opposing effects. Subtype-selective coupling of $α_2$C10, $α_2$C4, and $α_2$C2 adrenergic receptors to $G_i$ and $G_s$," *J. Biol. Chem.*, 267:15795-15801, 1992.

Eason et al., "The palmitoylated cysteine of the cytoplasmic tail of $α_{2A}$-adrenergic receptors confers subtype-specific agonist-promoted downregulation," *Proc. Natl. Acad. Sci. USA*, 91:11178-11182, 1994.

Engelhardt et al., "Progressive hypertrophy and heart failure in $β_1$-adrenergic receptor transgenic mice," *Proc. Natl. Acad. Sci. U.S.A.*, 96:7059-7064, 1999.

Eschenhagen et al., "Increased messenger RNA level of the inhibitory G protein α subunit $G_{iα-2}$ in human end-stage heart failure," *Circ. Res.*, 70:688-696, 1992.

Feng et al., "Variants in the $α_{2A}$ AR adrenergic receptor gene in psychiatric patients," *Am. J. Med. Genet.*, 81:405-410, 1998.

Franz et al., "Cardiomyopathies: from genetics to the prospect of treatment," *Lancet*, 358:1627-1637, 2001.

Fraser et al., "Cloning, sequence analysis, and permanent expression of a human $α_2$-adrenergic receptor in Chinese hamster ovary cells. Evidence for independent pathways of receptor coupling to adenylate cyclase attenuation and activation," *J. Biol. Chem.*, 264:11754-11761, 1989.

Freeman et al., "Genetic polymorphism of the $α_2$-adrenergic receptor is associated with increased platelet aggregation, baroreceptor sensitivity, and salt excretion in normotensive humans," *American Journal of Hypertension*, 8(9):863-869, 1995.

Frielle et al., "Cloning of the cDNA for the human $β_1$-adrenergic receptor," *Proc. Natl. Acad. Sci. USA*, 84:7920-7924, 1987.

Gavin et al., "$α_{2C}$-adrenoceptors mediate contractile responses to noradrenaline in the human saphenous vein," *Naunyn Schmiedeberg's Arch Pharmacol.*, 355:406-411, 1997.

GenBank, NCBI Sequence Viewer v2.0, Accession No. U72648, Nov. 1998, 10 pages.

Gerson et al., "Activity of the uptake-1 norepinephrine transporter as measured by I-123 MIBG in heart failure patients with a loss-of-function polymorphism of the presynaptic alpha2C-adrenergic receptor," *Journal of Nuclear Cardiology*, 10(6):583-589, 2003.

Givertz, "Underlying causes and survival in patients with heart failure," *N. Engl. J. Med.*, 342:I120-I122, 2000.

Green et al, "A polymorphism of the human $β_2$-adrenergic receptor within the fourth transmembrane domain alters ligand binding and functional properties of the receptor," *J. Biol. Chem.*, 268:23116-23121, 1993.

Green et al., "Amino-terminal polymorphisms of the human $β_2$-adrenergic receptor impart distinct agonist-promoted regulatory properties," *Biochemistry*, 33:9414-9419, 1994.

Green et al., "Influence of $β_2$-adrenergic receptor genotypes on signal transduction in human airway smooth muscle cells," *Am. J. Respir. Cell Mol. Biol.*, 13:25-33, 1995.

Gusella, "DNA polymorphism and human disease," *Ann. Rev. Biochem.*, 55:831-854, 1986.

Hall et al., "Association of Glu 27 $β_2$-adrenoceptor polymorphism with lower airway reactivity in asthmatic subjects," *The Lancet*, 345:1213-1214, 1995.

Hamid et al., "Localization of $β_2$-adrenoceptor messenger RNA in human and rat lung using in situ hybridization: correlation with receptor autoradiography," *European Journal of Pharmacology*, 206:133-138, 1991.

Heinonen et al., "Identification of a three-amino acid deletion in the $α_{2B}$-adrenergic receptor that is associated with reduced basal metabolic rate in obese subjects," *The Journal of Clinical Endocrinology and Metabolism*, 84(7):2429-2433, 1999.

Higashi et al., "Association of a genetic variation in the $β_3$-adrenergic receptor gene with coronary heart disease among Japanese," *Biochem. Biophys. Res. Comm.*, 232:728-730, 1997.

Himms-Hagen et al., "Effect of CL-316,243, a thermogenic $β_3$-agonist, on energy balance and brown and white adipose tissue in rats ," *Am. J. Physiol.*, 266:1371-1382, 1994.

Holroyd et al., "Evidence for $β_2$-adrenergic receptor (ADRB2) polymorphism at amino acid 16 as a risk factor for bronchial hyper-responsiveness (BHR)," *Am. J. Respir. Crit. Care Med.*, Abstract, 151:A673, 1995.

Ikezu et al., "Amino acids 356-372 constitute a $G_i$-activator sequence of the $α_2$-adrenergic receptor and have a Phe substitute in the G protein-activator sequence motif," *FEBS Lett.*, 311:29-32, 1992.

Iwai et al., "Suppressive effect of the Gly389 allele of the $β_1$-adrenergic receptor gene in the occurrence of ventricular tachycardia in dilated cardiomyopathy," *Circulation Journal*, 66:723-728, 2002.

Jewell-Motz and Liggett, "An acidic motif within the third intracellular loop of the $α_2$C2 adrenergic receptor is required for agonist-promoted phosphorylation and desensitization," *Biochemistry*, 34(37):11946-11953, 1995.

Jewell-Motz et al., "Agonist-mediated downregulation of $G_{αi}$ via the $α_2$-adrenergic receptor is targeted by receptor-$G_i$ interaction and is independent of receptor signaling and regulation," *Biochemistry*, 37:15720-15725, 1998.

Kass, "β-receptor polymorphisms: heart failure's crystal ball," *Nature Medicine*, 9(10):1260-1262, 2003.

Kobilka et al., "cDNA for the human β2-adrenergic receptor: a protein with multiple membrane-spanning domains and encoded by a gene whose chromosomal location is shared with that of the receptor for platelet-derived growth factor," *Proc. Natl. Acad. Sci. USA*, 84:46-50, 1987.

Kobilka et al., "Cloning, sequencing, and expression of the gene coding for the human platelet $\alpha_2$-adrenergic receptor," *Science*, 238:650-656, 1987.

Kornher and Livak, "Mutation detection using nucleotide analogs that alter electrophoretic mobility," *Nucl. Acids. Res.*, 17:7779-7784, 1989.

Krief et al., "Tissue distribution β3-adrenergic receptor mRNA in man," *J. Clin. Invest.*, 91:344-349, 1993.

Kumari et al., "Effect of clonidine on the human acoustic startle reflex," *Psychopharmacology*, 123:353-360, 1996.

Kuppuswamy et al., "Single nucleotide primer extension to detect genetic diseases: experimental application to hemophilia B (factor IX) and cystic fibrosis genes," *Proc. Natl. Acad. Sci. USA*, 88:1143-1147, 1991.

Kwoh et al., "Transcription-based amplification system and detection of amplified human immunodeficiency virus type 1 with a bead-based sandwich hybridization format," *Proc. Natl. Acad. Sci. USA*, 86:1173-1177, 1989.

Landegren et al., "A ligase-mediated gene detection technique," *Science*, 241:1077-1080, 1988.

Large et al., "Human beta-2 adrenoceptor gene polymorphisms are highly frequent in obesity and associate with altered adipocyte beta-2 adrenoceptor function," *J. Clin. Invest.*, 100:3005-3013, 1997.

Lentes et al., "A biallelic DNA polymorphism of the human beta-2-adrenergic receptor detected by Ban I-Adrbr-2," *Nucleic Acids Research*, 16(5):2359, 1988.

Li et al., "Do allelic variants in $\alpha_{2A}$ and $\alpha_{2C}$ adrenergic receptors predispose to hypertension in blacks?" *Hypertension*, 47:1140-1146, 2006.

Liggett et al., "Early and delayed consequences of $\alpha_2$-adrenergic receptor overexpression in mouse hearts," *Circ.*, 101:1707-1714, 2000.

Liggett et al., "The Ile164 $\beta_2$-adrenergic receptor polymorphism adversely affects the outcome of congestive heart failure," *J. Clin. Invest.*, 102:1534-1539, 1998.

Liggett, "β-adrenergic receptors in the failing heart: the good, the bad, and the unknown," *J. Clin. Invest.*, 107(8):947-948, 2001.

Lobmeyer et al., "Synergistic polymorphisms of $\beta_1$ and $\alpha_{2C}$-adrenergic receptors and the influence on left ventricular ejection fraction response to β-blocker therapy in heart failure," *Pharmacogenetics and Genomics*, 17(4):277-282, 2007.

Lomasney et al., "Expansion of the $\alpha_2$-adrenergic receptor family: cloning and characterization of a human $\alpha_2$-adrenergic receptor subtype, the gene for which is located on chromosome 2," *Proc. Natl. Acad. Sci. USA*, 87:5094-5098, 1990.

Lowell et al., "The potential significance of $\beta_3$ adrenergic receptors," *J. Clin. Invest.*, 95:923, 1995.

Luttrell et al., "G-protein-coupled receptors and their regulation: activation of the MAP kinase signaling pathway by G-protein-coupled receptors," *Advances in Second Messenger and Phosphoprotein Research*, 31:263-277, 1997.

Makaritsis et al., "Role of the $\alpha_{2B}$-adrenergic receptor in the development of salt-induced hypertension," *Hypertension*, 33(1):14-17, 1999.

Martin, "Thyrotropin-releasing hormone rapidly activates the phosphodiester hydrolysis of polyphosphoinositides in $GH_3$ pituitary cells. Evidence for the role of a polyphosphoinositide-specific phospholipase C in hormone action," *J. Biol. Chem.*, 258:14816-14822, 1983.

McQuitty et al., "Polymorphism in the human β2 adrenergic receptor gene detected by Restriction Endonuclease digestion with Fnu4HI," *Hum. Genet.*, 93:225, 1994.

Meisel et al., "Polymorphisms of adrenergic receptors and the risk of heart failure," *New England Journal of Medicine*, 348(5):468-470, 2003.

Michel et al., "Functional correlates of $\alpha_{2A}$-adrenoceptor gene polymorphism in the HANE study," *Nephrology, Dialysis, Transplantation*, 14(11):2657-2663, 1999.

Moore et al., "Racial differences in the frequencies of cardiac beta(1)-adrenergic receptor polymorphisms: analysis of c145A>G and c1165G>C," *Hum. Mutat.*, 14(3):271, 1999.

Morgan et al., "Yohimbine-facilitated acoustic startle reflex in humans," *Psychopharmacology*, 110:342-346, 1993.

Nickerson et al., "Automated DNA diagnostics using an ELISA-based oligonucleotide ligation assay," *Proc. Natl. Acad. Sci. USA*, 87:8923-8927, 1990.

Nyrén et al., "Solid phase DNA minisequencing by an enzymatic luminometric inorganic pyrophosphate detection assay," *Anal. Biochem.*, 208:171-175, 1993.

Okamoto and Nishimoto, "Detection of G protein-activator regions in $M_4$ subtype muscarinic, cholinergic, and $\alpha_2$-adrenergic receptors based upon characteristics in primary structure," *J. Biol. Chem.*, 267:8342-8346, 1992.

Orita et al., "Rapid and sensitive detection of point mutations and DNA polymorphisms using the polymerase chain reaction," *Genomics*, 5:874-879, 1989.

Palczewski et al., "Crystal structure of rhodopsin: a G protein-coupled receptor," *Science*, 289:739-745, 2000.

PCT International Preliminary Examination Report issued in International Application No. PCT/US2003/028135, mailed Jun. 13, 2006.

PCT International Preliminary Examination Report issued in International Application No. PCT/US2001/012575, mailed Sep. 13, 2005.

PCT International Preliminary Report on Patentability issued in International Application No. PCT/US2004/029838, mailed Mar. 13, 2006.

PCT International Preliminary Report on Patentability issued in International Application No. PCT/US2005/023293, mailed Jun. 19, 2007.

PCT International Search Report issued in International Application No. PCT/US2005/023293, mailed May 29, 2007.

PCT International Search Report issued in International Application No. PCT/US2004/029838, mailed Oct. 14, 2005.

PCT International Search Report issued in International Application No. PCT/US2003/028135, mailed Nov. 22, 2005.

PCT International Search Report issued in International Application No. PCT/US2001/012575, mailed Jan. 29, 2003.

PCT Invitation to Pay Additional Fees issued in International Application No. PCT/US2001/012575, mailed Nov. 11, 2002.

Pertl and Bianchi, "Fetal DNA in maternal plasma: emerging clinical applications," *Obstet. Gynecol.*, 98(3):483-490, 2001.

Prezant and Fischel-Ghodsian, "Trapped-oligonucleotide nucleotide incorporation (TONI) assay, a simple method for screening point mutations," *Hum. Mutat.*, 1:159-164, 1992.

Regan et al., "Cloning and expression of a human kidney cDNA for an $\alpha_2$-adrenergic receptor subtype," *Proc. Natl. Acad. Sci. USA*, 85:6301-6305, 1988.

Reihsaus et al., "Mutations in the gene encoding for the $\beta_2$-adrenergic receptor in normal and asthmatic subjects," *Am. J. Respir. Cell Mol. Biol.*, 8:334-339, 1993.

Reynisdottir et al., "Catecholamine resistance in fat cells of women with upper-body obesity due to decreased expression of beta$_2$-adrenoceptors," *Diabetologia*, 37:428-435, 1994.

Rosin et al., "Distribution of alpha 2C-adrenergic receptor-like immunoreactivity in the rat central nervous system," *J. Comp. Neurol.*, 372:135-165, 1996.

Rothwell and Stock, "A role for brown adipose tissue in diet-induced thermogenesis," *Nature*, 281:31-35, 1979.

Ruffolo et al., "Pharmacologic and therapeutic applications of $\alpha_2$-adrenoceptor subtypes," *Annu Rev Pharmacol Toxicol*, 33:243-279, 1993.

Sakai et al., "Genetic analysis of amplified DNA with immobilized sequence-specific oligonucleotide probes," *Proc. Natl. Acad. Sci. USA*, 86:6230-6234, 1989.

Sallinen et al., "Adrenergic $\alpha_{2C}$-receptors modulate the acoustic startle reflex, prepulse inhibition, and aggression in mice," *The Journal of Neuroscience*, 18:3035-3042, 1998.

Sallinen et al., "Genetic alteration of the $\alpha_2$-adrenoceptor subtype c in mice affects the development of behavioral despair and stress-induced increases in plasma corticosterone levels," *Mol. Psychiatry*, 4:443-452, 1999.

Sallinen et al., "Genetic alteration of $\alpha_{2C}$-adrenoceptor expression in mice: influence on locomotor, hypothermic, and neurochemical effects of dexmedetomidine, a subtype-nonselective $\alpha_2$-adrenoceptor agonist," *Mol. Pharmacol.*, 51:36-46, 1997.

Saulnier-Blache et al., "Analysis of the $\alpha_{2C}$-adrenergic receptor gene promoter and its cell-type-specific activity," *Mol. Pharmacol.*, 50:1432-1442, 1996.

Schramm and Limbird, "Stimulation of mitogen-activated protein kinase by G protein-coupled $\alpha_2$-adrenergic receptors does not require agonist-elicited endocytosis," *J. Biol. Chem.*, 274:24935-24940, 1999.

Schwinn et al., "The alpha 1C-adrenergic receptor: characterization of signal transduction pathways and mammalian tissue heterogeneity," *Mol. Pharmacol.*, 40:619-626, 1991.

Serikov et al., "Reduction of $[Ca^{2+}]_i$ restores uncoupled $\beta$-adrenergic signaling in isolated perfused transgenic mouse hearts," *Circulation Research*, 88:9-11, 2001.

Shi et al., "Distribution of alpha2-adrenoceptor mRNAs in the rat lumbar spinal cord in normal and axotomized rats," *NeuroReport*, 10:2835-2839, 1999.

Small and Liggett, "Identification and functional characterization of $\alpha_2$-adrenoceptor polymorphisms," *TRENDS in Pharmacological Studies*, 22(9):471-477, 2001.

Small et al., "Identification of adrenergic receptor polymorphisms," *Methods in Enzymology*, 343:459-475, 2002.

Small et al., "Polymorphic deletion of three intracellular acidic residues of the $\alpha_{2B}$-adrenergic receptor decreases G protein-coupled receptor kinase-mediated phosphorylation and desensitization," *The Journal of Biological Chemistry*, 276(7):4917-4922, 2001.

Smith et al., "Measurement of protein using bicinchoninic acid," *Anal. Biochem.*, 150:76-85, 1985.

Snapir et al., "An insertion/deletion polymorphism in the $\alpha_{2B}$-adrenergic receptor gene is a novel genetic risk factor for acute coronary events," *Journal of the American College of Cardiology*, 37(6):1516-1522, 2001.

Sokolov, "Primer extension technique for the detection of single nucleotide in genomic DNA," *Nucl. Acids. Res.*, 18:3671, 1990.

Supplementary European Search Report issued in European Application No. EP 05789151, mailed Sep. 5, 2008.

Supplementary European Search Report issued in European Application No. 04816181.4, mailed Oct. 11, 2006.

Supplementary Partial European Search Report issued in European Application No. EP 03794666.2, mailed Jul. 17, 2006.

Syvänen et al., "A primer-guided nucleotide incorporation assay in the genotyping of apolipoprotein E," *Genomics*, 8:684-692, 1990.

Syvänen et al., "Identification of individuals by analysis of biallelic DNA markers, using PCR and solid-phase minisequencing," *Amer. J. Hum. Genet.*, 52:46-59, 1993.

Tan et al., "Association between $\beta_2$-adrenoceptor polymorphism and susceptibility to bronchodilator desensitisation in moderately severe stable asthmatics," *Lancet*, 350:995-999, 1997.

Tan et al., "$\beta_2$-adrenoceptor polymorphism determines susceptibility to bronchodilator desensitisation in asthmatics," *Am. J. Respir. Crit. Care Med.*, Abstract, 155:A208, 1997.

Tanila et al., "Role of $\alpha_{2C}$-adrenoceptor subtype in spatial working memory as revealed by mice with targeted disruption of the $\alpha_{2C}$-adrenoceptor gene," *European Journal of Neuroscience*, 11:599-603, 1999.

Tepe et al., "Altering the receptor-effector ratio by transgenic overexpression of type V adenylyl cyclase: enhanced basal catalytic activity and function without increased cardiomyocyte $\beta$-adrenergic signalling," *Biochemistry*, 38:16706-16713, 1999.

Tesson et al., "Characterization of a unique genetic variant in the $\beta_1$-adrenoceptor gene and evaluation of its role in idiopathic dilated cardiomyopathy," *Journal of Molecular and Cellular Cardiology*, 31:1025-1032, 1999.

Trayhurn and Mercer, "Brown adipose tissue thermogenesis in obese animals," *Biochem. Soc. Trans.*, 14:236-239, 1986.

Tsujii and Bray, "Food intake of lean and obese Zucker rats following ventricular infusions of adrenergic agonists," *Brain Res.*, 587:226-232, 1992.

Turki et al., "Genetic polymorphisms of the $\beta_2$-adrenergic receptor in nocturnal and nonnocturnal asthma," *J. Clin. Invest.*, 95:1635-1641, 1995.

Turki et al., "Myocardial signaling defects and impaired cardiac function of a human $\beta_2$-adrenergic receptor polymorphism expressed in transgenic mice," *Proc. Natl. Acad. Sci.USA*, 93:10483-10488, 1996.

Ugozzoli et al., "Detection of specific alleles by using allele-specific primer extension followed by capture on solid support," *GATA*, 9:107-112, 1992.

Ungerer et al., "Altered expression of $\alpha$-adrenergic receptor kinase and $\beta_1$-adrenergic receptors in the failing human heart," *Circulation*, 87:454-463, 1993.

van Campen et al., "Ejection fraction improvement by $\beta$-blocker treatment in patients with heart failure: an analysis of studies published in the literature," *Journal of Cardiovascular Pharmacology*, 32(Suppl. 1):S31-S35, 1998.

Wagoner et al., "Polymorphisms of the $\beta_1$-adrenergic receptor predict exercise capacity in heart failure," *American Heart Journal*, 144(5):840-846, 2002.

Wagoner et al., "Polymorphisms of the $\beta_2$ adrenergic receptor ($\beta_2$AR) affect exercise capacity in patients with heart failure" *Circulation*, 94:8, Abstract, 1996.

Wagoner et al., "Polymorphisms of the $\beta_2$-adrenergic receptor determine exercise capacity in patients with heart failure," *Circulation Research*, 86:834-840, 2000.

Walker et al., "Isothermal in vitro amplification of DNA by a restriction enzyme/DNA polymerase system," *Proc. Natl. Acad. Sci. USA*, 89:392-396, 1992.

Wartell et al., "Detecting base pair substitutions in DNA fragments by temperature-gradient gel electrophoresis," *Nucl. Acids. Res.*, 18:2699-2706, 1990.

Wu et al., "The Ligation Amplification Reaction (LAR)—amplification of specific DNA sequences using sequential rounds of template-dependent ligation," *Genomics*, 4:560-569, 1989.

Yang-Feng et al., "Chromosomal organization of adrenergic receptor genes," *Proc. Natl. Acad. Sci. USA*, 87:1516-1520, 1990.

Yoshida et al., "Anti-obesity and anti-diabetic effects of CL 316,243, a highly specific $\beta_3$-adrenoceptor agnoist, in yellow KK mice," *Life Sciences*, 54:491-498, 1994.

Yussman et al., "Mitochondrial death protein Nix is induced in cardiac hypertrophy and triggers apoptotic cardiomyopathy," *Nature Medicine*, 8(7):725-730, 2002.

Altman et al., "Abnormal regulation of the sympathetic nervous system in $\alpha_{2A}$-adrenergic receptor knockout mice," *Mol. Pharmacol.*, 56:154-161, 1999.

Arner and Hoffstedt, "Adrenoceptor genes in human obesity," *Journal of Internal Medicine*, 245:667-672, 1999.

Baron and Siegel, "$p$-[$^{125}$I]Iodoclonidine, a novel radiolabeled agonist for studying central $\alpha_2$-adrenergic receptors," *Mol. Pharmacol.*, 38:348-356, 1990.

Cotton, "Current methods of mutation detection," *Mutation Research*, 285:125-144, 1993.

Dao et al., "Expression of altered $\alpha_2$-adrenergic phenotypic traits in normotensive humans at genetic risk of hereditary (essential) hypertension," *J Hypertens.*, 16(6):779-792, 1998.

de Chasseval and de Villartay, "High level transient gene expression in human lymphoid cells by SV40 large T antigen boost," *Nucleic Acids Res.*, 20(2):245-250, 1992.

Eason and Liggett, "Chimeric mutagenesis of putative G-protein coupling domains of the $\alpha_{2A}$-adrenergic receptor. Localization of two redundant and fully competent $G_i$ coupling domains," *J Biol Chem.*, 271(22):12826-12832, 1996.

Eason et al., "Contribution of ligand structure to activation of $\alpha_2$-adrenergic receptor subtype coupling to $G_s$," *Mol. Pharmacol.*, 45:696-702, 1994.

Eason et al., "Four consecutive serines in the third intracellular loop are the sites for $\beta$-adrenergic receptor kinase-mediated phosphorylation and desensitization of the $\alpha_{2A}$-adrenergic receptor," *The Journal of Biological Chemistry*, 270(9):4681-4688, 1995.

Exton, "Regulation of phosphoinositide phospholipases by hormones, neurotransmitters, and other agonists linked to G proteins," *Annu Rev Pharmacol Toxicol.*, 36:481-509, 1996.

Goldstein et al., "Sympathetic reactivity during a yohimbine challenge test in essential hypertension," *Hypertension.*, 18(5 Suppl):III40-III48, 1991.

Goodman and Gilman's *The Pharmacological Basis of Therapeutics*, Pergamon Press, 1990, New York, pp. 89-90.

Gratze et al. "β-2 adrenergic receptor variations affect resting blood pressure and agnoist-induced vasodilation in young adult Caucasians," *Hypertension*, 33:1425-1430, 1999.

Guyer et al., "Cloning, sequencing, and expression of the gene encoding the porcine $\alpha_2$-adrenergic receptor," *The Journal of Biological Chemistry*, 265(28):17307-17317, 1990.

Handy et al., "Diverse tissue expression of rat $\alpha_2$-adrenergic receptor genes," *Hypertension*, 21: 861-865, 1993.

Hausdorff et al., "Phosphorylation sites on two domains of the $\beta_2$-adrenergic receptor are involved in distinct pathways of receptor desensitization," *The Journal of Biological Chemistry*, 264:12657-12665, 1989.

Hein et al., "Gene substitution/knockout to delineate the role of $\alpha_2$-adrenoceptor subtypes in mediating central effects of catecholamines and imidazolines," *Annals New York Academy of Sciences*, 881:265-271, 1999.

Hellström et al., "The different effects of a Gln27Glu $\beta_2$-adrenoceptor gene polymorphism on obesity in males and in females," *Journal of Internal Medicine*, 245:253-259, 1999.

Ho et al., "Structural polymorphism in the $\alpha_{2B}$ adrenoceptor: no association with schizophrenia or clozapine responsiveness," *Am. J. Med. Genet.*, 81(6):510, Abstract No. 93, 1998.

Holmes et al., "Guanabenz. A review of its pharmacodynamic properties and therapeutic efficacy in hypertension," *Drugs*, 26(3):212-229, 1983.

Ishiyama-Shigemoto et al., "Association of polymorphisms in the β2-adrenergic receptor gene with obesity, hypertriglyceridaemia, and diabetes mellitus," *Diabetologia*, 42:98-101, 1999.

Jewell-Motz and Liggett, "G protein-coupled receptor kinase specificity for phosphorylation and desensitization of the $\alpha_2$-adrenergic receptor subtypes," *The Journal of Biological Chemistry*, 271(30):18082-18087, 1996.

Jewell-Motz et al., "$\alpha_{2A}/\alpha_{2C}$-adrenergic receptor third loop chimera show that agonist interaction with receptor subtype backbone establishes G protein-coupled receptor kinase phosphorylation," *The Journal of Biological Chemistry*, 275(37):28989-28993, 2000.

Kotanko et al., "Essential hypertension in African Caribbean associates with a variant of the $\beta_2$-adrenoceptor," *Hypertension*, 30:773-776, 1997.

Kurose and Lefkowitz, "Differential desensitization and phosphorylation of three cloned and transfected $\alpha_2$-adrenergic receptor subtypes," *J. Biol. Chem.*, 269:10093-10099, 1994.

Lakhlani et al., "Substitution of a mutant $\alpha_{2a}$-adrenergic receptor via "hit and run" gene targeting reveals the role of this subtype in sedative, analgesic, and anesthetic-sparing responses in vivo," *Proc Natl Acad Sci USA.*, 94(18):9950-9955, 1997.

Liggett et al., "Adrenergic receptor-coupled adenylyl cylase systems: regulation of receptor function by phosphorylation, sequestration and downregulation," In *Regulation of Cellular Signal Transduction Pathways by Desensitization and Amplification*, pp. 71-97, 1993.

Liggett et al., "Sites in the third intracellular loop of the $\alpha_{2A}$-adrenergic receptor confer short term agnoist-promoted desensitization," *The Journal of Biological Chemistry*, 267(7):4740-4746, 1992.

Liggett, "Pharmacogenetics of relevant targets in asthma," *Clin Exp Allergy*, 28 Suppl 1:77-79; discussion 80-81, 1998.

Limbird, "Receptors linked to inhibition of adneylate cyclase: additional signaling mechanisms," *FASEB J.*, 2:2686-2695, 1988.

Link et al., "Cardiovascular regulation in mice lacking $\alpha_{2A}$-adrenergic receptor subtypes b and c," *Science*, 273:803-805, 1996.

Lockette et al., "$\alpha_2$-adrenergic receptor gene polymorphism and hypertension in blacks," *Am J Hypertens.*, 8(4 Pt 1):390-394, 1995.

Luttrell et al., "Regulation of mitogen-activated protein kinase pathways by catecholamine receptors," *Adv. Pharmacol.*, 42:466-470, 1998.

MacMillan et al., "Central hypotensive effects of the $\alpha_{2a}$-adrenergic receptor subtype," *Science*, 273:801-805, 1996.

MacMillan et al., "$\alpha_2$-adrenergic receptor subtypes: subtle mutation of the $\alpha_{2A}$-adrenergic receptor in vivo by gene targeting strategies reveals the role of this subtype in multiple physiological settings," *Recent Prog Horm Res.*, 53:25-42, 1998.

Makaritsis et al., "Sympathoinhibitory function of the $\alpha_{2A}$-adrenergic receptor subtype," *Hypertension*, 34(3):403-407, 1999.

Martin-Guerrero et al., "The N251K functional polymorphism in the $\alpha_{2A}$-adrenoceptor gene is not associated with depression: a study in suicide completers," *Pyschopharmacology*, 184:82-86, 2006.

Meirhaeghe et al., "$\beta_2$-adrenoceptor gene polymorphism, body weight, and physical activity," *Lancet*, 353:896, 1999.

Munroe and Caufield, "Genetics of hypertension," *Current Opinion in Genetics & Development*, 10:325-329, 2000.

Newton, "Primers," in *PCR Essential Data*, Chapter 6, pp. 49-56, 1995.

Onions et al., "Genetic markers at the leptin (*OB*) locus are not significantly linked to hypertension in African Americans," *Hypertension*, 31(6):1230-1234, 1998.

Onorato et al., "Role of acidic amino acids in peptide substrates of the β-adrenergic receptor kinase and rhodopsin kinase," *Biochemistry*, 30:5118-5125, 1991.

Pitcher et al., "G protein-coupled receptor kinases," *Annu. Rev. Biochem.*, 67:653-692, 1998.

Pollin et al., "The Glu$^{12}$/Glu$^9$ mutation in the $\alpha_{2B}$-adrenergic receptor is associated with increased resting metabolic rate (RMR) in a Caucasian cohort," *Obesity Research*, 8:Supp 859, Abstract No. PE4, 2000.

Reihsaus et al., "Mutations in the gene encoding for the beta 2-adrenergic receptor in normal and asthmatic subjects," *Am. J. Respir. Cell Mol. Biol.*, 8:334-339, 1993.

Robinson and Hudson, "Andrenoceptor pharmacology," located online at http://www.tocris.com/adrenoceptor.htm, 1998. (Accessed on Mar. 19, 2001.).

Rohrer and Kobilka, "G protein-coupled receptors: functional and mechanistic insights through altered gene expression," *Physiological Reviews*, 78(1):35-52, 1998.

Sakane et al., "$\beta_2$-adrenoceptor gene polymorphism and obesity," *Lancet*, 353:1976, 1999.

Salonen et al., "An insertion/deletion polymorphism in the alpha-2b-adrenergic receptor gene is a novel genetic risk factor for acute coronary events," *Circulation*, 102(18):Supp 859, Abstract No. 4125, 2000.

Shenker et al., "A constitutively activating mutation of the luteinizing hormone receptor in familial male precocious puberty," *Nature*, 365(6447):652-654, 1993.

Small et al., "An Asn to Lys polymorphism in the third intracellular loop of the human $\alpha_{2A}$-adrenergic receptor imparts enhanced agonist-promoted $G_i$ coupling," *The Journal of Biological Chemistry*, 275(49):38518-38523, 2000.

Spiegel, "Defects in G protein-coupled signal transduction in human disease," *Annu Rev Physio.*, 58:143-170, 1996.

Svetkey et al., "Association of hypertension with $\beta_2$- and $\alpha_{2c10}$-adrenergic receptor genotype," *Hypertension*, 27(6):1210-1215, 1996.

Svetkey et al., "Preliminary evidence of linkage of salt sensitivity in black Americans at the $\beta_2$-adrenergic receptor locus," *Hypertension*, 29:918-922, 1997.

Tavares et al., "Localization of $\alpha_{2A}$- and $\alpha_{2B}$-adrenergic receptor subtypes in brain," *Hypertension*, 27:449-455, 1996.

Timmermann et al., "β-2 adrenoceptor genetic variation is associated with genetic predisposition to essential hypertension: the Bergen blood pressure study," *Kidney International*, 53:1455-1460, 1998.

\* cited by examiner

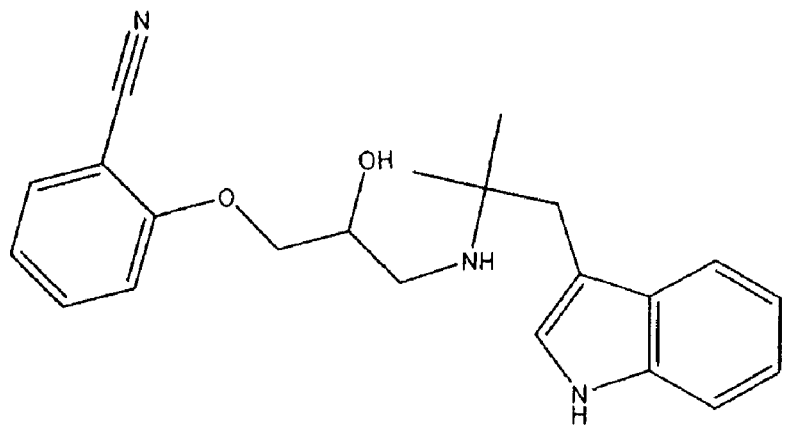
Bucindolol
2-(3-(1-(1H-indol-3-yl)-2-methylpropan-2-ylamino)-2-hydroxypropoxy)benzonitrile
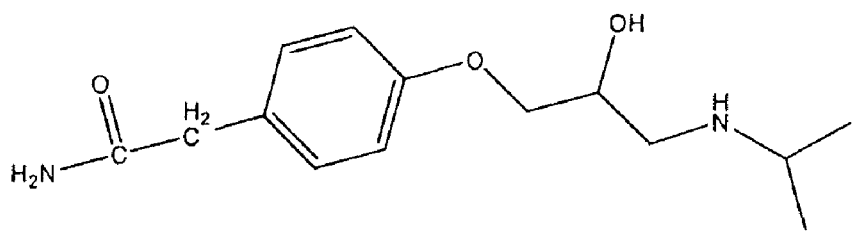
Atenolol
2-(4-(2-hydroxy-3-(isopropylamino)propoxy)phenyl)acetamide
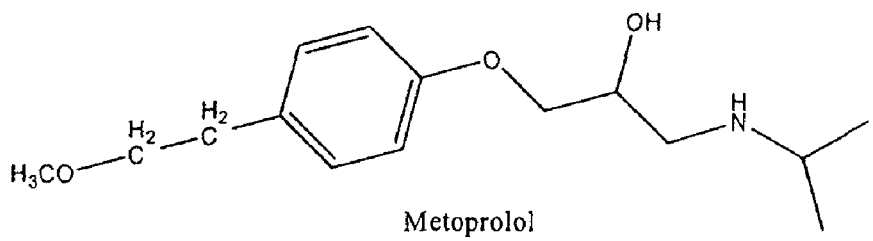
Metoprolol
1-(isopropylamino)-3-(4-(2-methoxyethyl)phenoxy)propan-2-ol
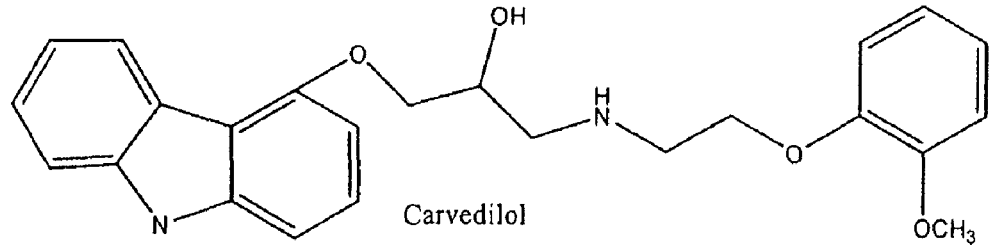
Carvedilol
[1-[carbazolyl-(4)-oxy]-3-[(2-methoxyphenoxyethyl)amino]-2-propanol]
FIG. 1

Anti-adrenergic Agents/treatments with Phase II or III Heart failure Clinical Trial Data, or in development

| Compound, (Device) | Pharmacologic properties (0-4+) | | | | | | |
|---|---|---|---|---|---|---|---|
| | β$_1$-AR blockade | β$_2$-AR blockade | α$_1$-AR blockade | ISA, human | GNMB* | Inverse agonism | Sympath-olysis |
| Metoprolol | ++++ | ++ | 0 | 0 | 0 | +++ | 0 |
| Bisoprolol | ++++ | ++ | 0 | 0 | 0 | +++ | 0 |
| Carvedilol | ++++ | +++ | ++++ | 0 | + | + | + |
| Bucindolol | ++++ | ++++ | + | 0 | + | 0 – + | +++ |
| Nebivolol | ++++ | + | 0 | 0 | 0 | ? | ? |
| Moxonidine | 0 | 0 | 0 | 0 | 0 | 0 | ++++ |
| Clonidine | 0 | 0 | 0 | 0 | 0 | 0 | ++++ |
| (Carotid sinus Stimulation) | 0 | 0 | 0 | 0 | 0 | 0 | ++++ |

*, guanine nucleotide modulatable or agonist binding, the ability to recognize β-ARs pre-coupled to αG$_s$

FIG. 2

Characteristics of NE change risk groups, patients treated with bucindolol (±SD) (1)

| Parameter | NE Δ >-244.5 (n = 153) | NE Δ ≤-244.5, + 145 (n = 551) | NE Δ >145 (n = 137) |
|---|---|---|---|
| Baseline NE, pg/ml | 932* ±544 | 422 ±189 | 409 ±199 |
| 3 mo NE Δ, pg/ml | -529* ±458 | -44 ±103 | 326* ±244 |
| Class III/IV | 86/14* | 93/7 | 93/7 |
| Baseline HR, BPM | 85.5* ±13.8 | 81.0 ±13.0 | 80.6 ±13.7 |
| HR change @ 3 mos | -13.6* ±14.8 | -9.7 ±12.4 | -7.1* ±12.8 |
| Age | 60.1 ±12.2 | 60.7 ±12.1 | 62.0 ±12.7 |
| Gender (%M/F) | 79/21 | 81/19 | 82/18 |

\*, p <.05 vs. intermediate group; +, p<.10 vs. intermediate group

FIG. 15

Characteristics of NE change risk groups, patients treated with bucindolol (±SD) (2)

| Parameter | NE Δ >-244.5 (n = 153) | NE Δ ≤-244.5, + 145 (n = 551) | NE Δ >145 (n = 137) |
|---|---|---|---|
| Number of deaths (%) | 52 (34%)* | 114 (21%) | 43 (31%) |
| Duration of CHF mos, median | 36.0 | 31.0 | 31.0 |
| Etiology (%Non-isc/Ischemic) | 46/54 | 42/58 | 31/69* |
| Race (% non-Black/Black) | 74/26# | 80/20 | 77/23 |
| LVEF, EF units (EFU) as % | 20.1* ±8.0 | 24.1 ±7.0 | 23.3 ±6.7 |
| RVEF, EFU | 32.0* ±13.4 | 36.5 ±13.2 | 32.2* ±13.0 |
| Change in LVEF @ 3 mos, EFU | 7.0# ±8.4 | 5.7 ±7.9 | 4.2* ±7.0 |

*, $p < .05$ vs. intermediate group; #, $p < .10$ vs. intermediate group

METHODS FOR TREATMENT WITH BUCINDOLOL BASED ON GENETIC TARGETING

This application is a divisional of U.S. patent application Ser. No. 11/226,908 filed Sep. 14, 2005, which claims priority to U.S. Provisional Patent Application No. 60/609,689 filed on Sep. 14, 2004 and U.S. Provisional Patent Application No. 60/610,706 filed on Sep. 17, 2004, all of which are hereby incorporated by reference in their entirety.

This invention was made with government support under grants HL052318, HL07071609, ES06096, HL071118, and HL48013 awarded by the National Institutes of Health. The government has certain rights in the invention.

BACKGROUND OF THE INVENTION

1. Field of the Invention

The present invention relates to pharmacogenetics and cardiology. More specifically, the present invention relates to methods for individualized heart failure therapy with bucindolol based on a patient's genotype of polymorphisms in adrenergic receptor genes, including the $\beta_1$-adrenergic receptor ($\beta_1$AR) gene and the $\alpha_{2c}$-adrenergic receptor ($\alpha_{2c}$AR) gene.

2. Description of Related Art

According to the American Heart Association (AHA), about 62 million Americans have some form of cardiovascular disease, which can include high blood pressure, coronary heart disease (heart attack and chest pain), stroke, birth defects of the heart and blood vessels, and congestive heart failure, and close to a million die from such conditions every year. The annual report of the AHA further states that cardiovascular disease kills more Americans than the next seven causes of death combined, including cancer. Surprisingly, slightly more females, overall, than males have cardiovascular disease. Heart disease accounted for 40% of all deaths in the U.S. in 1999. Despite recent treatment advances, mortality from heart failure is approximately 50% within 5 years.

In the United States alone there are approximately six million people, about 1.5% of the population, with chronic heart failure ("HF"), and 550,000 new patients are diagnosed each year. Medical therapy has made progress in treating HF, but morbidity and mortality remain high (Mann et al., 2005). The current standard of care in HF involves the use of inhibitors (ACE inhibitors, ARBs, and/or aldosterone receptor antagonists) of the renin-angiotensin-aldosterone system (RAAS), and n-blockers, which competitively inhibit β-adrenergic receptors on cardiac myocytes. β-blockers are effective in mortality reduction and are considered the most effective HF drug class overall, but still work in only 50-60% of treated patients. Moreover, the U.S. patient clinical data on the efficacy of approved β-blockers in mortality trials is less impressive, with published data from the only large, intention-to-treat mortality trial showing an increase in mortality in U.S. patients vs. placebo.

Accordingly, there is a substantial need for improved HF therapies that have higher efficacy and response rates, are better tolerated, and are better suited to subpopulations with special needs, such as diabetics. However, development of new agents against this therapeutic background has proved extremely challenging. Since 2001, of 13 Phase III trials in HF only three have been positive. Two of these positive trials were with an ARB (candesartan) (McMurray et al., 2003; Granger et al., 2003). The third positive trial, the A-HeFT Trial with BiDil (a combination of isosorbide dinitrate and hydralazine) was in a subset (African-Americans) that comprises only 12% of the American HF population (Taylor et al., 2004). Clearly, there is a continued need to develop the next generation of HF drugs.

While $\beta_1$ agonists are used for treating acute deterioration of patients with failing ventricular function, prolonged exposure of the heart from administered agonists, or the elevated catecholamine agonists produced by the body, leads to worsening heart failure. In contrast, β-adrenergic receptor antagonists (termed β-blockers) have emerged as a major treatment modality in chronic heart failure.

In the early 1990's, a group of U.S. heart failure investigators working with β-blocking agents in heart failure decided that a mortality trial was required in order to validate this still-controversial therapy. A group of U.S. drafted a protocol and grant application that was subsequently approved for funding by the VA cooperative Clinical Studies Program and the NHLBI. The approved protocol did not specify a drug, but rather provided that an optimal β-blocker would be selected based on potential for success and strength of Phase II data. The drugs that were considered were carvedilol, metoprolol tartrate, metoprolol succinate CR/XL, and bucindolol. Metoprolol tartrate was rejected because of less than promising effects on mortality from the MDC Trial (Waagstein et al., 1993); metoprolol succinate CR/XL was not selected because of a lack of efficacy and tolerability data in heart failure; and carvedilol was not selected in part because of poor tolerability in advanced heart failure (Krum et al. 1995). Bucindolol was the unanimous choice of the Selection Committee, based on its excellent tolerability (Eichhorn et al., 1997; Gilbert et al., 1990; Bristow et al., 1994; Pollock et al., 1990), efficacy (Gilbert et al., 1990; Bristow et al., 1994; Pollock et al., 1990; Eichhorn et al., 1990), and level of interest by its sponsor. Bucindolol thus became the subject of the Beta Blocker Evaluation of Survival Trial ("BEST"), the first mortality trial planned and initiated in HF.

The BEST trial began in 1995, and ended in 1999. After BEST was initiated three other mortality trials were planned and initiated, MERIT-HF with metoprolol succinate CR/XL (MERIT-HF Study Group, 1999), CIBIS-II with bisoprolol (CIBIS-II Investigators, 1999), and COPERNICUS with carvedilol (Packer et al., 2002). Due to the more rapid and less restrictive enrollment of these trials, CIBIS-II and MERIT-HF were completed before BEST, and both these trials had positive results.

The BEST Trial was terminated prematurely in 1999, prior to completion, due in part to a loss of equipoise by investigators, and an accelerated drop-in rate to open label β-blockers based on the knowledge of the other two positive trials (BEST Trial Investigators, 2001; Domanski et al., 2003). The sponsor elected not to proceed with the commercial development of bucindolol based on the results known at the time the Trial was stopped. While BEST investigators observed a benefit in Class III, non-African-Americans, that was similar to the positive results reported six months earlier in CIBIS II and MERIT-HF, the investigators observed poor results in Class IV and African-American patients. Moreover, BEST did not meet its primary endpoint of all-cause mortality (reduction of 10%, β=0.10) when the trial was stopped (BEST Trial Investigators, 2001). The investigators postulated that the differences between the results of other (3-blockers and bucindolol might be attributable to the "unique pharmacological properties of bucindolol" (BEST Trial Investigators, 2001), which highlights the perceived distinctions among the chemical and functional properties of this diverse class of compounds.

Moreover, even though most β-blocker trials in heart failure have shown group beneficial effects, there is substantial interindividual variability in outcome that is not explained by baseline clinical characteristics (CIBIS-II Investigators, 1999). Interindividual variability in the response to pharmacologic therapy is recognized with virtually all drugs. In circumstances such as the treatment of chronic heart failure with β-blockers—where morbidity and mortality are high, the titration algorithm is complex, the interindividual variability is substantial, and additional treatment options exist—assessing the likelihood of a favorable (or adverse) long-term response to drug therapy can have a significant impact on decision making. The approximately 50% 5-year mortality of patients with heart failure has prompted intense study of treatment options and has lead to multidrug regimens typically including a β-blocker, an angiotensin converting enzyme inhibitor (or angiotensin receptor antagonist), diuretics, and digoxin. β-blocker therapy is initiated in relatively stable patients, at low doses (i.e., about 10 mg), and slowly increased over a period of months to either a target dose, or a dose which is tolerated. Dosage adjustments of other drugs, or initiation of additional drugs is not uncommon during the up-titration period. Thus the treatment of heart failure with (3-blockers must be individualized. Indeed the statement "dosage must be individualized and closely monitored" is found in the prescribing information for the two β-blocker preparations approved for treating heart failure in the U.S. Furthermore, studies in animal models and humans suggest that β-blocker-promoted reversal of the cellular and global remodeling of the failing heart may require months of stable therapy (Lowes et al., 2002). Substantial variability in responses to (3-blockers has been noted, including left ventricular ejection fraction (LVEF) changes (van Campen et al., 1998), exercise tolerance (Bolger, 2003) and survival (Packe et al., 2001). Nevertheless, based on the preponderance of data, β-blocker therapy should be considered for most patients with chronic heart failure, assuming no contraindications such as volume overload, requirement for inotropic infusions, bradycardia, hemodynamic instability, and asthma.

Consequently, not only were there perceived differences among the various β-blockers—particularly bucindolol as compared to other β-blockers—but also variability had been observed among patients in their abilities to respond favorable to a particular β-blocker therapy. Evidence for the therapeutic value of bucindolol is needed, particularly evidence that explains these interindividual differences.

SUMMARY OF THE INVENTION

The present invention provides methods for individualized cardiovascular disease therapy based on the identification of polymorphisms in adrenergic receptors that affect an individual's response to bucindolol. In certain embodiments, it concerns individualized therapy for heart failure.

In certain embodiments, there are methods for evaluating bucindolol treatment for a patient comprising obtaining sequence information regarding at least one polymorphism in an adrenergic receptor gene of the patient, wherein the information is predictive of bucindolol efficacy in the patient. The sequence information may be nucleic acid sequence information and/or amino acid sequence information. In particular embodiments, the adrenergic receptor gene is $β_1AR$ or $α_{2c}AR$. In some cases, sequence information about a polymorphism in both genes is obtained.

Moreover, the polymorphisms include one at nucleotide position 1165 in the $β_1$-adrenergic receptor ($β_1AR$) gene that corresponds to amino acid position 389 in the encoded protein and another at nucleotide positions 964-975 of the $α_{2c}AR$ gene that corresponds to amino acid positions 322-325 in the encoded protein.

The invention is based on the determination by the inventors that being homozygous in the $β_1AR$ gene to encode an arginine at position 389 in the gene product provides the patient with a physiology that is amenable to treatment with bucindolol. In addition, the invention is based on the determination that a deletion in the $α_{2c}AR$ gene that leads to a deletion of amino acids 322-325 in the gene product is detrimental to treatment of later stages of heart failure with bucindolol. The term "treatment" will be understood to refer to therapy with respect to a patient diagnosed with a cardiovascular disease or with symptoms of a cardiovascular, as opposed to preventative measures.

It is generally understood that polymorphisms occur in the context of genes; however, in the case of polymorphisms that affect the encoded gene product, an alteration in that gene product may also be referred to as a polymorphism.

According to the invention, methods include assessing whether to prescribe or administer bucindolol to a patient with cardiovascular disease comprising obtaining information from the patient regarding his/her polymorphisms in adrenergic receptor genes and/or their encoded gene products that affect a response to bucindolol.

Therefore, the present invention is concerned with obtaining the information regarding polymorphisms in the $β_1AR$ and/or $α_{2c}AR$ proteins directly or as deduced by determining the nucleotide sequence at position 1165 on the $β_1AR$ gene and/or positions 964-975 on the $α_{2c}AR$ gene, and prescribing or administering bucindolol based on the obtained information. It will be understood that cognate nucleic acids for the $β_1AR$ or $α_{2c}AR$ protein include the mRNA transcript encoding the protein, both strands of any cDNA generated from the mRNA transcript, and both strands of the genomic DNA for the $β_1AR$ or $α_{2c}AR$ gene.

Knowledge about which polymorphism a cardiovascular disease patient has at position 389 of the $β_1AR$ and/or positions 322-325 of $α_{2c}AR$ provides the basis for assessing whether to administer or prescribe bucindolol to the patient.

The present invention further identifies patients with heart failure that will positively respond to treatment using β-blockers, specifically bucindolol.

The present invention also provides devices and compositions for the delivery of β-blockers, specifically bucindolol, to an individual in need of such therapy.

The method of the present invention comprises determining the genotype for a heart failure patient at the individual's $β_1AR$ gene, wherein the patient is likely to exhibit a positive response to a standard dose of bucindolol if the patient is not a carrier of $β_1Gly389$ (that is, having one or two Gly389 alleles). In an embodiment, bucindolol is prescribed for a heart failure patient who is homozygous for $β_1Arg389$. The method of the present invention further contemplates prescribing or administering a standard dose of bucindolol to a patient in need of such therapy based on knowing that the patient is "homozygous $β_1Arg389$," meaning both $β_1AR$ genes of the patient encode an arginine at position 389 in the gene products. Methods of the invention involve prescribing or administering bucindolol to patients who are homozygous $β_1Arg389$ and this is regardless of how it is determined that the patient has that genotype.

In further embodiments, the method of the present invention comprises determining the genotype for a heart failure patient at the individual's $α_{2c}AR$ gene, wherein the patient is likely to exhibit a positive response to a standard dose of bucindolol if the patient is not a carrier of $α_{2c}Del322-325$. In certain embodiments, bucindolol is prescribed for a heart failure patient who is homozygous wildtype for $\alpha_{2c}$ at amino acid positions 322-325 (i.e., the amino acids are not deleted). The method of the present invention further contemplates prescribing or administering a standard dose of bucindolol to a patient in need of such therapy based on knowing that the patient is "homozygous wildtype $\alpha_{2c}$AR," meaning the patient does not have a deletion in the $\alpha_{2c}$AR gene sequence that encodes amino acids 322-325 in $\alpha_{2c}$AR. Methods of the invention involve prescribing or administering bucindolol to patients who are homozygous wildtype for the deletion (not a deletion carrier) and this is regardless of how it is determined that the patient has that genotype.

It is contemplated that in certain situations, a patient may be genotyped for one of these polymorphisms and then a subsequent determination is done with respect to the other polymorphism; in this scenario, two different samples are evaluated. Alternatively, a single sample may be obtained and evaluated for two separate polymorphisms. In another embodiment, bucindolol is prescribed for a heart failure patient who has the diplotype of homozygous $\beta_1$Arg389 and homozygous wild type $\alpha_{2c}$AR. The method of the present invention further contemplates prescribing or administering a standard dose of bucindolol to a patient in need of such therapy based on knowing that the patient is homozygous for $\beta_1$Arg389 or for wild type $\alpha_{2c}$AR, or the diplotypic combination.

The method of the present invention also comprises determining whether individuals having similar pathophysiological states, such as but not limited to, dilated cardiomyopathy, ischemic cardiomyopathy, ischemic heart disease (angina, myocardial infarction), pheochromocytoma, migraines, cardiac arrhythmias, hypertension and various anxiety disorders are likely to positively respond to a standard dose of bucindolol based on whether the individual is homozygous for Arg389 at the individual's $\beta_1$AR gene (and not a carrier of the 389Gly) and/or whether the individual is homozygous wildtype for $\alpha_{2c}$AR gene and not a carrier of $\alpha_{2c}$Del322-325.

In certain embodiments, the invention concerns methods for evaluating bucindolol treatment for a patient comprising knowing either (i) the sequence at nucleotide position 1165 of one or both coding sequences of the patient's $\beta_1$AR genes or (ii) the amino acid at position 389 of the patient's $\beta_1$AR proteins, wherein the individual is being considered for treatment with bucindolol.

In further embodiments, the invention concerns methods for evaluating bucindolol treatment for a patient comprising knowing whether there is a deletion either (i) in the sequence at nucleotide positions 964-975 of one or both of the patient's $\alpha_{2c}$AR alleles or (ii) in the amino acids at positions 322-325 of the patient's $\alpha_{2c}$AR proteins, wherein the individual is being considered for treatment with bucindolol.

It is contemplated that not all of the patient's proteins will be evaluated in any embodiment of the invention but that a sample will be obtained and some of the proteins in the sample will be evaluated for their protein sequence.

It is also contemplated that the term "knowing" is used according to its ordinary and plain meaning to refer to having the specified information. It is contemplated that typically a medical practitioner will be evaluating whether to prescribe or administer a patient bucindolol and in making that evaluation the practitioner will order one or more tests regarding one or both of the patient's $\beta_1$AR alleles or their encoded proteins and/or regarding one or both of the patient's $\alpha_{2c}$AR alleles or their encoded proteins. In the context of the polymorphisms discussed herein, the terms "allele" and "gene" are used interchangeably.

Other aspects of the invention include methods for treating a patient with a heart condition may comprise administering or prescribing to the patient an effective amount of bucindolol, wherein the patient does not have detectable levels of a $\beta_1$AR protein with a glycine at position 389 or wherein the patient is homozygous for a cytosine at position 1165 in the nucleotide coding sequence of both $\beta_1$AR alleles. In either case a doctor or other medical practitioner may prescribe or administer bucindolol if they are aware that bucindolol is an appropriate medication for that patient by virtue of that patient having the Arg389/Arg389 polymorphism in the $\beta_1$AR gene.

Alternatively or additionally, methods for treating a patient with a heart condition may comprise administering or prescribing to the patient an effective amount of bucindolol, wherein the patient does not have detectable levels of a $\beta_{2c}$AR protein with a deletion of amino acids 322-325 or wherein the patient is homozygous for the presence of nucleotides 964-975 ("nondeletion") in the coding sequence of both $\alpha_{2c}$AR alleles. In either case a doctor or other medical practitioner may prescribe or administer bucindolol if they are aware that bucindolol is an appropriate medication for that patient by virtue of that patient not being a carrier of the Del322-325 polymorphism in the $\alpha_{2c}$AR gene, that is, not being heterozygous or homozygous for the deletion.

Additional methods include evaluating whether a heart failure patient will respond positively to a bucindolol comprising: a) obtaining information indicating i) the presence of a polymorphism at the coding position 1165 in the coding sequence of one or both $\beta_1$AR genes of the patient or ii) the presence of a polymorphism at the amino acid at position 389 of the $\beta_1$AR protein; and b) prescribing or administering bucindolol.

Moreover, other methods covered by the invention involve treating a patient with bucindolol comprising: a) obtaining information indicating i) the presence of a polymorphism at the coding position 1165 in the coding sequence of one or both $\beta_1$AR alleles of the patient or ii) the presence of a polymorphism at the amino acid at position 389 of the $\beta_1$AR protein; and b) either prescribing bucindolol therapy for the patient wherein the patient's genotype indicates the patient is homozygous Arg389 in the $\beta_1$AR protein or not prescribing bucindolol for the patient wherein the patient's genotype indicates the patient is not homozygous Arg389 in the $\beta_1$AR protein.

It is further contemplated that the invention concerns the use of bucindolol in the manufacture of a medicament for the treatment of a heart condition in patients with the Arg389/Arg389 polymorphism in their $\beta_1$AR genes. The embodiments discussed with respect to methods may be implemented in use of bucindolol in the manufacture of a medicament.

Also, the present invention concerns obtaining a biological sample from a patient who is being considered for treatment with bucindolol and evaluating it for the Arg389 polymorphism by determining either (i) the sequence at nucleotide position 1165 of one or both coding sequences of the patient's $\beta_1$AR genes or (ii) the amino acid at position 389 of the patient's $\beta_1$AR proteins. It is contemplated that if $\beta_1$AR proteins are evaluated, one might look for whether a sample contains any $\beta_1$AR proteins with a glycine at 389.

Further methods include evaluating whether a heart failure patient will respond positively to a bucindolol comprising: a) obtaining information indicating whether i) the nucleotide sequence at positions 964-975 has been deleted in one or both of the patient's $\alpha_{2c}$AR alleles or ii) the amino acid sequence at positions 322-325 has been deleted in the patient's $\alpha_{2c}$AR proteins; and b) prescribing or administering bucindolol. It is contemplated that if $\alpha_{2c}$AR proteins are evaluated, one might look for whether a sample contains any $\alpha_{2c}$AR proteins with the relevant deletion.

Moreover, other methods covered by the invention involve treating a patient with bucindolol comprising: a) obtaining information indicating whether i) the nucleotide sequence at positions 964-975 has been deleted in one or both of the patient's $\alpha_{2c}$AR alleles or ii) the amino acid sequence at positions 322-325 has been deleted in the patient's $a_{2c}$AR proteins; and b) either prescribing bucindolol therapy for the patient wherein the patient's genotype indicates the patient is homozygous wildtype in the $\alpha_{2c}$AR alleles or not prescribing bucindolol for the patient wherein the patient's genotype indicates the patient is not homozygous wildtype in the $\alpha_{2c}$AR protein.

It is further contemplated that the invention concerns the use of bucindolol in the manufacture of a medicament for the treatment of a heart condition in patients with the homozygous wildtype 322-325 polymorphism in their $\alpha_{2c}$AR alleles. The embodiments discussed with respect to methods may be implemented in use of bucindolol in the manufacture of a medicament.

Also, the present invention concerns obtaining a biological sample from a patient who is being considered for treatment with bucindolol and evaluating it for the Arg389 polymorphism in the $\beta_1$AR protein and/or the Del322-325 polymorphism in the $\alpha_{2c}$AR protein by determining (i) the sequence at nucleotide position 1165 of one or both coding sequences of the patient's $\beta_1$AR alleles; (ii) the amino acid at position 389 in the patient's $\beta_1$AR proteins; iii) whether there is a deletion in nucleotides 964-975 in the coding sequence of one or both $\alpha_{2c}$AR alleles; and/or iv) whether there is a deletion of amino acids 322-325 in the patient's $\alpha_{2c}$AR proteins.

To achieve these methods, a doctor, medical practitioner, or their staff may obtain a biological sample for evaluation. The sample may be analyzed by the practitioner or their staff, or it may be sent to an outside or independent laboratory. The medical practitioner may be cognizant of whether the test is providing information regarding the patient's $\beta_1$AR genes or alleles as distinguished from the encoded proteins, or the medical practitioner may be aware only that the test indicates directly or indirectly that the genotype of the patient reflects the Gly389/Gly389 phenotype ("homozygous Gly" sequence), the Arg389/Gly389 phenotype ("heterozygous" sequence), or the Arg389/Arg389 phenotype ("homozygous Arg" or "homozygous wild-type" sequence).

Similarly, the medical practitioner may be cognizant of whether the test is providing information regarding the patient's $\alpha_{2c}$AR genes or alleles as distinguished from the encoded proteins, or the medical practitioner may be aware only that the test indicates directly or indirectly that the genotype of the patient reflects the homozygous wildtype sequence (no deletion in either allele), the heterozygous Del322-325 phenotype ("heterozygous" sequence), or the Del322-325/Del322-325 phenotype ("homozygous deletion" sequence).

In some embodiments discussed in the Examples, a patient with either the heterozygous sequence or the homozygous Gly sequence with respect to $\beta_1$AR is referred to as a "Gly carrier." Likewise, a patient with either the heterozygous sequence or the homozygous deletion sequence with respect to $\alpha_{2c}$AR is referred to a "Del322-325 carrier" or a "deletion carrier."

In any of these circumstances, the medical practitioner "knows" the relevant information that will allow him or her to determine whether bucindolol is an appropriate medicinal option. It is contemplated that, for example, a laboratory conducts the test to determine that patient's genotype such its personnel also know the appropriate information. They may report back to the practitioner with the specific result of the test performed or the laboratory may simply report that bucindolol is appropriate drug based on the laboratory results.

In further embodiments, the patient's genotype at nucleotide position 1165 of the coding sequence of one or both $\beta_1$AR alleles is known. In the context of the present invention, whether position 1165 of the coding sequence contains a guanine or cystosine in one or both alleles is significant. This indicates what amino acid can be found at position 389 of the $\beta_1$AR protein sequence. A cytosine at position 1165 in the coding sequence encodes an arginine, while a guanine in the coding sequence encodes a glycine. In particular embodiments, the sequences at position 1165 in both $\beta_1$AR alleles of the patient are known. The result may be a guanine in both alleles, a cytosine in both alleles, or a guanine in one allele and a cytosine in the other allele.

In certain embodiments, the patient's genotype at nucleotide positions 964-975 of the coding sequence of one or both $\alpha_{2c}$AR alleles is known. In the context of the present invention, whether there is a deletion in one or both alleles of the $\alpha_{2c}$AR gene is significant. This indicates whether there is a deletion amino acid of amino acids 322-325 (amino acids 322, 323, 324, and 325) of the $\alpha_{2c}$AR protein sequence. In particular embodiments, whether there is a deletion of the nucleotide sequence corresponding to positions 964-975 in both $\beta_1$AR alleles of the patient is known.

Those of skill in the art readily understand that the coding sequence of a gene refers to the strand of the gene that is used for transcription of messenger RNA. The sequence of the coding sequence is complementary to the sequence of the transcribed transcript. Because of the complementary nature of sequences between a coding sequence and a noncoding sequence, the sequence of any coding sequence can be determined by knowing the sequence of the transcript, the noncoding strand, or the encoded protein. The nucleic acid sequence at that position in one or both alleles can be determined by a number of ways known to those of skill in the art. Such ways include, but are not limited to, chain terminating sequencing, restriction digestion, allele-specific polymerase reaction, single-stranded conformational polymorphism analysis, genetic bit analysis, temperature gradient gel electrophoresis, or ligase chain reaction.

Alternatively, the $\beta_1$AR protein sequence may be evaluated. In certain embodiments, the amino acid at position 389 in one or more of the patient's $\beta_1$AR protein is known. It is contemplated that any sample evaluated from the patient will contain multiple $\beta_1$AR proteins that can be analyzed. An analysis of these proteins can determine if the patient has $\beta_1$AR proteins with only an arginine at 389, only a glycine at 389, or a mixture of both types. Similarly, the $\alpha_{2c}$AR protein sequence may be evaluated. In particular embodiments, whether there is a deletion of amino acids 322-325 in one or more of the patient's $\alpha_{2c}$AR protein is known.

It is contemplated that any sample evaluated from the patient will contain multiple $\beta_1$AR and $\alpha_{2c}$AR proteins that may be analyzed. An analysis of these proteins can determine if the patient has $\beta_1$AR proteins with only an arginine at 389, only a glycine at 389, or a mixture of both types. Likewise, it may be determined whether the patient has $\alpha_{2c}$AR proteins with only the wildtype sequence at amino acids 322-325 (no deletion), only a deletion of the amino acids corresponding to 322-325, or a mixture of both types.

Methods for determining the sequence at a particular position in a protein are well known to those of skill in the art.

They may involve using an antibody, high pressure liquid chromatography, or mass spectroscopy.

As discussed above, the sequence of a particular position in the $\beta_1$AR gene or protein and/or $\alpha_{2c}$AR gene or protein may be known. Some methods of the invention involve determining the sequence in the $\beta_1$AR gene or protein sequence and/or $\alpha_{2c}$AR gene or protein sequence.

Consequently, it is contemplated that embodiments may involve obtaining a biological sample from a patient. A biological sample is a sample that contains biological material such as all or part of an organ, tissue, cells, nucleic acids, proteins, or other such macromolecules and substances. The sample may include sputum, serum, blood, plasma, spinal fluid, semen, lymphatic fluid, urine, stool, pleural effusion, ascites, a tissue sample, tissue biopsy, cell swab, or a combination thereof. In other embodiments of the invention, a sample may include cells that are from lung, skin, muscle, liver, renal, colon, prostate, breast, brain, bladder, small intestine, large intestine, cervix, stomach, pancreas, testes, ovaries, bone, marrow, or spine. In some embodiments, the sample is a whole blood, plasma or serum sample, while in other embodiments, the sample is obtained by lavage, smear, or swab of an area on or in the patient. In certain embodiments, the biological sample is a blood sample.

In some embodiments of the invention, the sequence of a patient's $\beta_1$AR genes and/or proteins and/or the sequence of a patient's $\alpha_{2c}$AR genes and/or proteins may already have been evaluated. It is contemplated that this analysis may have been done prior to the patient being considered for treatment with bucindolol or as part of a general examination. For example, the sequence of the patient's $\beta_1$AR genes and/or proteins, as well as his $\alpha_{2c}$AR genes and/or proteins may be determined and entered into a database or entered into the patient's medical history. In this case, a medical practitioner may come to know what the sequence is by obtaining a patient history regarding the sequence i) at position 1165 in the coding sequence of one or both $\beta_1$AR alleles or ii) at position 389 in the amino acids sequence of the $\beta_1$AR protein; iii) at position 964-975 in the coding sequence of one or both $\alpha_{2c}$AR alleles; and/or iv) at positions 322-325 in the amino acids sequence of the $\alpha_{2c}$AR protein.

The present invention also involves reporting the results of a determination of the nucleic acid or protein sequence at the relevant position in the $\beta_1$AR alleles or protein and/or the $\alpha_{2c}$AR alleles or protein. In certain embodiments, methods include preparing a report containing the results of determining (i), (ii), (iii), and/or (iv) described in the previous paragraph. Such a report would identify the patient by name, social security number, and/or other identification number or qualifier. It may also contain the actual data as a result of the determination or a summary of that data.

In some embodiments, methods include identifying a patient possibly in need of treatment with a bucindolol. A patient for which bucindolol is being considered as a treatment option may have symptoms of or may have been diagnosed with a medical condition, such as heart failure, dilated cardiomyopathy, ischemic heart disease, pheochromocytoma, migraines, cardiac arrhythmias, hypertension or an anxiety disorder. In certain embodiments, the patient has symptoms of or has been diagnosed with ischemic heart disease, which may specifically be angina and/or a myocardial infarction. In particular cases, a patient has symptoms of or has been diagnosed with heart failure. The heart failure may be considered advanced heart failure, though the invention may not be limited to such patients. The term "advanced heart failure" is used according to its ordinary and plain meaning in the field of cardiology. In some embodiments, a patient being prescribed bucindolol may have class III or class IV heart failure according to the NYHA classification system. The NYHA classification system is one evaluation system, however, it is contemplated that the invention is not limited in this way and that this is meant to be illustrative rather than limiting. Patients may be classified by another such system. It is further contemplated that patients may be classified by a different methodology but that the invention would be implemented similarly.

In other embodiments, however, a patient may have signs or symptoms of heart failure but not advanced heart failure. In such a situation the patient may have been or may be characterized as a class I or II heart failure patient according to the NYHA classification system. In these embodiments, the patient may be genotyped for the Arg389 $\beta_1$ polymorphism, in which case a person with the Arg/Arg phenotype is a candidate for bucindolol treatment. Consequently, methods of the invention can involve preventing heart failure in a patient by determining whether the patient has Arg389/Arg389 polymorphism and administering bucindolol if they do. Particular patients might be particularly suited for this including, but not limited to, those patients with symptoms of heart failure, with risk factors of heart failure, or with a familial or prior history of heart failure.

Additionally, methods may involve administering or prescribing other therapeutic agents or performing a surgical or other interventional strategy for treating the patient.

According to the present invention, methods may further involve prescribing or administering bucindolol to the patient after knowing that the patient's genotype at the 389 polymorphism is Arg389/Arg389, also known as the homozygous arginine genotype. Additionally or alternatively, bucindolol may be prescribed or administered after knowing that the patient has the homozygous wildtype $\alpha_{2c}$AR polymorphism (does not carry a deletion of nucleotides 964-975 in either allele of the $\alpha_{2c}$AR gene). Moreover, it may be the case that a patient who does not exhibit either or both genotypes will not be prescribed or administered bucindolol. The patient may be prescribed or administered a n-blocker that is specifically not bucindolol.

In additional embodiments, methods can involve knowing whether there is a deletion in (iii) the nucleotide sequence at positions 964-975 in the coding sequence of one or both of the patient's $\alpha_{2c}$AR genes or (iv) the amino acid sequence at positions 322-325 of one or more of the patient's $\alpha_{2c}$AR proteins. This may be known in addition to or independently of whether the patient's genotype in the $\beta_1$AR gene at position 1165 (389 in the protein).

If an advanced heart failure (that is, NYHA class III or IV) patient exhibits a homozygous $\alpha_{2c}$AR Del322-325 genotype and the patient does not exhibit the Arg389/Arg389 genotype, it is contemplated the patient will not be prescribed or administered bucindolol. In certain embodiments, the patient is identified as a patient whose race is Black. Alternatively, if a patient does not exhibit a homozygous $\alpha_{2c}$AR Del322-325 genotype, the patient may be prescribed or administered bucindolol.

Other information may also be considered in determining whether bucindolol is an appropriate drug for the patient. This may include race, gender, age, previous surgeries, heart failure stage, patient history regarding cardiovascular disease, diagnosis of other diseases or conditions, risks for other diseases or condition, drug allergies, drug toxicity, and/or other medications being taken.

Therefore, it is contemplated that the invention also concerns doing a diplotype analysis or obtaining the results of a diplotype analysis. In particular embodiments, the diplotype analysis involves evaluating directly or indirectly the polymorphism (1) at position 389 of $\beta_1AR$ so as to determine whether a patient has an Arg389/Arg389 genotype and (2) at position 322-325 of $\alpha_{2c}AR$ so as to determine whether the patient has a Del322-325/Del322-325 genotype. Other polymorphisms may be included in the haplotype, particularly those that are affected or affect the patient's ability to respond favorably to bucindolol as a therapeutic agent.

Any embodiment discussed with respect to one aspect of the invention applies to other aspects of the invention as well. This includes embodiments discussed with respect to each of $\beta_1AR$ and $\alpha_{2c}AR$. Specifically, any embodiment discussed with respect to $\beta_1AR$ genes, alleles, or protein may be implemented with respect to $\alpha_{2c}AR$ genes, alleles, or proteins, and vice versa.

The embodiments in the Example section are understood to be embodiments of the invention that are applicable to all aspects of the invention.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. The chemical structures of several β-blockers, including bucindolol, is depicted.

FIG. 2. Comparison chart of different anti-adrenergic agents and treatments based on Phase II or III heart failure clinical trial data or other development data.

FIG. 15. Characteristics of norepinephrine change in risk groups and patients treated with bucindolol. Standard deviations (SD) are included in chart.

FIG. 16. Additional characteristics of norepinephrine change in risk groups and patients treated with bucindolol. Standard deviations (SD) are included in chart.

DESCRIPTION OF ILLUSTRATIVE EMBODIMENTS

Figure 3:
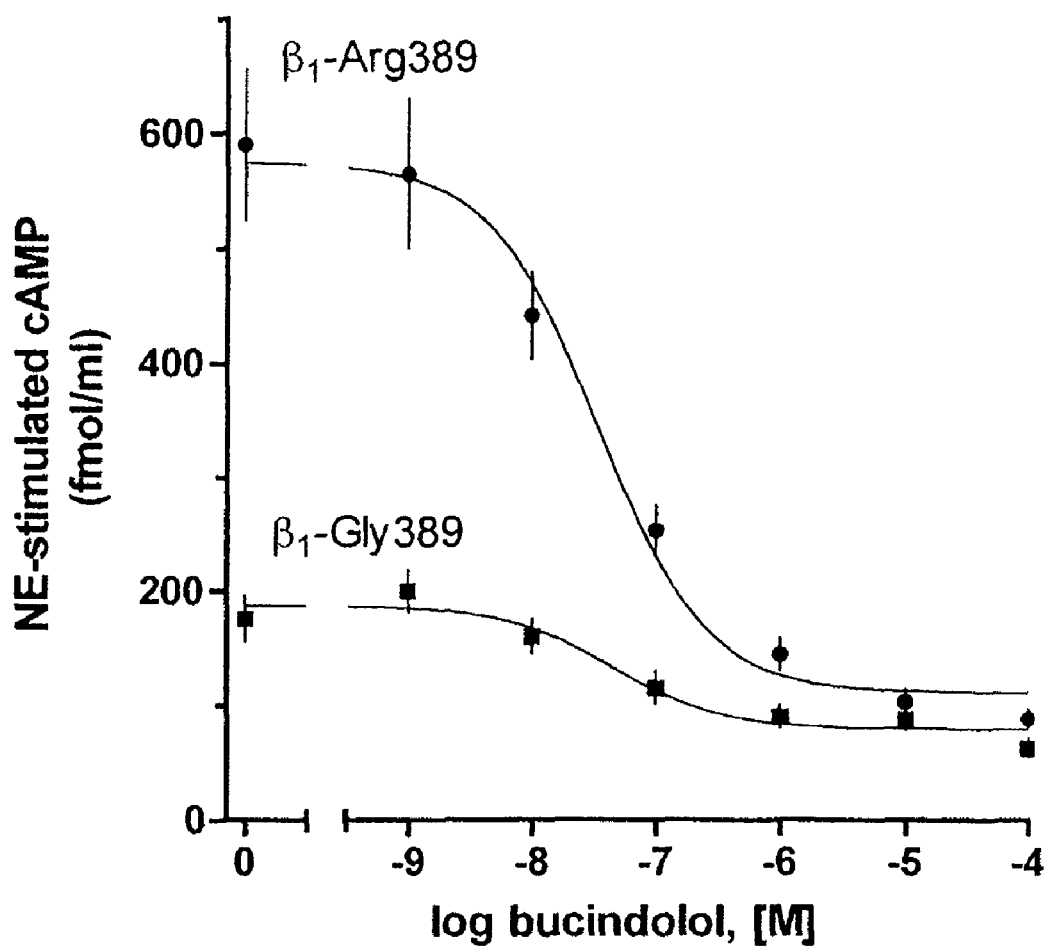
FIG. 3. This figure illustrates the allele-specific effects of bucindolol in cells stably expressing $\beta_1Arg389$- or $\beta_1Gly389$. Results are mean±SE of 4 experiments.

The inventors of the present invention were confronted with the data that bucindolol appeared to provide less favorable therapeutic responses in certain patient subgroups and a less favorable response than other β-blockers by certain criteria. They hypothesized that the interindividual variability in the response to bucindolol in heart failure (HF) is due to genetic variability and determined the basis for this. In doing so, the inventors were able to make a significant case for the therapeutic value of bucindolol and its appropriateness for the treatment of heart failure in humans.

The genetic variability of the $\beta_1$AR at amino acid 389 of the protein (nucleic acid 1165 of the gene) was evaluated. This was based on the properties of the two receptors, denoted here as Arg389 and Gly389, as ascertained in transfected cells, where basal and agonist-stimulated adenylyl cyclase activities are approximately 3-fold greater for the Arg receptor (Mason et al., 1999). However, prior to the current studies, it was not clear whether patients with Arg389, or Gly389, would benefit most from bucindolol treatment. For example, the enhanced function of Arg389 may have made it impossible for bucindolol to act as an effective antagonist. The ultimate test of the hypothesis, where death, cardiac transplantation or HF hospitalizations (heart failure exacerbations in actual patient treated with placebo or bucindolol) were evaluated, had not been carried-out.

The present invention thus approached the question of whether the Arg (or Gly) 389 ($\beta_1$AR allele represents a pharmacogenetic locus for predicting response to (β-blockers in heart failure using a three-tiered approach involving investigations in transfected cells (see Example 1 discussed in detail below), transgenic mice (see Example 2 discussed in detail below) and a large multicenter placebo-controlled clincal trial (see Example 3 discussed in detail below). The clinical study is denoted BEST (β-blocker Evalutation Survival Trial). In the transfected cells, functional antagonism by bucindolol of norepinephrine-stimulated cAMP was assessed. Even though the Arg389 receptor displayed markedly higher norepinephrine-stimulated cAMP production, bucindolol antagonized the response. The absolute decrease in cAMP production was substantially greater for Arg389 vs Gly389 expressing cells, which is due to the high norepinephrine stimulation of Arg389 and the efficacy of bucindolol to fully antagonize the response. Approximately 80% inhibition of the Arg389 cAMP response was observed at 0.1 μM bucindolol, which is comparable to plasma concentrations of the drug at the doses used in BEST (unpublished data). These results suggested that in patients a greater change in cardiac $\beta_1$AR activity from bucindolol treatment might be possible in those with the $\beta_1$-Arg389 compared to the $\beta_1$-Gly389 genotype, and potentially result in a more favorable clinical response. In the transgenic mouse studies, the inventors examined the effect of β-blockade over a 6 month period on the expression of key signaling and $Ca^{2+}$-handling proteins in the heart. With the Gly389 mice, there was no effect of treatment on expression of these proteins. On the other hand, an overall treatment effect from β-blockade was noted in the Arg389 mice, with changes that are consistent with reverse remodeling at the molecular level. Next, the archived DNA from BEST, a study which provided extensive phenotyping and matched placebo group, was utilized; due to the transfected cells and transgenic mice results, the inventors had an a priori hypothesis that $\beta_1$-Arg389 would be the most favorable genotype for survival. Here, a dominant model was assumed. Thus, the two genotype groups were Arg389 homozygotes and patients with one or two Gly389 alleles (i.e., homozygous for Gly or heterozygotes; this group is termed "Gly389 carriers"). The clinical endpoint results from BEST indicate no mortality, heart failure hospitalization or mortality+heart failure hospitalization benefit of bucindolol treatment in patients who are $\beta_1$-Gly389 carriers, but clinically relevant improvements in all three outcomes in $\beta_1$-Arg389 homozygous patients treated with bucindolol as compared to placebo. Baseline clinical parameters including heart rate, blood pressure and LVEF, or the etiology of heart failure, were not predictive of endpoint response in the entire cohort that included all $\beta_1$AR gene variants. Furthermore, there was no apparent effect of the $\beta_1$-Gly49 polymorphism on these relationships. Taken together, then, the results from these studies strongly suggest that position 389 variant of $\beta_1$AR is a predictor of the response to bucindolol in heart failure.

Moreover, a role for the genetic variant in the α2cAR gene was also postulated for bucindolol efficacy. The inventors of the present invention hypothesized that the interindividual variability in the response to bucindolol in heart failure is due to genetic variability of the $\alpha_{2c}$AR gene. The present invention thus approached the question of whether the $\alpha_{2c}$Del322-325 AR allele represents a pharmacogenetic locus for predicting response to bucindolol in heart failure using BEST, a large multicenter placebo-controlled trial (see Examples discussed in detail below). The archived DNA from BEST, a study that provided extensive phenotyping and matched placebo group, was utilized. Here, a dominant model was assumed. Thus, the two genotype groups were 1) $\alpha_{2c}$ wild-type homozygotes (patients with no deletion in 322-325 on either allele) and $\alpha_{2c}$Del322-325 heterozygotes or homozygotes (patients with the deletion in one or both alleles, referred to as "$\alpha_{2c}$Del322-325 carriers"). The clinical endpoint results from BEST indicate no mortality, heart failure hospitalization or mortality plus heart failure hospitalization benefit of bucindolol treatment in patients who are $\alpha_{2c}$Del322-325 carriers, but clinically relevant improvements in all three outcomes in $\alpha_{2c}$ wild-type homozygous patients treated with bucindolol as compared to placebo. Baseline clinical parameters including heart rate, blood pressure and LVEF, or the etiology of heart failure, were not predictive of endpoint response in the entire cohort that included all $\alpha_{2c}$AR gene variants. Taken together, then, the results from these studies strongly suggest that the $\alpha_{2c}$Del322-325 polymorphism is a predictor of the response to bucindolol in heart failure.

Therefore, the present invention concerns methods that utilize the genetic relationship between the Arg389 $\beta_1$AR polymorphism and bucindolol therapy and between the Del322-325 $\alpha_{2c}$AR polymorphism and bucindolol therapy.

I. Adrenergic Receptors and β-Blockers

Treatment for heart failure has involved targeting adrenergic receptors (AR). There are at least nine sub-types of adrenergic receptors (Dohlman et al., 1991; and Liggett et al., 1993), of which at least three sub-types are β-adrenergic receptors.

A potential role for common genetic variants in susceptibility, progression and response to treatment is suggested by familial clustering of phenotypes, reduced penetrance in familial cardiomyopathies and marked interindividual variations in progression and treatment outcomes. While polymorphisms in adrenergic receptors have been identified, there has been no study involving patients data in which a correlation between any polymorphism and a clinical response to a therapeutic agent has been identified. The present invention concerns two polymorphisms: 1) the polymorphism encoding the amino acid at position 389 in $\beta_1$-AR and 2) the polymorphism encoding amino acids 322-325 in $\alpha_{2c}$-AR. However, the relationship between these particular genetic variant and any treatment outcome had not been established with any clinical evidence prior to the present invention, nor had any correlation been demonstrated with bucindolol.

A. $\beta_1$ Adrenergic Receptor

The $\beta_1$ adrenergic receptor ($\beta_1$-AR) is the principle sub-type expressed on cardiac myocytes. The human heart expresses both the $\beta_1$AR and the $\beta_2$AR subtypes (Bristow et al, 1986; Bristow et al., 1988). Each receptor mediates positive inotropic and chronotropic responses to endogenous catecholamines and exogenously administered agonists (Bristow et al., 1986; Brodde et al., 1986; Brodde et al., 1992).

The $\beta_1$AR triggers the heart's contractile response when activated, as it is by norepinephrine. In addition, the $\beta_1$ receptor has a central role in the progression of cardiomyopathy and other disease pathways. Increased activation of this receptor and its associated myopathic and arrhythmic pathways plays a major role in the natural history of heart failure. Once the cardiomyopathic process has begun, chronic $\beta_1$-adrenergic activation accelerates disease progression, as the failing heart tries to compensate for its impaired functioning by releasing more norepinephrine and increasing $\beta_1$-receptor signaling. The theory of β-receptor blockade rests in part on counteracting this cardiomyopathic pathway by blocking the $\beta_1$-receptor and reducing norepinephrine signaling.

The $\beta_1$ adrenergic receptor has been cloned and sequenced (Frielle et al., 1987). The gene has been localized to chromosome q24-q26 of chromosome 10 (Yang-Feng et al., 1990). The human $\beta_1$AR has a deduced amino acid sequence of 477 amino acids.

At coding nucleotide position 1165 of the $\beta_1$AR gene, either cytosine or guanine can be found in the human population, which results in either Arg or Gly being encoded at amino acid position 389 (Mason et al., 1999). This position is within an intracellular domain of the receptor that is involved with coupling to the stimulatory G-protein, G. In fibroblasts transfected to express equal levels of the two receptors, the $\beta_1$-Arg389 receptor display substantially greater stimulation of adenylyl cyclase compared to $\beta_1$-Gly389 (Mason et al., 1999). A less common polymorphism of the $\beta_1$AR, Gly49, has also been identified but there are discrepant reports as to its functional implications (Rathz et al., 2002; and Levin et al., 2002).

The $\beta_1$-AR 389Arg/Arg polymorphism is actually the most prevalent form of the $\beta_1$ adrenergic receptor and is present in about 50% of the U.S. population (slightly less in African-Americans). The other variant of this receptor has a glycine (Gly) at the 389 position and is considered the wild type only because it was cloned first. The presence of an arginine (Arg) at codon 389 is the preferred (and only) structure of this receptor in all other known non-human animal species, and the 389 region is in an important functional domain. The 389Arg/Arg is also the highest functioning variation of this receptor (Mason et al., 1999); its signal transducing efficacy is 3-4 times greater than for Gly heterozygotes or Gly/Gly at the 389 position (see Examples and Mason et al., 1999). The increased signal transduction capacity of the $\beta_1$-AR 389Arg/Arg applies to cAMP generation (Mason et al. 1999), isolated human heart muscle contraction (Mason et al. 1999), and production of cardiomyopathy in transgenic mice (Mialet Perez et al., 2003).

Certain β-blockers have been evaluated in the context of specific genetic variations with varying results. Sofowora et al. reported that patients who are homozygous for Gly389 are less sensitive to the effects of atenolol, a selective β-adrenergic receptor, based on hemodynamic responses, suggesting to the authors that the variation may be relevant particularly to resting blood pressure responses. Johnson et al. (1993) reported that homozygotes for Arg389 were more likely to respond to metoprolol, a selective (β-blocker, as measured by blood pressure. Perez et al. (2003) evaluated position 389 variants of the $\beta_1$AR in the context of intact cardiac function using targeted transgenesis in mice. In these transgenic mice overexpressing either homyzgous Arg or Gly at the 389 position, Arg/Arg mice had a greater loss of isoproterenol responsiveness for increases in myocardial function, and a greater degree of cardiomyopathy as measured by myocardial dysfunction, degree of chamber remodeling, and histology. They also reported a greater improvement in left ventricular function in patients treated with carvedilol, a non-selective β-blocker, that was associated with the Arg389 polymorphism, in either the homozygous or heterozygous state.

Liu et al. (2003) report finding that a greater response (in terms of changes in heart rate) to metoprolol was associated with Arg389 compared to Gly389. The authors also warned about extending the results beyond their patient pool, which was healthy, young, male Chinese volunteers. They specifically say that the study did not look at any long-term effects of metoprolol with respect to the polymorphisms.

A review article published in 2004(Lohse, 2004) noted that while the Arg389 polymorphism might be relevant to the benefit from treatment of β-blockers, there had been no study regarding the influence of β-adrenergic receptor polymorphisms on responsive to β-blockers in heart failure. Another review indicated that while some studies suggested that polymorphisms in adrenergic receptors might alter the response to treatment with β-blockers, firm conclusions or recommendations for patient management could not be made because of the low patient numbers in the different studies Moreover, several reports did not detect any correlation between a polymorphism at 389 of the $\beta_1$-AR and the treatment response to a β-blocker. Thus, there is a distinguishing point with respect to the present disclosure, although the specification points to a reference of White et al. (see argument #1 below), which allegedly looked at metoprolol-treated heart failure patients as assessed by mortality or the combined endpoint of mortality+heart failure hospitalization, and found no association. O'Shaughnessy et al. (2000) reported that no difference was seen in blood pressure or heart rate response to beta blockade (atenolol or bisoprolol—both antagonists) due to 389 polymorphism. Another paper, Joseph et al. (2004), also observed no difference in receptor affinity for β-blockers with 389 polymorphism. Furthermore, a recent study reported being unable to find any evidence of "a pharmacogenetic effect" on metoprolol treatment with respect to the Arg389 polymorphism. White et al., *Eur. J. Heart Fail.* 5:463-8, 2003.

Therefore, a correlation between the effectiveness of β-blockers as a class of therapeutic agents and the 389 polymorphism in $β_1$-AR had not been established. Furthermore, no correlation could be made regarding bucindolol particularly, which differs from the other β-blockers in several important respects. Because the differences among the various β-blockers is significant, the effects of the $β_1$AR-389 variants on β-blocker response may be dependent on the specific agent.

The present disclosure provides data that when the BEST data is evaluated in the context of individual genotype, particularly at the Arg389 polymorphism, bucindolol has substantial therapeutic efficacy. This data is surprising given that in the BEST study the mortality effects observed in the total population studied were lower than what had been observed with other n-blockers such as carvedilol, metoprolol CR/XL and bisoprolol. Furthermore, the scientific data provided herein demonstrate for the first time a correlation between the therapeutic efficacy of bucindolol and two genetic variaants.

In detail, the invention provides a method for determining whether bucindolol should be prescribed to a patient wherein; the identity of a polymorphic nucleotide or amino acid site of a $β_1$ AR and a $α_{2c}$-AR is determined and based on the results of that diagnostic test bucindolol is either prescribed or not. Similarly, based on the genotype, another medication may be prescribed for patient with the unfavorable $β_1$AR genotype, so as to attempt to gain improved clinical response. In both scenarios, drug treatment decisions are based on the $β_1$AR genotype of the patient.

Thus, the invention concerns methods for evaluating bucindolol therapy for a patient, particularly a heart failure patient, based on whether the individual is homozygous Arg389 at the $β_1$AR gene, homozygous for the wild type form of the $α_{2c}$AR at amino acid position 322-325, or both. Alternatively, the present invention concerns a method concerning the diplotype of $β_1$AR389Gly carrier and $α_{2c}$ARDel322-325 carrier.

B. $α_{2c}$ Adrenergic Receptor

The $α_{2c}$-ARs are located on cardiac sympathetic nerve terminals, and regulate the prejunctional neuronal release of norepinephrine into the synaptic cleft area. Binding of norepinephrine to $α_{2c}$-ARs invokes a negative feedback sympatholytic response that attenuates further neuronal norepinephrine release. Murine gene ablation models implicate the $α_{2c}$-ARs as being principally responsible for controlling the chronic steady rate of norepinephrine release. (Hein et al., 1999). In this way the $α_{2c}$-AR has a "protective" role in the heart, buffering against the chronically elevated levels of norepinephrine encountered in the failing human heart.

A human genetic polymorphism has been reported for the α2c-AR gene, ADRA2C. (Small et al., 2000). A loss of 12 nucleotides in ADRA2C translates to a deletion of four consecutive amino acids ($α_{2c}$Del322-325) in the third intracellular loop of the receptor. (Small et al., 2000). This deletion polymorphism is much more common in African-Americans, with a 0.4 allele frequency compared to 0.04 in non-African-Americans. Overall, this polymorphism is present in about 15% of the U.S. population.

In contrast to the Arg389 polymorphism, the 322-325 Del polymorphism of the $α_{2c}$ adrenergic receptor is an uncommon and low-functioning variation of this receptor (Small et al., 2000). Loss of these four residues predicts a reduction in receptor function, which is supported by cellular transfection experiments where receptor function is curtailed by 50-85%. (Small et al., 2000). The $α_{2c}$ receptor ordinarily tonically inhibits norepinephrine release prejunctionally in adrenergic nerve terminals (Hein et al., 1999).

The 322-325 deletion essentially destroys receptor function (Small et al., 2000) leading to higher levels of norepinephrine and adrenergic drive (Neumister et al., 2005). The consequence of diminished inhibitory control is that basal norepinephrine release is constitutively increased resulting in a higher state of sympathetic activity. (Hein et al., 1999). In heart failure this becomes of particular interest as $α_{2c}$Del322-325 receptors lack the "protective" braking effect against increased sympathetic drive.

The $α_{2c}$Del322-325 receptor polymorphism, present in one study as a homozygous genotype in only 7.4% of Caucasians but in 52.6% of Blacks with chronic heart failure, results in loss of function as assessed by inhibition of adenylyl cyclase stimulation (Small et al., 2002). This defect has functional consequences on $α_{2c}$-AR function and has been interchangeably referred to as both "polymorphism" and a "mutation" reflecting the characteristics of relative commonness in populations and its profound structural/functional effects, respectively. Throughout this proposal the variant is referred to primarily as a "polymorphism" to reflect that this is a common variant present in many subjects with heart failure. Its importance, however, stems from its functional consequences, profoundly diminishing receptor activity. Based on the effects of genetic ablation in mice, the wild type, fully functional $α_{2c}$ receptor is prejunctionally inhibitory to norepinephrine release; as the knockout mice display a loss of this inhibition that leads to increased norepinephrine levels and pathological hypertrophy. (Hein et al., 1999). The clinical importance in humans of this polymorphism was illustrated a study that identified the $α_{2c}$Del322-325 genotype as a risk factor for heart failure; having an unadjusted odds ratio for heart failure of 5.54 (95% CI 2.68, 11.45; p<0.001) in Blacks homozygous for this genotype as compared to heterozygotes and noncarriers. (Small et al., 2002). In conjunction with the $β_1$Arg389 variant the effect was more pronounced with an unadjusted odds ratio of 12.67 (95% CI 2.70, 59.42; p=0.001). However, in contrast to the present disclosure, there has been no indication that these polymorphism are relevant from a therapeutic perspective.

C. β-Blockers

While $β_1$ agonists such as dobutamine, are used for treating acute deterioration of patients with failing ventricular function, prolonged exposure of the heart from administered agonists, or the elevated endogenous catecholamine agonists produced by the body, leads to worsening heart failure. Indeed $β_1$AR and $β_2$AR become desensitized in heart failure, which is thought to be a mechanism of self-protection against the high levels of catecholamines that exist in heart failure. The administration of β antagonists can improve ventricular function and clinical outcomes, presumably by blocking these deleterious effects of catecholamines. And indeed, cardiac βAR expression and function improve during β blockade treatment of heart failure. The vast majority of the deleterious effects of catecholamines, and the success of β blocker therapy is due to variants of the $\beta_1AR$ subtype. (Zhu et al., 2001; and Bristow et al., 2003).

β-adrenergic receptor antagonists (also termed (β-blockers) have emerged as a major treatment modality in chronic heart failure. Initially these agents were thought to be contraindicated in heart failure, since increased adrenergic drive was thought to be critical for supporting the failing heart. In fact, in early experience with the $1^{st}$ generation compound propranolol, administration of standard doses was frequently associated with worsening of heart failure (Stephen, 1968). However, using low starting doses and slow up-titration, $2^{nd}$ generation (selective $\beta_1$-blockers) or $3^{rd}$ generation (nonselective β-blocker-vasodilators) generation compounds have been shown to reverse contractile dysfunction as well as structural and molecular remodeling, and to improve heart failure morbidity and mortality (Bristow, 2000); CIBIS-II Investigators and Committees. The cardiac insufficiency bisoprolol study II: a (CIBIS-II, 1999); MERIT-HF Study Group. Effect of metoprolol CR/XL in chronic heart failure: Metoprolol CR/XL Randomized Intervention Trial in Congestive Heart Failure (MERIT-HF, 1999). Packer et al. (2001); BEST Trial Investigators, (2001); Lowes et al., 2002). In part, these beneficial effects are thought to be due to a protection of the failing heart, which has limited metabolic and physiologic reserves, from persistent adverse biological effects mediated by elevated norepinephrine levels found in the syndrome (Bristow, 2000; Cohn et al., 1984; and Liggett, 2001). In addition, β-blockers have been shown to partially reverse the molecular phenotype of heart failure (Lowes et al., 2002), so these agents are capable of both preventing and reversing progressive myocardial failure and remodeling Eichhorn and Bristow, Circulation 1996).

Interestingly, recent studies have shown that the heart rate and/or blood pressure response to the β-blockers metoprolol and atenolol is greater in normotensive Arg389 individuals compared to Gly389 individuals (Liu et al., 2003; and Sofowora et al., 2003). And, in hypertensives the blood pressure response to metoprolol is greater in Arg389 compared to Gly389 patients (Johnson et al., 2003). One published study in heart failure has found no apparent association or trend between $\beta_1AR$ polymorphisms and the combined response of hospitalizations and death to metoprolol treatment (White et al., 2003). In this study, though, metoprolol-treated patients were not directly compared to placebo patients by genotype, and approximately 45% of the patients had mild heart failure (NYHA Class II), and the mean follow-up period was only 12 months. Such differences may account for this potential discrepancy. However, bucindolol and metoprolol have some notable differences in their pharmacologic properties (Bristow, 2000; and Bristow et al., 1997). In particular, bucindolol lowers norepinephrine, dilates the peripheral vasculature, and more potently blocks the human $\beta_1$-adrenergic receptor.

While a common pharmacologic property of all β-blocking agents that have been used to treat HF is that they block the $\beta_1AR$, which in the failing human heart has been estimated to transduce up to approximately 90% of the pathologic adrenergic stimulation (Zhu et al., 2001; and Bristow et al., 2003), the available β-blockers have a number of distinguishing properties including βAR-subtype selectivity, affinity for $\alpha_1AR$, partial agonist activity, sympatholysis (Bristow et al., 2004) and vasodilation (Bristow, 2000; and Bristow et al., 1997).

The chemical structure of some β-blockers is provided in FIG. 1, which shows that these agents have significant structural differences. Moreover, they have different pharmacological properties. As is shown in FIG. 2, a comparison of different anti-adrenergic agents in development or in Phase II or III clinical trials depicts these differences. Carvedilol, for instance, is an efficient $\beta_1$-AR and $\beta_2$-AR blocker, as well as an $\alpha_1$-AR blocker. In contrast, bucindolol is a weak $\alpha_1$-AR blocker, and metoprolol and bisoprolol do not block $\alpha_1$-AR at all. Significantly, bucindolol is unique among β-blockers in its sympatholytic properties, in contrast to carvedilol, metoprolol, and bisoprolol, which have no such properties. Compared to other β-blocking agents bucindolol uniquely lowers systemic norepinephrine levels (Lowes et al., 2000; Bristow et al., 1997; BEST NEJM, Bristow, 2004), and is a full agonist for the $\beta_3$-adrenergic receptor (Strosberg, 1997).

Bucindolol is a 3rd generation, β-blocker-vasodilator with the chemical name and structure of (2-{2-hydroxy-3{{2-(3-indolyl)-1,1-dimethylethyl}amino}propoxy}-benzonitrile hydrochloride). It was first developed for hypertension, and then for heart failure. Because of its low inverse agonist and vasodilator properties the nonselective β-blockade of bucindolol is relatively well tolerated by heart failure patients, and in part for this reason in 1994 bucindolol was selected by the NIH and VA Cooperative Clinical Trials Group to test the hypothesis that a β-blocker could reduce mortality in advanced heart failure. The test of this hypothesis was the BEST Trial, which was conducted between May 31, 1995 and Jul. 29, 1999.

The Beta-blocker Evaluation of Survival Trial ("BEST") was stopped prematurely on recommendation of the Data and Safety Monitoring Committee, at a time when the hazard ratio for the primary endpoint of all-cause mortality was 0.90 (C.I.s 0.78-1.02) (BEST Investigators, 2001; Domanski et al., 2003). However, the results for the entire BEST cohort were positive for the high order secondary endpoint of mortality or heart failure hospitalization, which was reduced by bucindolol by 19% with a p value of <0.0001 (Domanski et al., 2003). This endpoint is in fact increasingly viewed as the preferred primary endpoint for HF pivotal trials.

The reasons why BEST was stopped were 1) confirmation by BEST Trial data generated in Class III, non-Black patients of the then recently published information from CIBIS-II (CIBIS Investigators, 1999) and MERIT-HF (MERIT-HF Study Group, 1999) trials that these types of heart failure patients have a substantial survival benefit from β-blockade, 2) increasing loss of equipoise among investigators, who believed that the efficacy of β-blockade in heart failure had been demonstrated, and 3) inefficacy and trends toward adverse events in subgroups (Class IV and Blacks) that had not been previously investigated in n-blocker heart failure trials. Further development of bucindolol was then abandoned because it was not clear bucindolol could be successfully marketed, even if approved.

Therefore, in this large survival trial in which the end point evaluation was overall survival, the BEST clinical trial was terminated early because of confirmation of benefit that had recently been shown in other trials, and the inability to extend the efficacy of bucindolol to patient subgroups that had not been previously evaluated in large scale clinical trials (BEST Investigators, 2001). At that time, there was no significant difference in mortality observed between those treated with bucindolol or with a placebo. In distinct contrast to the results of BEST, similar studies with the β-adrenergic antagonists bisoprolol (termed "CIBIS-II" trial), metoprolol (termed "MERIT-HF" trial), and carvedilol "COPERNICUS" trial) reported very favorable differences (34-35% reductions in mortality) between those treated with the antagonists and those treated with a placebo. The BEST investigators speculated that one possible explanation for the difference in the results "may derive from the unique pharmacological properties of bucindolol."

In the CIBIS-II trial, the study was also stopped early, but because the mortality rates were significantly less in those treated with bisoprolol. CIBIS-II Investigators, 1999. Similarly, in the MERIT-HF study with metoprolol, the study was ended prematurely because the predefined criterion had been met and exceeded. MERIT-HF Study Group, 1999. The COPERNICUS study involving carvedilol was also halted early because of the significant benefits observed with treatment. Packer et al., 2001. The BEST investigators noted that their results raised questions about the equivalency of β-blockers.

Moreover, in previous non-mortality studies with carvedilol (Yancy et al., 2001), no response differences were observed between black and non-black subjects, which is another specific, and relevant distinction with respect to bucindolol. In the BEST trial, black patients with advanced heart failure showed a worse outcome than non-blacks. Bristow, 1997.

One review of the different trials stated, "No clear explanation can be proposed for the reduced benefit obtained with bucindolol in the BEST study." Bouzamondo et al., 2001 (finding that if the BEST trial is excluded, the evidence indicates risk reduction achieved with β-blocker treatment). While the authors say their study suggests that different heart failure populations subgroups have a different response to β-blocker therapy, they do not exclude the possibility that the different β-blockers have different properties, nor do they say that polymorphisms are the reason. See also Sallach et al., 2003. ("While some authorities have suggested that [the difference with the BEST trial] was due to the patient population examined, others feel that the lack of mortality reduction is due to bucindolol itself").

Therefore, there are therapeutic differences between bucindolol and other β-blockers, and there was a significant question regarding the therapeutic efficacy of bucindolol overall. Consequently, any relationship between bucindolol and particular genetic variants was not evident.

The benefit of retrospective analysis based on the genetic data disclosed herein highlights the unique pharmacologic features of bucindolol that contribute to its effectiveness in treating heart failure patients. Two of these features are also instrumental in the interaction of the drug with the adrenergic receptor gene variants.

The first of these features is sympatholysis, or the ability of a drug to lower adrenergic drive directly (lower norepinephrine levels in blood and tissue). As noted above, among β-blockers that have been used to treat heart failure, bucindolol is unique in this regard (BEST Trial Investigators, 2001; Lowes et al., 2000; Bristow et al., 2004). The sympatholytic effects of bucindolol are likely due to $\beta_2$-receptor blockade coupled with not enough $\alpha_1$-blockade to activate adrenergic drive, and low inverse agonist activity for $\beta_1$- and β2-receptors to minimize adrenergic activation based on myocardial depression. Other properties of bucindolol that could contribute to sympatholysis are nitric oxide generation and $\beta_3$-receptor agonism (Strosberg, 1997). These latter two properties plus or minus a weak $\alpha_1$-receptor blockade likely account for the mild vasodilator properties of bucindolol (Gilbert et al., 1990) which, unlike carvedilol, are not powerful enough to trigger reflex adrenergic activation.

When present in modest amounts, (smaller reductions in norepinephrine) sympatholysis is a favorable property, contributing to the therapeutic anti-adrenergic effect of bucindolol. This is a potentially superior mechanism of action to simple β-blockade, as excess norepinephrine is removed from the system. Norepinephrine is toxic to heart muscle and in excess amounts triggers various cardiac disease pathways. However, when exaggerated, sympatholysis can be harmful, and can increase mortality (Bristow et al. 2004). As discussed below, genetic targeting of bucindolol allows this property to function only in a favorable manner.

Figure 13:
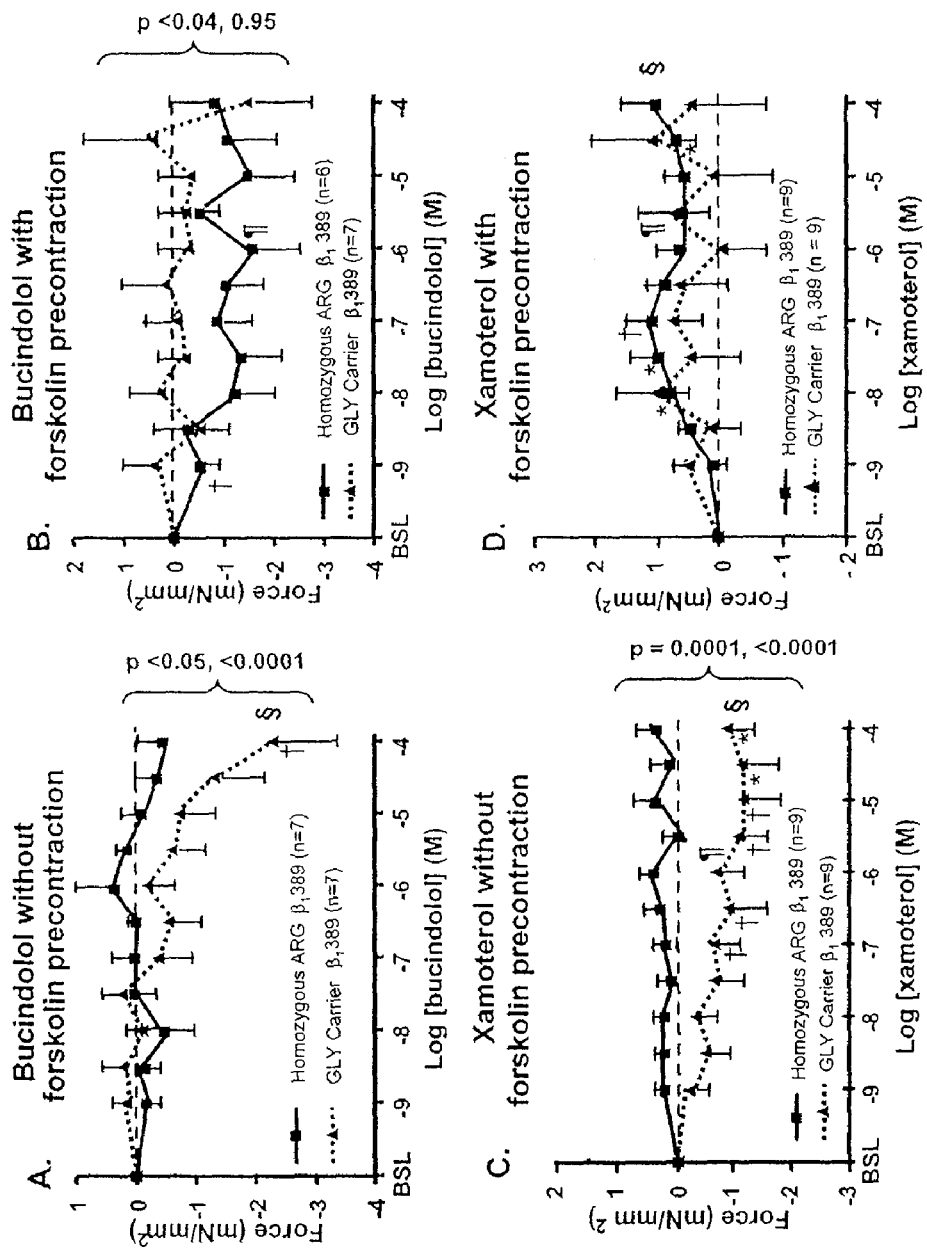
FIGS. 13A-D. Effect of increasing doses of bucindolol or xamoterol on peak systolic force (mN/mm²) in isolated right ventricular trabeculae from failing human hearts. Dose-response curves were performed without (bucindolol, panel A; xamoterol, panel C) and with (bucindolol, panel B; xamoterol, panel D) pretreatment by $10^{-5}$ M forskolin to enhance β-AR signal transduction. In the forskolin pretreatment experiments, forskolin-alone trabeculae were allowed to incubate throughout the treatment period, and any effects on force were subtracted from the bucindolol or xamoterol-treated trabeculae. *, =p<0.05 vs. baseline tension; †, p<0.10 vs. baseline tension; §, p<0.05 vs. slope of 0 for entire curve; ¶, p<0.05 vs. slope of 0 for doses of $10^{-9}$ M to $10^{-6}$ M; p values associated with brackets are for test for interaction between curve slopes, with 1st p valur for doses between $10^{-9}$ M to $10^{-6}$ M, and 2nd p value for entire curve.

The second pharmacologic property of bucindolol that interacts with a pharmacogenetic target is high affinity $\beta_1$-receptor blockade (Hershberger et al., 1990; Asano et al., 2001). Bucindolol has high affinity for human $\beta_1$-receptors, as well as for $\beta_2$-receptors (Hershberger et al., 1990). In addition, through a non-agonist effect on either translation or protein turnover, bucindolol lowers $\beta_1$-receptor density (Asano et al., 2001). Because it is so well tolerated, bucindolol can be administered at very high β-blocking doses, and each of these properties contributes to its salutary effects on the high functioning human $\beta_1$-receptor 389Arg/Arg gene variant (Examples, Mason et al., 1999). Although bucindolol has intrinsic sympathomimetic activity (USA) in rat myocardium in functioning human cardiac tissue bucindolol is devoid of ISA (Bristow et al., 1994; Sederberg et al., 2000; Bristow et al., 1998, Example 7). This can clearly be seen in FIG. 13, panels A and B, where no significant increase in force development occurs in isolated failing human right ventricular trabeculae, even in the presence of signal transduction augmentation with the diterpene compound forskolin, in either the $\beta_1$AR Arg/Arg or Gly carrier genotypes. In contrast, as shown in FIG. 13 panel C, xamoterol as a positive control ISA compound exhibits an increase in force in both low and high signal transduction activation in the $\beta_1$AR Arg/Arg genotype, but only in the high activation state rendered by forskolin pretreatment in Gly carriers. Finally, as shown in FIG. 13, in preparations of isolated human heart, bucindolol has unique effects on $\beta_1$AR Arg/Arg vs Gly carrier receptors. Under conditions of low levels of signal transduction (low receptor activation) in the failing heart (Panel A), bucindolol functions as a neutral antagonist (no agonist or inverse agonist activity) at the human myocardial $\beta_1$Arg/Arg receptor, but when signal transduction is high as when adenylyl cyclase is directly activated by forskolin (Panel B), bucindolol functions as an inverse agonist, inactivating the receptor as indicated by a statistically significant slope factor up to the highest concentration achievable in plasma by therapeutic doses, $10^{-6}$ M. No such effect occurs in Gly carrier receptors, where bucindolol functions as an inverse agonist in low activation states, and a neutral antagonist in the presence of forskolin. These data suggest that bucindolol is uniquely effective in antagonizing high activation states of the $\beta_1$389Arg/Arg receptor, the form of the receptor that would be expected to be the most cardiomyopathic.

These properties are likely reasons for the surprising and unexpected results that were observed with the Arg389 genetic variant in the $\beta_1$AR and the Del322-325 genetic variant in $\alpha_{2c}$AR in the context of bucindolol treatment.

II. Analysis of Polymorphism

Because the genetic variants are in coding regions of the $\beta_1$-AR and α-AR genes and affect the encoded protein, the presence of the Arg389 or Del322-325 polymorphism can be determined from either the sequence of the nucleic acid or the protein. As a result, a variety of different methodologies can be employed for this purpose.

A. Nucleic Acids

Certain embodiments of the present invention concern various nucleic acids, including amplification primers, oligonucleotide probes, and other nucleic acid elements involved in the analysis of genomic DNA. In certain aspects, a nucleic acid comprises a wild-type, a mutant, or a polymorphic nucleic acid.

The terms "β$_1$-adrenergic receptor" polymorphisms or "β$_1$AR" polymorphisms, therefore, are terms of art and refer to polymorphisms in the nucleic acid or amino acid sequence of a β$_1$-adrenergic receptor gene or gene product. For reference purposes only, GenBank Accession No. J03019 (Gly389) and AF169007 (Arg389) (both of which are herein incorporated by reference) are examples of Gly- and Arg-389 forms of the β$_1$-adrenergic receptor gene sequence, respectively.

Also, the terms "α$_{2c}$-adrenergic receptor" polymorphisms or "α$_{2c}$AR" polymorphisms, therefore, are terms of art and refer to polymorphisms in the nucleic acid or amino acid sequence of a α$_{2c}$-adrenergic receptor gene or gene product. For reference purposes only, GenBank Accession No. NM00683 corresponds to wildtype (non-deletion) and AF280400 corresponds to the deletion (both of which are herein incorporated by reference).

For the purposes of identifying the location of a polymorphism, the first nucleotide of the start codon of the coding region (the adenine of the ATG in a DNA molecule and the adenine of the AUG in an RNA molecule) of the β$_1$AR gene or α$_{2c}$-AR is considered nucleotide "1" and the numbers progress according along the coding sequence. Similarly, the first amino acid of the translated protein product (the methionine) is considered amino acid "1".

The term "nucleic acid" is well known in the art. A "nucleic acid" as used herein will generally refer to a molecule (i.e., a strand) of DNA or RNA comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length. A "gene" refers to coding sequence of a gene product, as well as introns and the promoter of the gene product.

In some embodiments, nucleic acids of the invention comprise or are complementary to all or 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1165, 1200, 1300, 1400, 1500 or more contiguous nucleotides, or any range derivable therein, of the human β$_1$AR cDNA sequence with either a cytosine or guanine at position 1165 in the cDNA sequence or of the α$_{2c}$AR cDNA sequence with nucleotides 964-975 present or absent. One of skill in the art knows how to design and use primers and probes for hybridization and amplification, including the limits of homology needed to implement primers and probes.

These definitions generally refer to a single-stranded molecule, but in specific embodiments will also encompass an additional strand that is partially, substantially or fully complementary to the single-stranded molecule. Thus, a nucleic acid may encompass a double-stranded molecule or a triple-stranded molecule that comprises one or more complementary strand(s) or "complement(s)" of a particular sequence comprising a molecule. As used herein, a single stranded nucleic acid may be denoted by the prefix "ss", a double stranded nucleic acid by the prefix "ds", and a triple stranded nucleic acid by the prefix "ts."

In particular aspects, a nucleic acid encodes a protein, polypeptide, or peptide. In certain embodiments, the present invention concerns novel compositions comprising at least one proteinaceous molecule. As used herein, a "proteinaceous molecule," "proteinaceous composition," "proteinaceous compound," "proteinaceous chain," or "proteinaceous material" generally refers, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein.

1. Preparation of Nucleic Acids

A nucleic acid may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemical synthesis using phosphotriester, phosphite or phosphoramidite chemistry and solid phase techniques such as described in European Patent 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959, 463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 2001, incorporated herein by reference).

2. Purification of Nucleic Acids

A nucleic acid may be purified on polyacrylamide gels, cesium chloride centrifugation gradients, chromatography columns or by any other means known to one of ordinary skill in the art (see for example, Sambrook et al., 2001, incorporated herein by reference). In some aspects, a nucleic acid is a pharmacologically acceptable nucleic acid. Pharmacologically acceptable compositions are known to those of skill in the art, and are described herein.

In certain aspects, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

3. Nucleic Acid Segments

In certain embodiments, the nucleic acid is a nucleic acid segment. As used herein, the term "nucleic acid segment," are fragments of a nucleic acid, such as, for a non-limiting example, those that encode only part of a $\beta_1AR$ gene locus or a $\beta_1AR$ gene sequence, or part of the $\alpha_{2c}AR$ gene locus or gene sequence. Thus, a "nucleic acid segment" may comprise any part of a gene sequence, including from about 2 nucleotides to the full length gene including promoter regions to the polyadenylation signal and any length that includes all the coding region.

Various nucleic acid segments may be designed based on a particular nucleic acid sequence, and may be of any length. By assigning numeric values to a sequence, for example, the first residue is 1, the second residue is 2, etc., an algorithm defining all nucleic acid segments can be created:

n to n+y where n is an integer from 1 to the last number of the sequence and y is the length of the nucleic acid segment minus one, where n+y does not exceed the last number of the sequence. Thus, for a 10-mer, the nucleic acid segments correspond to bases 1 to 10, 2 to 11, 3 to 12 . . . and so on. For a 15-mer, the nucleic acid segments correspond to bases 1 to 15, 2 to 16, 3 to 17 . . . and so on. For a 20-mer, the nucleic segments correspond to bases 1 to 20, 2 to 21, 3 to 22 . . . and so on. In certain embodiments, the nucleic acid segment may be a probe or primer. As used herein, a "probe" generally refers to a nucleic acid used in a detection method or composition. As used herein, a "primer" generally refers to a nucleic acid used in an extension or amplification method or composition.

4. Nucleic Acid Complements

The present invention also encompasses a nucleic acid that is complementary to a nucleic acid. A nucleic acid is "complement(s)" or is "complementary" to another nucleic acid when it is capable of base-pairing with another nucleic acid according to the standard Watson-Crick, Hoogsteen or reverse Hoogsteen binding complementarity rules. As used herein "another nucleic acid" may refer to a separate molecule or a spatial separated sequence of the same molecule. In preferred embodiments, a complement is a hybridization probe or amplification primer for the detection of a nucleic acid polymorphism.

As used herein, the term "complementary" or "complement" also refers to a nucleic acid comprising a sequence of consecutive nucleobases or semiconsecutive nucleobases (e.g., one or more nucleobase moieties are not present in the molecule) capable of hybridizing to another nucleic acid strand or duplex even if less than all the nucleobases do not base pair with a counterpart nucleobase. However, in some diagnostic or detection embodiments, completely complementary nucleic acids are preferred.

5. Nucleic Acid Detection and Evaluation

Genotyping was performed using methods exactly as previously described in Small et al., (2002), which is incorporated herein by reference. It will be understood by the skilled artisan that other standard techniques are available for genotyping and any technique may be used with the present invention. General methods of nucleic acid detection methods are provided below, followed by specific examples employed for the identification of polymorphisms, including single nucleotide polymorphisms (SNPs).

The particular genotyping method used to determine the genotype of an individual in need of a β-blocker therapy is not part of the present invention, but in short involves isolating from the individual a nucleic acid mixture comprising the two copies of the $\beta_1AR$ gene, or a fragment thereof, that are present in the individual, and determining the identity of the nucleotide pair at position 1165 in the $\beta_1AR$ or determining whether there is a deletion of nucleotides 964-975 in the $\alpha_{2c}AR$ gene. Preferred polymorphisms and polymorphic sites in a gene for a $\beta_1AR$ and $\alpha_{2c}AR$ include the following in Table 1:

TABLE 1

| $\beta_1$-Adrenergic Receptor Polymorphism | | | | |
|---|---|---|---|---|
| Nucleotide Position | Nucleotide | Amino Acid Position | Amino Acid | Designations |
| 1165 | G or C | 389 | Gly or Arg | Gly389, Arg389 |
| $\alpha_{2c}$-Adrenergic Receptor Polymorphism | | | | |
| Nucleotide Position | Nucleotide | Amino Acid Positions | Amino Acid | Designations |
| 964-975 | deletion | 322-325 | deletion | $\alpha_{2c}$Del322-325 |

These polymorphisms in have been previously reported. Wild-type $\beta_1AR$ nucleotide sequences generally comprise a guanine at nucleotide 1165. Wild-type $\beta_1AR$ protein sequences generally comprise a glycine at amino acid 389. What is considered wild-type $\alpha_{2c}AR$ nucleotide sequences generally mean there is no deletion of nucleotides 964-975 and therefore no deletion of amino acids 322-325.

Those in the art will readily recognize that nucleic acid molecules may be double-stranded molecules and that reference to a particular site on one strand refers, as well, to the corresponding site on a complementary strand. Thus, in defining a polymorphic site, reference to an adenine, a thymine (uridine), a cytosine, or a guanine at a particular site on the plus (sense or coding) strand of a nucleic acid molecule is also intended to include the thymine (uridine), adenine, guanine, or cytosine (respectively) at the corresponding site on a minus (antisense or noncoding) strand of a complementary strand of a nucleic acid molecule. Thus, reference may be made to either strand and still comprise the same polymorphic site and an oligonucleotide may be designed to hybridize to either strand. Throughout the text, in identifying a polymorphic site, reference is made to the sense strand, only for the purpose of convenience.

Typically, the nucleic acid mixture is isolated from a biological sample taken from the individual, such as a blood sample or tissue sample using standard techniques such as disclosed in Jones (1963) which is hereby incorporated by reference. Suitable tissue samples include whole blood, semen saliva, tears, urine, fecal material, sweat, buccal, skin and hair. The nucleic acid mixture may be comprised of genomic DNA, mRNA, or cDNA and, in the latter two cases, the biological sample must be obtained from an organ in which the $\beta_1AR$ gene is expressed. Furthermore it will be understood by the skilled artisan that mRNA or cDNA preparations would not be used to detect polymorphisms located in introns or in 5' and 3' nontranscribed regions. If a $\beta_1AR$ gene fragment is isolated, it must contain the polymorphic site(s) to be genotyped.

The ability to predict a patient's response to a β-agonist is useful for physicians in making decisions about how to treat a patient having heart failure. A patient whose genotype indicates the patient will probably respond well to the agonist would be a better candidate for β-blocker therapy than a patient who is likely to exhibit an intermediate response or no response, and the physician would be able to determine with less trial and error which individuals should receive an alternative form of therapy.

In the genotyping methods used in the present invention, the identity of a nucleotide (or nucleotide pair) at a polymorphic site may be determined by amplifying a target region(s) containing the polymorphic site(s) directly from one or both copies of the $\beta_1AR$ gene and/or $\alpha_{2c}AR$ gene present in the individual and the sequence of the amplified region(s) determined by conventional methods. It will be readily appreciated by the skilled artisan that only one nucleotide will be detected at a polymorphic site in individuals who are homozygous at that site, while two different nucleotides will be detected if the individual is heterozygous for that site. The polymorphism may be identified directly, known as positive-type identification, or by inference, referred to as negative-type identification. For example, where a SNP is known to be guanine and cytosine in a reference population, a site may be positively determined to be either guanine or cytosine for an individual homozygous at that site, or both guanine and cytosine, if the individual is heterozygous at that site. Alternatively, the site may be negatively determined to be not guanine (and thus cytosine/cytosine) or not cytosine (and thus guanine/guanine).

The target region(s) may be amplified using any oligonucleotide-directed amplification method, including but not limited to polymerase chain reaction (PCR) (U.S. Pat. No. 4,965,188), ligase chain reaction (LCR) (Barany et al., 1991; WO90/01069), and oligonucleotide ligation assay (OLA) (Landegren et al., 1988). Oligonucleotides useful as primers or probes in such methods should specifically hybridize to a region of the nucleic acid that contains or is adjacent to the polymorphic site. Typically, the oligonucleotides are between 10 and 35 nucleotides in length and preferably, between 15 and 30 nucleotides in length. Most preferably, the oligonucleotides are 20 to 25 nucleotides long. The exact length of the oligonucleotide will depend on many factors that are routinely considered and practiced by the skilled artisan.

Other known nucleic acid amplification procedures may be used to amplify the target region including transcription-based amplification systems (U.S. Pat. No. 5,130,238; EP 329,822; U.S. Pat. No. 5,169,766, WO89/06700) and isothermal methods (Walker et al., 1992).

A polymorphism in the target region may also be assayed before or after amplification using one of several hybridization-based methods known in the art. Typically, allele-specific oligonucleotides are utilized in performing such methods. The allele-specific oligonucleotides may be used as differently labeled probe pairs, with one member of the pair showing a perfect match to one variant of a target sequence and the other member showing a perfect match to a different variant. In some embodiments, more than one polymorphic site may be detected at once using a set of allele-specific oligonucleotides or oligonucleotide pairs.

Hybridization of an allele-specific oligonucleotide to a target polynucleotide may be performed with both entities in solution, or such hybridization may be performed when either the oligonucleotide or the target polynucleotide is covalently or noncovalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Allele-specific oligonucleotides may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the allele-specific oligonucleotide or target nucleic acid.

The genotype for one or more polymorphic sites in the $\beta_1AR$ gene of an individual may also be determined by hybridization of one or both copies of the gene, or a fragment thereof, to nucleic acid arrays and subarrays such as described in WO 95/11995. The arrays would contain a battery of allele-specific oligonucleotides representing each of the polymorphic sites to be included in the genotype or haplotype.

The identity of polymorphisms may also be determined using a mismatch detection technique, including but not limited to the RNase protection method using riboprobes (Winter et al., 1985; Meyers et al., 1985) and proteins which recognize nucleotide mismatches, such as the *E. coli* mutS protein (Modrich, 1991). Alternatively, variant alleles can be identified by single strand conformation polymorphism (SSCP) analysis (Orita et al., 1989; Humphries, et al., 1996) or denaturing gradient gel electrophoresis (DGGE) (Wartell et al., 1990; Sheffield et al., 1989).

A polymerase-mediated primer extension method may also be used to identify the polymorphism(s). Several such methods have been described in the patent and scientific literature. Extended primers containing a polymorphism may be detected by mass spectrometry as described in U.S. Pat. No. 5,605,798. An other primer extension method is allele-specific PCR (Ruano et al., 1989); Ruano et al., 1991; WO 93/22456; Turki et al., 1995).

Polymorphic variation at nucleotide position 1165 of the human $\beta_1AR$ gene can also be detected using differential digestion of DNA by certain restriction enzymes (Small et al., 2002) or by any other method that identifies the nucleotide at position 1165 of the $\beta_1AR$ gene.

a. Hybridization

The use of a probe or primer of between 7, 8, 9, 10, 11, 12, 13, 14, 15, 16, 17, 18, 19, 20, 21, 22, 23, 24, 25, 50, 60, 70, 80, 90, or 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting a specific polymorphism. It is generally appreciated that conditions can be rendered more stringent by the addition of increasing amounts of formamide. For example, under highly stringent conditions, hybridization to filter-bound DNA may be carried out in 0.5 M $NaHPO_4$, 7% sodium dodecyl sulfate (SDS), 1 mM EDTA at 65° C., and washing in 0.1×SSC/0.1% SDS at 68° C. (Ausubel et al., 1989).

Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Under low stringent conditions, such as moderately stringent conditions the washing may be carried out for example in 0.2×SSC/0.1% SDS at 42° C. (Ausubel et al., 1989). Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples. In other aspects, a particular nuclease cleavage site may be present and detection of a particular nucleotide sequence can be determined by the presence or absence of nucleic acid cleavage.

In general, it is envisioned that the probes or primers described herein will be useful as reagents in solution hybridization, as in PCR, for detection of expression or genotype of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

b. Amplification of Nucleic Acids

Nucleic acids used as a template for amplification may be isolated from cells, tissues or other samples according to standard methodologies (Sambrook et al., 2001). In certain embodiments, analysis is performed on whole cell or tissue homogenates or biological fluid samples with or without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to the $\beta_1AR$ gene locus, or variants thereof, and fragments thereof are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids that contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected, analyzed or quantified. In certain applications, the detection may be performed by visual means. In certain applications, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA) (described in further detail below), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846, 709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, Great Britain Application 2 202 328, and in PCT Application PCT/US89/01025, each of which is incorporated herein by reference in its entirety. Qbeta Replicase, described in PCT Application PCT/US87/00880, may also be used as an amplification method in the present invention.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation Other nucleic acid amplification procedures include transcription-based amplification systems (TAS), including nucleic acid sequence based amplification (NASBA) and 3SR (Kwoh et al., 1989; PCT Application WO 88/10315, incorporated herein by reference in their entirety). European Application 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990; Ohara et al., 1989).

c. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 2001). Separated amplification products may be cut out and eluted from the gel for further manipulation. Using low melting point agarose gels, the separated band may be removed by heating the gel, followed by extraction of the nucleic acid.

Separation of nucleic acids may also be effected by spin columns and/or chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized, with or without separation. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 2001). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

d. Other Assays

Other methods for genetic screening may be used within the scope of the present invention, for example, to detect mutations in genomic DNA, cDNA and/or RNA samples. Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCR™ (see above), single-strand conformation polymorphism analysis ("SSCP") and other methods well known in the art.

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. The use of RNase I for mismatch detection is described in literature from Promega Biotech. Promega markets a kit containing RNase I that is reported to cleave three out of four known mismatches. Others have described using the MutS protein or other DNA-repair enzymes for detection of single-base mismatches.

Alternative methods for detection of deletion, insertion or substitution mutations that may be used in the practice of the present invention are disclosed in U.S. Pat. Nos. 5,849,483, 5,851,770, 5,866,337, 5,925,525 and 5,928,870, each of which is incorporated herein by reference in its entirety.

e. Specific Examples of Polymorphism Nucleic Acid Screening Methods

Spontaneous mutations that arise during the course of evolution in the genomes of organisms are often not immediately transmitted throughout all of the members of the species, thereby creating polymorphic alleles that co-exist in the species populations. Often polymorphisms are the cause of genetic diseases. Several classes of polymorphisms have been identified. For example, variable nucleotide type polymorphisms (VNTRs), arise from spontaneous tandem duplications of di- or trinucleotide repeated motifs of nucleotides. If such variations alter the lengths of DNA fragments generated by restriction endonuclease cleavage, the variations are referred to as restriction fragment length polymorphisms (RFLPs). RFLPs are been widely used in human and animal genetic analyses.

Another class of polymorphisms are generated by the replacement of a single nucleotide. Such single nucleotide polymorphisms (SNPs) rarely result in changes in a restriction endonuclease site. Thus, SNPs are rarely detectable restriction fragment length analysis. SNPs are the most common genetic variations and occur once every 100 to 300 bases and several SNP mutations have been found that affect a single nucleotide in a protein-encoding gene in a manner sufficient to actually cause a genetic disease. SNP diseases are exemplified by hemophilia, sickle-cell anemia, hereditary hemochromatosis, late-onset alzheimer disease etc.

Several methods have been developed to screen polymorphisms and some examples are listed below. The reference of Kwok and Chen (2003) and Kwok (2001) provide overviews of some of these methods; both of these references are specifically incorporated by reference.

SNPs relating to ABCC2 can be characterized by the use of any of these methods or suitable modification thereof. Such methods include the direct or indirect sequencing of the site, the use of restriction enzymes where the respective alleles of the site create or destroy a restriction site, the use of allele-specific hybridization probes, the use of antibodies that are specific for the proteins encoded by the different alleles of the polymorphism, or any other biochemical interpretation.

i. DNA Sequencing

The most commonly used method of characterizing a polymorphism is direct DNA sequencing of the genetic locus that flanks and includes the polymorphism. Such analysis can be accomplished using either the "dideoxy-mediated chain termination method," also known as the "Sanger Method" (Sanger et al., 1975) or the "chemical degradation method," also known as the "Maxam-Gilbert method" (Maxam et al., 1977). Sequencing in combination with genomic sequence-specific amplification technologies, such as the polymerase chain reaction may be utilized to facilitate the recovery of the desired genes (Mullis et al., 1986; European Patent Application 50,424; European Patent Application. 84,796, European Patent Application 258,017, European Patent Application. 237,362; European Patent Application. 201,184; U.S. Pat. Nos. 4,683,202; 4,582,788; and 4,683,194), all of the above incorporated herein by reference.

ii. Exonuclease Resistance

Other methods that can be employed to determine the identity of a nucleotide present at a polymorphic site utilize a specialized exonuclease-resistant nucleotide derivative (U.S. Pat. No. 4,656,127). A primer complementary to an allelic sequence immediately 3'- to the polymorphic site is hybridized to the DNA under investigation. If the polymorphic site on the DNA contains a nucleotide that is complementary to the particular exonucleotide-resistant nucleotide derivative present, then that derivative will be incorporated by a polymerase onto the end of the hybridized primer. Such incorporation makes the primer resistant to exonuclease cleavage and thereby permits its detection. As the identity of the exonucleotide-resistant derivative is known one can determine the specific nucleotide present in the polymorphic site of the DNA.

iii. Microsequencing Methods

Several other primer-guided nucleotide incorporation procedures for assaying polymorphic sites in DNA have been described (Komher et al., 1989; Sokolov, 1990; Syvanen 1990; Kuppuswamy et al., 1991; Prezant et al., 1992; Ugozzoll et al., 1992; Nyren et al., 1993). These methods rely on the incorporation of labeled deoxynucleotides to discriminate between bases at a polymorphic site. As the signal is proportional to the number of deoxynucleotides incorporated, polymorphisms that occur in runs of the same nucleotide result in a signal that is proportional to the length of the run (Syvanen et al., 1990).

iv. Extension in Solution

French Patent 2,650,840 and PCT Application WO91/02087 discuss a solution-based method for determining the identity of the nucleotide of a polymorphic site. According to these methods, a primer complementary to allelic sequences immediately 3'- to a polymorphic site is used. The identity of the nucleotide of that site is determined using labeled dideoxynucleotide derivatives which are incorporated at the end of the primer if complementary to the nucleotide of the polymorphic site.

v. Genetic Bit Analysis or Solid-Phase Extension

PCT Application WO92/15712 describes a method that uses mixtures of labeled terminators and a primer that is complementary to the sequence 3' to a polymorphic site. The labeled terminator that is incorporated is complementary to the nucleotide present in the polymorphic site of the target molecule being evaluated and is thus identified. Here the primer or the target molecule is immobilized to a solid phase.

vi. Oligonucleotide Ligation Assay (OLA)

This is another solid phase method that uses different methodology (Landegren et al., 1988). Two oligonucleotides, capable of hybridizing to abutting sequences of a single strand of a target DNA are used. One of these oligonucleotides is biotinylated while the other is detectably labeled. If the precise complementary sequence is found in a target molecule, the oligonucleotides will hybridize such that their termini abut, and create a ligation substrate. Ligation permits the recovery of the labeled oligonucleotide by using avidin. Other nucleic acid detection assays, based on this method, combined with PCR have also been described (Nickerson et al., 1990). Here PCR is used to achieve the exponential amplification of target DNA, which is then detected using the OLA.

vii. Ligase/Polymerase-Mediated Genetic Bit Analysis

U.S. Pat. No. 5,952,174 describes a method that also involves two primers capable of hybridizing to abutting sequences of a target molecule. The hybridized product is formed on a solid support to which the target is immobilized. Here the hybridization occurs such that the primers are separated from one another by a space of a single nucleotide. Incubating this hybridized product in the presence of a polymerase, a ligase, and a nucleoside triphosphate mixture containing at least one deoxynucleoside triphosphate allows the ligation of any pair of abutting hybridized oligonucleotides. Addition of a ligase results in two events required to generate a signal, extension and ligation. This provides a higher specificity and lower "noise" than methods using either extension or ligation alone and unlike the polymerase-based assays, this method enhances the specificity of the polymerase step by combining it with a second hybridization and a ligation step for a signal to be attached to the solid phase.

viii. Invasive Cleavage Reactions

Invasive cleavage reactions can be used to evaluate cellular DNA for a particular polymorphism. A technology called INVADER® employs such reactions (e.g., de Arruda et al., 2002; Stevens et al., 2003, which are incorporated by reference). Generally, there are three nucleic acid molecules: 1) an oligonucleotide upstream of the target site ("upstream oligo"), 2) a probe oligonucleotide covering the target site ("probe"), and 3) a single-stranded DNA with the target site ("target"). The upstream oligo and probe do not overlap but they contain contiguous sequences. The probe contains a donor fluorophore, such as fluoroscein, and an acceptor dye, such as Dabcyl. The nucleotide at the 3' terminal end of the upstream oligo overlaps ("invades") the first base pair of a probe-target duplex. Then the probe is cleaved by a structure-specific 5' nuclease causing separation of the fluorophore/quencher pair, which increases the amount of fluorescence that can be detected. See Lu et al., 2004.

In some cases, the assay is conducted on a solid-surface or in an array format.

ix. Other Methods To Detect SNPs

Several other specific methods for polymorphism detection and identification are presented below and may be used as such or with suitable modifications in conjunction with identifying polymorphisms of the $\beta_1AR$ gene in the present invention. Several other methods are also described on the SNP web site of the NCBI on the World Wide Web at ncbi.nlm.nih.gov/SNP, incorporated herein by reference.

In a particular embodiment, extended haplotypes may be determined at any given locus in a population, which allows one to identify exactly which SNPs will be redundant and which will be essential in association studies. The latter is referred to as 'haplotype tag SNPs (htSNPs)', markers that capture the haplotypes of a gene or a region of linkage disequilibrium. See Johnson et al. (2001) and Ke and Cardon (2003), each of which is incorporated herein by reference, for exemplary methods.

The VDA-assay utilizes PCR amplification of genomic segments by long PCR methods using TaKaRa LA Taq reagents and other standard reaction conditions. The long amplification can amplify DNA sizes of about 2,000-12,000 bp. Hybridization of products to variant detector array (VDA) can be performed by a Affymetrix High Throughput Screening Center and analyzed with computerized software.

A method called Chip Assay uses PCR amplification of genomic segments by standard or long PCR protocols. Hybridization products are analyzed by VDA, Halushka et al. (1999), incorporated herein by reference. SNPs are generally classified as "Certain" or "Likely" based on computer analysis of hybridization patterns. By comparison to alternative detection methods such as nucleotide sequencing, "Certain" SNPs have been confirmed 100% of the time; and "Likely" SNPs have been confirmed 73% of the time by this method.

Other methods simply involve PCR amplification following digestion with the relevant restriction enzyme. Yet others involve sequencing of purified PCR products from known genomic regions.

In yet another method, individual exons or overlapping fragments of large exons are PCR-amplified. Primers are designed from published or database sequences and PCR-amplification of genomic DNA is performed using the following conditions: 200 ng DNA template, 0.5 µM each primer, 80 µM each of dCTP, dATP, dTTP and dGTP, 5% formamide, 1.5 mM $MgCl_2$, 0.5 U of Taq polymerase and 0.1 volume of the Taq buffer. Thermal cycling is performed and resulting PCR-products are analyzed by PCR-single strand conformation polymorphism (PCR-SSCP) analysis, under a variety of conditions, e.g., 5 or 10% polyacrylamide gel with 15% urea, with or without 5% glycerol. Electrophoresis is performed overnight. PCR-products that show mobility shifts are reamplified and sequenced to identify nucleotide variation.

In a method called CGAP-GAI (DEMIGLACE), sequence and alignment data (from a PHRAP.ace file), quality scores for the sequence base calls (from PHRED quality files), distance information (from PHYLIP dnadist and neighbour programs) and base-calling data (from PHRED '-d' switch) are loaded into memory. Sequences are aligned and examined for each vertical chunk ('slice') of the resulting assembly for disagreement. Any such slice is considered a candidate SNP (DEMIGLACE). A number of filters are used by DEMIGLACE to eliminate slices that are not likely to represent true polymorphisms. These include filters that: (i) exclude sequences in any given slice from SNP consideration where neighboring sequence quality scores drop 40% or more; (ii) exclude calls in which peak amplitude is below the fifteenth percentile of all base calls for that nucleotide type; (iii) disqualify regions of a sequence having a high number of disagreements with the consensus from participating in SNP calculations; (iv) removed from consideration any base call with an alternative call in which the peak takes up 25% or more of the area of the called peak; (v) exclude variations that occur in only one read direction. PHRED quality scores were converted into probability-of-error values for each nucleotide in the slice. Standard Baysian methods are used to calculate the posterior probability that there is evidence of nucleotide heterogeneity at a given location.

In a method called CU-RDF (RESEQ), PCR amplification is performed from DNA isolated from blood using specific primers for each SNP, and after typical cleanup protocols to remove unused primers and free nucleotides, direct sequencing using the same or nested primers.

In a method called DEBNICK (METHOD-B), a comparative analysis of clustered EST sequences is performed and confirmed by fluorescent-based DNA sequencing. In a related method, called DEBNICK (METHOD-C), comparative analysis of clustered EST sequences with phred quality >20 at the site of the mismatch, average phred quality >=20 over 5 bases 5'-FLANK and 3' to the SNP, no mismatches in 5 bases 5' and 3' to the SNP, at least two occurrences of each allele is performed and confirmed by examining traces.

In a method identified by ERO (RESEW), new primers sets are designed for electronically published STSs and used to amplify DNA from 10 different mouse strains. The amplification product from each strain is then gel purified and sequenced using a standard dideoxy, cycle sequencing technique with $^{33}P$-labeled terminators. All the ddATP terminated reactions are then loaded in adjacent lanes of a sequencing gel followed by all of the ddGTP reactions and so on. SNPs are identified by visually scanning the radiographs.

In another method identified as ERO (RESEQ-HT), new primers sets are designed for electronically published murine DNA sequences and used to amplify DNA from 10 different mouse strains. The amplification product from each strain is prepared for sequencing by treating with Exonuclease I and Shrimp Alkaline Phosphatase. Sequencing is performed using ABI Prism Big Dye Terminator Ready Reaction Kit (Perkin-Elmer) and sequence samples are run on the 3700 DNA Analyzer (96 Capillary Sequencer).

FGU-CBT (SCA2-SNP) identifies a method where the region containing the SNP were PCR amplified using the primers SCA2-FP3 and SCA2-RP3. Approximately 100 ng of genomic DNA is amplified in a 50 ml reaction volume containing a final concentration of 5 mM Tris, 25 mM KCl, 0.75 mM $MgCl_2$, 0.05% gelatin, 20 µmol of each primer and 0.5 U of Taq DNA polymerase. Samples are denatured, annealed and extended and the PCR product is purified from a band cut out of the agarose gel using, for example, the QIAquick gel extraction kit (Qiagen) and is sequenced using dye terminator chemistry on an ABI Prism 377 automated DNA sequencer with the PCR primers.

In a method identified as JBLACK (SEQ/RESTRICT), two independent PCR reactions are performed with genomic DNA. Products from the first reaction are analyzed by sequencing, indicating a unique FspI restriction site. The mutation is confirmed in the product of the second PCR reaction by digesting with Fsp I.

In a method described as KWOK(1), SNPs are identified by comparing high quality genomic sequence data from four randomly chosen individuals by direct DNA sequencing of PCR products with dye-terminator chemistry (see Kwok et al., 1996). In a related method identified as KWOK(2) SNPs are identified by comparing high quality genomic sequence data from overlapping large-insert clones such as bacterial artificial chromosomes (BACs) or P1-based artificial chromosomes (PACs). An STS containing this SNP is then developed and the existence of the SNP in various populations is confirmed by pooled DNA sequencing (see Taillon-Miller et al., 1998). In another similar method called KWOK(3), SNPs are identified by comparing high quality genomic sequence data from overlapping large-insert clones BACs or PACs. The SNPs found by this approach represent DNA sequence variations between the two donor chromosomes but the allele frequencies in the general population have not yet been determined. In method KWOK(5), SNPs are identified by comparing high quality genomic sequence data from a homozygous DNA sample and one or more pooled DNA samples by direct DNA sequencing of PCR products with dye-terminator chemistry. The STSs used are developed from sequence data found in publicly available databases. Specifically, these STSs are amplified by PCR against a complete hydatidiform mole (CHM) that has been shown to be homozygous at all loci and a pool of DNA samples from 80 CEPH parents (see Kwok et al., 1994).

In another such method, KWOK (OverlapSnpDetectionWithPolyl)ayes), SNPs are discovered by automated computer analysis of overlapping regions of large-insert human genomic clone sequences. For data acquisition, clone sequences are obtained directly from large-scale sequencing centers. This is necessary because base quality sequences are not present/available through GenBank. Raw data processing involves analyzed of clone sequences and accompanying base quality information for consistency. Finished ('base perfect', error rate lower than 1 in 10,000 bp) sequences with no associated base quality sequences are assigned a uniform base quality value of 40 (1 in 10,000 bp error rate). Draft sequences without base quality values are rejected. Processed sequences are entered into a local database. A version of each sequence with known human repeats masked is also stored. Repeat masking is performed with the program "MASKERAID." Overlap detection: Putative overlaps are detected with the program "WUBLAST." Several filtering steps followed in order to eliminate false overlap detection results, i.e. similarities between a pair of clone sequences that arise due to sequence duplication as opposed to true overlap. Total length of overlap, overall percent similarity, number of sequence differences between nucleotides with high base quality value "high-quality mismatches." Results are also compared to results of restriction fragment mapping of genomic clones at Washington University Genome Sequencing Center, finisher's reports on overlaps, and results of the sequence contig building effort at the NCBI. SNP detection: Overlapping pairs of clone sequence are analyzed for candidate SNP sites with the 'POLYBAYES' SNP detection software. Sequence differences between the pair of sequences are scored for the probability of representing true sequence variation as opposed to sequencing error. This process requires the presence of base quality values for both sequences. High-scoring candidates are extracted. The search is restricted to substitution-type single base pair variations. Confidence score of candidate SNP is computed by the POLYBAYES software.

In method identified by KWOK (TaqMan assay), the TaqMan assay is used to determine genotypes for 90 random individuals. In method identified by KYUGEN(Q1), DNA samples of indicated populations are pooled and analyzed by PLACE-SSCP. Peak heights of each allele in the pooled analysis are corrected by those in a heterozygote, and are subsequently used for calculation of allele frequencies. Allele frequencies higher than 10% are reliably quantified by this method. Allele frequency=0 (zero) means that the allele was found among individuals, but the corresponding peak is not seen in the examination of pool. Allele frequency=0-0.1 indicates that minor alleles are detected in the pool but the peaks are too low to reliably quantify.

In yet another method identified as KYUGEN (Method1), PCR products are post-labeled with fluorescent dyes and analyzed by an automated capillary electrophoresis system under SSCP conditions (PLACE-SSCP). Four or more individual DNAs are analyzed with or without two pooled DNA (Japanese pool and CEPH parents pool) in a series of experiments. Alleles are identified by visual inspection. Individual DNAs with different genotypes are sequenced and SNPs identified. Allele frequencies are estimated from peak heights in the pooled samples after correction of signal bias using peak heights in heterozygotes. For the PCR primers are tagged to have 5'-ATT or 5'-GTT at their ends for post-labeling of both strands. Samples of DNA (10 ng/ul) are amplified in reaction mixtures containing the buffer (10 mM Tris-HCl, pH 8.3 or 9.3, 50 mM KCl, 2.0 mM $MgCl_2$), 0.25 µM of each primer, 200 µM of each dNTP, and 0.025 units/µl of Taq DNA polymerase premixed with anti-Taq antibody. The two strands of PCR products are differentially labeled with nucleotides modified with R110 and R6G by an exchange reaction of Klenow fragment of DNA polymerase I. The reaction is stopped by adding EDTA, and unincorporated nucleotides are dephosphorylated by adding calf intestinal alkaline phosphatase. For the SSCP: an aliquot of fluorescently labeled PCR products and TAMRA-labeled internal markers are added to deionized formamide, and denatured. Electrophoresis is performed in a capillary using an ABI Prism 310 Genetic Analyzer. Genescan softwares (P-E Biosystems) are used for data collection and data processing. DNA of individuals (two to eleven) including those who showed different genotypes on SSCP are subjected for direct sequencing using big-dye terminator chemistry, on ABI Prism 310 sequencers. Multiple sequence trace files obtained from ABI Prism 310 are processed and aligned by Phred/Phrap and viewed using Consed viewer. SNPs are identified by PolyPhred software and visual inspection.

In yet another method identified as KYUGEN (Method2), individuals with different genotypes are searched by denaturing HPLC (DHPLC) or PLACE-SSCP (Inazuka et al., 1997) and their sequences are determined to identify SNPs. PCR is performed with primers tagged with 5'-ATT or 5'-GTT at their ends for post-labeling of both strands. DHPLC analysis is carried out using the WAVE DNA fragment analysis system (Transgenomic). PCR products are injected into DNASep column, and separated under the conditions determined using WAVEMaker program (Transgenomic). The two strands of PCR products that are differentially labeled with nucleotides modified with R110 and R6G by an exchange reaction of Klenow fragment of DNA polymerase I. The reaction is stopped by adding EDTA, and unincorporated nucleotides are dephosphorylated by adding calf intestinal alkaline phosphatase. SSCP followed by electrophoresis is performed in a capillary using an ABI Prism 310 Genetic Analyzer. Genescan softwares (P-E Biosystems). DNA of individuals including those who showed different genotypes on DHPLC or SSCP are subjected for direct sequencing using big-dye terminator chemistry, on ABI Prism 310 sequencer. Multiple sequence trace files obtained from ABI Prism 310 are processed and aligned by Phred/Phrap and viewed using Consed viewer. SNPs are identified by PolyPhred software and visual inspection. Trace chromatogram data of EST sequences in Unigene are processed with PHRED. To identify likely SNPs, single base mismatches are reported from multiple sequence alignments produced by the programs PHRAP, BRO and POA for each Unigene cluster. BRO corrected possible misreported EST orientations, while POA identified and analyzed non-linear alignment structures indicative of gene mixing/chimeras that might produce spurious SNPs. Bayesian inference is used to weigh evidence for true polymorphism versus sequencing error, misalignment or ambiguity, misclustering or chimeric EST sequences, assessing data such as raw chromatogram height, sharpness, overlap and spacing; sequencing error rates; context-sensitivity; cDNA library origin, etc.

In method identified as MARSHFIELD(Method-B), overlapping human DNA sequences which contained putative insertion/deletion polymorphisms are identified through searches of public databases. PCR primers which flanked each polymorphic site are selected from the consensus sequences. Primers are used to amplify individual or pooled human genomic DNA. Resulting PCR products are resolved on a denaturing polyacrylamide gel and a PhosphorImager is used to estimate allele frequencies from DNA pools.

f. Linkage Disequilibrium

Polymorphisms in linkage disequilibrium with another polymorphism in which identification of one polymorphism is predictive of the identity of the linked polymorphism. "Linkage disequilibrium" ("LD" as used herein, though also referred to as "LED" in the art) refers to a situation where a particular combination of alleles (i.e., a variant form of a given gene) or polymorphisms at two loci appears more frequently than would be expected by chance. "Significant" as used in respect to linkage disequilibrium, as determined by one of skill in the art, is contemplated to be a statistical p or a value that may be 0.25 or 0.1 and may be 0.1, 0.05. 0.001, 0.00001 or less. The polymorphism at position 389 in the $\beta_1AR$ protein may be determined by evaluating the nucleic acid sequence of a polymorphism in linkage disequilibrium with the 389 polymorphism. The invention may be implemented in this manner with respect to one or more polymorphisms so as to allow haplotype analysis. "Haplotype" is used according to its plain and ordinary meaning to one skilled in the art. It refers to a collective genotype of two or more alleles or polymorphisms along one of the homologous chromosomes.

B. Evaluating the Protein

Alternatively, polymorphic variation can be determined by any method that detects an amino acid variation at position 389 of the $\beta_1AR$ protein. The invention should not be limited by any particular method for achieving this. For example, a sample of fluid or tissue may be obtained from an individual and the amino acid at position 389 of the $\beta_1AR$ protein is determined. Such detection can be by various methods including antibody based assays, (Western blots, ELISA) or amino acid analysis (high pressure liquid chromatography or mass spectroscopy) could be used that would detect whether the protein has Arg or Gly.

Therefore, in certain embodiments, the present invention concerns compositions comprising at least one proteinaceous molecule, such as a $\beta_1AR$ protein or an protein that binds $\beta_1AR$ protein, such as an antibody. As used herein, a "proteinaceous molecule," "proteinaceous composition," "proteinaceous compound," "proteinaceous chain" or "proteinaceous material" generally refers, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials. The nucleotide and protein, polypeptide and peptide sequences for various genes have been previously disclosed, and may be found at computerized databases known to those of ordinary skill in the art. One such database is the National Center for Biotechnology Information's Genbank and GenPept databases (http://www.ncbi.nlm.nih.gov/). The coding regions for these known genes may be amplified and/or expressed using the techniques disclosed herein or as would be know to those of ordinary skill in the art. Alternatively, various commercial preparations of proteins, polypeptides and peptides are known to those of skill in the art.

1. Protein Purification

It may be desirable to purify $\beta_1AR$ from a sample or purify a protein that binds $\beta_1AR$, such as an antibody. Such techniques are widely employed and the invention is not intended to be limited with respect to protein purification. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention may concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

A variety of techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (e.g., alter pH, ionic strength, and temperature).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand also should provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

2. Antibodies

Another embodiment of the present invention are antibodies, in some cases, a human monoclonal antibody immunoreactive with the polypeptide sequence of human $\beta_1 AR$. It is understood that antibodies can be used for detecting $\beta_1 AR$, particularly a $\beta_1 AR$ that is the result of a particular polymorphism. It is contemplated that antibodies particularly useful in the context of the present invention are those that differentially bind a $\beta_1 AR$ protein with a Gly389 compared to a $\beta_1 AR$ protein with a Arg389 so as to distinguish between the two populations.

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Harlow et al., 1988; incorporated herein by reference).

a. Antibody Generation

In certain embodiments, the present invention involves antibodies. For example, all or part of a monoclonal may be used in determining the amino acid at position 389. As detailed above, in addition to antibodies generated against full length proteins, antibodies also may be generated in response to smaller constructs comprising epitopic core regions, including wild-type and mutant epitopes. The techniques for preparing and using various antibody-based constructs and fragments are well known in the art. Means for preparing and characterizing antibodies are also well known in the art (See, e.g., Harlow and Lane, 1988; incorporated herein by reference).

Monoclonal antibodies (mAbs) are recognized to have certain advantages, e.g., reproducibility and large-scale production, and their use is generally preferred. The invention thus provides monoclonal antibodies of the human, murine, monkey, rat, hamster, rabbit and even chicken origin.

The methods for generating monoclonal antibodies (mAbs) generally begin along the same lines as those for preparing polyclonal antibodies. Briefly, a polyclonal antibody may be prepared by immunizing an animal with an immunogenic polypeptide composition in accordance with the present invention and collecting antisera from that immunized animal. Alternatively, in some embodiments of the present invention, serum is collected from persons who may have been exposed to a particular antigen. Exposure to a particular antigen may occur a work environment, such that those persons have been occupationally exposed to a particular antigen and have developed polyclonal antibodies to a peptide, polypeptide, or protein. In some embodiments of the invention polyclonal serum from occupationally exposed persons is used to identify antigenic regions in the gelonin toxin through the use of immunodetection methods.

A wide range of animal species can be used for the production of antisera. Typically the animal used for production of antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin also can be used as carriers. Means for conjugating a polypeptide to a carrier protein are well known in the art and include glutaraldehyde, m-maleimidobenzoyl-N-hydroxysuccinimide ester, carbodiimide and bis-biazotized benzidine.

As also well known in the art, the immunogenicity of a particular immunogen composition can be enhanced by the use of non-specific stimulators of the immune response, known as adjuvants. Suitable molecule adjuvants include all acceptable immunostimulatory compounds, such as cytokines, toxins or synthetic compositions.

Adjuvants that may be used include IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion also is contemplated. MHC antigens may even be used. Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant.

In addition to adjuvants, it may be desirable to coadminister biologic response modifiers (BRM), which have been shown to upregulate T cell immunity or down-regulate suppressor cell activity. Such BRMs include, but are not limited to, Cimetidine (CIM; 1200 mg/d) (Smith/Kline, Pa.); low-dose Cyclophosphamide (CYP; 300 $mg/m^2$) (Johnson/Mead, N.J.), cytokines such as γ-interferon, IL-2, or IL-12 or genes encoding proteins involved in immune helper functions, such as B-7.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization.

A second, booster injection also may be given. The process of boosting and titering is repeated until a suitable titer is achieved. When a desired level of immunogenicity is obtained, the immunized animal can be bled and the serum isolated and stored, and/or the animal can be used to generate mAbs.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified polypeptide, peptide or domain, be it a wild-type or mutant composition. The immunizing composition is administered in a manner effective to stimulate antibody producing cells.

mAbs may be further purified, if desired, using filtration, centrifugation and various chromatographic methods such as HPLC or affinity chromatography. Fragments of the monoclonal antibodies of the invention can be obtained from the monoclonal antibodies so produced by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It also is contemplated that a molecular cloning approach may be used to generate mAbs. For this, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

b. Immunodetection Methods

As discussed, in some embodiments, the present invention concerns immunodetection methods for binding, purifying, removing, determining, and/or otherwise detecting biological components such as antigenic regions on polypeptides and peptides. The immunodetection methods of the present invention can be used to identify antigenic regions of a peptide, polypeptide, or protein that has therapeutic implications, particularly in reducing the immunogenicity or antigenicity of the peptide, polypeptide, or protein in a target subject.

Immunodetection methods include enzyme linked immunosorbent assay (ELISA), radioimmunoassay (RIA), immunoradiometric assay, fluoroimmunoassay, chemiluminescent assay, bioluminescent assay, and Western blot, though several others are well known to those of ordinary skill. The steps of various useful immunodetection methods have been described in the scientific literature, such as, e.g., Doolittle et al., 1999; Gulbis et al., 1993; De Jager et al., 1993; and Nakamura et al., 1987, each incorporated herein by reference.

In general, the immunobinding methods include obtaining a sample suspected of containing a protein, polypeptide and/or peptide, and contacting the sample with a first antibody, monoclonal or polyclonal, in accordance with the present invention, as the case may be, under conditions effective to allow the formation of immunocomplexes.

These methods include methods for purifying a protein, polypeptide and/or peptide from organelle, cell, tissue or organism's samples. In these instances, the antibody removes the antigenic protein, polypeptide and/or peptide component from a sample. The antibody will preferably be linked to a solid support, such as in the form of a column matrix, and the sample suspected of containing the protein, polypeptide and/or peptide antigenic component will be applied to the immobilized antibody. The unwanted components will be washed from the column, leaving the antigen immunocomplexed to the immobilized antibody to be eluted.

The immunobinding methods also include methods for detecting and quantifying the amount of an antigen component in a sample and the detection and quantification of any immune complexes formed during the binding process. Here, one would obtain a sample suspected of containing an antigen or antigenic domain, and contact the sample with an antibody against the antigen or antigenic domain, and then detect and quantify the amount of immune complexes formed under the specific conditions.

In terms of antigen detection, the biological sample analyzed may be any sample that is suspected of containing an antigen or antigenic domain, such as, for example, a tissue section or specimen, a homogenized tissue extract, a cell, an organelle, separated and/or purified forms of any of the above antigen-containing compositions, or even any biological fluid that comes into contact with the cell or tissue, including blood and/or serum.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

i. ELISAs

As detailed above, immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

In one exemplary ELISA, antibodies are immobilized onto a selected surface exhibiting protein affinity, such as a well in a polystyrene microtiter plate. Then, a test composition suspected of containing the antigen, such as a clinical sample, is added to the wells. After binding and/or washing to remove non-specifically bound immune complexes, the bound antigen may be detected. Detection is generally achieved by the addition of another antibody that is linked to a detectable label. This type of ELISA is a simple "sandwich ELISA." Detection may also be achieved by the addition of a second antibody, followed by the addition of a third antibody that has binding affinity for the second antibody, with the third antibody being linked to a detectable label. The ELISA may be based on differential binding of an antibody to a protein with Arg389 versus Gly389.

In another exemplary ELISA, the samples suspected of containing the antigen are immobilized onto the well surface and/or then contacted with antibodies. After binding and/or washing to remove non-specifically bound immune complexes, the bound anti-antibodies are detected. Where the initial antibodies are linked to a detectable label, the immune complexes may be detected directly. Again, the immune complexes may be detected using a second antibody that has binding affinity for the first antibody, with the second antibody being linked to a detectable label.

Another ELISA in which the antigens are immobilized, involves the use of antibody competition in the detection. In this ELISA, labeled antibodies against an antigen are added to the wells, allowed to bind, and/or detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. An example of a washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. This may be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

ii. Immunohistochemistry

The antibodies of the present invention may also be used in conjunction with both fresh-frozen and/or formalin-fixed, paraffin-embedded tissue blocks prepared for study by immunohistochemistry (IHC). For example, immunohistochemistry may be utilized to characterize Fortilin or to evaluate the amount Fortilin in a cell. The method of preparing tissue blocks from these particulate specimens has been successfully used in previous IHC studies of various prognostic factors, and/or is well known to those of skill in the art (Brown et al., 1990; Abbondanzo et al., 1990; Allred et al., 1990).

Briefly, frozen-sections may be prepared by rehydrating 50 mg of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections.

III. Therapy

Once the genotype or the protein sequence of $\beta_1$-AR of the individual is determined a therapeutic course of treatment may be individualized. In a preferred embodiment of the method, the trait of interest is a clinical response exhibited by a patient to some therapeutic treatment, for example, response to a drug such as but not limited to a $\beta$-blocker, such as bucindolol, targeting $\beta_1$AR or response to a therapeutic treatment for a medical condition. As used herein, "medical condition" includes but is not limited to any condition or disease manifested as one or more physical and/or psychological symptoms for which treatment is desirable, and includes previously and newly identified diseases and other disorders having similar pathophysiological states, such as but not limited to, heart failure, pheochromocytoma, migraines, cardiac arrhythmias, hypertension, dilated cardiomyopathy, ischemic heart disease (cardiomyopathy, ischemic heart disease (cardiomyopathy, angina, myocardial infarction), and various anxiety disorders. As used herein the term "clinical response" means any or all of the following: a quantitative measure of the efficacy or potency of the therapy and adverse events (i.e., side effects).

Thus homozygous $\beta_1$Arg389 individuals having a medical condition can be placed on a therapy that includes $\beta$-blockers such as but not limited to bucindolol. The $\beta$-blocker may be administered alone or in combination with at least one other agent, such as a stabilizing compound. The $\beta$-blocker may also be administered in combination with a medical device that would have previously been contraindicated by the disease state that required the device. For example, normally a heart failure patient with bradycardia would not receive a $\beta$-blocker. But if the genotype of the individual is Arg389 (the favorable genotype) a pacemaker could be implanted, to prescribe bucindolol.

A. Routes of Administration

Administration of the $\beta$-blocker may be by any number of routes including, but not limited to oral, intravenous, intramuscular, intra-arterial, intramedullary, intrathecal, intraventricular, intradermal, intratracheal, intravesicle, intraocular, transdermal, subcutaneous, intraperitoneal, intranasal, enteral, topical, sublingual, or rectal. Further details on techniques for formulation and administration may be found in the latest edition of Remington's Pharmaceutical Sciences (Maack Publishing Co., Easton, Pa.). In certain embodiments bucindolol is formulated for oral administration.

B. Formulations

Where clinical applications are contemplated, pharmaceutical compositions will be prepared in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector or cells, dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or cells of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal or intravenous injection, or by direct injection into cardiac tissue. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For oral administration the polypeptides of the present invention generally may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

1. Controlled/Extended/Sustained/Prolonged Release Administration

Another aspect of this invention provides methods of treating heart failure patients by delivering the β-blocker to a patient, having a homozygous β1Arg389 genotype, as a controlled release formulation. As used herein, the terms "controlled," "extended," "sustained," or "prolonged" release of the composition of the present invention will collectively be referred to herein as "controlled release," and includes continuous or discontinuous, and linear or non-linear release of the composition of the present invention. There are many advantages for a controlled release formulation of β-blockers.

a. Tablets

A controlled release tablet suitable for purposes of this invention is disclosed in U.S. Pat. No. 5,126,145, which is incorporated by reference herein. This tablet comprises, in admixture, about 5-30% high viscosity hydroxypropyl methyl cellulose, about 2-15% of a water-soluble pharmaceutical binder, about 2-20% of a hydrophobic component such as a waxy material, e.g., a fatty acid, and about 30-90% active ingredient.

b. Films

This invention further provides a prophylaxis for or method of treating a patient having a homozygous β1Arg389 genotype following an invasive cardiac procedure comprising administering biodegradable, biocompatible polymeric film comprising a β-blocker, such as bucindolol, to a patient. The polymeric films are thin compared to their length and breadth. The films typically have a uniform selected thickness between about 60 micrometers and about 5 mm. Films of between about 600 micrometers and 1 mm and between about 1 mm and about 5 mm thick, as well as films between about 60 micrometers and about 1000 micrometers, and between about 60 and about 300 micrometers are useful in the manufacture of therapeutic implants for insertion into a patient's body. The films can be administered to the patient in a manner similar to methods used in adhesion surgeries. For example, a β-blocker, such as bucindolol, film formulation can be sprayed or dropped onto a cardiac tissue site or artery during surgery, or a formed film can be placed over the selected tissue site. In an alternative embodiment, the film can be used as controlled release coating on a medical device such as a stent, as is discussed in further detail below.

Either biodegradable or nonbiodegradable polymers may be used to fabricate implants in which the β-blocker is uniformly distributed throughout the polymer matrix. A number of suitable biodegradable polymers for use in making the biodegradable films of this invention are known to the art, including polyanhydrides and aliphatic polyesters, preferably polylactic acid (PLA), polyglycolic acid (PGA) and mixtures and copolymers thereof, more preferably 50:50 copolymers of PLA:PGA and most preferably 75:25 copolymers of PLA:PGA. Single enantiomers of PLA may also be used, preferably L-PLA, either alone or in combination with PGA. Polycarbonates, polyfumarates and caprolactones may also be used to make the implants of this invention.

The amount of the β-blocker, such as bucindolol, to be incorporated into the polymeric films of this invention is an amount effective to show a measurable effect in treating diseases having similar pathophysiological states, such as but not limited to, heart failure, pheochromocytoma, migraines, cardiac arrhythmias, hypertension, aschemia, cardiomyopathy, and various anxiety disorders. The composition of the present invention can be incorporated into the film by various techniques such as by solution methods, suspension methods, or melt pressing.

c. Transdermal Patch Device

Transdermal delivery involves delivery of a therapeutic agent through the skin for distribution within the body by circulation of the blood. Transdermal delivery can be compared to continuous, controlled intravenous delivery of a drug using the skin as a port of entry instead of an intravenous needle. The therapeutic agent passes through the outer layers of the skin, diffuses into the capillaries or tiny blood vessels in the skin and then is transported into the main circulatory system.

Transdermal patch devices which provide a controlled, continuous administration of a therapeutic agent through the skin are well known in the art. Such devices, for example, are disclosed in U.S. Pat. Nos. 4,627,429; 4,784,857; 5,662,925; 5,788,983; and 6,113,940, which are all incorporated herein by reference. Characteristically, these devices contain a drug impermeable backing layer which defines the outer surface of the device and a permeable skin attaching membrane, such as an adhesive layer, sealed to the barrier layer in such a way as to create a reservoir between them in which the therapeutic agent is placed. In one embodiment of the present invention a formulation of the β-blocker is introduced into the reservoir of a transdermal patch and used by a patient who is homozygous Arg389 at the β1AR genes.

d. Medical Devices

Another embodiment contemplates the incorporation of a β-blocker, such as bucindolol, into a medical device that is then positioned to a desired target location within the body, whereupon the β-blocker elutes from the medical device. As used herein, "medical device" refers to a device that is introduced temporarily or permanently into a mammal for the prophylaxis or therapy of a medical condition. These devices include any that are introduced subcutaneously, percutaneously or surgically to rest within an organ, tissue or lumen. Medical devices include, but are not limited to, stents, synthetic grafts, artificial heart valves, artificial hearts and fixtures to connect the prosthetic organ to the vascular circulation, venous valves, abdominal aortic aneurysm (AAA) grafts, inferior venal caval filters, catheters including permanent drug infusion catheters, embolic coils, embolic materials used in vascular embolization (e.g., PVA foams), mesh repair materials, a Dracon vascular particle orthopedic metallic plates, rods and screws and vascular sutures.

In one embodiment, the medical device such as a stent or graft is coated with a matrix. The matrix used to coat the stent or graft according to this invention may be prepared from a variety of materials. A primary requirement for the matrix is that it be sufficiently elastic and flexible to remain unruptured on the exposed surfaces of the stent or synthetic graft.

C. Dosages

The amount of bucindolol that is administered or prescribed to the patient can be about, at least about, or at most about 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500 mg, or any range derivable therein. Alternatively, the amount administered or prescribed may be about, at least about, or at most about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0 mg/kg, or any range derivable therein, with respect to the weight of the patient.

When provided in a discrete amount, each intake of bucindolol can be considered a "dose." A medical practitioner may prescribe or administer multiple doses of bucindolol over a particular time course (treatment regimen) or indefinitely. It is contemplated that bucindolol Bucindolol may be administered 1, 2, 3, 4, 5, 6, 7, 8, 9, 10, 11, 12, 13, 14, 15, 16, 17, 18, 19, 20, 30, 40, 50, 60, 70, 80, or more times or any range derivable therein. It is further contemplated that the drug may be taken for an indefinite period of time or for as long as the patient exhibits symptoms of the medical condition for which bucindolol was prescribed or administered. Also, the drug may be administered every 2, 3, 4, 5, 6, 7, 8, 9, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months or more, or any range derivable therein. Alternatively, it may be administered systemically over any such period of time and be extended beyond more than a year.

D. Other Therapeutic Options

In certain embodiments of the invention, methods may involve administering a beta blocker that is not bucindolol or that is an ionotrope, a diuretic, ACE-I, AII antagonist, BNP, $Ca^{++}$-blocker, or an HDAC inhibitor. These agents may be prescribed or administered instead of or in addition to bucindolol after the $β_1$-AR and/or $α_{2c}$-AR polymorphisms are evaluated.

As a second therapeutic regimen, the agent may be administered or taken at the same time as bucindolol, or either before or after bucindolol. The treatment may improve one or more symptoms of pathologic cardiac hypertrophy or heart failure such as providing increased exercise capacity, increased cardiac ejection volume, decreased left ventricular end diastolic pressure, decreased pulmonary capillary wedge pressure, increased cardiac output or cardiac index, lowered pulmonary artery pressures, decreased left ventricular end systolic and diastolic dimensions, decreased left and right ventricular wall stress, decreased wall tension and wall thickness, increased quality of life, and decreased disease-related morbidity and mortality.

In another embodiment, it is envisioned to use bucindolol in combination with other therapeutic modalities. Thus, in addition to the therapies described above, one may also provide to the patient more "standard" pharmaceutical cardiac therapies. Examples of other therapies include, without limitation, other beta blockers, anti-hypertensives, cardiotonics, anti-thrombotics, vasodilators, hormone antagonists, iontropes, diuretics, endothelin antagonists, calcium channel blockers, phosphodiesterase inhibitors, ACE inhibitors, angiotensin type 2 antagonists and cytokine blockers/inhibitors, and HDAC inhibitors.

Combinations may be achieved by contacting cardiac cells with a single composition or pharmacological formulation that includes both agents, or by contacting the cell with two distinct compositions or formulations, at the same time, wherein one composition includes the expression construct and the other includes the agent. Alternatively, the therapy using bucindolol may precede or follow administration of the other agent(s) by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would typically contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either bucindolol, or the other agent will be desired. In this regard, various combinations may be employed. By way of illustration, where the bucindolol is "A" and the other agent is "B", the following permutations based on 3 and 4 total administrations are exemplary:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are likewise contemplated.

1. Pharmacological Therapeutic Agents

Pharmacological therapeutic agents and methods of administration, dosages, etc., are well known to those of skill in the art (see for example, the "Physicians Desk Reference", Klaassen's "The Pharmacological Basis of Therapeutics", "Remington's Pharmaceutical Sciences", and "The Merck Index, Eleventh Edition", incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

Non-limiting examples of a pharmacological therapeutic agent that may be used in the present invention include an antihyperlipoproteinemic agent, an antiarteriosclerotic agent, an antithrombotic/fibrinolytic agent, a blood coagulant, an antiarrhythmic agent, an antihypertensive agent, a vasopressor, a treatment agent for congestive heart failure, an antianginal agent, an antibacterial agent or a combination thereof.

In addition, it should be noted that any of the following may be used to develop new sets of cardiac therapy target genes as β-blockers were used in the present examples (see below). While it is expected that many of these genes may overlap, new gene targets likely can be developed.

a. Antihyperlipoproteinemics

In certain embodiments, administration of an agent that lowers the concentration of one of more blood lipids and/or lipoproteins, known herein as an "antihyperlipoproteinemic," may be combined with a cardiovascular therapy according to the present invention, particularly in treatment of athersclerosis and thickenings or blockages of vascular tissues. In certain aspects, an antihyperlipoproteinemic agent may comprise an aryloxyalkanoic/fibric acid derivative, a resin/bile acid sequesterant, a HMG CoA reductase inhibitor, a nicotinic acid derivative, a thyroid hormone or thyroid hormone analog, a miscellaneous agent or a combination thereof i. Aryloxyalkanoic Acid/Fibric Acid Derivatives Non-limiting examples of aryloxyalkanoic/fibric acid derivatives include beclobrate, enzafibrate, binifibrate, ciprofibrate, clinofibrate, clofibrate (atromide-S), clofibric acid, etofibrate, fenofibrate, gemfibrozil (lobid), nicofibrate, pirifibrate, ronifibrate, simfibrate and theofibrate.

ii. Resins/Bile Acid Sequesterants

Non-limiting examples of resins/bile acid sequesterants include cholestyramine (cholybar, questran), colestipol (colestid) and polidexide.

iii. HMG CoA Reductase Inhibitors

Non-limiting examples of HMG CoA reductase inhibitors include lovastatin (mevacor), pravastatin (pravochol) or simvastatin (zocor).

iv. Nicotinic Acid Derivatives

Non-limiting examples of nicotinic acid derivatives include nicotinate, acepimox, niceritrol, nicoclonate, nicomol and oxiniacic acid.

v. Thyroid Hormones and Analogs

Non-limiting examples of thyroid hormones and analogs thereof include etoroxate, thyropropic acid and thyroxine.

vi. Miscellaneous Antihyperlipoproteinemics

Non-limiting examples of miscellaneous antihyperlipoproteinemics include acifran, azacosterol, benfluorex, β-benzalbutyramide, carnitine, chondroitin sulfate, clomestrone, detaxtran, dextran sulfate sodium, 5,8, 11, 14, 17-eicosapentaenoic acid, eritadenine, furazabol, meglutol, melinamide, mytatrienediol, ornithine, γ-oryzanol, pantethine, pentaerythritol tetraacetate, α-phenylbutyramide, pirozadil, probucol (lorelco), β-sitosterol, sultosilic acid-piperazine salt, tiadenol, triparanol and xenbucin.

b. Antiarteriosclerotics

Non-limiting examples of an antiarteriosclerotic include pyridinol carbamate.

c. Antithrombotic/Fibrinolytic Agents

In certain embodiments, administration of an agent that aids in the removal or prevention of blood clots may be combined with administration of a modulator, particularly in treatment of atherscleosis and vasculature (e.g., arterial) blockages. Non-limiting examples of antithrombotic and/or fibrinolytic agents include anticoagulants, anticoagulant antagonists, antiplatelet agents, thrombolytic agents, thrombolytic agent antagonists or combinations thereof.

In certain aspects, antithrombotic agents that can be administered orally, such as, for example, aspirin and wafarin (coumadin), are preferred.

i. Anticoagulants

A non-limiting example of an anticoagulant include acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin.

ii. Antiplatelet Agents

Non-limiting examples of antiplatelet agents include aspirin, a dextran, dipyridamole (persantin), heparin, sulfinpyranone (anturane) and ticlopidine (ticlid).

iii. Thrombolytic Agents

Non-limiting examples of thrombolytic agents include tissue plaminogen activator (activase), plasmin, pro-urokinase, urokinase (abbokinase) streptokinase (streptase), anistreplase/APSAC (eminase).

d. Blood Coagulants

In certain embodiments wherein a patient is suffering from a hemmorage or an increased likelihood of hemmoraging, an agent that may enhance blood coagulation may be used. Non-limiting examples of a blood coagulation promoting agent include thrombolytic agent antagonists and anticoagulant antagonists.

i. Anticoagulant Antagonists

Non-limiting examples of anticoagulant antagonists include protamine and vitamine K1.

ii. Thrombolytic Agent Antagonists and Antithrombotics

Non-limiting examples of thrombolytic agent antagonists include amiocaproic acid (amicar) and tranexamic acid (amstat). Non-limiting examples of antithrombotics include anagrelide, argatroban, cilstazol, daltroban, defibrotide, enoxaparin, fraxiparine, indobufen, lamoparan, ozagrel, picotamide, plafibride, tedelparin, ticlopidine and triflusal.

e. Antiarrhythmic Agents

Non-limiting examples of antiarrhythmic agents include Class I antiarrythmic agents (sodium channel blockers), Class II antiarrythmic agents (beta-adrenergic blockers), Class II antiarrythmic agents (repolarization prolonging drugs), Class IV antiarrhythmic agents (calcium channel blockers) and miscellaneous antiarrythmic agents.

i. Sodium Channel Blockers

Non-limiting examples of sodium channel blockers include Class IA, Class IB and Class IC antiarrhythmic agents. Non-limiting examples of Class IA antiarrhythmic agents include disppyramide (norpace), procainamide (pronestyl) and quinidine (quinidex). Non-limiting examples of Class IB antiarrhythmic agents include lidocaine (xylocalne), tocamide (tonocard) and mexiletine (mexitil). Non-limiting examples of Class IC antiarrhythmic agents include encamide (enkaid) and flecamide (tambocor).

ii. Beta Blockers

Non-limiting examples of a beta blocker, otherwise known as a β-adrenergic blocker, a β-adrenergic antagonist or a Class II antiarrhythmic agent, include acebutolol (sectral), alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol (brevibloc), indenolol, labetalol, levobunolol, mepindolol, metipranolol, metoprolol, moprolol, nadolol, nadoxolol, nifenalol, nipradilol, oxprenolol, penbutolol, pindolol, practolol, pronethalol, propanolol (inderal), sotalol (betapace), sulfinalol, talinolol, tertatolol, timolol, toliprolol and xibinolol. In certain aspects, the beta blocker comprises an aryloxypropanolamine derivative. Non-limiting examples of aryloxypropanolamine derivatives include acebutolol, alprenolol, arotinolol, atenolol, betaxolol, bevantolol, bisoprolol, bopindolol, bunitrolol, butofilolol, carazolol, carteolol, carvedilol, celiprolol, cetamolol, epanolol, indenolol, mepindolol, metipranolol, metoprolol, moprolol, nadolol, nipradilol, oxprenolol, penbutolol, pindolol, propanolol, talinolol, tertatolol, timolol and toliprolol.

iii. Repolarization Prolonging Agents

Non-limiting examples of an agent that prolong repolarization, also known as a Class III antiarrhythmic agent, include amiodarone (cordarone) and sotalol (betapace).

iv. Calcium Channel Blockers/Antagonist

Non-limiting examples of a calcium channel blocker, otherwise known as a Class IV antiarrythmic agent, include an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazinde derivative (e.g., cinnarizine, flunarizine, lidoflazine) or a micellaneous calcium channel blocker such as bencyclane, etafenone, magnesium, mibefradil or perhexyline. In certain embodiments a calcium channel blocker comprises a long-acting dihydropyridine (nifedipine-type) calcium antagonist.

v. Miscellaneous Antiarrhythmic Agents

Non-limiting examples of miscellaneous antiarrhymic agents include adenosine (adenocard), digoxin (lanoxin), acecamide, ajmaline, amoproxan, aprindine, bretylium tosylate, bunaftine, butobendine, capobenic acid, cifenline, disopyranide, hydroquinidine, indecamide, ipatropium bromide, lidocaine, lorajmine, lorcamide, meobentine, moricizine, pirmenol, prajmaline, propafenone, pyrinoline, quinidine polygalacturonate, quinidine sulfate and viquidil.

f. Antihypertensive Agents

Non-limiting examples of antihypertensive agents include sympatholytic, alpha/beta blockers, alpha blockers, anti-angiotensin II agents, beta blockers, calcium channel blockers, vasodilators and miscellaneous antihypertensives.

i. Alpha Blockers

Non-limiting examples of an alpha blocker, also known as an α-adrenergic blocker or an α-adrenergic antagonist, include amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an alpha blocker may comprise a quinazoline derivative. Non-limiting examples of quinazoline derivatives include alfuzosin, bunazosin, doxazosin, prazosin, terazosin and trimazosin.

ii. Alpha/Beta Blockers

In certain embodiments, an antihypertensive agent is both an alpha and beta adrenergic antagonist. Non-limiting examples of an alpha/beta blocker comprise labetalol (normodyne, trandate).

iii. Anti-Angiotension II Agents

Non-limiting examples of anti-angiotension II agents include include angiotensin converting enzyme inhibitors and angiotension II receptor antagonists. Non-limiting examples of angiotension converting enzyme inhibitors (ACE inhibitors) include alacepril, enalapril (vasotec), captopril, cilazapril, delapril, enalaprilat, fosinopril, lisinopril, moveltopril, perindopril, quinapril and ramipril. Non-limiting examples of an angiotensin II receptor blocker, also known as an angiotension II receptor antagonist, an ANG receptor blocker or an ANG-II type-1 receptor blocker (ARBS), include angiocandesartan, eprosartan, irbesartan, losartan and valsartan.

iv. Sympatholytics

Non-limiting examples of a sympatholytic include a centrally acting sympatholytic or a peripherially acting sympatholytic. Non-limiting examples of a centrally acting sympatholytic, also known as an central nervous system (CNS) sympatholytic, include clonidine (catapres), guanabenz (wytensin) guanfacine (tenex) and methyldopa (aldomet). Non-limiting examples of a peripherally acting sympatholytic include a ganglion blocking agent, an adrenergic neuron blocking agent, a β-adrenergic blocking agent or a alpha1-adrenergic blocking agent. Non-limiting examples of a ganglion blocking agent include mecamylamine (inversine) and trimethaphan (arfonad). Non-limiting of an adrenergic neuron blocking agent include guanethidine (ismelin) and reserpine (serpasil). Non-limiting examples of a β-adrenergic blocker include acenitolol (sectral), atenolol (tenormin), betaxolol (kerlone), carteolol (cartrol), labetalol (normodyne, trandate), metoprolol (lopressor), nadanol (corgard), penbutolol (levatol), pindolol (visken), propranolol (inderal) and timolol (blocadren). Non-limiting examples of alpha1-adrenergic blocker include prazosin (minipress), doxazocin (cardura) and terazosin (hytrin).

v. Vasodilators

In certain embodiments a cardiovasculator therapeutic agent may comprise a vasodilator (e.g., a cerebral vasodilator, a coronary vasodilator or a peripheral vasodilator). In certain preferred embodiments, a vasodilator comprises a coronary vasodilator. Non-limiting examples of a coronary vasodilator include amotriphene, bendazol, benfurodil hemisuccinate, benziodarone, chloracizine, chromonar, clobenfurol, clonitrate, dilazep, dipyridamole, droprenilamine, efloxate, erythrityl tetranitrane, etafenone, fendiline, floredil, ganglefene, herestrol bis(β-diethylaminoethyl ether), hexobendine, itramin tosylate, khellin, lidoflanine, mannitol hexanitrane, medibazine, nicorglycerin, pentaerythritol tetranitrate, pentrinitrol, perhexyline, pimethylline, trapidil, tricromyl, trimetazidine, trolnitrate phosphate and visnadine.

In certain aspects, a vasodilator may comprise a chronic therapy vasodilator or a hypertensive emergency vasodilator. Non-limiting examples of a chronic therapy vasodilator include hydralazine (apresoline) and minoxidil (loniten). Non-limiting examples of a hypertensive emergency vasodilator include nitroprusside (nipride), diazoxide (hyperstat IV), hydralazine (apresoline), minoxidil (loniten) and verapamil.

vi. Miscellaneous Antihypertensives

Non-limiting examples of miscellaneous antihypertensives include ajmaline, γ-aminobutyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzolimine, pargyline, pempidine, pinacidil, piperoxan, primaperone, a protoveratrine, raubasine, rescimetol, rilmenidene, saralasin, sodium nitrorusside, ticrynafen, trimethaphan camsylate, tyrosinase and urapidil.

In certain aspects, an antihypertensive may comprise an arylethanolamine derivative, a benzothiadiazine derivative, a N-carboxyalkyl(peptide/lactam) derivative, a dihydropyridine derivative, a guanidine derivative, a hydrazines/phthalazine, an imidazole derivative, a quanternary ammonium compound, a reserpine derivative or a suflonamide derivative.

Arylethanolamine Derivatives. Non-limiting examples of arylethanolamine derivatives include amosulalol, bufuralol, dilevalol, labetalol, pronethalol, sotalol and sulfinalol.

Benzothiadiazine Derivatives. Non-limiting examples of benzothiadiazine derivatives include althizide, bendroflumethiazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothizide, hydroflumethizide, methyclothiazide, meticrane, metolazone, paraflutizide, polythizide, tetrachlormethiazide and trichlormethiazide.

N-carboxyalkyl(peptide/lactam) Derivatives. Non-limiting examples of N-carboxyalkyl(peptide/lactam) derivatives include alacepril, captopril, cilazapril, delapril, enalapril, enalaprilat, fosinopril, lisinopril, moveltipril, perindopril, quinapril and ramipril.

Dihydropyridine Derivatives. Non-limiting examples of dihydropyridine derivatives include amlodipine, felodipine, isradipine, nicardipine, nifedipine, nilvadipine, nisoldipine and nitrendipine.

Guanidine Derivatives. Non-limiting examples of guanidine derivatives include bethanidine, debrisoquin, guanabenz, guanacline, guanadrel, guanazodine, guanethidine, guanfacine, guanochlor, guanoxabenz and guanoxan.

Hydrazines/Phthalazines. Non-limiting examples of hydrazines/phthalazines include budralazine, cadralazine, dihydralazine, endralazine, hydracarbazine, hydralazine, pheniprazine, pildralazine and todralazine.

Imidazole Derivatives. Non-limiting examples of imidazole derivatives include clonidine, lofexidine, phentolamine, tiamenidine and tolonidine.

Quanternary Ammonium Compounds. Non-limiting examples of quanternary ammonium compounds include azamethonium bromide, chlorisondamine chloride, hexamethonium, pentacynium bis(methylsulfate), pentamethonium bromide, pentolinium tartrate, phenactropinium chloride and trimethidinium methosulfate.

Reserpine Derivatives. Non-limiting examples of reserpine derivatives include bietaserpine, deserpidine, rescinnamine, reserpine and syrosingopine.

Suflonamide Derivatives. Non-limiting examples of sulfonamide derivatives include ambuside, clopamide, furosemide, indapamide, quinethazone, tripamide and xipamide.

vii. Vasopressors

Vasopressors generally are used to increase blood pressure during shock, which may occur during a surgical procedure. Non-limiting examples of a vasopressor, also known as an antihypotensive, include amezinium methyl sulfate, angiotensin amide, dimetofrine, dopamine, etifelmin, etilefrin, gepefrine, metaraminol, midodrine, norepinephrine, pholedrine and synephrine.

g. Treatment Agents for Congestive Heart Failure

Non-limiting examples of agents for the treatment of congestive heart failure include anti-angiotension II agents, afterload-preload reduction treatment, diuretics and inotropic agents.

i. Afterload-Preload Reduction

In certain embodiments, an animal patient that can not tolerate an angiotension antagonist may be treated with a combination therapy. Such therapy may combine administration of hydralazine (apresoline) and isosorbide dinitrate (isordil, sorbitrate).

ii. Diuretics

Non-limiting examples of a diuretic include a thiazide or benzothiadiazine derivative (e.g., althiazide, bendroflumethazide, benzthiazide, benzylhydrochlorothiazide, buthiazide, chlorothiazide, chlorothiazide, chlorthalidone, cyclopenthiazide, epithiazide, ethiazide, ethiazide, fenquizone, hydrochlorothiazide, hydroflumethiazide, methyclothiazide, meticrane, metolazone, paraflutizide, polythizide, tetrachloromethiazide, trichlormethiazide), an organomercurial (e.g., chlonnerodrin, meralluride, mercamphamide, mercaptomerin sodium, mercumallylic acid, mercumatilin dodium, mercurous chloride, mersalyl), a pteridine (e.g., furtherene, triamterene), purines (e.g., acefylline, 7-morpholinomethyltheophylline, pamobrom, protheobromine, theobromine), steroids including aldosterone antagonists (e.g., canrenone, oleandrin, spironolactone), a sulfonamide derivative (e.g., acetazolamide, ambuside, azosemide, bumetanide, butazolamide, chloraminophenamide, clofenamide, clopamide, clorexolone, diphenylmethane-4,4'-disulfonamide, disulfamide, ethoxzolamide, furosemide, indapamide, mefruside, methazolamide, piretanide, quinethazone, torasemide, tripamide, xipamide), a uracil (e.g., aminometradine, amisometradine), a potassium sparing antagonist (e.g., amiloride, triamterene) or a miscellaneous diuretic such as aminozine, arbutin, chlorazanil, ethacrynic acid, etozolin, hydracarbazine, isosorbide, mannitol, metochalcone, muzolimine, perhexyline, ticrnafen and urea.

iii. Inotropic Agents

Non-limiting examples of a positive inotropic agent, also known as a cardiotonic, include acefylline, an acetyldigitoxin, 2-amino-4-picoline, aminone, benfurodil hemisuccinate, bucladesine, cerberosine, camphotamide, convallatoxin, cymarin, denopamine, deslanoside, digitalin, digitalis, digitoxin, digoxin, dobutamine, dopamine, dopexamine, enoximone, erythrophleine, fenalcomine, gitalin, gitoxin, glycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strphanthin, sulmazole, theobromine and xamoterol.

In particular aspects, an intropic agent is a cardiac glycoside, a beta-adrenergic agonist or a phosphodiesterase inhibitor. Non-limiting examples of a cardiac glycoside includes digoxin (lanoxin) and digitoxin (crystodigin). Non-limiting examples of a β-adrenergic agonist include albuterol, bambuterol, bitolterol, carbuterol, clenbuterol, clorprenaline, denopamine, dioxethedrine, dobutamine (dobutrex), dopamine (intropin), dopexamine, ephedrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. Non-limiting examples of a phosphodiesterase inhibitor include aminone (inocor).

iv. Antianginal Agents

Antianginal agents may comprise organonitrates, calcium channel blockers, beta blockers and combinations thereof.

Non-limiting examples of organonitrates, also known as nitrovasodilators, include nitroglycerin (nitro-bid, nitrostat), isosorbide dinitrate (isordil, sorbitrate) and amyl nitrate (aspirol, vaporole).

2. Surgical Therapeutic Agents

In certain aspects, the secondary therapeutic agent may comprise a surgery of some type, which includes, for example, preventative, diagnostic or staging, curative and palliative surgery. Surgery, and in particular a curative surgery, may be used in conjunction with other therapies, such as the present invention and one or more other agents.

Such surgical therapeutic agents for vascular and cardiovascular diseases and disorders are well known to those of skill in the art, and may comprise, but are not limited to, performing surgery on an organism, providing a cardiovascular mechanical prostheses, angioplasty, coronary artery reperfusion, catheter ablation, providing an implantable cardioverter defibrillator to the subject, mechanical circulatory support or a combination thereof. Non-limiting examples of a mechanical circulatory support that may be used in the present invention comprise an intra-aortic balloon counterpulsation, left ventricular assist device or combination thereof.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Transfected Cells

A. Methods

Chinese hamster fibroblasts (CHW cells) were stably transfected with the human Arg389 and Gly389 cDNAs as previously described (Mason et al., 1999). Lines with equivalent levels of expression as determined by radioligand binding were studied to ascertain the antagonist effect of bucindolol on norepinephrine stimulated cAMP accumulation. Cells in monolayers were treated with 10 μM norepinephrine in the absence and presence of various concentrations of bucindolol for 20 min at 37° C. and [$^3$H]cAMP isolated by column chromatography (Salomon, 1991).

B. Results: Response to Bucindolol in Transfected Cells

Expression levels in CHW cells of the receptors for the functional antagonism studies were 123±19 and 137±16 fmol/mg for Arg389 and Gly389 cell lines, respectively. Cells were exposed to 10 μM of the agonist norepinephrine, in the absence or presence of varying concentrations of bucindolol, and cAMP levels determined. As shown in FIG. 3, Arg389 displayed a greater cAMP stimulation to norepinephrine in the absence of bucindolol compared to Gly389, which represents the primary phenotypes of the two receptors (Mason et al., 1999). Despite the substantially greater degree of norepinephrine-mediated stimulation of the Arg389 receptor, bucindolol effectively antagonized the response. The difference in the absolute decrease in cAMP production afforded by bucindolol was greater for cells expressing β1-Arg389: bucindolol caused a maximal decrease of 435±80 fmol/ml cAMP in Arg389 cells compared to 115±23 fmol/ml cAMP in Gly389 cells (P<0.008, N=4). The potency of bucindolol was not found to be different for the response (ED50=46±4.5 and 35±11 nM, respectively, P=0.94, N=4). In additional experiments bucindolol alone at concentrations up to 10 μM caused no stimulation of cAMP in cells expressing either receptor variant (data not shown). These results thus indicated that the Arg389 receptor may provide for a greater clinical response to bucindolol in heart failure treatment.

Example 2

Response to β-Blockade in Transgenic Mice

Using the α-myosin heavy chain promoter, transgenic mice with targeted ventricular expression of the human β1AR (Arg389 or Gly389 forms) were utilized to ascertain allele-specific responses to chronic administration of the β-blocker propranolol. Expression levels of the two receptors were equivalent. The generation of these mice and their partial characterization has recently been reported in detail elsewhere (Perez et al., 2003). For the current studies, 3-month-old mice of both genotypes, as well as nontransgenic mice, were treated with propranolol (0.5 mg/ml) in their drinking water, or water without propranolol (control) continuously for 6 months. Hearts were then removed and ventricular protein extracts prepared. These were subjected to Western blotting to ascertain expression of the following proteins using methods previously described (Perez et al., 2003): Gαs, Gαi2, G-protein coupled receptor kinase-2 (GRK2), adenylyl cyclase type 5 (AC5), total phospholamban (T-PLN), phosphorylated phospholamban (P-PLN) and sarcoplasmic endoplasmic reticulum calcium ATPase-2A (SERCA). Treatment effect was assessed by comparing expression of the proteins of untreated and propranolol treated mice, within genotype, by ANOVA. The study was approved by the University of Cincinnati Animal Use and Care Committee.

Figure 4:
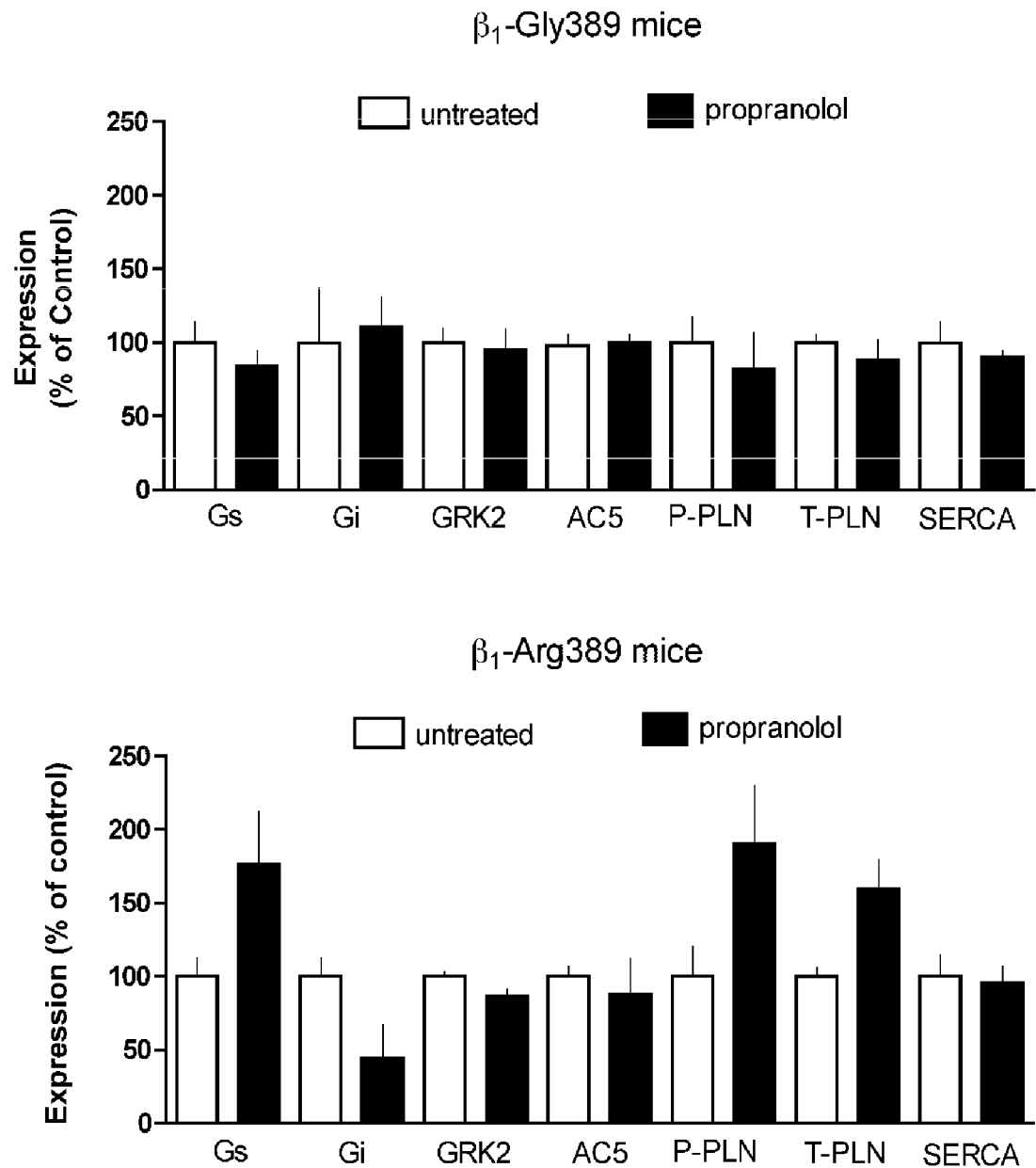
FIG. 4. Bar graph illustrates a response to β-blockade in transgenic mice with targeted overexpression of Gly389 and Arg389 $\beta_1AR$ to the heart. Shown are mean (±SE) results from Western blots for the indicated proteins from hearts of $\beta_1$-Arg389 and $\beta_1$-Gly389 mice (n=3-4 in each group). Data are normalized to the control (untreated) values. An overall treatment response to propranolol was found only in hearts from the $\beta_1$-Arg389 mice (P<0.002 by ANOVA).

As recently reported (Perez et al., 2003), transgenic mice with targeted expression of β1-Gly389 or β1-Arg389 to the heart exhibit multiple alterations over time (observed as early as 6-months of age), in the expression of certain cardiac signaling and Ca++ handling proteins. To assess the potential for a genotype-specific response to long-term β-blockade, 3 month-old mice expressing each β1AR genotype were treated with placebo or the β-blocker propranolol for six months, the ventricles removed and protein extracts prepared. Western blots were utilized to quantitate expression of the indicated proteins, comparing the changes in expression by treatment within β1AR genotype groups. As shown in FIG. 4, propranolol treatment had no effect (P=0.67) on expression of the indicated proteins in hearts from Gly389 mice. In contrast, an overall treatment response (either increases or decreases in expression) was observed with propranolol treatment in hearts from Arg389 mice (P<0.002). The directions of these trends induced by β-blockade, which included increases in Gαs, P-PLN and T-PLN, and decreases in Gαi and GRK2, are all considered restorative biochemical responses in the context of the hypertrophied/failing heart (Liggett, 2001). Taken together, then, the protein expression profiles associated with chronic β-blockade in this transgenic mouse model suggest that a more favorable response to the β-blocker bucindolol might be expected in β1-Arg389 heart failure patients compared to those with the β1-Gly389 genotype.

Example 3

Bucindolol Vs. Placebo Clinical Study

A. Materials and Methods

1. Patient Population

Patients who participated in the Beta Blocker Evaluation of Survival Trial (BEST), (Lowes et al., 2002) and who consented for DNA substudies, were genotyped at the coding β1AR polymorphic sites. Enrollment in BEST was from May 31, 1995 to Dec. 31, 1998; the study design has been described in detail elsewhere (BEST Trial Investigators, 2001; and Lowes et al., 2002). Briefly, the study was a randomized, multicenter, placebo-controlled trial of the 3rd generation, nonselective β-blocker-vasodilator bucindolol (Bristow, 2000) in 2708 patients with Class III/IV heart failure (BEST Trial Investigators, 2001). Those receiving the active drug were administered 3 mg bucindolol twice daily for the first week, and up-titrated as tolerated on a weekly basis to 50 mg twice daily (or 100 mg twice daily for patients weighing >75 kg). Of the 2708 patients, 1040 consented for the substudy and had adequate DNA prepared from a blood sample. The study was approved by the BEST DNA Oversight Committee and the University of Cincinnati Institutional Review Board.

2. Genotyping

DNA was extracted from whole blood using standard techniques (Jones, 1963). Genotyping was performed using methods exactly as previously described in detail (Small et al., 2002). For the β1AR, variations at coding nucleotides 145 and 1165 were delineated, which correspond to amino acids 49 and 389. These alleles are designated as β1-Ser49, 131-Gly49 and β1-Arg389, β1-Gly389. All the DNA samples were successfully genotyped at the β1AR-389 locus and 1030 were successfully genotyped at β1AR-49.

3. Statistical Analysis

The primary endpoints were all-cause mortality, hospitalizations adjudicated by an endpoints committee (BEST Trial Investigators, 2001) to be due to heart failure, and the combined endpoint of death or heart failure hospitalization. The variants at amino acid position 389 of the β1AR (Arg and Gly) were considered the primary genotypes hypothesized to influence β-blocker efficacy. Continuous clinical variables are reported as mean±SD, and comparisons were by t-test or Wilcoxon rank-sum tests. Categorical variables are reported as proportions and comparisons were by chi-square or Fisher's exact tests. Cumulative survival curves were constructed by Kaplan-Meier methods (Kaplan et al., 1958); and SAS (r) proprietary software, release 6.12. Cary, N. C.: SAS Institute, 1996). The Cox proportional-hazards regression model was used to examine the effects of treatment stratified by the indicated genotype. Results were adjusted for age, sex, race, and, as indicated, the β1-Gly49 polymorphism. Because of the limited number of comparisons, and an a priori hypothesis that was based on cell, transgenic, and other human studies (Kaplan et al., 1958); and SAS (r) proprietary software, release 6.12. Cary, N. C.: SAS Institute, 1996; Perez et al., 2003); and Wagoner et al., 2002), the P values <0.05 were considered to as significant, without adjustments for multiple comparisons.

B. Results

The results from the transfected cells and transgenic mice prompted genotyping patients from BEST, a trial of the β3-blocker bucindolol in the treatment of Class III-IV heart failure which included a placebo arm (BEST Trial Investigators, 2001). Most demographic and baseline clinical characteristics were not statistically different between those who participated in the DNA substudy compared to those who did not. Of particular note, age, sex, NYHA class and heart failure etiology were not different. Minor and clinically insignificant differences between DNA substudy participants vs non-participants were noted in baseline heart rates (−1.3 bpm), systolic blood pressures (+1.7 mmHg), weight (+1.9 kg), LVEF (+0.9%) and percentage of non-whites (−5%). The overall allele frequency of Arg389 was 67%, which is similar to the reported allele frequency of this polymorphism in the general population (Mason et al., 1999) and in heart failure cohorts (Smal et al., 2002).

The characteristics of the patients grouped by the primary hypothesis genotypes (β1AR-389) and treatment, are provided in Table 2. There were no differences in age, sex, race, heart failure etiology, NYHA class, or baseline LVEF between groups stratified by placebo, bucindolol treatment, or genotype. As can be seen, the number of homozygous Gly389 individuals was relatively small (52 placebo, 42 bucindolol). Therefore, Arg homozygotes were compared to Gly carriers (those having either one or two Gly alleles). The four cohorts, grouped by treatment and genotype, then, each consisted of >200 subjects (Table 2).

TABLE 2

| | Placebo Group N = 525 | | | | Bucindolol Group N = 515 | | | |
|---|---|---|---|---|---|---|---|---|
| | Arg homozygous N = 236 | Arg/Gly heterozygous N = 237 | Gly homozygous N = 52 | Gly carriers N = 289 | Arg homozygous N = 257 | Arg/Gly heterozygous N = 216 | Gly homozygous N = 42 | Gly carriers N = 258 |
| Age - mean (std) | 60.5 (11.8) | 60.3 (12.4) | 59.6 (13.2) | 60.2 (12.5) | 59.8 (11.8) | 61.6 (12.0) | 56.6 (14.2) | 60.8 (12.5) |
| Sex - N (%) | | | | | | | | |
| Male | 187 (79%) | 183 (77%) | 42 (81%) | 225 (78%) | 206 (80%) | 173 (80%) | 34 (81%) | 207 (80%) |
| Female | 49 (21%) | 54 (23%) | 10 (19%) | 64 (22%) | 51 (20%) | 43 (20%) | 8 (19%) | 51 (20%) |
| Race - N (%) | | | | | | | | |
| Non-black | 212 (90%) | 182 (77%) | 33 (63%) | 215 (74%) | 215 (84%) | 165 (76%) | 26 (62%) | 191 (74%) |
| Black | 24 (10%) | 55 (23%) | 19 (37%) | 74 (26%) | 42 (16%) | 51 (24%) | 16 (38%) | 67 (26%) |

TABLE 2-continued

| | Placebo Group N = 525 | | | | Bucindolol Group N = 515 | | | |
|---|---|---|---|---|---|---|---|---|
| | Arg homozygous N = 236 | Arg/Gly heterozygous N = 237 | Gly homozygous N = 52 | Gly carriers N = 289 | Arg homozygous N = 257 | Arg/Gly heterozygous N = 216 | Gly homozygous N = 42 | Gly carriers N = 258 |
| Etiology - N (%) | | | | | | | | |
| Ischemic | 145 (61%) | 137 (58%) | 34 (65%) | 171 (59%) | 138 (54%) | 129 (60%) | 23 (55%) | 152 (59%) |
| Non-ischemic | 91 (39%) | 100 (42%) | 18 (35%) | 118 (41%) | 119 (46%) | 87 (40%) | 19 (45%) | 106 (41%) |
| NYHA Functional Class - N (%) | | | | | | | | |
| III | 223 (94%) | 217 (92%) | 48 (92%) | 265 (92%) | 242 (94%) | 194 (90%) | 36 (86%) | 230 (89%) |
| IV | 13 (6%) | 20 (8%) | 4 (8%) | 24 (8%) | 15 (6%) | 22 (10%) | 6 (14%) | 28 (11%) |
| LVEF % - mean (std) | 23.3 (7.0) | 24.2 (7.1) | 23.6 (6.8) | 24.1 (7.0) | 23.4 (7.2) | 23.7 (7.1) | 22.6 (6.9) | 23.5 (7.1) |

Baseline Characteristics of patients in BEST stratified by treatment and genotype. Data are mean ± SD.

Figure 5:
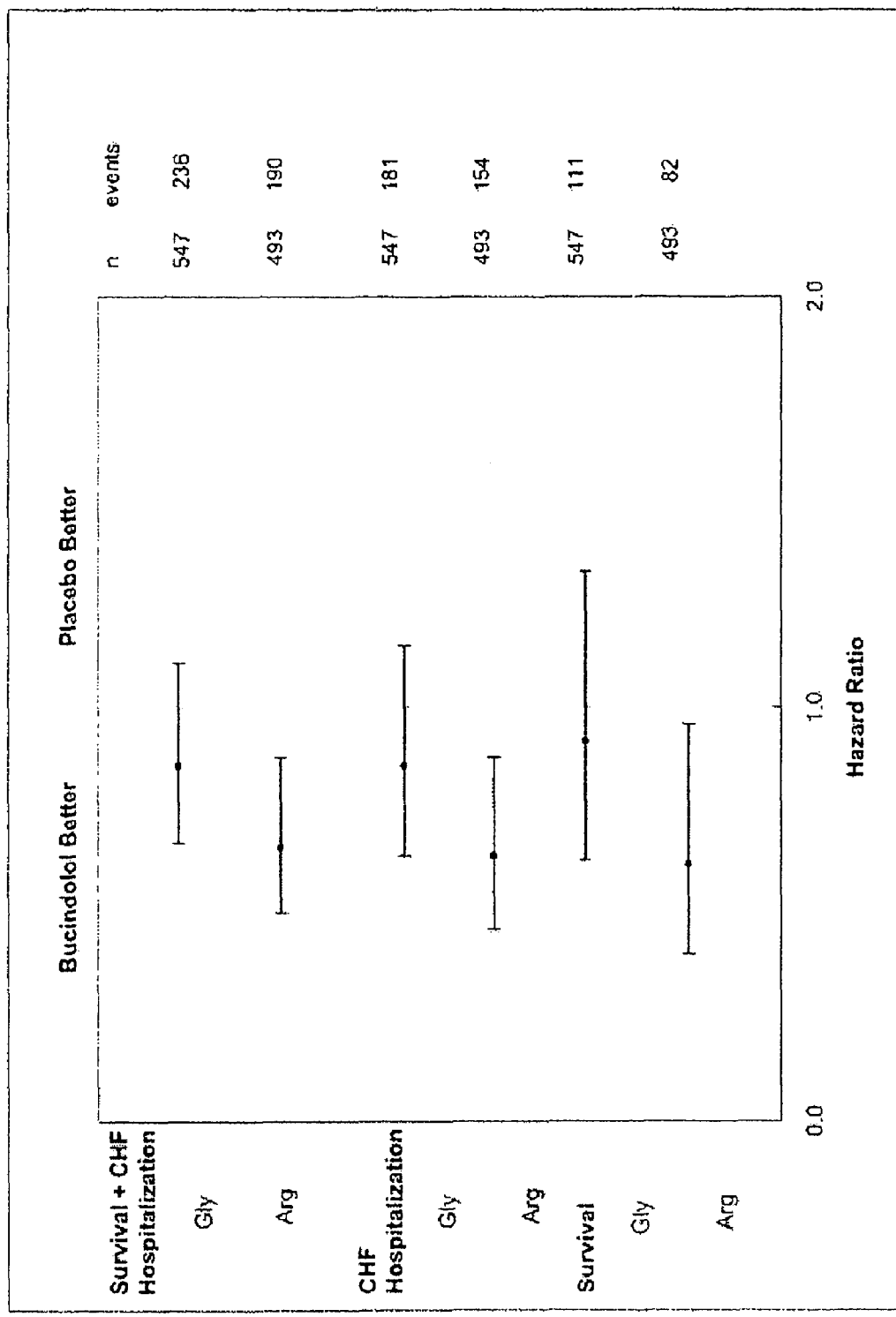
FIG. 5. This illustrates the hazard ratios and 95% confidence intervals for heart failure outcomes stratified by $\beta_1AR$ genotype.
Figure 6:
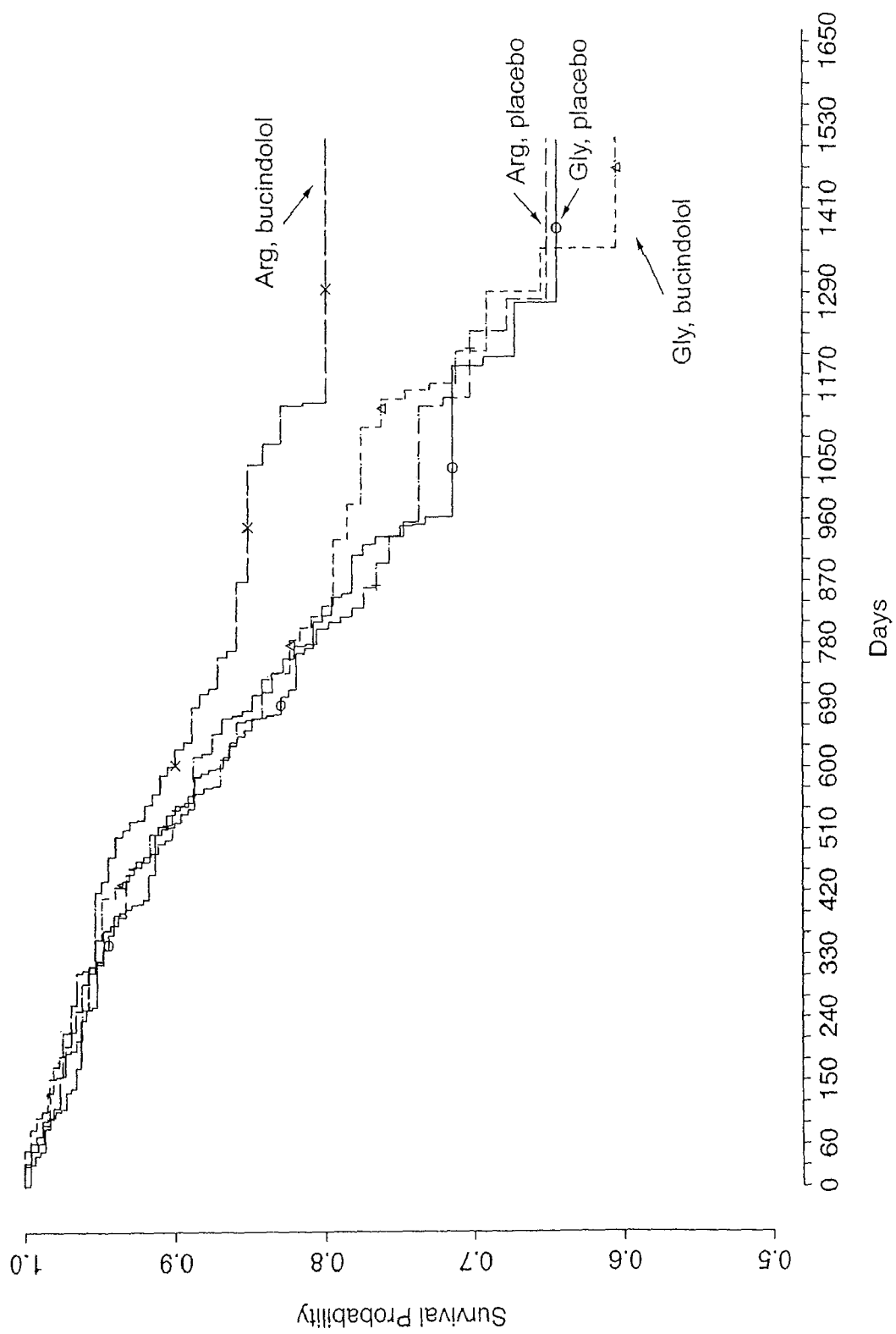
FIG. 6. This graph illustrates the survival of patients in the bucindolol-placebo study stratified by treatment and $\beta_1AR$ genotype.

Survival of placebo and bucindolol treated patients stratified by β1AR-389 genotype is shown in FIGS. 5 and 6. Individual comparisons adjusted for age, sex, and race revealed that homozygous Arg389 bucindolol-treated patients had increased survival compared to Arg389 placebo-treated patients (hazard ratio=0.62, 95% CI=0.40 to 0.96, P=0.03). Thus, the improvement in survival due to bucindolol in the Arg389 patients amounted to 38% over placebo. This same comparison in Gly carriers revealed no difference in survival curves (hazard ratio=0.90, 95% CI=0.62 to 1.30, P=0.57), indicative of no treatment response to bucindolol. There was also an apparent influence of β1AR genotype on the heart failure hospitalization response to bucindolol (FIG. 5). A decrease in hospitalizations with bucindolol treatment in homozygous Arg389 patients was observed compared to placebo patients with the same genotype (hazard ratio=0.64, 95% CI=0.46-0.88, P=0.006). Gly389 carriers showed no benefit of the drug compared to placebo in terms of hospitalizations (hazard ratio=0.86, 95% CI=0.64 to 1.15, P=0.298). For the combined outcome of heart failure hospitalizations or death, a bucindolol-associated favorable treatment effect (FIGS. 5 and 7) was evident for Arg389 patients compared to placebo (hazard ratio=0.66, 95% CI=0.50 to 0.88, P=0.004), but was not apparent in bucindolol-treated Gly389 carriers vs placebo (hazard ratio=0.87, 95% CI=0.67 to 1.11, P=0.250). Adjustments for the position 49 variants ([3]-Ser49, β1-Gly49) had no significant effect on any of the above results. With such adjustment (including age, sex and race) the hazard ratio for survival for β1-Arg389 homozygotes was 0.62, 95% CI=0.40 to 0.97, P=0.035; for β1-Gly389 carriers there remained no apparent treatment effect (hazard ratio=0.89, 95% CI=0.61 to 1.30, P=0.56). Similarly, adjustment for position 49 had no appreciable effect on the hazard ratios for hospitalizations: for Arg389 homozygotes the hazard ratio=0.63, 95% CI=0.45 to 0.86, P=0.007; for Gly389 carriers the hazard ratio=0.85, 95% CI=0.63 to 1.14, P=0.54. The results for the combined outcome of death and hospitalizations stratified by β1-389 genotype were also not modified by the β1-49 genotypes.

Example 4

Mortality Risks Associated with Sympatholysis in Some Best Patients

Systemic venous norepinephrine measurements as part of the BEST Trial core protocol were among the strongest baseline predictors of mortality, with Ln norepinephrine associated with 1.8 and 1.6 fold increases in mortality risk by univariate and multivariate analyses, respectively. Surprisingly, as shown below, the change in norepinephrine at 3 months had a complex relationship to mortality that was dependent on the treatment group. In the bucindolol- but not in the placebo-treated group a substantial number of patients (18% of the subject population) exhibited decreased norepinephrine levels that were associated with a 1.7 fold higher risk of subsequent mortality.

Most, but not all, studies indicate that adrenergic activity is a major determinant of outcome in chronic heart failure (CHF) (Cohn et al., 1984; Kaye et al., 1995; Isnard et al., 2000; Rockman et al., 1989). In addition, cardiac adrenergic activity is the first neurohormonal marker that becomes elevated in subjects with left ventricular dysfunction (Runquist et al., 1997). These observations form the cornerstone of the rationale for β-blocker therapy of heart failure (Bristow, 2000).

On the other hand, adrenergic support is an important compensatory mechanism in the failing heart, serving to maintain resting myocardial performance in a relatively normal range (Port et al., 2001). When adrenergic drive is rapidly reduced in subjects with chronic heart failure myocardial function may worsen (Gaffney et al., 1963), and treatments which substantially lower adrenergic drive may increase serious adverse events including mortality (Cohn et al., 2003; Swedberg et al., 2002). Based on these observations it appears that "sympatholytic" pharmacological lowering of adrenergic activity may affect heart failure natural history quite differently from β-blockade.

Although baseline adrenergic activity has been examined in numerous CHF outcome studies as well as in clinical trials (Benedict et al., 1996; Swedberg et al., 1996; Francis et al., 1993; Anand et al., 2003), until recently only relatively small numbers (typically hundreds) of subjects have been investigated in these studies (Anand et al., 2003). In addition, the relationship of temporal behavior of norepinephrine as a potential determinant of natural history has been examined in only two other trials (Swedberg et al., 1990; Anand et al., 2003) and never in a large CHF cohort, placebo-controlled study employing a powerful anti-adrenergic agent. Thus, the effects of baseline levels and changes in adrenergic activity on clinical outcomes in the BEST were investigated, as well as and the interaction of bucindolol, a β-blocker with sympatholytic properties on clinical outcomes.

A. Methods

1. Clinical Protocol

The BEST protocol and the main outcomes have been previously described (Mason et al., 1999; Small et al., 2002). Because of an initial delay in setting up the procedures, collection of blood samples for norepinephrine in all randomized patients began 6 months after trial initiation. As a result, 2126 of the 2708 randomized subjects in BEST had at least a baseline norepinephrine sample collected and measured.

2. Norepinephrine Sample Collection and Measurements

Peripheral venous NE samples were drawn at baseline, 3 and 12 months by inserting a 21 gauge butterfly needle into an arm vein and placing the subject in a quiet room in a supine position for 30 minutes. The initial 3 ml of blood was discarded, and then 5 ml of blood was withdrawn and immediately transferred to pre-chilled 5 ml tubes containing EDTA. Within 30 min plasma was separated and frozen at $-70°$ C. Sites shipped samples on dry ice to a central laboratory (LabCorp, Raritan, N.J.) every 3 mo, where the samples were stored at $-85°$ C. and assayed within 3 weeks. NE was measured by HPLC-electrochemical detection using the Bio-Rad HPLC method (Bio-Rad Laboratories Hercules, Calif.). Quality control included re-measuring all samples with initial values of <200 pg/ml or >2000 pg/ml, from the $2^{nd}$ stored tube; and routinely (every 20 samples) measuring known amounts.

3. Statistical Methods

Means and standard deviations (SD) for continuous data, and proportions or percentages for categorical data are presented. T-tests or Wilcoxon rank sum tests were used for continuous data, and chi-square or Fisher's exact test for categorical data. An alpha level of 0.05 (2 tailed, unadjusted) was used to indicate statistical significance.

Norepinephrine levels at baseline, or the change at 3 months were used to predict survival and the combined endpoint of mortality+CHF hospitalization. Absolute and log transformed data were initially analyzed. Because of skewness in norepinephrine levels natural log(Ln) transformed data were used in multivariate Cox proportional hazards regression models.

A Maximum Likelihood based method (Kalbfleisch et al., 1980) was used to categorize changes in norepinephrine into 3 groups for prediction of mortality or mortality+CHF hospitalization. This partitioning method finds the optimal split of norepinephrine values that maximize the likelihood of the resulting Cox proportional hazards model. In addition, a flexible cubic spline analysis (Green et al., 1994) was used to determine the shape and significance level of the relationship of norepinephrine changes at 3 months to survival.

B. Results

1. Study Population

The baseline demographic and population descriptor data in subjects in whom at least a baseline norepinephrine was drawn were not different from the entire study population (BEST Trial Investigators, 2001).

2. Norepinephrine Data

Figure 8:
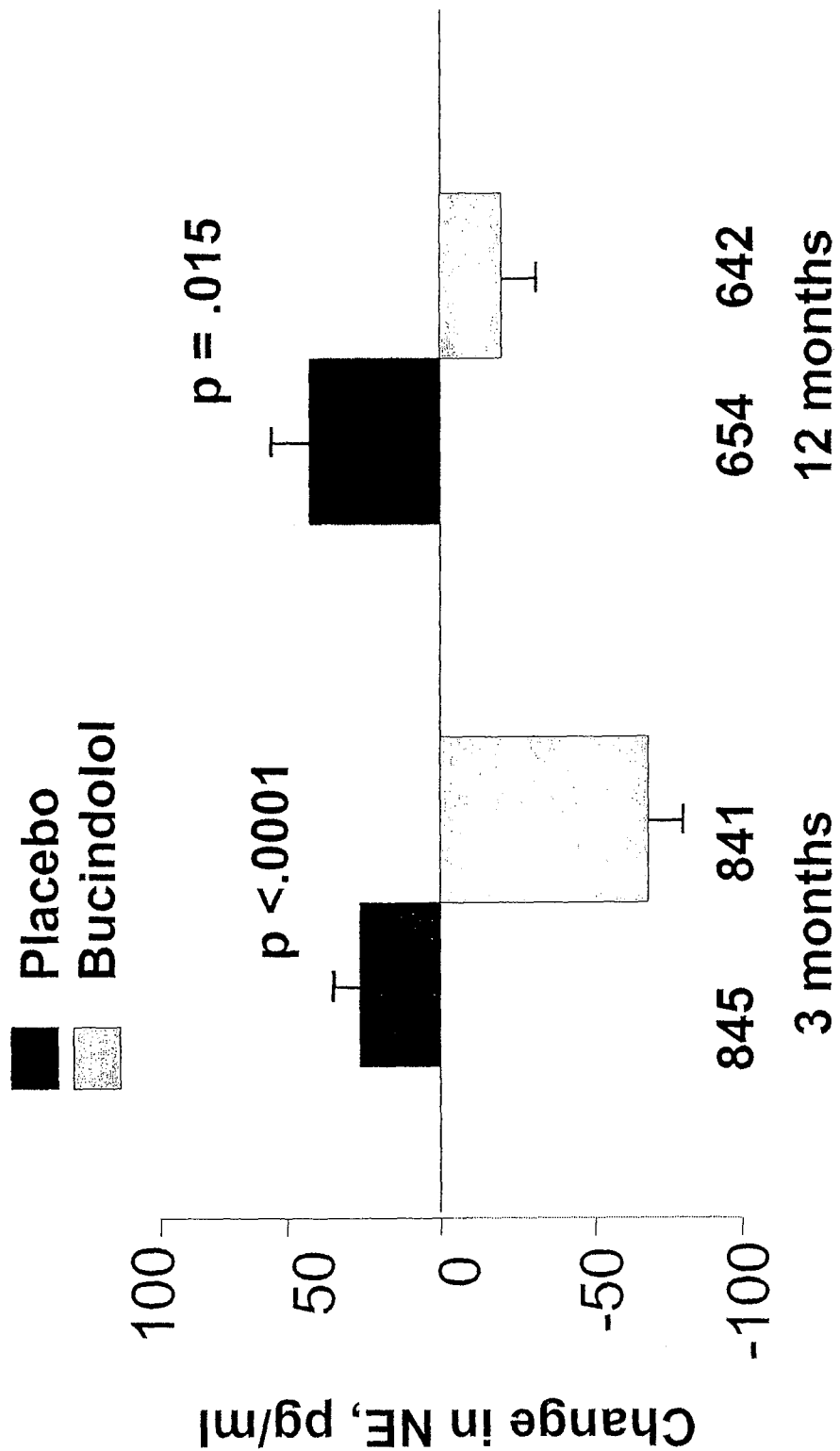
FIG. 8. Change from baseline norepinephrine levels±SEM at 3 months and 12 months, by treatment group. In both A and B The numbers under the bars are the numbers of patients in each group who had baseline and interval measurements at each timepoint; p values are for a comparison of change in each treatment group.

Baseline norepinephrine mean values were 501±316 pg/ml in the placebo group (n=1061), and 529±370 pg/ml in the bucindolol group (n=1065, p=0.061 vs. placebo). By paired t analysis at 3 (p=0.0085) and 12 (p=0.0002) months the placebo group exhibited a statistically significant increase in norepinephrine, while the bucindolol group exhibited significant decreases at 3 months (p=0.0001) and a trend (p=0.067) for a decrease at 12 months (FIG. 8). Between-group changes in norepinephrine were highly statistically significant at 3 (p<0.0001) and 12 (p<0.0001) months. Relative to changes in the placebo group, the decrease in norepinephrine in the bucindolol group was by 19% and 13% at 3 and 12 months, respectively.

Figure 9:
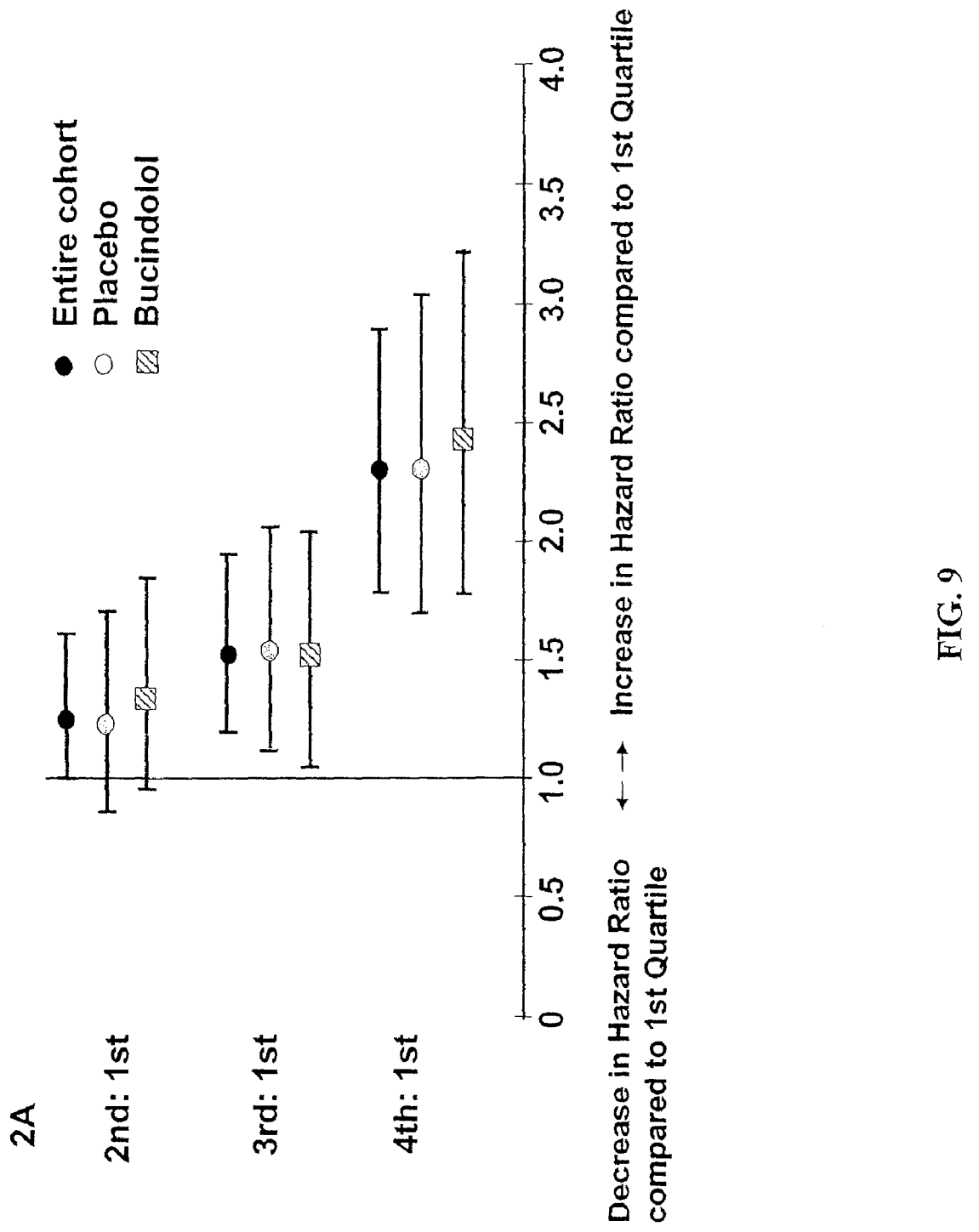
FIG. 9. Hazard ratios relative to the first quartile for all-cause mortality, by quartile of baseline norepinephrine. The norepinephrine cut points defining quartiles are: $1^{st}$, $\leq 304$ pg/ml; $2^{nd}$, 305 pg/ml to 436 pg/ml; $3^{rd}$, 437 pg/ml to 635 pg/ml; $4^{th}$, $\geq 636$ pg/ml. Numbers of patients per quartile are: Placebo group $1^{st}$ 294, $2^{nd}$ 255, $3^{rd}$ 248, $4^{th}$ 264; Bucindolol group $1^{st}$ 239, $2^{nd}$ 274, $3^{rd}$ 284, $4^{th}$ 267.
Figure 10:
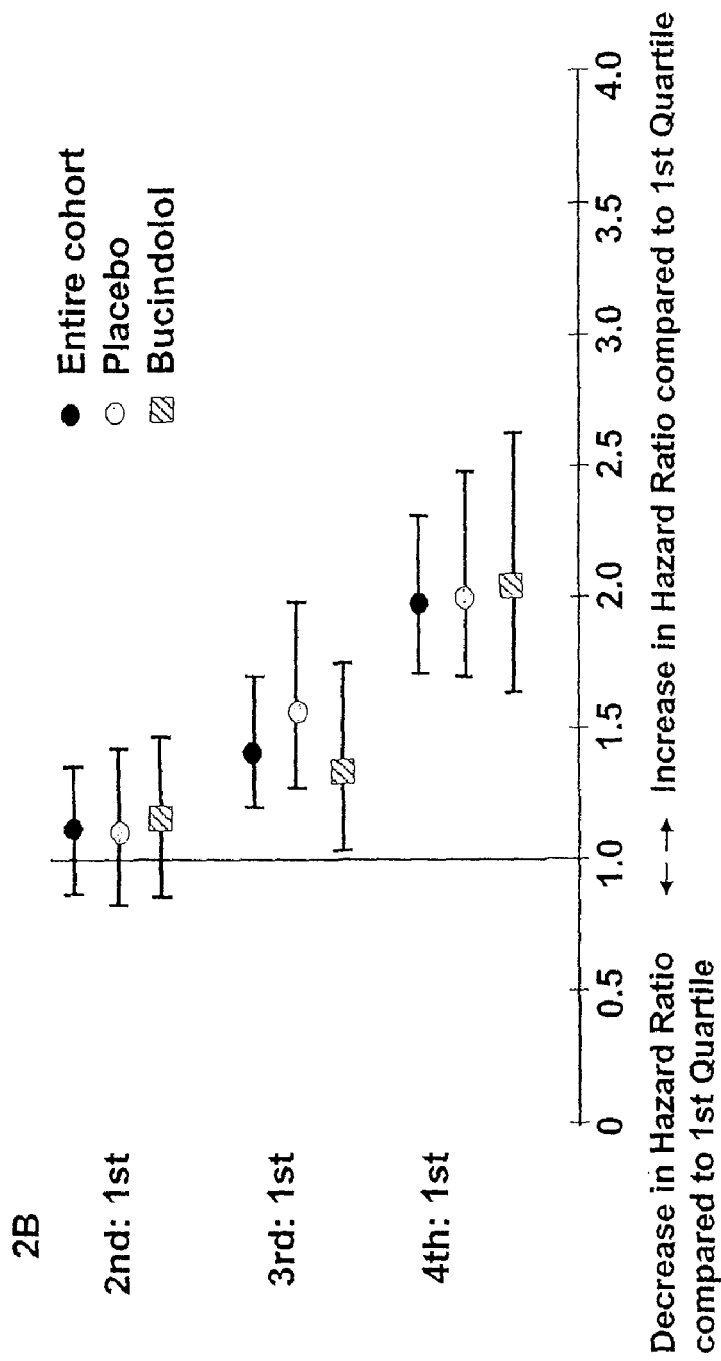
FIG. 10. Hazard ratios relative to the first quartile for the combined endpoint of all-cause mortality+CHF hospitalization, by quartile of baseline norepinephrine.

3. Baseline Norepinephrine as a Predictor of Mortality or the Combined Endpoint of Mortality+CHF Hospitalization FIG. 9 plots the hazard ratios for total mortality risk for baseline norepinephrine values, by quartiles relative to the first quartile assigned a hazard ratio (HR) of 1.0. For the entire cohort and for each treatment group there is a progressive increase in mortality risk with increasing quartile. Similar results were obtained for the combined endpoint of mortality+CHF hospitalization (FIG. 10).

Table 3 gives the univariate and multivariate analyses of baseline norepinephrine and other protocol prespecified potential modifiers of mortality. Ln norepinephrine yielded a univariate HR (95% confidence limits) of 1.82 (1.58-2.09), p<0.001. On multivariate analysis Ln norepinephrine was among the most powerful predictors of mortality.

4. Change in Norepinephrine as a Predictor of Mortality or the Combined Endpoint of Mortality+CHF Hospitalization The relationships of quartile changes in norepinephrine at 3 months to subsequent mortality or mortality+CHF hospitalization are shown in Table 4, where HRs are calculated relative to the 1st quartile of change. The quartile analysis was performed in order to keep the norepinephrine change/quartile the same in the placebo and bucindolol groups, with the cut points derived from the entire cohort. This created 2 quartiles of norepinephrine reduction ($1^{st}$ and $2^{nd}$), and 2 of norepinephrine increase ($3^{rd}$ and $4^{th}$). Both absolute norepinephrine change in pg/ml and % change from baseline value are given in Table 4. Because of the sympatholytic effect of bucindolol there were more bucindolol patients in the $1^{st}$ quartile and more placebo patients in the $4^{th}$ quartile.

As can be observed in Table 4, for absolute norepinephrine change vs. mortality the placebo group exhibited a trend for an increased risk in the 4th/1st quartile, with an HR of 1.38, p=0.099), and no trends for differences in mortality in the 2nd or 3rd quartiles relative to the 1st. For mortality+CHF hospitalization, in the placebo group the $4^{th}$ quartile:1st had a significant HR of 1.46 (p=0.011). In contrast, the bucindolol group exhibited no trends for an increased risk in the $4^{th}:1^{st}$ quartiles for either clinical outcome, but a decreased risk in mortality in the 3rd quartile relative to the $1^{st}$ (HR 0.66, p=0.046) and a trend (p=0.22) for a decreased risk in the $3^{rd}:1^{st}$ quartile for mortality+CHF hospitalization.

For norepinephrine % change there were increases or trends for increases in risk in the placebo $3^{rd}:1^{st}$ and $4^{th}:1^{st}$ quartiles, for both mortality and mortality+CHF hospitalization. In contrast, in the bucindolol group there were no such trends for an increased HR in the $3^{rd}$ or $4^{th}$ quartile relative to the $1^{st}$ for either clinical endpoint, and similar to the absolute norepinephrine change there was a trend for a decreased HR (0.77) in the $3^{rd}:1^{st}$ quartile (p=0.21).

Table 4 also gives HRs by treatment group expressed as bucindolol:placebo, for each norepinephrine quartile by absolute or % change. For mortality, the bucindolol:placebo HR was significantly <unity (reduction in mortality by bucindolol compared to placebo) in the $3^{rd}$ quartiles for either absolute (HR=0.63) or % (HR=0.56) norepinephrine change. For mortality+CHF hospitalization a similar pattern was observed, except that HRs in the $4^{th}$ quartiles were also significantly reduced. In contrast to mortality, for mortality+CHF hospitalization the $2^{nd}$ quartile yielded a nearly significant (p=0.067) increase in the bucindolol:placebo HR for absolute change, and a significant (p=0.021) increase (HR=1.39) for % change.

Figure 11:
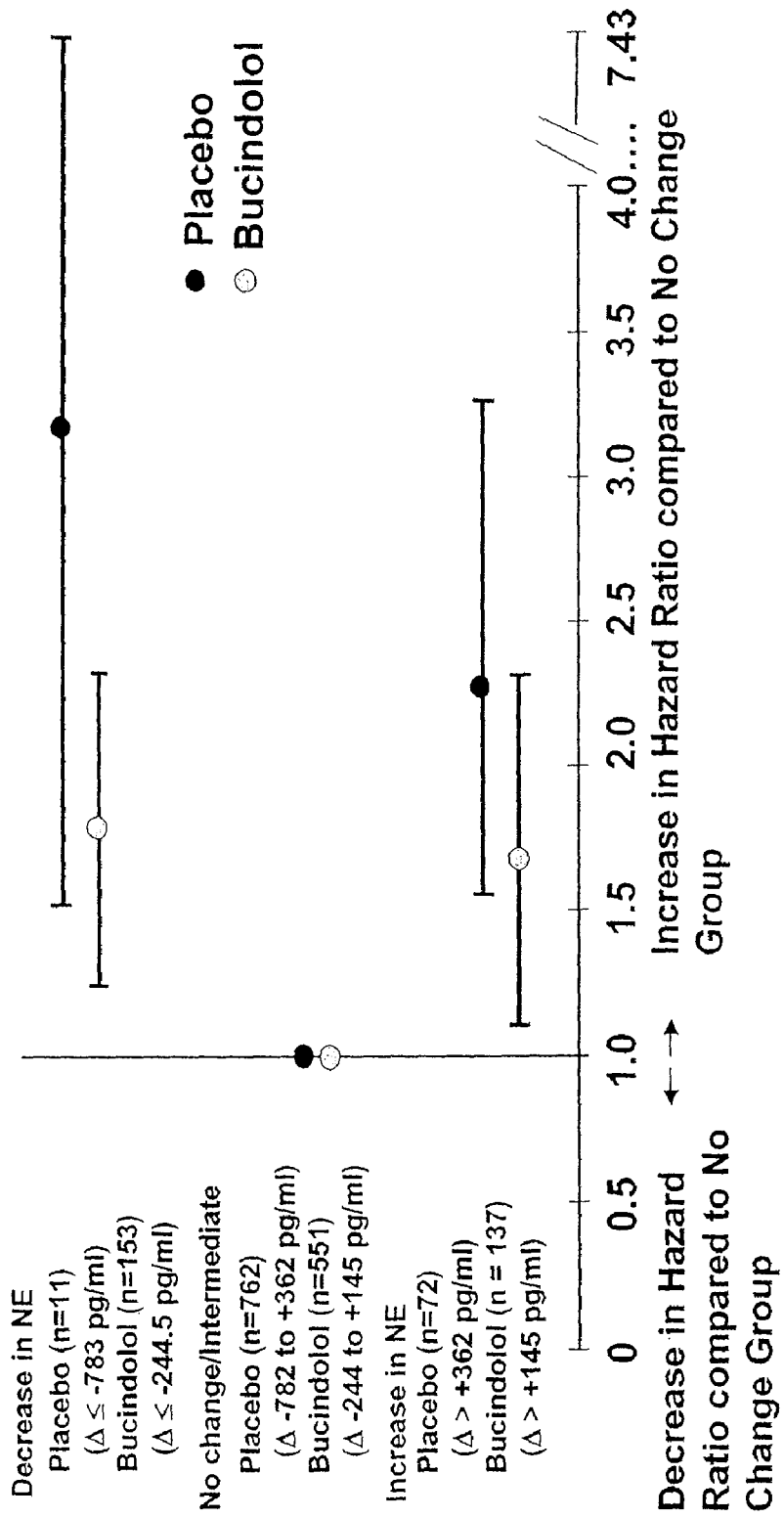
FIG. 11. Likelihood analysis for change in norepinephrine at 3 months vs. subsequent all-cause mortality, Placebo and Bucindolol treatment groups.

In order to further explore the treatment-associated differential mortality risk associated with norepinephrine change, a likelihood-based method (Bristow, 1984) was employed. As shown in FIG. 11, separate likelihood analysis within each treatment group identified 11 subjects in the placebo group and 153 subjects in the bucindolol group who were at respective higher risks (HR 3.31, p=0.004; HR 1.69, p=0.002) of subsequent mortality with norepinephrine reduction at 3 months. The reductions in norepinephrine in these risk groups were by ≧783 pg/ml in the placebo group, and ≧244.5 pg/ml in the bucindolol group. FIG. 11 also illustrates that subgroups with an increase in norepinephrine at 3 months were identified at higher mortality risk, in both treatment groups.

Because the likelihood based method provides maximal optimization of norepinephrine change cut points predictive of increased mortality, we employed less discriminatory fitting using flexible cubic spline fitting (Fowler and Bristow, 1985). The best fit by this method was a U-shaped, nonlinear curve with 5 knots and 3 degrees of freedom, with respective Chi-Square values for the bucindolol-treated group, placebo-treated group and entire cohort of 13.2 (p=0.0042), and 11.1 (p=0.011) and 32.5 (p<0.0001).

5. Characteristics of Subjects with an Increase or Decrease in Norepinephrine Associated with Increased Mortality Risk Characteristics of the mortality high-risk subgroups identified at both ends of the norepinephrine change spectrum by likelihood-based analysis, compared to the respective intermediate change groups serving as controls, are shown in Table 5. The 153 subjects in the bucindolol subgroup identified at higher mortality risk with norepinephrine reduction had high baseline norepinephrine levels and an average decrease in norepinephrine at 3 months of 529 pg/ml. These subjects also had lower LVEFs and RVEFs, and higher heart rates compared to the intermediate change control group, which had little or no norepinephrine change (−44 pg/ml). The 153 bucindolol-treated subjects with marked norepinephrine reduction also had a higher percentage of Class IV subjects, and a trend (p=0.088) towards more Black vs. Non-Black subjects as compared to the intermediate change group. Of the 52 deaths that occurred in these 153 subjects, 79% were classified as cardiac and 63%, 27% and 2% were attributed to sudden cardiac death, pump failure and myocardial infarction, respectively. In contrast, the subgroup treated with bucindolol that had a higher mortality risk associated with an increase in norepinephrine (n=137) had lower baseline RVEFs, similar baseline LVEFs but a significantly less LVEF increase at 3 months compared to the intermediate change group. In this subgroup the % Class IV and Non-Black/Black distribution did not differ from the intermediate group. In this subgroup 35 of the 43 deaths were cardiovascular, but the minority were sudden (34% vs. 51% pump failure and 6% due to myocardial infarction).

C. Discussion

Baseline norepinephrine data from the BEST Trial confirm and extend previous reports of a positive relationship between level of adrenergic activation and adverse clinical outcomes. The data on baseline norepinephrine indicate that this parameter is as strong a predictor of clinical outcomes as has been identified in a CHF population. Surprisingly, in BEST the increased risk conferred by a higher baseline norepinephrine level was not substantially lowered by anti-adrenergic therapy, as mortality or mortality+CHF hospitalization hazard ratios progressively increased with increasing norepinephrine quartile in both the bucindolol and placebo treatment groups. One possibility for this lack of protective effect by bucindolol in the higher baseline norepinephrine quartiles was a sympatholytic effect occurring in subjects with the most advanced CHF and the greatest degree of myocardial dysfunction.

On the other hand, bucindolol conferred a clinically protective effect in quartiles of patients exhibiting an increase in adrenergic activity at 3 months. No such reduction in clinical endpoints was observed in quartiles of norepinephrine reduction. In fact, for mortality+CHF hospitalization the $2^{nd}$ quartile of norepinephrine reduction exhibited evidence of increased risk in bucindolol-treated patients. Moreover, when quartiles of norepinephrine 3 month change were referenced to the $1^{st}$ quartile (which had the greatest degree of reduction) the $3^{rd}$:$1^{st}$ quartile relationship exhibited evidence of an increase in mortality in the $1^{st}$ quartile for the bucindolol group, but not for the placebo group. These suggestions of an adverse effect of bucindolol in patients exhibiting a reduction in norepinephrine at 3 months prompted additional analyses of the sympatholytic effects of this unique β-blocking agent.

Compared to placebo, bucindolol reduced norepinephrine by 19% at 3 months. This compares to a 24% relative reduction in norepinephrine at 3 months by the central sympatholytic agent moxonidine in the MOXCON Trial (Cohn et al., 2003). As in MOXCON, the sympatholytic effects of bucindolol appeared to be associated with an increased risk for adverse clinical outcomes, particularly for sudden death. In addition to the evidence within quartiles of norepinephrine reduction discussed above, likelihood-based analysis identified 18% of the bucindolol group with a marked norepinephrine reduction (by >224 pg/ml) who had a 1.65 fold increased risk for mortality, while only 1% of the placebo-treated patients were identified as being at increased risk for mortality with marked norepinephrine reduction. This analysis also revealed an increased risk for mortality in patients with an increase in norepinephrine, but in similar numbers of bucindolol- and placebo-treated patients. The increased risk of mortality at both ends of the spectrum of 3 month norepinephrine change was confirmed by flexible cubic spine fitting, which yielded a statistically significant U-shaped curve for both the bucindolol- and placebo-treated groups.

The subgroup of bucindolol-treated subjects with a reduction in norepinephrine identified by likelihood analysis to be at increased risk of mortality were comprised of patients with more advanced (Class IV vs. III) heart failure, higher baseline norepinephrine levels, more depressed LV and RV function, and a trend for a greater proportion of Blacks vs. non-Blacks. Thus the sympatholytic effects of bucindolol likely led to adverse outcomes in a subset of subjects with severe myocardial dysfunction who were likely dependent on adrenergic activity for cardiac functional support, but such a mechanism has not been proved by our data and other explanations are possible.

The only previously published clinical trial data on the relationship of changes in systemic adrenergic activity to outcomes are from CONSENSUS (Swedberg et al., 1990), where neurohormonal changes at 6 weeks were unrelated to outcome in 239 subjects, and Val-HeFT (Anand et al., 2003) where in 4301 patients absolute changes in norepinephrine at 4 months did not but % changes did predict differences in subsequent mortality in both the placebo- and valsartan-treted groups. However, unlike in Val-HeFT, a positive relationship was found between increasing absolute levels of norepinephrine and increasing mortality or mortality+CHF hospitalization risk. The major new finding of the current study is that both decreases and increases in adrenergic activity can be associated with adverse clinical outcomes in a chronic heart failure population. The mitigating effect of bucindolol on these risks indicates that the adverse effects of increases in norepinephrine can be abrogated by concurrent administration of anti-adrenergic therapy, as opposed to the risks conferred by baseline norepinephrine measured prior to initiation of therapy.

In summary, a comprehensive investigation of systemic adrenergic activity as estimated from peripheral venous norepinephrine levels measured in the BEST Trial indicates that in advanced CHF 1) baseline norepinephrine is a predictor of adverse clinical outcomes but not therapeutic response, 2) both increases and decreases in norepinephrine at 3 months predict adverse outcomes, and 3) bucindolol mitigates the risk of increases in norepinephrine, but through its sympatholytic properties places certain types of patients at clinical risk from reductions in norepinephrine.

TABLE 3

Multivariate analysis baseline NE

| Covariate | Hazard Ratio (95% CI) | P Value |
|---|---|---|
| Ln NE as Univariate | 1.82 (1.58-2.09) | <0.001 |
| Multivariate Analysis | | |
| Ln NE | 1.61 (1.40-1.85) | <0.001 |
| CAD (CAD vs. no CAD) | 1.68 (1.42-2.01) | <0.001 |
| LVEF (≤20% vs. >20%) | 1.46 (0.25-1.71) | <0.001 |
| Race (Black vs. non-Black) | 1.26 (1.04-1.50) | 0.016 |
| Gender (male vs. female) | 1.04 (0.84-1.28) | 0.724 |
| NYHA (IV vs. III) | 1.61 (1.28-2.01) | <.001 |

TABLE 4

Effect of change in norepinephrine (NE) at 3 months on subsequent mortality (M) or mortality + CHF hospitalization (M + H) in the placebo and bucindolol groups, and treatment effects of bucindolol compared to placebo by norepinephrine change quartile, hazard ratio and (95% confidence intervals)

| NE Change Absolute, pg/ml | Mortality hazard ratios by NE change quartile relative to 1st quartile | | | Crude mortality (%) and bucindolol/placebo hazard ratios by NE change quartile | | | |
|---|---|---|---|---|---|---|---|
| | 2nd/1st | 3rd/1st | 4th/1st | 1st | 2nd | 3rd | 4th |
| Placebo (P): M | 0.98 (0.65-1.48) | 1.01 (0.68-1.51) | 1.38 (0.94-2.03) | 24.5 | 27.2 | 27.5 | 37.5 |
| M + H | 1.21 (0.89-1.64) | 1.11 (0.82-1.50) | 1.46 (1.09-1.96) | | | | |
| Bucindolol (B): M | 0.99 (0.70-1.41) | 0.66 (0.43-0.99) | 1.15 (0.80-1.65) | 26.1 | 25.7 | 17.7* | 28.6 |
| M + H | 1.00 (0.75-1.32) | 0.83 (0.61-1.12) | 1.10 (0.82-1.47) | | | | |
| B/P: M | — | — | — | 0.96 (0.65-1.43) | 0.98 (0.68-1.43) | 0.63 (0.41-0.96) | 0.80 (0.57-1.14) |
| M + H | | | | 1.19 (0.88-1.61) | 1.30 (0.98-1.72) | 0.58 (0.43-0.78) | 0.74 (0.56-0.98) |
| % Change | | | | | | | |
| Placebo (P): M | 1.21 (0.80-1.84) | 1.42 (0.96-2.10) | 1.37 (0.92-2.04) | 23.1 | 27.3 | 32.1 | 29.2 |
| M + H | 1.27 (0.93-1.72) | 1.33 (0.99-1.78) | 1.35 (1.00-1.81) | | | | |
| Bucindolol (B): M | 1.14 (0.80-1.62) | 0.77 (0.51-1.16) | 1.19 (0.83-1.71) | 25.2 | 26.0 | 18.8 | 29.1 |
| M + H | 1.18 (0.89-1.56) | 0.91 (0.67-1.24) | 1.18 (0.88-1.58) | | | | |
| B/P: M | — | — | — | 1.03 (0.69-1.54) | 0.98 (0.68-1.42) | 0.56 (0.38-0.84) | 0.90 (0.63-1.29) |
| M + H | | | | 1.14 (0.84-1.54) | 1.39 (1.05-1.85) | 0.65 (0.48-0.88) | 0.66 (0.50-0.88) |

Quartiles are: absolute NE change in pg/ml, 1st <−144 (placebo n = 155, bucindolol n = 268); 2nd −144 to <−9 (placebo n = 206, bucindolol n = 214), 3rd −9 to 111 (placebo n = 236, bucindolol n = 186), 4th >111 (placebo n 248, bucindolol n = 173); % NE change, 1st <−30.2 (placebo n = 160, bucindolol n = 262), 2nd −30.2 to <−2.5 (placebo n = 198, bucindolol n = 223), 3rd −2.5 to 31.1 (placebo n = 240, bucindolol n = 181), 4th >31.1 (placebo n = 247, bucindolol n = 175). *p < .05 vs 1st quartile, Fisher's Exact Test

TABLE 5

Demographic characteristics of likelihood-determined subgroups with increased risk associated with changes (Δ) in norepinephrine (NE, in pg/ml) by reductions (Redxn) or increases (Incr) vs. the Intermediate (Inter) NE change subgroups. NE is in pg/ml; data in mean ± SD; *, $p < .05$ vs. Inter; #, $p < .10$ vs. Inter

| Parameter | Placebo Redxn (Δ NE ≦ −783) | Placebo Inter (Δ NE > −783, ≦ 362) | Placebo Incr (Δ NE > 362) | Bucindolol Redxn (Δ NE ≦ −244.5) | Bucindolol Inter (Δ NE −244.5, ≦ +145) | Bucindolol Incr (Δ NE > 145) |
|---|---|---|---|---|---|---|
| Number of subjects | n = 11 | n = 762 | n = 72 | n = 153 | n = 551 | n = 137 |
| Baseline NE, pg/ml | 1500* ± 405 | 464 ± 245 | 514 ± 328 | 932* ± 544 | 422 ± 189 | 409 ± 199 |
| NE change @ 3 mos, pg/ml | −1024* ± 220 | −16 ± 188 | 642* ± 335 | −529* ± 458 | −44 ± 103 | 326* ± 244 |
| NE change @ 12 mos, pg/ml | −667* ± 528 | 45 ± 268 | 297* ± 560 | −349* ± 347 | 17.5 ± 216 | 161* ± 246 |
| Number of deaths (%) | 6 (55%)* | 200 (26%) | 34 (47%)* | 52 (34%)* | 114 (21%) | 43 (31%)* |
| Age (years) | 63.6 ± 9.8 | 60.3 ± 11.9 | 64.7* ± 10.8 | 60.1 ± 12.2 | 60.7 ± 12.1 | 62.0 ± 12.7 |
| Gender (% M/F) | 64/36 | 80/20 | 82/18 | 79/21 | 81/19 | 82/18 |
| Race (% Non-Black/Black) | 73/27 | 80/20 | 82/18 | 74/26# | 80/20 | 77/23 |
| NYHA Class (% III/IV) | 82/18 | 92/8 | 83/17* | 86/14* | 93/7 | 93/7 |
| Duration of CHF, mos, median | 73.0# | 39.0 | 36.0 | 36.0 | 36.0 | 31.0 |
| Etiology (% Non-ischemic/Ischemic) | 45/55 | 42/58 | 29/71* | 46/54 | 42/58 | 31/69* |
| Baseline Heart Rate (HR, BPM) | 79.2 ± 12.4 | 81.6 ± 12.8 | 78.3* ± 12.3 | 85.5* ± 13.8 | 81.0 ± 13.0 | 80.6 ± 13.7 |
| HR change @ 3 mos | −5.5 ± 17.0 | −2.3 ± 12.5 | 1.0* ± 13.3 | −13.6* ± 14.8 | −9.7 ± 12.4 | −7.1* ± 12.8 |
| HR change @ 12 mos | −10.7# ± 13.2 | −2.6 ± 13.5 | −1.8 ± 13.5 | −12.6* ± 14.4 | −7.9 ± 13.5 | −8.1 ± 14.6 |
| Systolic BP (SBP, mm Hg) | 111 ± 20 | 118 ± 18 | 116 ± 19 | 116 ± 19 | 118 ± 18 | 120 ± 18.2 |
| Change in SBP @ 3 mos | 4.7 ± 13.8 | 0.0 15.4 | −0.1 ± 18.1 | −0.7 ± 18.2 | −0.5 ± 15.7 | −4.7* ± 16.4 |
| Change in SBP @ 12 mos | 5.6 ± 19.5 | 0.7 ± 18.1 | 1.9 ± 21.0 | 2.7 ± 20.1 | 0.7 ± 18.0 | −0.9 ± 16.8 |
| LVEF, EF units (EFU) as %) | 22.8 ± 6.6 | 23.1 ± 7.2 | 23.3 ± 7.6 | 20.1* ± 8.0 | 24.1 ± 7.0 | 23.3 ± 6.7 |
| Change in LVEF @ 3 mos, EFU | 0.2 ± 6.4 | 2.3 ± 6.6 | 0.6* ± 7.2 | 7.0# ± 8.4 | 5.7 ± 7.9 | 4.2* ± 7.0 |
| Change in LVEF @ 12 mos, EFU | 5.7 ± 11.9 | 3.3 ± 8.7 | 1.4 ± 7.6 | 8.8 ± 9.2 | 7.3 ± 10.4 | 7.1 ± 8.8 |

Example 5

Prevalence of A2C-Adrenergic Receptor Genetic Variants in Best

The table below gives the prevalence (%) of $\alpha_{2c}$-adrenergic receptor genetic variants (WT/WT=homozygous wild type, WT/DEL=heterozygotes, DEL/DEL=homozygous $\alpha_{2c}$Del322-325) in BEST, comparison to that originally reported by Liggett's group (Small et al., 2002). Samples from BEST were evaluated by using primers to amplify by PCR a region of the $\alpha_{2c}$AR sequence that covers the deletion and then running the amplification reaction over a gel that was capable of resolving a 12-base pair difference in length between products with or without the deletion.

TABLE 6

| | Non-Black | | | Black | | | Entire Cohort | | |
|---|---|---|---|---|---|---|---|---|---|
| Study | WT/WT | WT/DEL | DEL/DEL | WT/WT | WT/DEL | DEL/DEL | WT/WT | WT/DEL | DEL/DEL |
| BEST | 91.6 | 8.2 | 0.2 | 33.8 | 47.8 | 18.4 | 80.0 | 16.1 | 3.9 |
| Small, et al CHF | 86.4 | 6.2 | 7.4 | 29.5 | 17.9 | 52.6 | 58.5 | 11.9 | 29.6 |
| Small, controls | 94.3 | 3.8 | 1.9 | 34.5 | 48.8 | 16.6 | 67.7 | 23.8 | 8.5 |

As can be seen in the above table, the frequency of the α2cDel322-325 allele is much greater in Black populations vs. non-Black, in BEST 0.423 vs. 0.043 (p<0.0001). Secondly, in Blacks in BEST the α2cDel322-325 allele frequency is not as high as in Small et al's Black CHF patients (0.615, p<0.0001), but is similar to that in Small et al's Black controls (0.411, p=0.85). These differences probably reflect the relatively small sample sizes employed in Small et al.'s (n=78 Black CHF patient, 84 Black controls) and the BEST trial (n=207 Blacks in the DNA substudy).

In humans increased adrenergic drive associated with the $α_{2c}$Del322-325 polymorphism has only been assumed, and has not been directly investigated.

One possible reason for the small difference in baseline norepinephrine between α2cDel322-325 homozygotes and α2c wild type controls that is directly addressed in this proposal, is that systemic venous norepinephrine is not a good surrogate indicator of cardiac adrenergic drive, and in chronic heart failure changes in cardiac adrenergic drive can occur in the absence of changes insystemic norepinephrine.

The results of baseline and 3-month change in norepinephrine by α2c receptor type is shown in Table 7:

TABLE 7

Norepinephrine (NE), mean ± SD, and (n) from the BEST Trial, by α2c Receptor Type; *p < .05 vs. placebo change

| α2c Receptor Type | Baseline NE, pg/ml | Change in NE (pg/ml) at 3 mos | | |
|---|---|---|---|---|
| | | Placebo | Bucindolol | All |
| α2c wild type homozyg. or heterozyg. | 479 ± 264 (710) | 12 ± 274 (305) | −50* ± 227 (304) | −19 ± 254 (609) |
| α2cDel322-325 homozygotes | 521 ± 350 (161) | 51 ± 323 (60) | −153* ± 468 (67) | −57 ± 417 (127) |

As seen in Table 7, the baseline levels or change in systemic venous NE in BEST strongly support the above-stated hypotheses regarding effects of the α2cDel322-325 receptor variant on baseline adrenergic drive; there is only a nonsignificant trend in favor of the α2cDel322-325 homozygotes for a higher baseline norepinephrine at 3 months. On the other hand, it can be readily appreciated in Table 7 that the decrease in norepinephrine with bucindolol is much larger in α2cDel322-325 homozygotes than in α2c wild type homozygotes or heterozygotes.

Example 6

Expansion of Examples 3 and 4

A. Materials and Methods
1. Ex Vivo Human Ventricular Studies

Nonfailing hearts were obtained from local potential organ donors whose hearts were not transplanted because of physical or ABO blood type incompatibility. Failing hearts were from patients with end-stage heart failure due to ischemic or non-ischemic dilated cardiomyopathies who underwent cardiac transplantation. The demographic characteristics of the hearts are provided in Results. The contractile response of isolated, field stimulated, human trabeculae was assessed as previously described {1755; a-c}. Trabeculae of uniform size (1 to 2×6 to 8 mm) were mounted in 80 ml muscle bath chambers in Tyrode's solution at pH 7.45 bubbled with 95% $O_2$-5% $CO_2$ at 36°. After equilibration, a tension of 75% of Lmax was applied to each individual trabeculum. Field-stimulation by a 5-ms pulse at 10% above threshold was then applied, and after equilibration full dose-response curves to isoproterenol, bucindolol or xamoterol were performed using the indicated concentrations and application of increasing doses every 5 minutes. In experiments in which forskolin was used to enhance signal transduction {e,f}, $10^{-6}$ M of this adenylyl cyclase activator was applied to the tissue baths 15-20 minutes prior to the performance of dose-response curves, and allowed to achieve stability of tension response. Systolic tension at each dose was calculated as the stimulated tension in $mN/mm^2$ minus baseline tension. The maximum tension, concentration of isoproterenol that produced 50% of the maximum developed tension ($EC_{50}$) and curve slope were computed by nonlinear repeated measures analysis of covariance. A statistically significant negative or positive curve slope on grouped data was used to identify negative or positive inotropic effects, respectively, and curve slope differences between genotypic groups were detected by a test for interaction. Statistical methods were employed as described in Examples 3 and 4.

2. Transfected Cells, radioligand binding, cAMP assays

Chinese hamster fibroblasts were stably transfected using constructs previously described so as to separately express the human $β_1$-Arg389 or $β_1$-Gly389 receptors. $β_1$AR expression, and affinity for bucindolol, were determined by radioligand binding studies with $^{125}$I-cyanopindolol ($^{125}$I-CYP), using 1 μM propranolol to define nonspecific binding as described. Whole cell cAMP accumulation studies were carried out by the [$^3$H]-adenine method using two lines with equivalent expression levels of the two receptors as indicated. Attached cells were exposed to vehicle (basal), 10 μM norepinephrine or 10 uM norepinephrine with the indicated concentrations of bucindolol for 15 min at 37° C.

Figure 12:
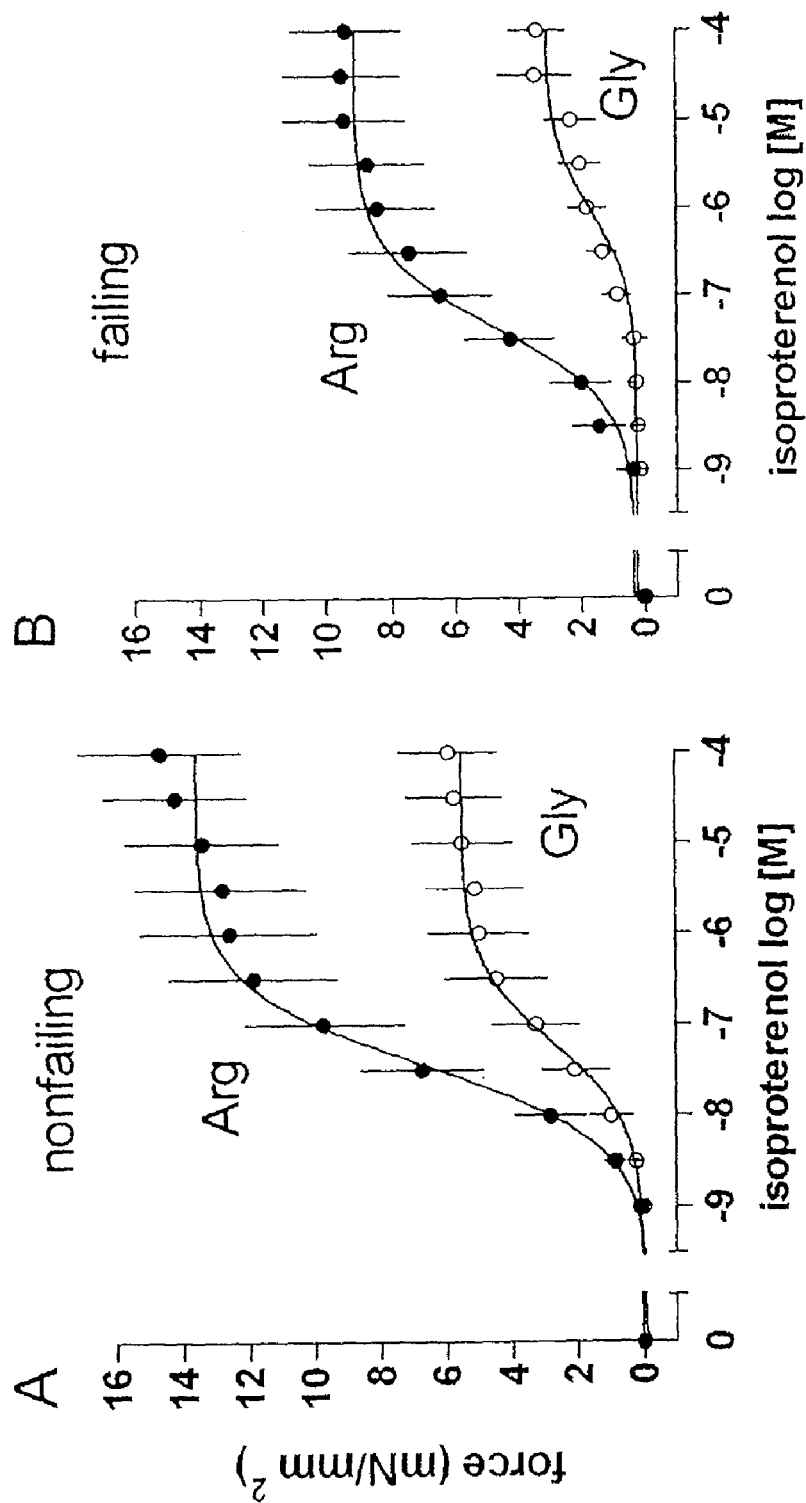
FIG. 12. Nonfailing and failing human ventricular ex vivo contractile responses correlate with $\beta_1AR$ genotype. Right ventricular trabeculae were utilized from nonfailing and failing human hearts as described in Methods. Trabeculae from 11 hearts were studied in each of the four groups. All Arg strps were from homozygous subjects. The Gly carriers consisted of 10 hetozygotes in the nonfailing and 9 in the failing groups, with the remainder being homozygotes for Gly. The maximal response derived from the dose response curves was greater for Arg389, both in the nonfailing (P=0.01) and failing (P=0.008) studies.

B. Results
1. Human Ventricular Ex Vivo Contractile Responses Correlate with $β_1$AR Genotype In these studies isolated right ventricular trabeculae from human hearts were utilized to ascertain the effects of genotype on contraction using the relevant tissue, under endogenous expression, in the absence and presence of ventricular failure. The pre-explant LVEF in the nonfailing group was 0.61+0.13 for Arg and 0.53+0.15 for Gly, and in the failing group=0.21+0.11 for Arg and 0.17+0.07 for Gly. Five of 11 failing Arg and six of 11 failing Gly patients had ischemic dilated cardiomyopathies, with all the other failing hearts being nonischemic dilated cardiomyopathies. The ages of the nonfailing hearts were: Arg 39±16 years, Gly 43±20 years (p=0.64). For failing hearts the ages were: Arg 48±15 years, Gly 54±8 years, p=0.26). The gender distribution in nonfailing hearts was 3 males and 8 females in Arg, and 5 males and 6 females in Gly. In Failing hearts the gender distribution was 8 males and 3 females in Arg, and 2 males and 9 females in Gly. Shown in FIG. 12 are systolic tension responses to isoproterenol in right ventricular trabeculae removed from nonfailing and failing human hearts, stratified by the $\beta_1$AR-389 genotype. In nonfailing hearts, the responses differed between genotypes, with maximal tensions being higher for $\beta_1$-Arg389 homozygotes (13±2.5 vs 5.2±1.4 mN/mm$^2$ for $\beta_1$-Gly389 carriers, P=0.01). Importantly, this same phenotype, with an even greater allele-specific relative difference, was observed in trabeculae from failing hearts: maximal isoproterenol-stimulated tensions were 9.4±1.9 mN/mm$^2$ for $\beta_1$-Arg389 and 2.4±0.60 mN/mm$^2$ for $\beta_1$-Gly389 (P=0.008).

A second group of 23 failing hearts was used to assess the inotropic effects of bucindolol, the $\beta_1$-AR selective partial agonist xamoterol {d}, and isoproterenol in isolated right ventricular trabeculae. This group's LVEF averaged 0.18±0.09, with 10 nonischemic and 13 ischemic dilated cardiomyopathies. The average age was 52±11, and there were 20 males and 3 females. Thirteen of the 23 hearts were homozygous for Arg389, while 10 were Gly carriers (all heterozygotes). There were no differences between Arg homozygotes and Gly carriers with respect to LVEF, age, etiology of cardiomyopathy, and gender. In 8 of the 23 hearts bucindolol and xamoterol experiments were performed; the other 15 hearts had either xamoterol or bucindolol dose-response curves performed without the other agent. All 23 hearts had full isoproterenol dose-response curves performed.

The results of the isoproterenol dose-response between the two genotypic groups was quite similar to results shown in FIG. 12. In data not shown, there was a marked difference in dose-response in favor of the Arg/Arg genotype, with highly significant (p<0.001) differences in curve slope by test for interaction and a difference in maxima (Arg, xxxx; Gly, yyyy, p<0.05). As can be seen in FIG. 3, bucindolol alone produced a negative inotropic effect in both genotypic groups (negative slopes in both, both p values <0.01, nonsignificant test for interaction between curve slopes). In the presence of forskolin pretreatment the Arg hearts retained a negative curve slope (P<0.05), but the slope of the Gly dose response curve was not different from 0. (p=0.25). In the absence of forskolin (FIG. 13C), xamoterol produced a positive inotropic effect in the Arg hearts, but a negative inotropic effect in Gly trabeculae (both slope p values <0.05) Xamoterol when applied with forskolin pretreatment produced a positive inotropic effect in both genotypic groups (positive curve slopes in both genotypes, p=<0.05), with the Arg/Arg hearts having a greater inotropic effect that reached significance compared to baseline at xamoterol doses of $3\times10^{-8}$ M and $10^{-7}$ M.

2. Functional Antagonism of NE Stimulated cAMP in Transfected Cells

For these studies cells expressing equivalent levels (fmol/mg, n=4) of the Arg389 (123±19) and Gly389 (137±16) human $\beta_1$ARs were utilized. Basal levels of cAMP were 72±8.5 and 59±9.1 fmol/well. Initial cAMP accumulation experiments in the presence of bucindolol up to 10 μM showed no evidence for intrinsic sympathomimetic activity (USA) at either receptor. To examine functional antagonism, cells were exposed to 10 μM of the agonist norepinephrine, in the absence or presence of varying concentrations of bucindolol, and cAMP levels determined. As shown in FIG. 13, Arg389 displayed a greater cAMP stimulation to agonist in the absence of bucindolol compared to Gly389, which represents the primary phenotypes of the two receptors as noted earlier {998}. Despite the substantially greater degree of NE-mediated stimulation of the Arg389 receptor, bucindolol effectively antagonized the response. The difference in the absolute decrease in cAMP production afforded by bucindolol was greater for cells expressing $\beta_1$-Arg389: bucindolol caused a maximal decrease of 435±80 fmol/ml cAMP in Arg389 cells compared to 115±23 fmol/ml cAMP in Gly389 cells (P=0.008, n=4). The potency of bucindolol was not found to be different for the response (EC$_{50}$=46±4.5 and 35±11 nM, respectively, P=0.94, n=4). In addition, in $^{125}$I-CYP competition binding studies the affinity for bucindolol was not different between $\beta_1$-Arg389 (pK$_i$=9.6±0.04) and $\beta_1$-Gly389 receptors (pK$_i$=9.6±0.11, n=3). These findings indicate that bucindolol is capable of antagonizing the enhanced response of $\beta_1$-Arg389.

3. Mechanism of the Therapeutic Advantage to the Arg389 Genotype

Increased adrenergic activity, typically identified by elevated systemic venous norepinephrine levels, supports compromised myocardial function in heart failure patients but contributes to the progression of heart failure {h}. This complex relationship between adrenergic activity and outcomes was observed in BEST, where an increase in baseline norepinephrine was independently associated with adverse outcomes, but marked withdrawal of adrenergic activation was associated with increased mortality {i}. Unlike other β-blockers that have been used to treat heart failure, bucindolol has potent sympatholytic properties, and in BEST 18% of patients treated with bucindolol exhibited exaggerated norepinephrine lowering at three months associated with a 1.7 fold increased risk of subsequent mortality {i}, reminiscent of increased mortality of patients in the MOXCON Trial treated with the pure sympatholytic agent moxonidine {j}. Although the increased mortality risk of exaggerated symapholysis is not completely understood, it probably involves loss of adrenergically-mediated contractility support to the failing heart. Patients who are Arg homozygous could therefore potentially tolerate the loss of norepinephrine signaling better than Gly carriers, because as shown in FIGS. 12 and 13, even low levels of catecholamine agonist produce an increase in force in Arg homozygotes. The other mechanism by which Arg homozygotes could gain a therapeutic advantage to treatment by bucindolol would be antagonism of a greater degree of adverse $\beta_1$-AR signaling, as implied in FIG. 3. In order to determine which of these mechanisms may have accounted for the more favorable therapeutic effect of bucindolol in Arg homozygotes vs. Gly carriers, the inventors compared mortality effects by baseline norepinephrine and by norepinephrine change at 3 months (Table 8). As can be seen in Table 8, the hazard ratio of Arg homozygotes to Gly carriers for mortality decreases with increasing baseline norepinephrine, suggesting a progressive advantage to bucindolol-treated Arg homozygotes with increasing adrenergic drive. For the change in norepinephrine analysis, the inventors compared mortality in Arg homozygotes to Gly carriers in groups previously identified as being at an increased risk for mortality related to a marked reduction (by >244 pg/ml at three months of therapy) in norepinephrine, a reference group with little or no change in norepinephrine (−244 to 145 pg/ml) not at risk for increased mortality, and a group at increased risk for mortality because of an increase in norepinephrine (by >145 pg/ml). As can be seen in Table 8, there is no advantage to Arg homozygotes in the subgroup at increased risk for mortality from exaggerated sympatholysis (Group 1); the hazard ratio of 1.07 indicates a negligible advantage of Gly carriers in this group. On the other hand, as for baseline norepinephrine, there is a decreasing hazard ratio with increasing norepinephrine rise at 3 months, to the point that in the increasing norepinephrine group the advantage to Arg homozygotes is by a relatively better mortality reduction of 64% (p=0.08). These norepinephrine change and baseline data indicate that the bucindolol therapeutic advantage for the Arg homozygous state of the $\beta_1$AR is directly related to the degree of adrenergic activity, and not to protection against sympatholysis.

TABLE 8

Bucindolol-treated patients in BEST DNA substudy with norepinephrine (NE) measurements (pg/ml, n = 439)

| NE Group | Mortality hazard ratio, Arg/Arg:Gly carrier | 95% C.I. | Cox p value | # Events |
|---|---|---|---|---|
| BSL NE (n) | | | | |
| 64-356 (146) | 0.90 | 0.37, 2.22 | 0.82 | 19 |
| 358-545 (144) | 0.74 | 0.37, 1.51 | 0.41 | 31 |
| 546-2571 (149) | 0.68 | 0.32, 1.47 | 0.33 | 29 |
| *Change in NE @ 3 mos (n) | | | | |
| Group 1, <−244 (70) | 1.07 | 0.41, 2.78 | 0.89 | 17 |
| Group 2, −244 to 145 (248) | 0.82 | 0.43, 1.59 | 0.56 | 36 |
| Group 3, >145 (54) | 0.36 | 0.11, 1.15 | 0.08 | 14 |

BSL = baseline.
*NE change in the bucindolol group at 3 months (mos) was related to subsequent survival outcome; the cutpoints are from the previously-published[1] likelihood analysis from the entire cohort. In that analysis compared to Group 2, Group had a 1.69 fold (p < .05) increase in mortality, and Group 3 a 1.65 fold (p < .05) increase in mortality.

Example 7

Additional Analysis from Best Trial

Figure 14:
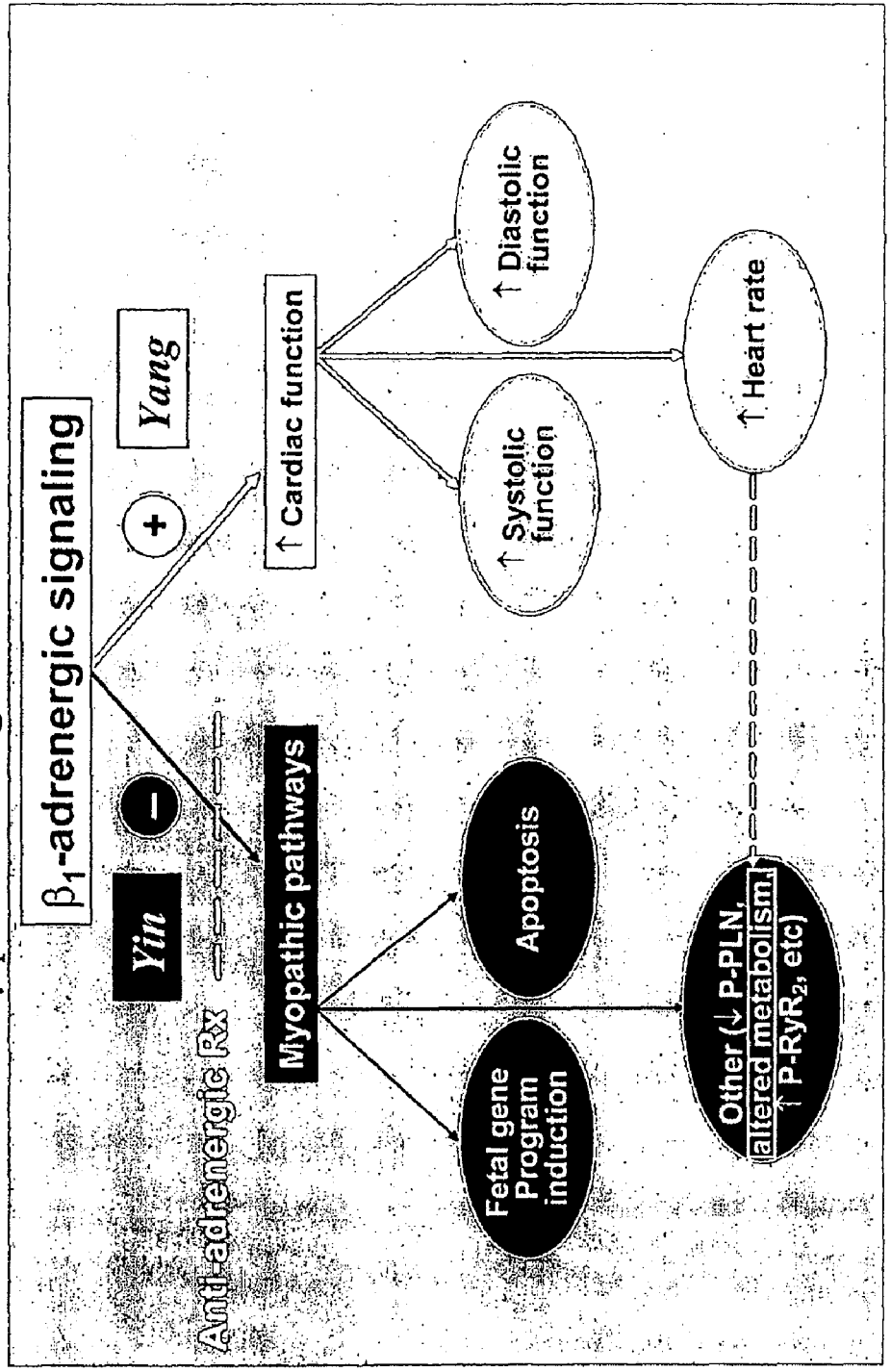
FIG. 14. Antithetical consequences of chronic myocardial $\beta_1$ adrenergic stimulation.

In chronic heart failure the activation of adrenergic nervous system has dual, seemingly antithetical consequences (FIG. 14). On the one hand, ongoing adrenergic activation provides important support to the failing heart, and pharmacologic abolishment of this support by sympatholytic agents increases mortality (Bristow et al., 2004; Cohn et al., 2003). On the other hand, chronic β-adrenergic stimulation is cardiomyopathic, and β-adrenergic receptor blockade can improve the dilated cardiomyopathy phenotype and clinical outcomes. The challenge of anti-adrenergic therapy is to not substantially interfere with adrenergic support, while inhibiting the adverse effects. The strategy of starting with low doses of reversible, mass action/competitive β-blocking agents has been largely successful in dealing with this delicate balance, particularly in less advanced heart failure patients.

It is clear that in BEST bucindolol encountered difficulty with balancing the effects of anti-adrenergic therapy, by withdrawing support excessively in Class IV patients (Anderson et al., 2003). Class IV patients treated with bucindolol had a statistically significant, 1.7 fold increase in the combined endpoint of death or heart failure hospitalization over the first 6 months of treatment, whereas Class III patients had no such early adverse effect and overall had a highly significant (p=0.0001), 22% reduction in event rate. The subgroup of patients with the large sympatholytic response to bucindolol was overrepresented in Class IV patients, as would be expected, since this subgroup has very high baseline norepinephrine levels (FIG. 15). The subgroup of patients with the large sympatholytic response to bucindolol also had a worse LV and RV function, as would be expected (FIG. 16).

There was a 1.7 fold increase in mortality in BEST in the subgroup (18% of the treated cohort) that experienced profound sympatholysis (reduction in norepinephrine by ≧244.5 pg/ml). This subgroup result is similar to that in the MOX-CON Trial, in patients who received the "pure" sympatholytic agent moxonidine (Cohn et al., 2003). There appear to be two pharmacogenetic ways in which patients can be protected from this adverse effect: 1) they have the wild type version of the $\alpha_{2c}$ receptor, which is one of the determinates of norepinephrine release (Bristow 2000); 2) they have the high functioning variant of the $\beta_1$ receptor, which presumably allows them to withstand loss of norepinephrine signaling. Thus, prescreening for the presence of either the wild-type $\alpha_{2c}$AR or $\beta_1$AR-389Arg/Arg identifies patient populations who have a reduction in mortality if respectively 29% (p=0.031) or 38% (p=0.030).

Figure 17:
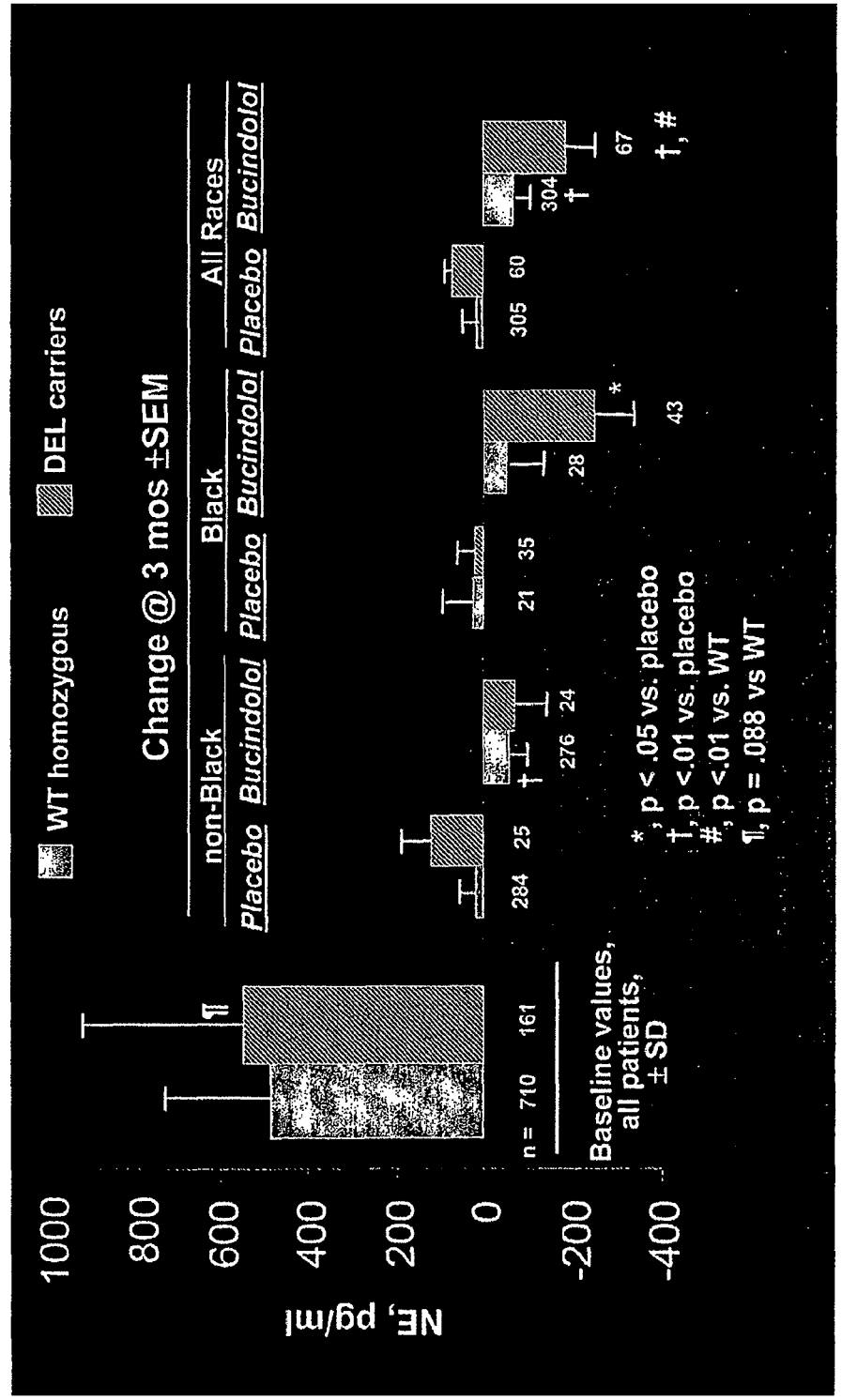
FIG. 17. Illustration of correlation between $\alpha_{2c}AR$ genotype and systemic norepinephrine levels in BEST patients.
Figure 18:
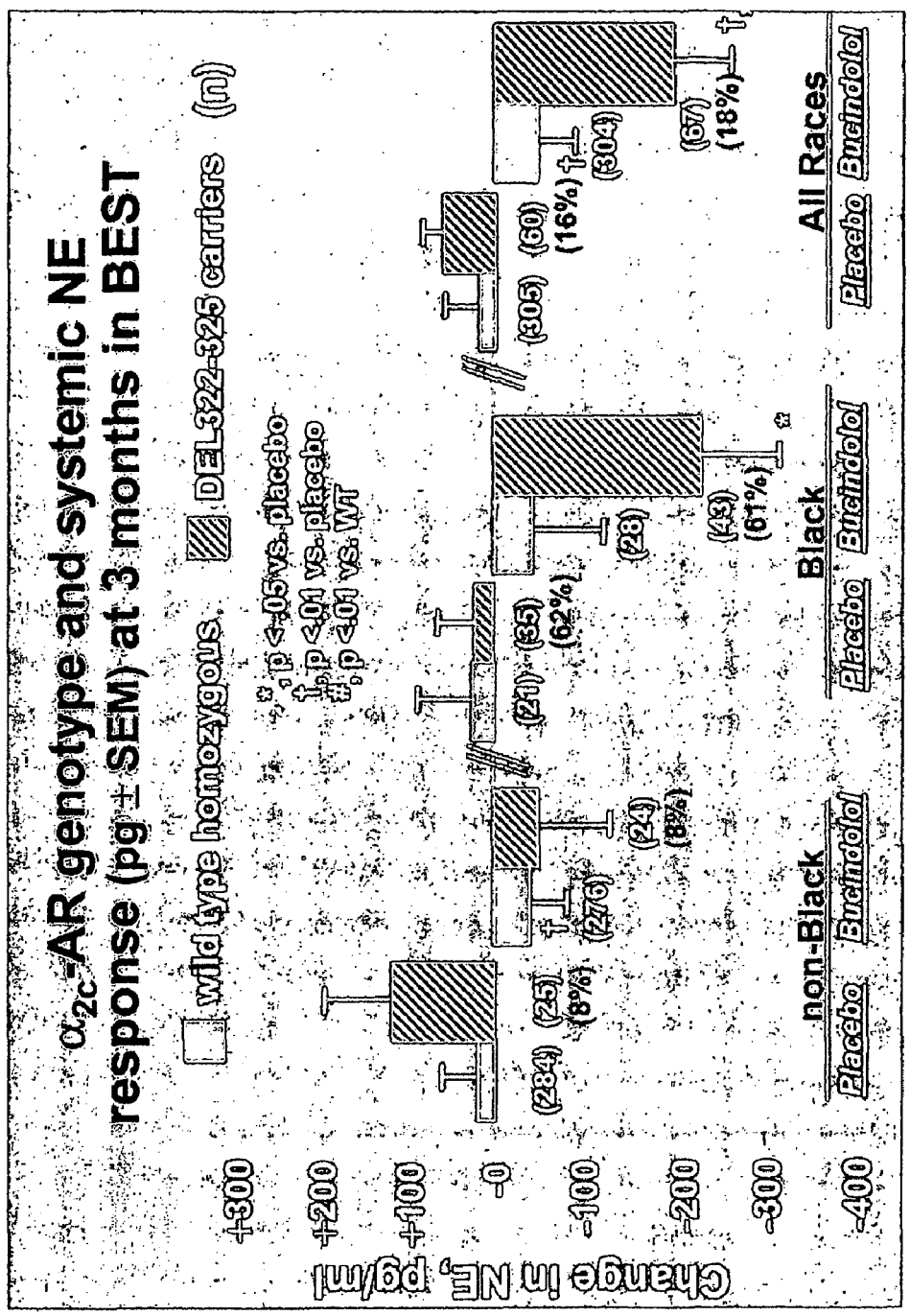
FIG. 18. Illustration of correlation between $\alpha_{2c}$AR genotype and systemic norepinephrine response (pg±SEM) in BEST patients after three months.
Figure 19:
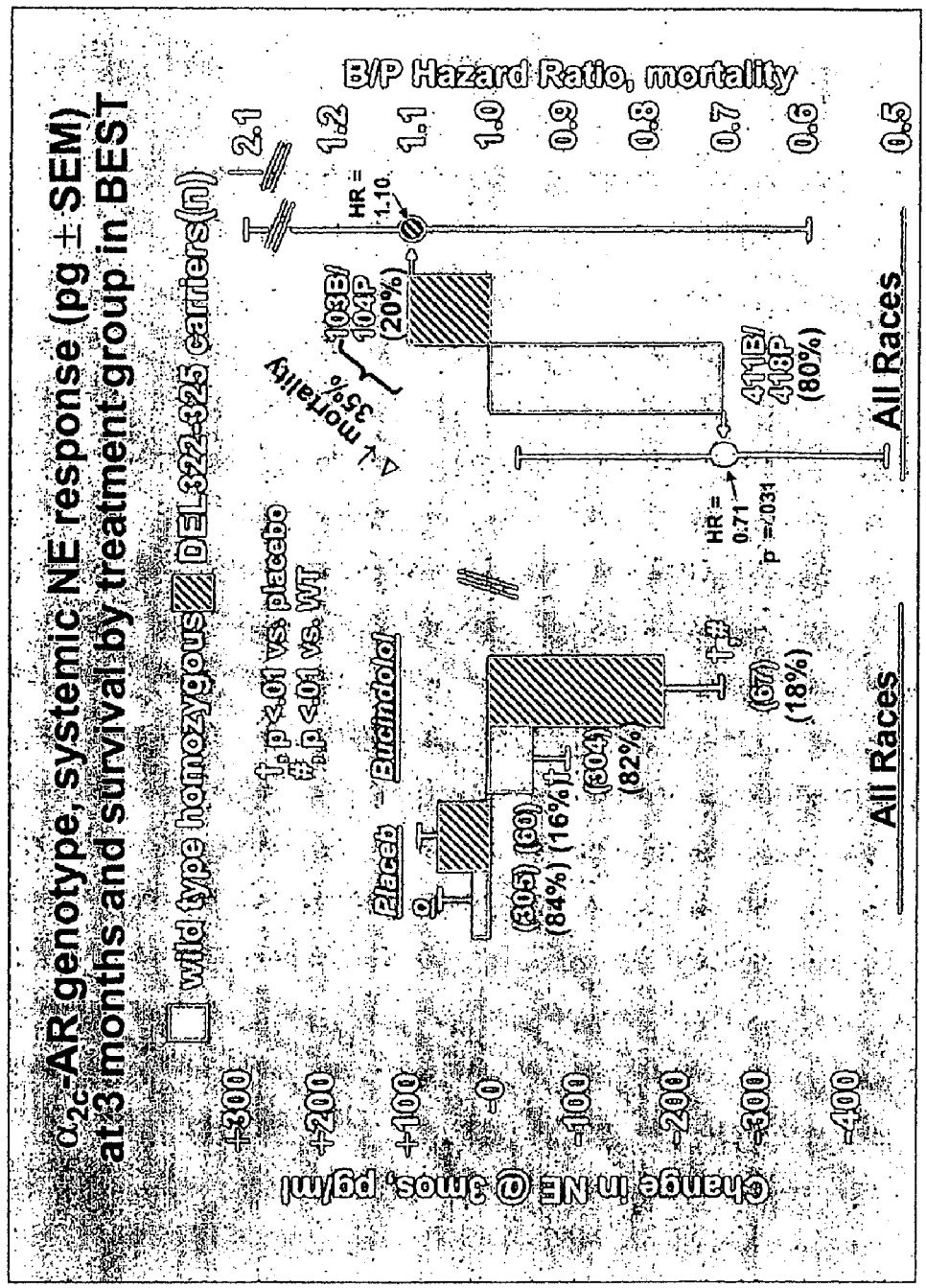
FIG. 19. Correlations between $\alpha_{2c}$AR genotype, systemic norepinephrine response (pg±SEM) in BEST patients after three months, and survival by treatment group among BEST patients.

In the Black subgroup, it appears to be a specific pharmacogenomic profile present in substantial numbers of patients that led to inefficacy and a trend for adverse outcomes with bucindolol treatment. Blacks have a much higher (approximately 10 fold) allele frequency for a loss of function variant of the $\alpha_{2c}$ receptor, involving deletion of amino acids 322-325 in the 3rd intracytoplasmic loop of the receptor protein (Small et al., 2000). Such a loss of function in the $\alpha_{2c}$AR would be expected to increase adrenergic drive, as the normal prejunctional adrenergic inhibitory action of $\alpha_2$ receptors is compromised (Brum et al. 2002). Subjects in BEST and in particular Blacks who were heterozygous or homozygous ($\alpha_{2c}$AR-Del322-325 carriers) for this gene variant had a trend for an increased systemic norepinephrine at baseline, and had a much greater sympatholytic response to bucindolol (FIG. 17). Indeed, approximately 61% of Black subjects in BEST were $\alpha_{2c}$AR-Del322-325 carriers, compared to 8% of non-Blacks (FIG. 18). In subjects who were $\alpha_{2c}$AR-Del322-325 carriers, there was a 10% increase in mortality in the bucindolol treated cohort, compared to a 29% reduction in mortality (p=0.031) in subjects who had the wild type $\alpha_{2c}$AR (FIG. 19).

Figure 20:
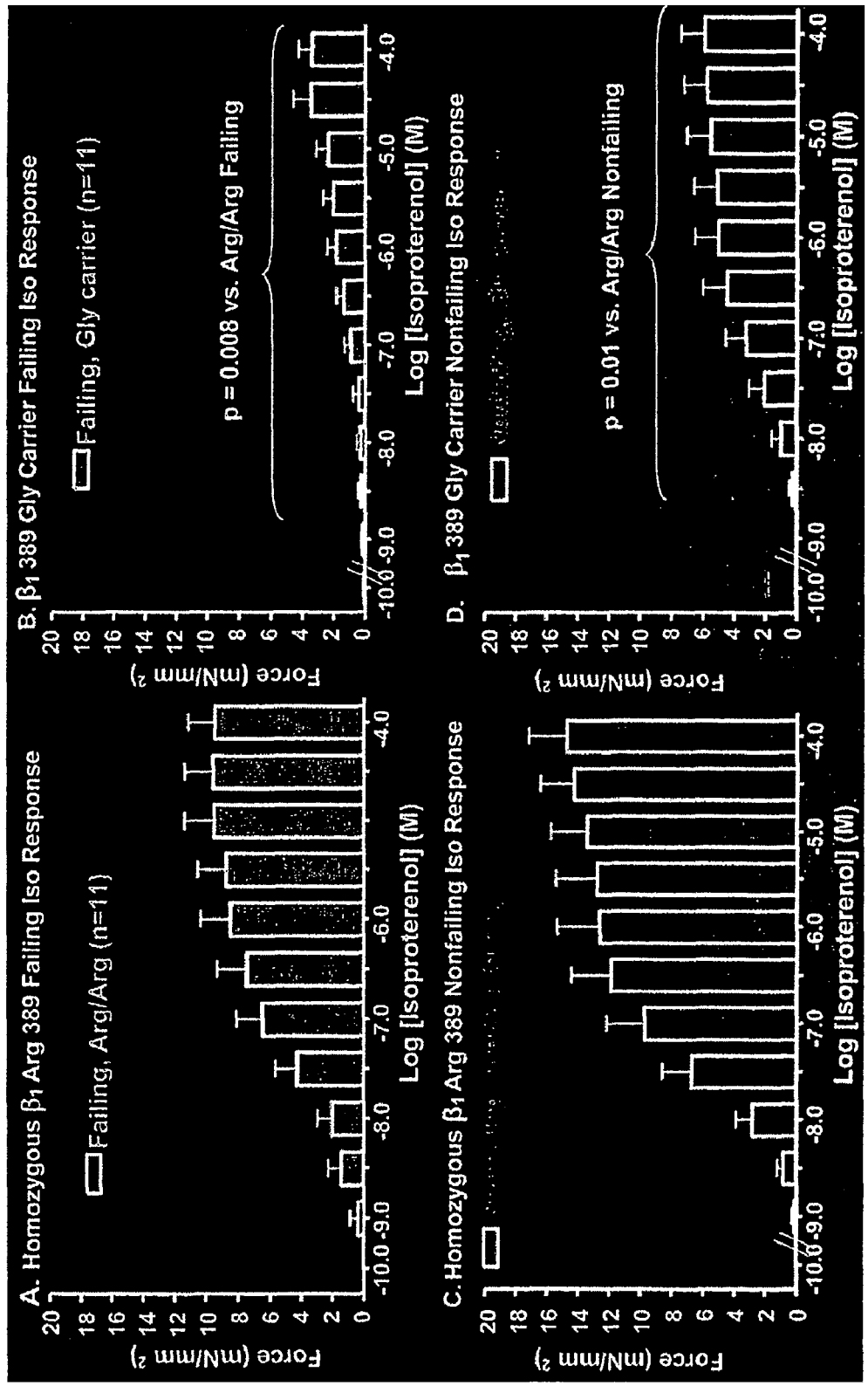
FIGS. 20A-D. Effect of $\beta_1$AR Arg/Gly 389 gene variants on isoproterenol response in isolated human RV trabeculae. A. Homozygous $\beta_1$AR Arg 389 failing Iso response. B. $\beta_1$-AR Gly 389 carrier failing Iso response. C. Homozygous $\beta_1$AR Arg 389 nonfailing Iso response. D. $\beta_1$AR 389 Gly carrier nonfailing Iso response.
Figure 21:
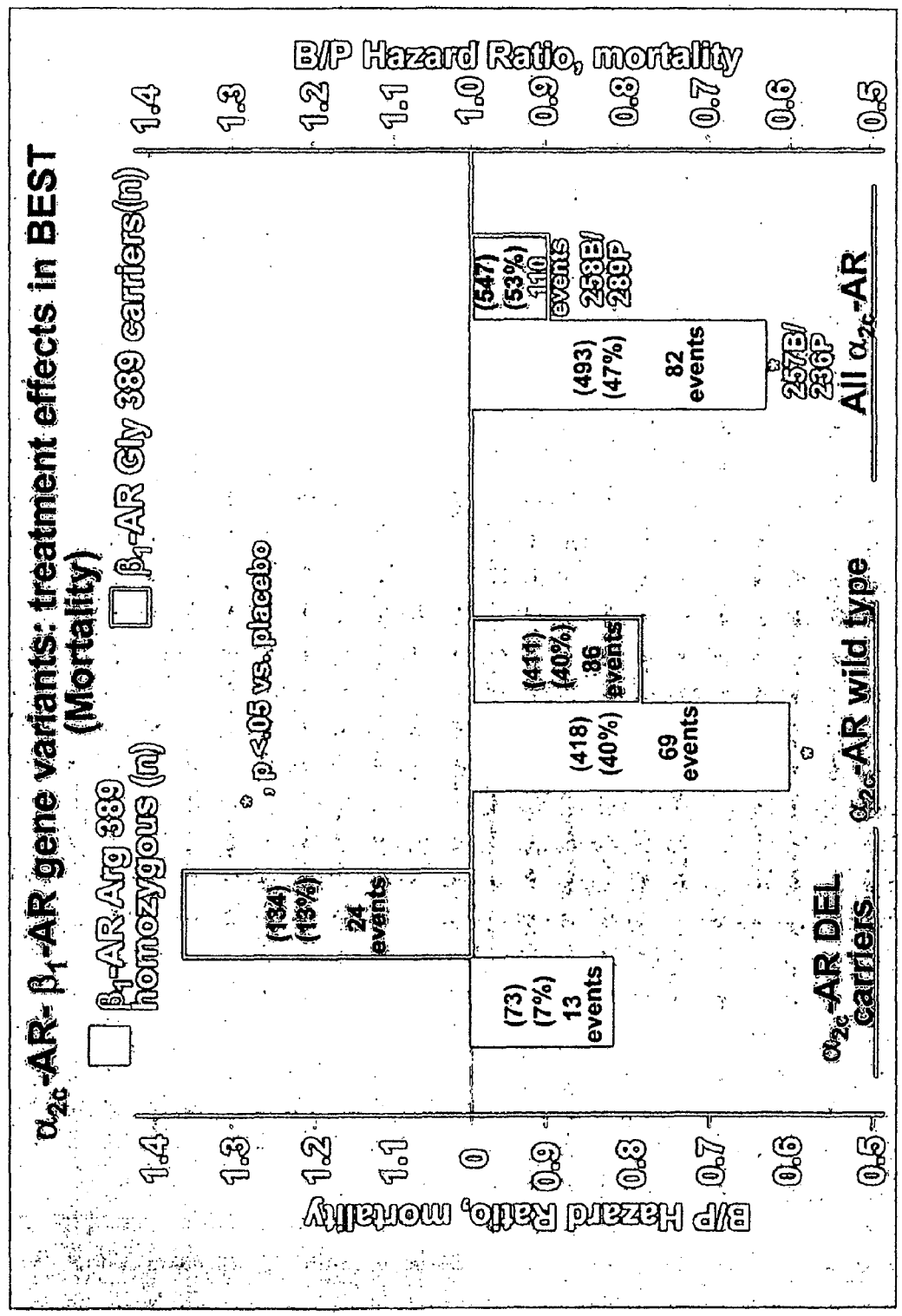
FIG. 21. $\alpha_{2c}$AR and $\beta_1$AR gene variants: treatment effects in BEST (mortality).

Another way to be protected against the sympatholytic effect of bucindolol is to have the high functioning, 389Arg/Arg variant of the $\beta_1$AR (FIG. 15) (Mason et al., 1999), possessed by 47% of the BEST population. As shown in FIG. 20 and Example 4, whether an individual is 389Arg/Arg (Arg homozygous) vs. a 389Gly carrier for the $\beta_1$AR is probably a major determinant of response to β-agonists, even more so than the presence or absence of heart failure. It would be expected that individuals who are $\beta_1$AR-389Arg/Arg would be relatively resistant to the adverse effects of sympatholysis, since even lower levels of norepinephrine would produce a relatively robust inotropic response (FIG. 20). That in fact appears to be the case, as shown in FIG. 19. FIG. 21 indicates that in patients who are $\alpha_{2c}$AR-Del322-325 carriers, the presence of the $\beta_1$AR-389Arg/Arg receptor converts a 36% increase in mortality in $\beta_1$AR-389Gly carriers to an 18% mortality reduction.

Figure 7:
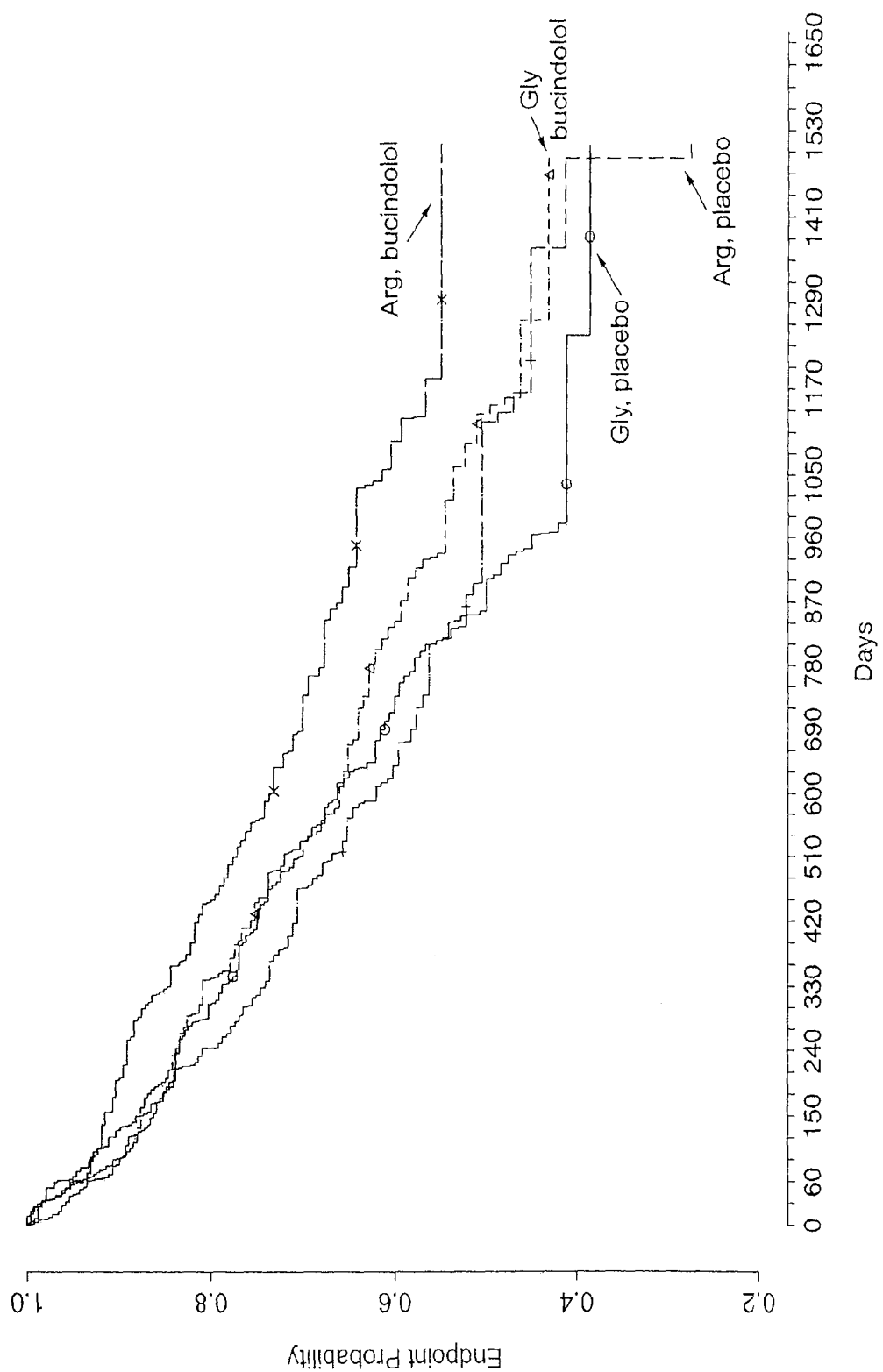
FIG. 7. This graph illustrates the probability of reaching the combined endpoint of death or heart failure hospitalizations in the bucindolol-placebo study stratified by treatment and $\beta_1AR$ genotype.

In addition to protecting against the myocardial depression resulting from sympatholysis, the $\beta_1$AR-389Arg/Arg genotype confers a greater, "hyper-response" to bucindolol (FIGS. 5-7). This is likely because the high functioning $\beta_1$AR-389Arg/Arg variant confers a greater degree of cardiomyopathy. Because of its higher function, the absolute degree of inhibition of signal transduction by bucindolol is much greater, translating into more potential for benefit in patients with the $\beta_1$AR-389Arg/Arg genotype.

Figure 22:
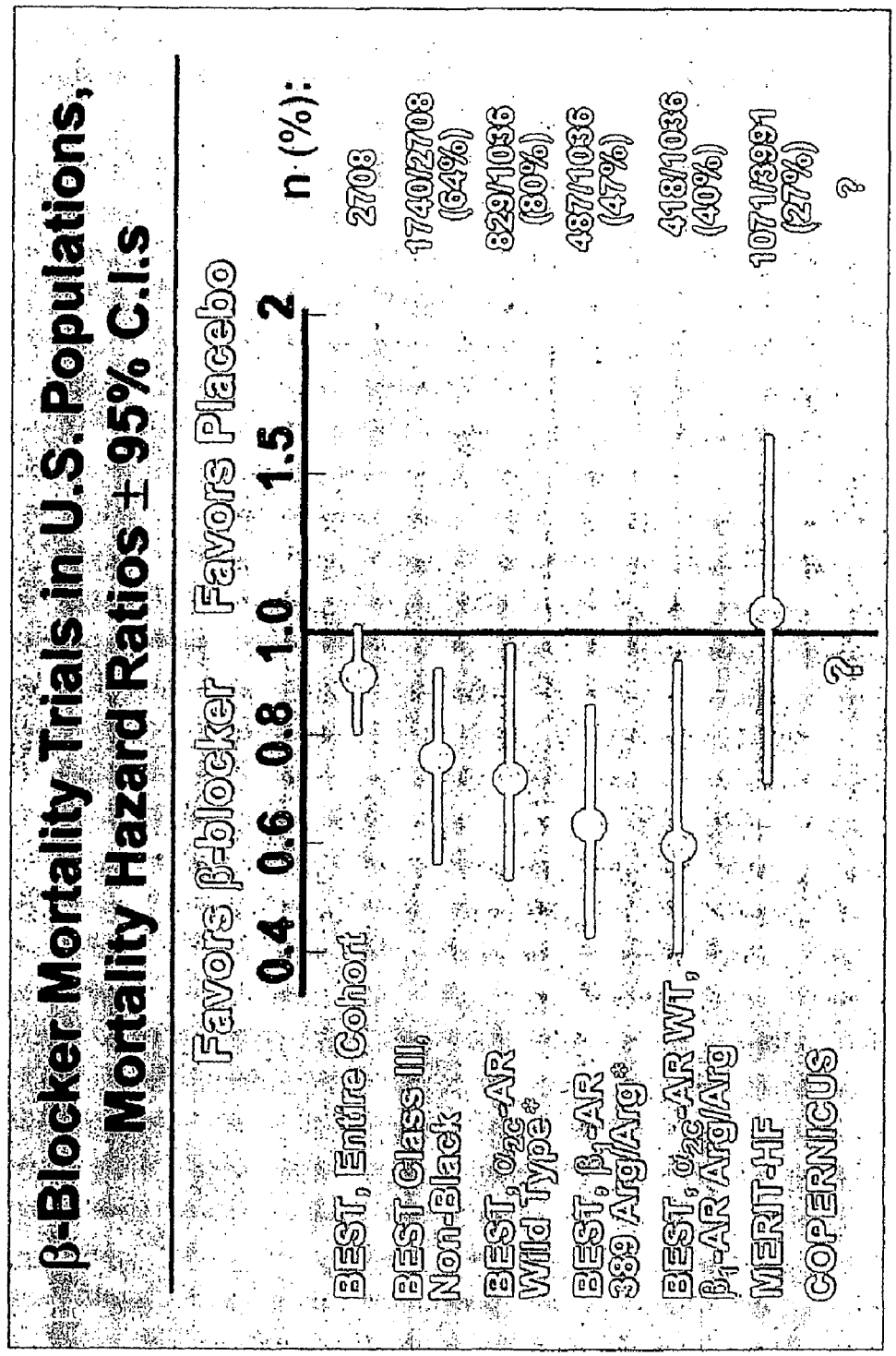
FIG. 22. β-blocker mortality trials in U.S. populations, mortality hazard ratios ±95% C.I.s.

As shown in FIG. 21 and FIG. 20, patients who had the 389Arg/Arg receptor variant had a greater mortality reduction response to bucindolol, in the entire cohort (38% reduction in mortality (p=0.030) vs. a nonsignificant, 10% reduction in Gly carriers), and in the $\alpha_{2c}$AR wild type patients (40% reduction in mortality, (p=0.037), vs. a nonsignificant, 22% reduction in Gly carriers). Therefore, the presence or absence of the hyper-responder marker $\beta_1$AR-389Arg/Arg genotype, is the major determinant of bucindolol response in advanced heart failure patients. FIG. 22 illustrates the progression of increasing efficacy for mortality reduction in BEST using gene variants to define subpopulations. For comparison, the only other $\beta$-blocker heart failure mortality trial to enroll a relatively large number (>500) of U.S. patients, MERIT-HF, is also plotted on FIG. 7. As can be seen, the reduction in mortality in BEST increases from an nonsignificant 10% in the entire cohort to 29% in the 80% of patients who were $\alpha_{2c}$AR wild type, to 38% in the 47% of patients who were $\beta_1$AR-389Arg/Arg, to 40% in the 40% of patients who were both $\alpha_{2c}$AR wild type and $\beta_1$AR-389Arg/Arg. In comparison, the hazard ration for metoprolol CR/XL in U.S. patients enrolled in MERIT-HF was 1.05 (Wedel et al., 2001).

Although it is possible that the $\beta_1$AR-389 genotype-specific data generated from BEST are generally valid for all $\beta$-blockers, there are good reasons to consider that the findings may apply only to bucindolol. First, as discussed above the $\beta_1$AR-389Arg/Arg genotype avoids the adverse effects of sympatholysis, and sympatholysis is unique to bucindolol among $\beta$-blockers used to treat heart failure. Second, to maximally inhibit signaling through the high functioning $\beta_1$AR-389Arg/Arg receptor, it may actually be useful to decrease norepinephrine and block the receptor, a combination of properties possessed only by bucindolol. Finally, the gene variant data generated in the BEST trial with bucindolol may be considered to be valid only in advanced, Class III-IV heart failure. It may well be that in less advanced (NYHA Class I-II) heart failure bucindolol would be the drug of choice in subjects with a combination of $\alpha_{2c}$AR-Del322-325 carrier plus $\beta_1$AR-389Arg/Arg, since sympatholysis and loss of myocardial function support would be less of an issue in this patient population, and individuals who have the haplotype of $\alpha_{2c}$AR-Del/Del+$\beta_1$AR-389Arg/Arg have a 10 fold increased risk of developing heart failure (Small et al., 2002). Bucindolol could potentially be the ultimate therapy for these patients, because it lowers norepinephrine (thereby dealing with the impact of the $\alpha_{2c}$AR-Del322-325 allele), and blocks the $\beta_1$AR.

Figure 23:
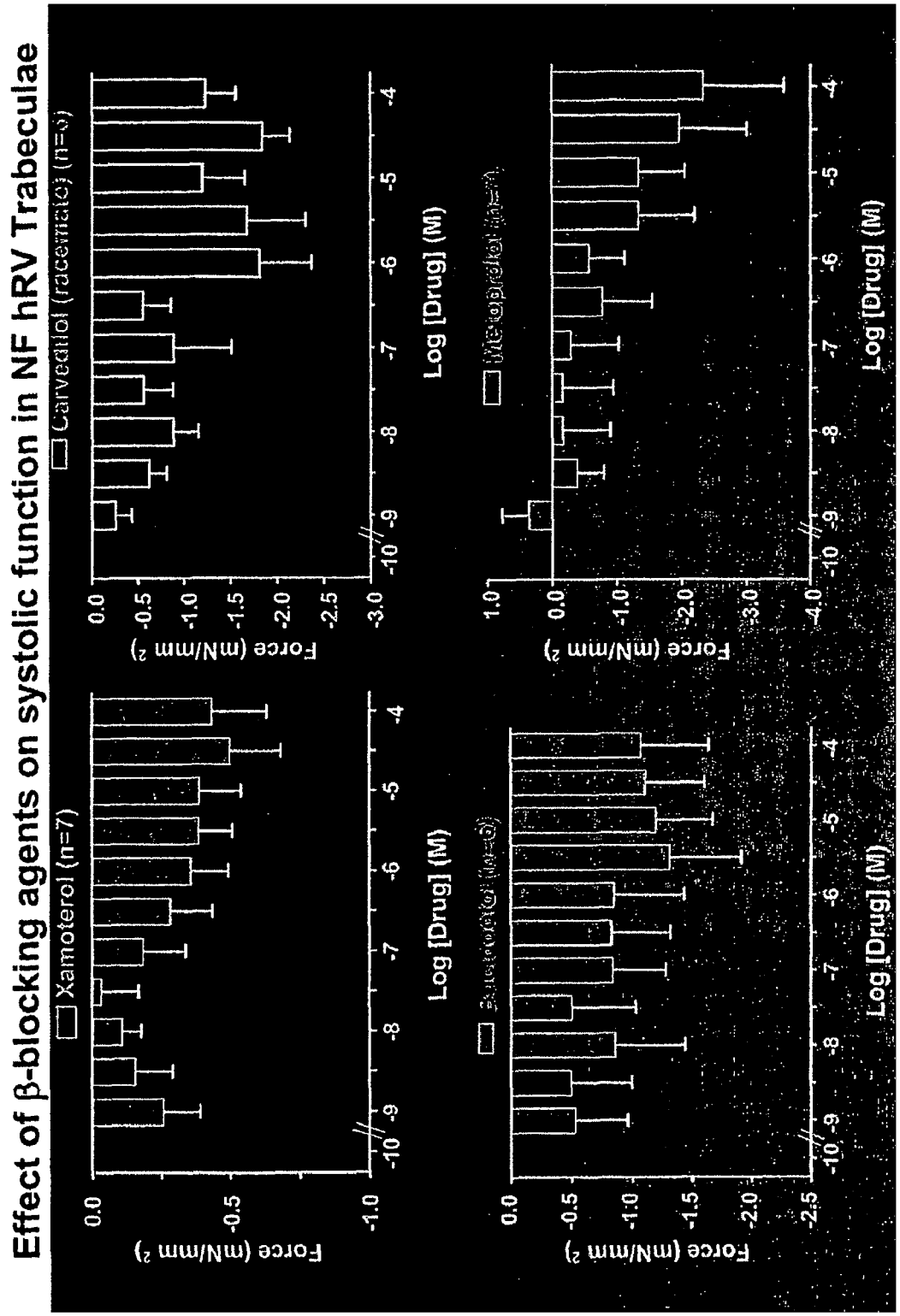
FIG. 23. Effect of β-blocking agents on systolic function in NF hRV trabeculae.
Figure 24:
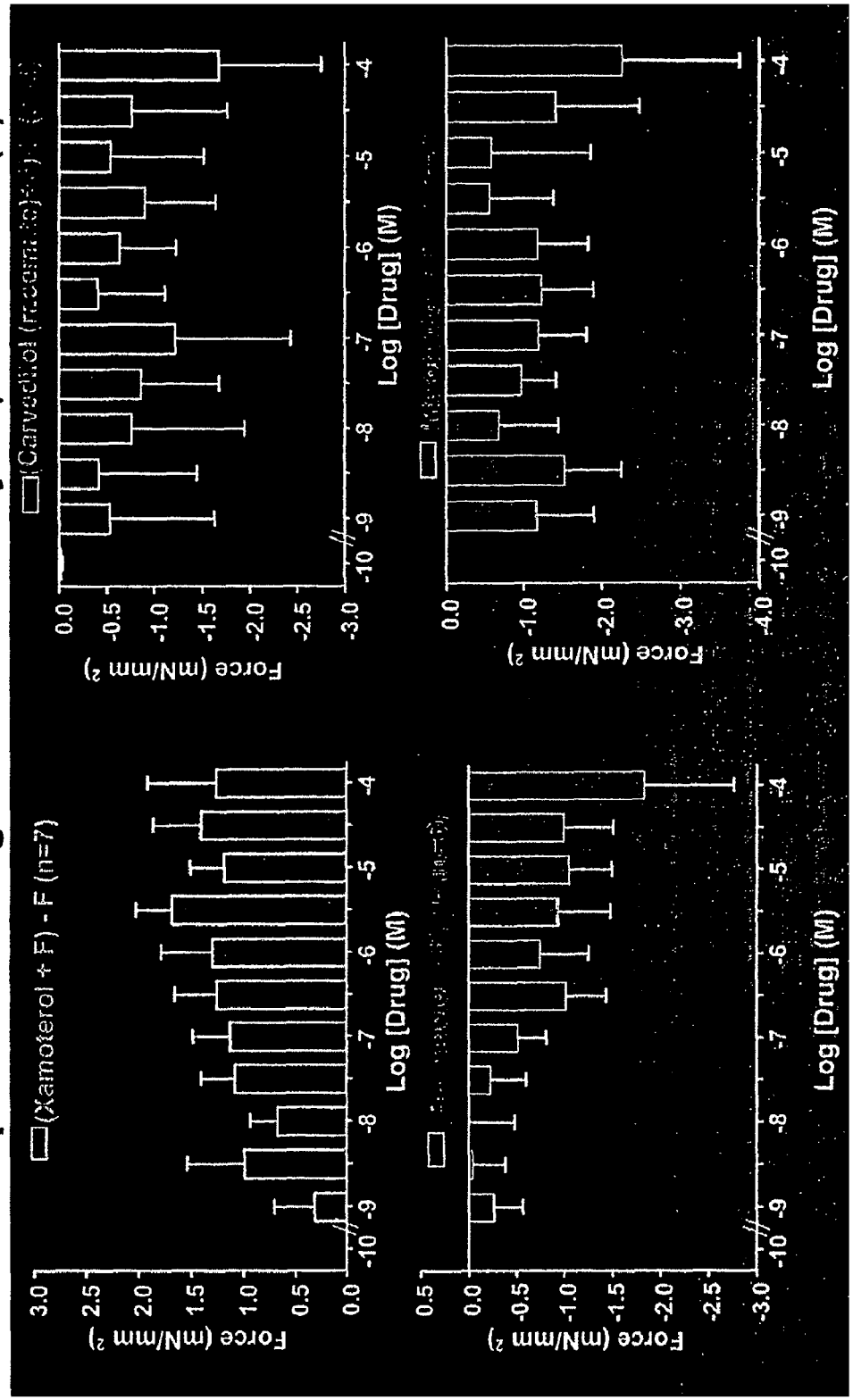
FIG. 24. Effect of β-blocking agents on systolic function in NF hRV trabeculae with amplification of signal transduction by 10 μM forskolin (F) treatment.
Figure 25:
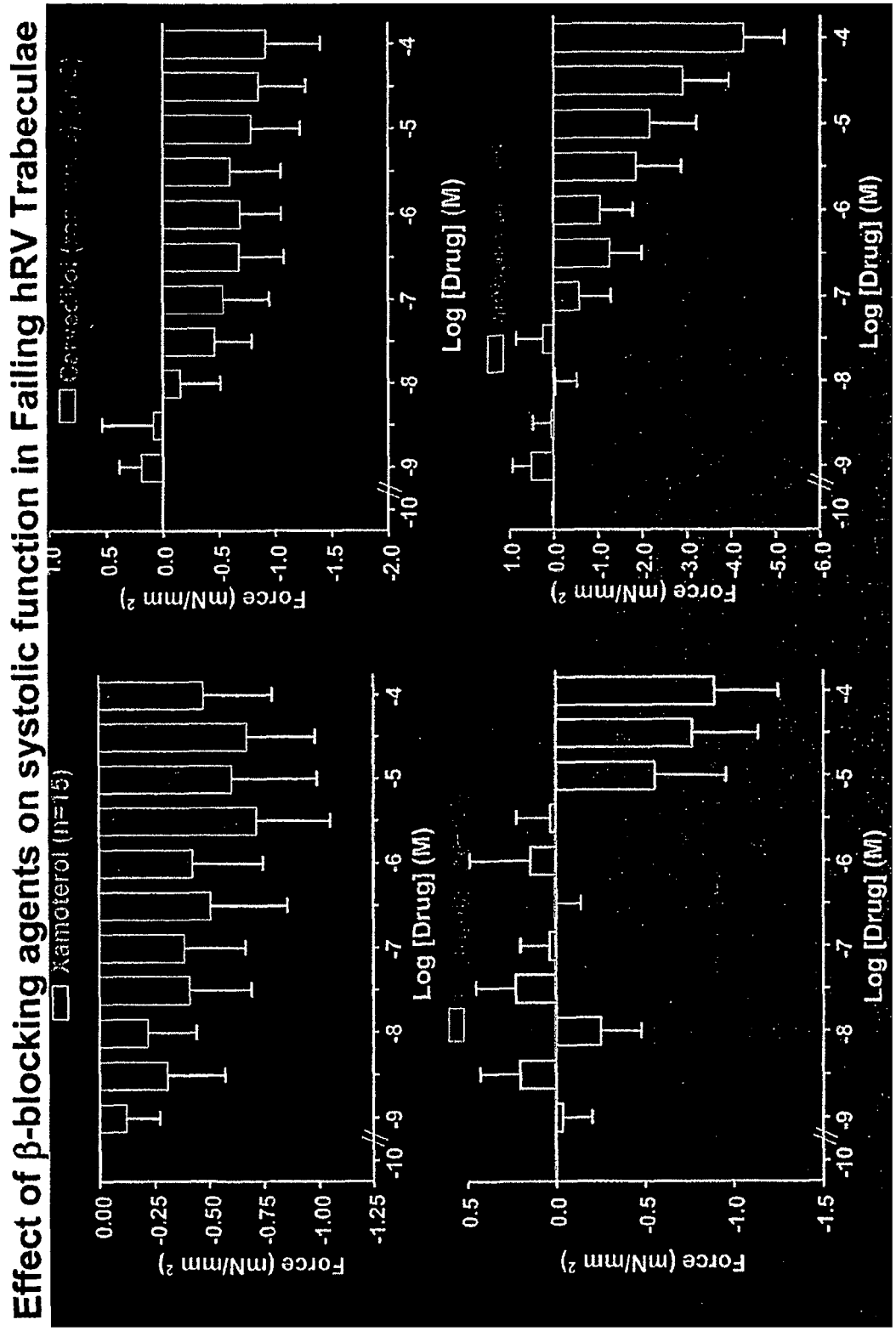
FIG. 25. Effect of β-blocking agents on systolic function in failing hRV trabeculae.
Figure 26:
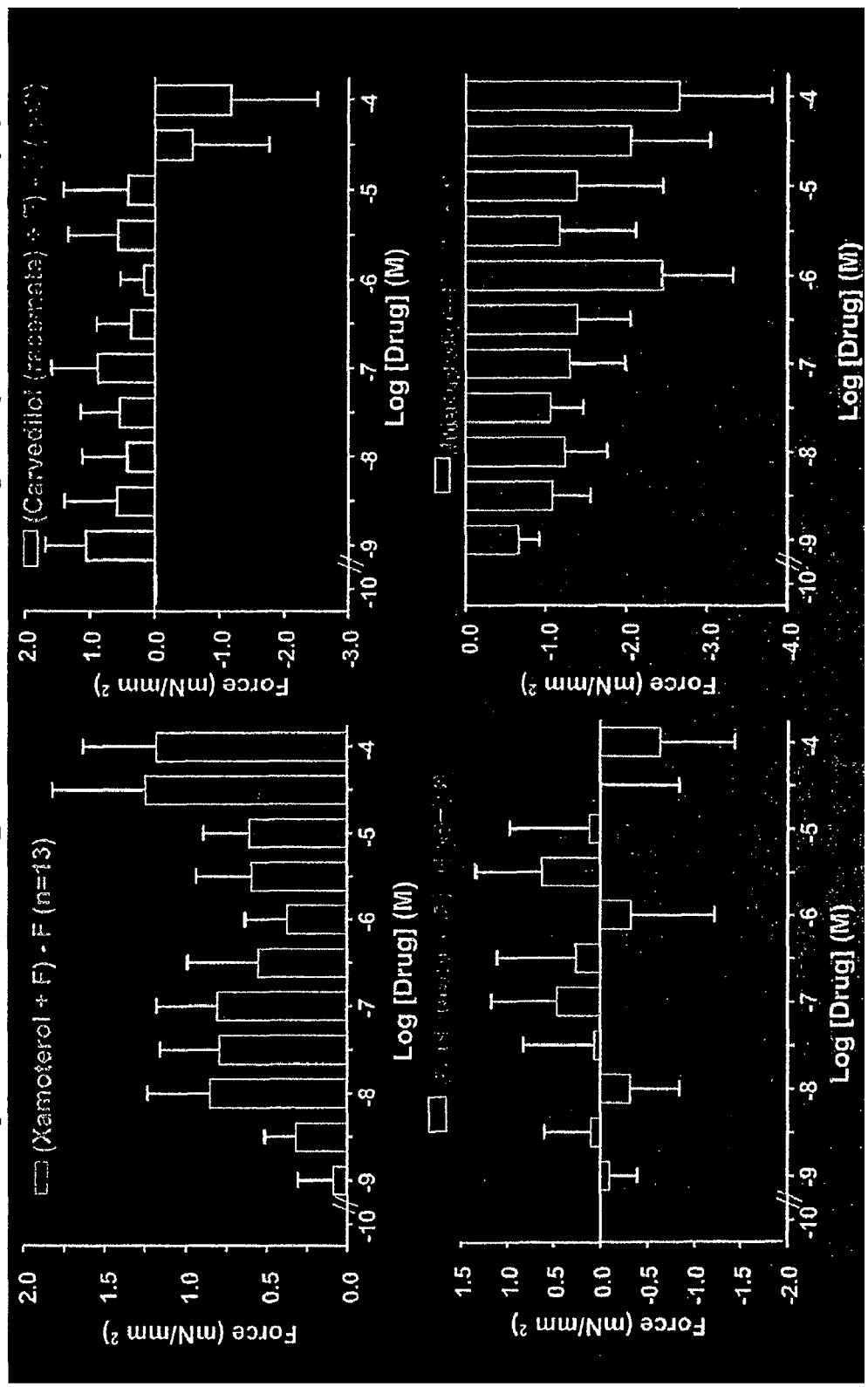
FIG. 26. Effect of β-blocking agents on systolic function in failing hRV trabeculae with amplification of signal transduction by 10 μM forskolin (F) treatment.

There has been controversy in the literature as to whether bucindolol has intrinsic sympathomimetic activity (ISA) in the human heart, a property that has been offered as the explanation for bucindolol's BEST Trial results. Although bucindolol clearly has ISA in rodent myocardium, extensive studies from the inventors indicate that bucindolol has extremely low inverse agonist activity without any ISA, in functioning human ventricular myocardium. As shown in Bristow et al., 1998, bucindolol does not increase nighttime heart rate on Holter monitoring, considered to be the most sensitive indicator of ISA in the human heart and a test capable of easily identifying the ISA of xamoterol or celiprolol (Xameterol Study Group, 1990; Silke et al., 1997). In addition, extensive studies performed by the inventors in isolated human heart preparations, bucindolol exhibited no evidence of ISA in nonfailing (FIGS. 23 and 24) or failing human hearts (FIGS. 25 and 26). In fact, in failing heart, carvedilol gives more of a positive inotropic signal than bucindolol, in forskolin pretreated preparations (required to augment signal transduction for detection of weak ISA) (FIG. 26). In BEST, the more favorable response of bucindolol in high functioning $\beta_1$AR-389 Arg/Arg variant is further evidence against ISA of bucindolol in human ventricular myocardium.

Example 8

Best Trial Revisited

A DNA substudy of BEST, conducted in 1040 patients, tested prospective hypotheses regarding two adrenergic receptor polymorphisms that, based on work in model systems (Mialet et al., 2003) or in epidemiological heart failure studies (Small et al., 2002), had the potential to interact with the treatment effect of bucindolol. These two adrenergic receptor gene variants, both of which exhibit differential allele frequencies in Blacks vs. non-Black populations, were found to markedly affect treatment outcomes in BEST. The first was the $\alpha_{2c}$ DEL 322-325 polymorphism, a loss of function gene variant that increases adrenergic drive and predisposes to an exaggerated sympatholytic effect of bucindolol. Patients who were $\alpha_{2c}$ DEL 322-325 carriers and were treated with bucindolol had an average reduction in norepinephrine at 3 months of 153±57 (SEM) pg/ml, compared to a reduction of 50±13 pg/ml in $\alpha_{2c}$ WT/WT patients treated with bucindolol (p=0.008). In BEST such exaggerated sympatholytic responses were associated with a statistically significant, 1.7 fold increase in mortality (Bristow et al., 2004). There were two clinical or demographic subgroups who were predisposed to marked sympatholysis, Class IV patients and Blacks, the only two subgroups who had mortality hazard ratios >1.0 in BEST (BEST Writing Committee, 2001). The allele frequency of $\alpha_{2c}$ DEL 322-325 was 0.42 in Blacks, and 0.04 in non-Blacks (p<0.0001). As shown in column 3 of Table 9, patients in BEST who were homozygous wild type (WT/WT) for the $\alpha_{2c}$-adrenergic receptor had a 30% reduction in all-cause mortality (p=0.031) and a 41% reduction in cardiovascular mortality (p=0.004), whereas patients who were carriers of the DEL 322-325 polymorphism had a 9% increase (p=NS) in all-cause mortality, and 3% increase in cardiovascular mortality (p=NS). Overall, 80% of the BEST trial, which was comprised of 24% Blacks, was $\alpha_{2c}$ WT/WT, including 34% of Blacks. Thus simply screening for the presence of the DEL 322-325 polymorphism and treating only the 85% of the U.S. population who are homozygous wild type for the $\alpha_{2c}$-adrenergic receptor would eliminate the increased sympatholysis/mortality risk of bucindolol in advanced heart failure populations, and enhance its therapeutic profile. As developed below, patients who are $\alpha_{2c}$ DEL 322-325 carriers may be treated with bucindolol if they have the 13, 389Arg/Arg genotype (genotype prevalence in BEST of 0.32 in Blacks and 0.51 in non-Blacks), so the population eligible for bucindolol is 85%+6%=91% of the total U.S. heart failure population, based on racial percentages of 12% Black and 88% non-Black. In addition, over 50% of Blacks (34%+21%=55%) could be treated with bucindolol using genotype selection.

The other adrenergic receptor polymorphism found to influence the treatment effect of bucindolol in BEST was the $\beta_1$ 389Arg/Gly SNP, where the Arg/Arg higher functioning variant conferred a "hyper-response" to bucindolol (Table 9, column 5) compared to the presence of the Gly allele ("Gly carriers" column 6, Table 9). The evidence that the 389Arg/Arg variant exhibits higher signal transduction function than Gly carrier variants was provided in the information package of the Mar. 28, 2005 meeting, and the evidence that the 389Arg allele is more cardiomyopathic than the 389Gly has been published by Dr. Liggett's group (Mialet et al., 2003). As can be seen in Table 9, patients in BEST who were 389Arg/Arg had a 38% (p=0.030) reduction in all-cause mortality, and a 46% reduction in cardiovascular mortality (p=0.015) from bucindolol, compared to respective mortality reductions of 10% and 22% (both p=NS) in patients who were 389Gly carriers. Since there is no evidence that carvedilol (Small et al., 2002) or metoprolol CR/XL (White et al., 2003) possess a markedly differentiated therapeutic response between $\beta_1$ 389Arg/Arg and $\beta_1$ 389Gly carriers, it is likely that bucindolol's salutary effects in patients with the $\beta_1$ 389Arg/Arg receptor gene variant are due to the combination of lowering norepinephrine signaling and receptor competitive antagonism. In that regard, Dr. Bristow's group has presented evidence based on physiologic and molecular/bio marker data that heart failure patients treated with full therapeutic doses of β-blocking agents exhibit evidence of ongoing myocardial adrenergic signaling (Lowes et al., 2001), and so lowering of norepinephrine in patients with the $\beta_1$ 389Arg/Arg high functioning receptor variant may offer additional benefit.

Moreover, patients who were both $\beta_1$ 389Arg/Arg and $\alpha_{2c}$-WT/WT (column 8, Table 9) had a 40% reduction in all-cause mortality (p=0.037), a 47% reduction in cardiovascular mortality (p=0.020), and a 39% reduction in mortality+heart failure hospitalization (p=0.002), or therapeutic responses that are much greater than in the entire BEST cohort or in the cognate opposite diplotypes. In that regard, column 11 in Table 9 indicates that patients who were both $\alpha_{2c}$ DEL 322-325 and $\beta_1$ 389Gly carriers had a 35% increase in all-cause mortality, and a 36% increase in CV mortality in BEST. The obvious explanation for these adverse responses is that advanced heart failure patients who have the low-functioning 389Gly carrier $\beta_1$-adrenergic receptor cannot tolerate the exaggerated sympatholytic response associated with the $\alpha_{2c}$ DEL carrier state. In contrast, patients with the high functioning (389Arg/Arg) $\beta_1$-receptor, which is characterized by robust responses to low concentrations of catecholamines, have no such adverse effect on total or cardiovascular mortality (Table 9, column 9). Although the relatively small number of patients and events precluded statistical significance for either mortality endpoint in the {$\alpha_{2c}$ DEL 322-325 and $\beta_1$ 389Gly carrier} subgroup, the congruence of these findings with both the sympatholytic data and the molecular pharmacology of the adrenergic receptor polymorphisms argues for their scientific and clinical importance when the issue is patient safety.

In BEST, the $\beta_1$ 389Arg/Arg allele frequency was 0.72 in non-Blacks, but only 0.57 in Blacks (p<0.0001). Thus in BEST Blacks had a higher frequency of an allele that predisposed to increased mortality ($\alpha_{2c}$ DEL 322-325), and a lower frequency of the "hyper-response" $\beta_1$ 389Arg/Arg allele. Both of these genetic differences in American Blacks likely contributed to the trend towards an adverse outcome in this demographic group (BEST Writing Committee, 2001).

The pharmacogenomic substudies of BEST used prospective hypotheses based on the anticipated pharmacologic interaction of bucindolol with specific adrenergic receptor polymorphisms that had been previously extensively investigated in model and human systems. Accordingly, it is believed that these pharmacogenomic hypotheses are more valid than standard, retrospectively derived, subgroup analyses.

The pharmacogenetic data analyzed from the BEST trial are included below. The population that agreed to the DNA substudy and pharmacogenomic analysis was not different from the entire cohort in baseline characteristics. In addition, there was no evidence of a gene dose effect for either polymorphism; heterozygote effects were the same or greater as in homozygotes. Because of this, both the $\alpha_{2c}$ DEL 322-325 and $\beta_1$ 389Gly alleles are assumed to act as dominant negatives.

TABLE 9

| Endpoint | BEST entire cohort bucindolol (n = 2708) mean f/u 2.0 yrs | BEST $\alpha_{2c}$ wt/wt bucindolol (n = 829/1036) mean f/u 2.0 yrs | BEST $\alpha_{2c}$ DEL carrier bucindolol (n= 207/1036) mean f/u 2.0 yrs | BEST $\beta_1$ 389Arg/Arg bucindolol (n = 493/1040) mean f/u 2.0 yrs | BEST $\beta_1$ 389 Gly carrier bucindolol (n = 547/1040) mean f/u 2.0 yrs |
|---|---|---|---|---|---|
| Mortality | 0.90; 860 Ev (0.78, 1.02) p = 0.10 | 0.70; 155 Ev (0.51, 0.97) p = 0.031 | 1.09; 37 Ev (0.57, 2.08) p = 0.79 | 0.62; 82 Ev (0.40, 0.96) p = 0.030 | 0.90; 111 Ev (0.62, 1.30) p = 0.57 |
| CV Mortality | 0.86; 731 Ev (0.74, 0.99) p = 0.040 | 0.59; 130 Ev (0.42, 0.85) p = 0.004 | 1.03; 32 Ev (0.52, 2.07) p = 0.92 | 0.54; 66 Ev (0.33, 0.89) p = 0.015 | 0.78; 97 Ev (0.52, 1.18) p = 0.24 |
| Mortality + HF Hospitalization | 0.81; 1421 Ev (0.73, 0.90) p < 0.0001 | 0.72; 341 Ev (0.59, 0.90) p = 0.003 | 0.89; 84 Ev (0.58, 1.37) p = 0.60 | 0.66; 190 Ev (0.50, 0.88) p = 0.004 | 0.87; 236 Ev (0.62, 1.30) p = 0.25 |
| HF Hospitalization | 0.78; 1045 Ev (0.69, 0.88); p < 0.001 | 0.74; 267 Ev (0.58, 0.95) p = 0.016 | 0.76; 67 Ev (0.47, 1.24) p = 0.27 | 0.64; 154 (0.48, 0.90) p = 0.006 | 0.86; 181 Ev (0.64, 1.15) p = 0.30 |

| | BEST $\beta_1$ 389Arg/Arg + $\alpha_{2c}$ WT/WT bucindolol (n = 418/1036) mean f/u 2.0 | BEST $\beta_1$ 389Arg/Arg + $\alpha_{2c}$ DEL carriers bucindolol (n = 73/1036) mean f/u 2.0 | BEST $\beta_1$ 389 Gly carriers + $\alpha_{2c}$ WT/WT bucindolol (n = 411/1036) mean f/u 2.0 | BEST $\beta_1$ 389 Gly carriers + DEL carriers bucindolol (n = 134/1036) mean f/u 2.0 | MERIT-HF US Pts metoprolol CR/XL (n = 1071/3991) mean f/u 1.0 |
|---|---|---|---|---|---|

TABLE 9-continued

| Endpoint | yrs | yrs | yrs | yrs | yrs |
|---|---|---|---|---|---|
| Mortality | 0.60; 69 Ev<br>(0.38, 0.97)<br>p = 0.037 | 0.71; 13 Ev<br>(0.24, 2.11)<br>p = 0.53 | 0.82; 86 Ev<br>(0.54, 1.26)<br>p = 0.37 | 1.35; 24 Ev<br>(0.61, 3.02)<br>p = 0.46 | 1.05; 100 Ev<br>0.71, 1.56<br>p = NS |
| CV Mortality | 0.53; 56 Ev<br>(0.31, 0.90)<br>p = 0.020 | 0.58; 73 Ev<br>(0.17, 2.02)<br>p = 0.39 | 0.67; 411 Ev<br>(0.42, 1.07)<br>p = 0.09 | 1.36; 22 Ev<br>(0.59, 3.15)<br>p = 0.47 | ~0.96; 90 Ev<br>p = NS |
| Mortality + HF<br>Hospitalization | 0.61; 156 Ev<br>(0.44, 0.84)<br>p = 0.002 | 0.85; 34 Ev<br>(0.43, 1.69)<br>p = 0.64 | 0.86; 185 Ev<br>(0.64, 1.16)<br>p = 0.32 | 0.81; 50 Ev<br>(0.46, 1.43)<br>p = 0.47 | ~0.84; 200 Ev<br>(0.61, 1.12)<br>p = NS |
| HF<br>Hospitalization | 0.59; 126 Ev<br>(.41, .84)<br>p = 0.004 | 0.81; 73 Ev<br>(0.38, 1.72)<br>p = 0.59 | 0.93; 411 Ev<br>(0.67, 1.29)<br>p = 0.66 | 0.62; 134 Ev<br>(0.32, 1.21)<br>p = 0.16 | NA |

Effects of β-blockers vs. placebo in the only available/published data from intention-to-treat mortality trials conducted in U.S. heart failure patients.
Ev = Events; NA, not available Example 9

Additional Studies: Design I

Figure 27:
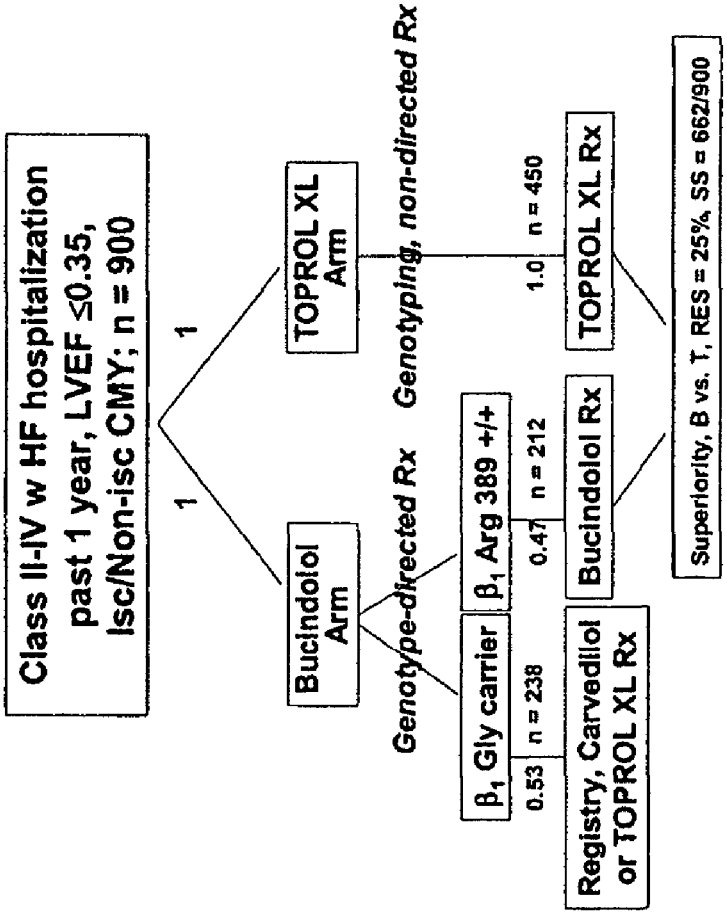
FIG. 27. Study Design I.

For ethical reasons it is no longer possible to perform placebo-controlled trials with β-blockers in patients with heart failure caused by a primary or secondary dilated cardiomyopathy. This leaves as design options non-inferiority or superiority studies against an active β-blocker control, or alternatively comparison of the bucindolol response between gene variants. A non-inferiority design option would appear to be eliminated by the lack of receptor gene variant data for any other agent (among other Phase III trials only MERIT-HF had a pharmacogenomic substudy (Small et al., 2002), and that was too small to reach any meaningful conclusions). Shown in FIG. 27 as Study Design I is a possible study scheme that would compare the combination of genotype targeting and bucindolol to non-targeted therapy with metoprolol CR/XL, using a primary endpoint of time to death or heart failure hospitalization. In Design I, patients randomized to bucindolol who are $β_1$AR-389Gly carriers would not be entered into the study, since based on BEST data the response to bucindolol is not sufficient to warrant further evaluation. These patients would instead enter a registry where a minimum of information, likely confined to vital status, would be captured as they are treated in whatever way their treating physicians choose. The primary comparison of Design I would be between $β_1$AR-389Arg/Arg patients treated with bucindolol, and all genotypes treated with metoprolol CR/XL (TOPROL XL) non-targeted therapy. The total randomized sample size for Design I would be 900, with 662 subjects participating in the primary outcome comparison.

Example 10

Additional Studies: Design II

In Study Design II (FIG. 28) for an additional study design, patients with symptomatic and advanced heart failure (reinforced by the heart failure hospitalization history over the preceding year; therefore, patients who are Class II at the time of screening are allowed in the trial) and LVEFs ≦0.35 (the general description of the BEST Trial population) are initially screened for the absence of the $α_{2c}$ 322-325 DEL polymorphism, in the carrier state (either heterozygous or homozygous). This restriction eliminates much of the adverse effect of sympatholysis from bucindolol, primarily manifested as a trend for increased mortality in BEST (hazard ratio 1.09, column 4, Table 9) and in MOXCON, and it is anticipated that bucindolol would have a slight advantage compared to metoprolol CR/XL in the remaining genotypes being treated in a pure $α_{2c}$ homozygous wild type (WT/WT) adrenergic receptor background.

The primary endpoint of the trial is noninferiority against metoprolol CR/XL (TOPROL-XL), using the 95% upper confidence limit (UCL) of the time to mortality plus heart failure hospitalization endpoint hazard ratio that was measured in the MERIT-HF trial (Hjalmarson et al. 2000). Though the MERIT-HF Trial included all genotypes, only 208 (5.2%) of the 3991 enrolled patients were Black. Alpha$_{2c}$ 322-325 DEL carriers are highly over-represented in Black subjects (in the BEST Trial the $α_{2c}$ 322-325 DEL allele frequency was 0.423 in Blacks vs. 0.043 in non-Blacks, while the DEL carrier prevalence was 66% in Blacks, vs. 8% in non-Blacks). Therefore, the MERIT-HF Trial was likely approximately 90% $α_{2c}$ wild type, or comparable genotypically to the proposed study population in Design II. In addition, since metoprolol CR/XL has no sympatholytic effects there is no reason to expect a differential response to metoprolol CR/XL in $α_{2c}$ wild type vs. DEL carriers. The 95% upper confidence limit for the hazard ratio (UCL) for bucindolol:metoprolol CR/XL ("noninferiority margin") has been determined from the formula (Hasselblad et al., 2001) {(UCL bucindolol:metoprolol CR/XL)*(UCL metoprolol CR/XL: placebo)≦1.0}; using the MERIT-HF entire cohort UCL of 0.80 for metoprolol:placebo yields x*0.80≦1.0, or a noninferiority margin x≦1.25. The 1.25 value was then reduced to 1.16, to provide greater certainty on noninferiority. The target UCL of 1.16 is also the value obtained when scaling the MERIT-HF hazard ratio/UCL up from the observed values of 0.69/0.80 to a hazard ratio of 1.0. The power estimate of 85% for a 2-sided α=≦0.05 was then determined from an expected hazard ratio of 0.90 (the slight advantage of bucindolol in an $α_{2c}$ WT/WT population, gained through bucindolol's better inhibition of $β_1$-389 Arg/Arg and/or its myocardial $β_2$-receptor blockade).

Support for an advantage of bucindolol over metoprolol CR/XL is provided by the U.S. enrolled patients in MERIT-HF (Table 9), who when treated with metoprolol CR/XL had a mortality increase of 5% and a mortality+HF hospitalization decrease of 16%. In contrast, in BEST the entire cohort had a mortality reduction of 10% (p=0.10) and a mortality+HF hospitalization decrease of 19% (p<0.0001), while the $α_{2c}$ wild type patients had a mortality reduction of 30% (p=0.031), and a mortality plus HF hospitalization reduction of 28% (p=0.003). Dividing the hazard ratios (0.72/0.84) yields an expected hazard ratio of 0.86, and an effect size for bucindolol vs. metoprolol CR/XL of 1.00-0.86, or 0.14. Thus it is not unreasonable to expect a 10% difference in favor of bucindolol vs. metoprolol CR/XL in a U.S. population that is $\alpha_{2c}$ WT/WT. By the criterion proposed in FIG. 28, regardless of the bucindolol/metoprolol hazard ratio, if the UCL is <1.16, the conclusion would be that bucindolol is noninferior to metoprolol CR/XL for effects on time to mortality or HF hospitalization, in an advanced HF population that is 100% $\alpha_{2c}$-adrenergic receptor homozygous wild type.

The second part of the trial design is intended to provide additional evidence that pharmacogenomically targeted bucindolol is superior to non-targeted metoprolol CR/XL, as a secondary endpoint. Here the population treated with bucindolol is $\beta_1$-389 Arg/Arg patients who also are $\alpha_{2c}$ wild type. In BEST 47% of the entire cohort was $\beta_1$-389 Arg/Arg, as were 50% of the $\alpha_{2c}$ wild type patients. As shown in Table 9, the diplotype of $\beta_1$-389 Arg/Arg+$\alpha_{2c}$ wild type exhibited a 40% reduction in mortality (p=0.037), a 39% reduction in mortality+HF hospitalization (p=0.002), and a 41% reduction in HF hospitalization (p=0.004). The expected hazard ration for mortality+HF hospitalizations for bucindolol:metoprolol CR/XL (MERIT U.S. data) would be 0.61/0.84, or 0.73. Using an effect size of 27% in bucindolol-treated $\beta_1$-389 Arg/Arg+$\alpha_{2c}$ wild type diplotype patients vs. metoprolol CR/XL yields a power calculation of 81%. Thus in the proposed trial shown in FIG. 28, the noninferiority margin for the primary endpoint is conservatively based on the entire cohort results of MERIT-HF, while the power calculations for both the primary and secondary endpoints incorporate an expected advantage of bucindolol in the selected genotypes, based on actual data in U.S. populations for both bucindolol and metoprolol CR/XL. Support for the validity of this comparison is that in the BEST Trial DNA substudy, $\beta_1$-389 Arg/Arg patients treated with placebo had identical event rates to $\beta_1$-389 Gly carrier patients treated with placebo (FIGS. 6 and 7). In other words, as shown in FIG. 7, the more favorable event rate in $\beta_1$-389 Arg/Arg patients treated with bucindolol is entirely due to the treatment effect, not to a better natural history of patients with the $\beta_1$-389 Arg/Arg genotype. This 1st order secondary endpoint will provide clinicians with further evidence that genotype targeting with bucindolol produces better clinical results than non-targeted therapy with an approved heart failure β-blocker.

Figure 28:
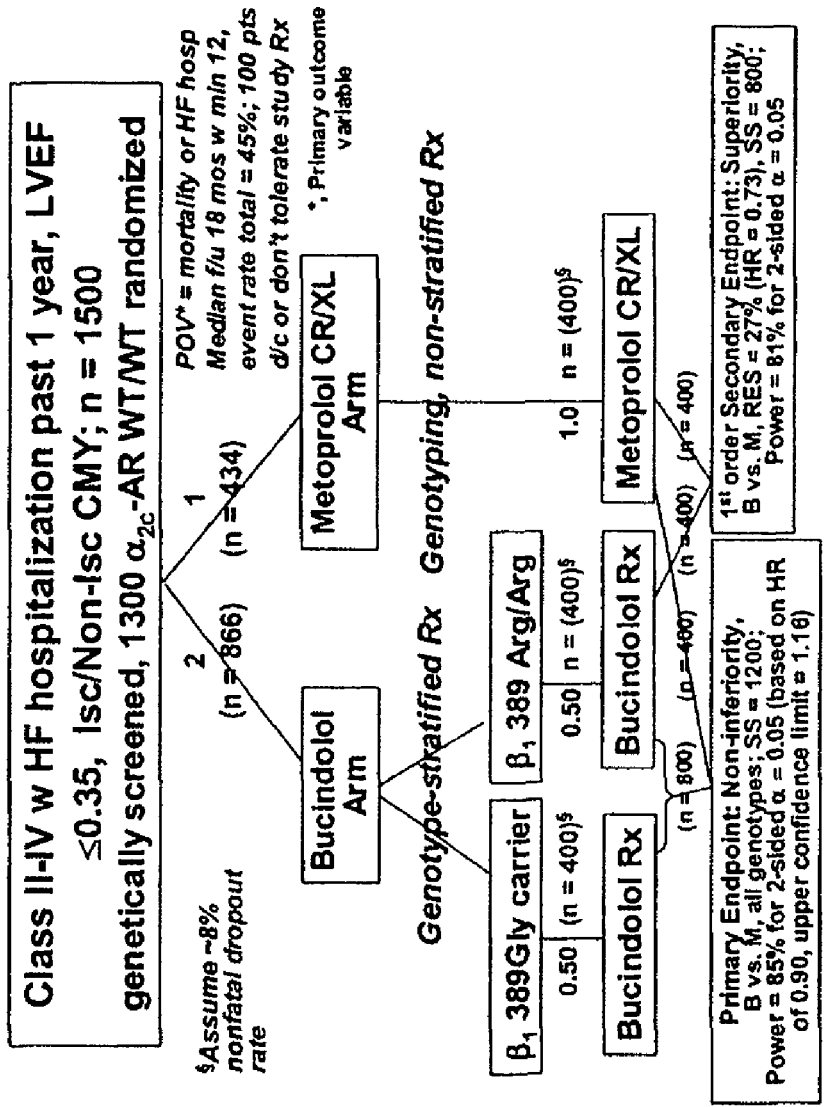
FIG. 28. Study Design II.

In the trial design shown in FIG. 28, the population treated with bucindolol is $\beta_1$-389 Arg/Arg patients who also are $\alpha_{2c}$ wild type. In BEST 47% of the entire cohort was $\beta_1$-389 Arg/Arg, as were 50% of the $\alpha_{2c}$ wild type patients. As shown in Table 9, the diplotype of $\beta_1$-389 Arg/Arg+$\alpha_{2c}$ wild type exhibited a 40% reduction in mortality (p=0.037), a 39% reduction in mortality plus HF hospitalization (p=0.002), and a 41% reduction in HF hospitalization (p=0.004). The expected hazard ration for mortality plus HF hospitalizations for bucindolol:metoprolol CR/XL (MERIT U.S. data) would be 0.61/0.84, or 0.73. Using an effect size of 27% in bucindolol-treated $\beta_1$-389 Arg/Arg plus $\alpha_{2c}$ wild type diplotype patients vs. metoprolol CR/XL yields a power calculation of 81%. Thus in the proposed trial shown in FIG. 28, the noninferiority margin for the primary endpoint is conservatively based on the entire cohort results of MERIT-HF, while the power calculations for both the primary and secondary endpoints incorporate an expected advantage of bucindolol in the selected genotypes, based on actual data in U.S. populations for both bucindolol and metoprolol CR/XL.

Example 11

Additional Studies: Design III

Figure 29:
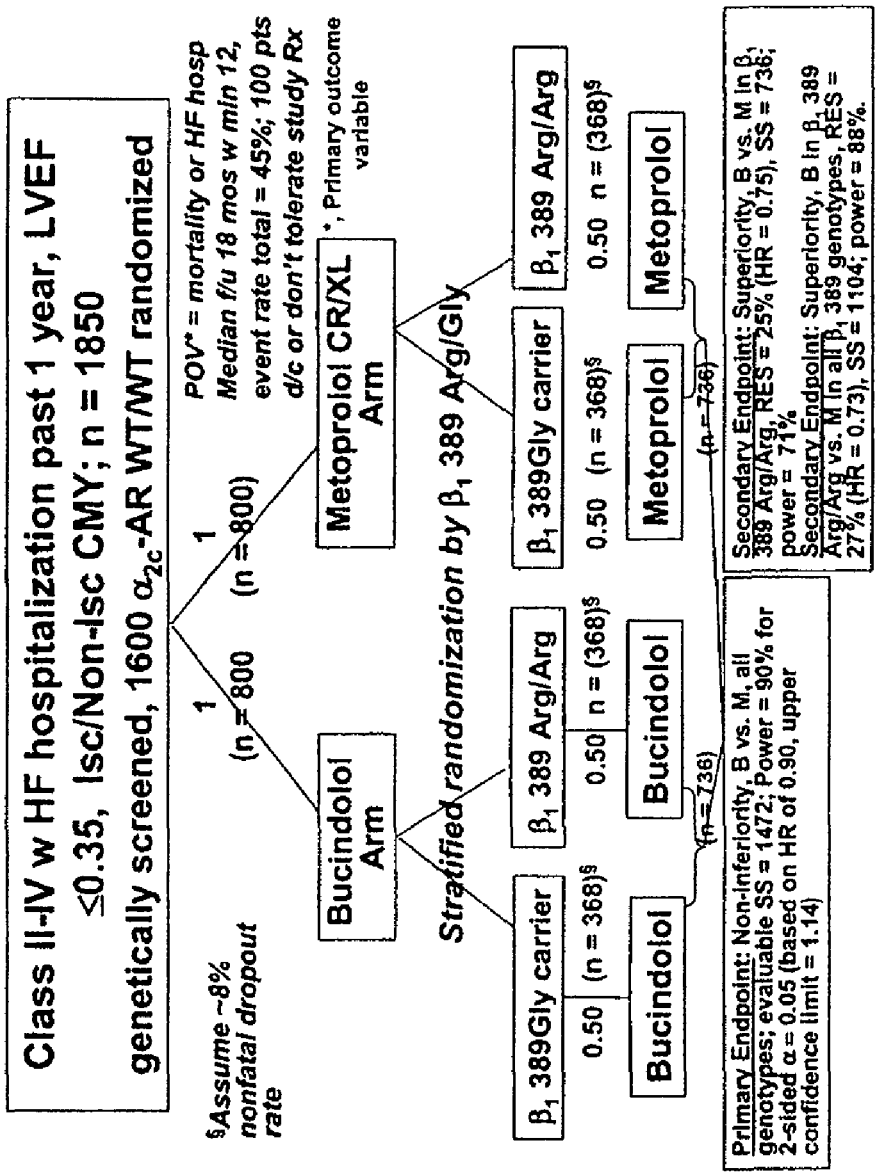
FIG. 29. Study Design III.

In case the noninferiority margin of 1.16, which provides a 36% preservation of the treatment effect of metoprolol CR/XL over placebo, is deemed insufficient for demonstrating efficacy, another design is proposed. An UCL of 1.14, which would preserve 50% of the metoprolol CR/XL vs. placebo treatment effect at 90% power, was considered acceptable. Therefore, the design shown in FIG. 28 has been adjusted to achieve this goal, with a power of 90% (FIG. 29). The increase in statistical power required to lower the UCL has been accomplished by increasing the sample size from 1300 to 1600, and to a lesser extent by converting from a 2:1 to a 1:1 randomization between bucindolol and metoprolol CR/XL. Also, in response to agency feedback we have added another secondary endpoint, bucindolol vs. metoprolol CR/XL in $\beta_1$-389 Arg/Arg patients. The power estimate for this secondary endpoint, based on an expected effect size of 25%, is 71%, while the power estimate for the other secondary endpoint, based on an expected effect size of 27%, is 88%. The former effect size of 25% was difficult to estimate because of limited data with metoprolol CR/XL in a $\beta_1$-389 Arg/Arg population; the only data available suggest little or no enhancement of the metoprolol CR/XL treatment effect compared to placebo (White et al., 2003). The effect size of 27% for the other secondary endpoint is based on U.S. MERIT-HF data as discussed above.

The foregoing description is considered as illustrative only of the principles of the invention. Further, since numerous modifications and changes will readily occur to those skilled in the art, it is not desired to limit the invention to the exact construction and process as described above. Accordingly, all suitable modifications and equivalents may be resorted to falling within the scope of the invention as defined by the claims that follow. The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,582,788
U.S. Pat. No. 4,627,429
U.S. Pat. No. 4,659,774
U.S. Pat. No. 4,683,194
U.S. Pat. No. 4,683,195
U.S. Pat. No. 4,683,202
U.S. Pat. No. 4,683,202
U.S. Pat. No. 4,683,202
U.S. Pat. No. 4,784,857
U.S. Pat. No. 4,800,159
U.S. Pat. No. 4,816,571
U.S. Pat. No. 4,883,750
U.S. Pat. No. 4,946,773
U.S. Pat. No. 4,959,463
U.S. Pat. No. 4,965,188

U.S. Pat. No. 5,126,145
U.S. Pat. No. 5,130,238
U.S. Pat. No. 5,141,813
U.S. Pat. No. 5,169,766
U.S. Pat. No. 5,264,566
U.S. Pat. No. 5,279,721
U.S. Pat. No. 5,428,148
U.S. Pat. No. 5,554,744
U.S. Pat. No. 5,574,146
U.S. Pat. No. 5,602,244
U.S. Pat. No. 5,605,798
U.S. Pat. No. 5,645,897
U.S. Pat. No. 5,662,925
U.S. Pat. No. 5,705,629
U.S. Pat. No. 5,788,983
U.S. Pat. No. 5,840,873
U.S. Pat. No. 5,843,640
U.S. Pat. No. 5,843,650
U.S. Pat. No. 5,843,651
U.S. Pat. No. 5,843,663
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,849,481
U.S. Pat. No. 5,849,483
U.S. Pat. No. 5,849,486
U.S. Pat. No. 5,849,487
U.S. Pat. No. 5,849,497
U.S. Pat. No. 5,849,546
U.S. Pat. No. 5,849,547
U.S. Pat. No. 5,851,770
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,337
U.S. Pat. No. 5,866,366
U.S. Pat. No. 5,900,481
U.S. Pat. No. 5,905,024
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779,
U.S. Pat. No. 5,919,626
U.S. Pat. No. 5,919,630
U.S. Pat. No. 5,922,574
U.S. Pat. No. 5,925,517
U.S. Pat. No. 5,925,525
U.S. Pat. No. 5,928,862
U.S. Pat. No. 5,928,869
U.S. Pat. No. 5,928,870
U.S. Pat. No. 5,928,905
U.S. Pat. No. 5,928,906
U.S. Pat. No. 5,929,227
U.S. Pat. No. 5,932,413
U.S. Pat. No. 5,932,451

U.S. Pat. No. 5,935,791
U.S. Pat. No. 5,935,825
U.S. Pat. No. 5,939,291
U.S. Pat. No. 5,942,391
U.S. Pat. No. 5,952,174
U.S. Pat. No. 6,113,940
U.S. Pat. No. 4,656,127
U.S. Pat. No. 4,682,195
Abbondanzo et al., *Breast Cancer Res. Treat.*, 16:182(151), 1990.
Allred et al., *Arch. Surg.*, 125(1):107-113, 1990.
Anand et al., *Circulation*, 107(9):1278-1283, 2003.
Anderson et al., *J. Card. Fail.*, 9:266-277, 2003.
Asano et al., *J. Cardiovasc. Pharmacol.*, 37:678-691, 2001.
Ausubel et al., In: *Current Protocols in Molecular Biology*, John, Wiley & Sons, Inc, New York, 1989.
Barany, et al., *Proc. Natl. Acad. Sci. USA*, 88:189-193, 1991
Bellus, *J. Macromol. Sci. Pure Appl. Chem.*, A31(1): 1355-1376, 1994.
Benedict et al., *Circulation*, 94(4):690-697, 1996.
BEST Trial Investigators, *N. Engl. J. Med.*, 344(22):1659-1667, 2001.
Bolger, *Int J Cardiol*, 92(1):1-8, 2003.
Bouzamondo et al., *Fund. Clin. Pharmacol.*, 15:95-109, 2001.
Bristow et al, *Circ. Res.*, 59(3):297-309, 1986.
Bristow et al., *Cardiovasc/Drugs Ther.*, 11:291-296, 1997.
Bristow et al., *Circulation*, 110:1437-1442, 2004.
Bristow et al., *Circulation*, 89(4):1632-1642, 1994.
Bristow et al., *Clin. Cardiol.*, 21(12 Suppl 1):13-13, 1998.
Bristow et al., *J Card Fail.*, 9(6):444-53, 2003.
Bristow et al., *Mol. Pharmacol.*, 35:296-303, 1988.
Bristow, *Circulation*, 101:558-569, 2000.
Brodde et al., *J. Cardiovasc., Pharmacol.*, 8:1235-1242, 1986.
Brodde et al., *Z. Kardiol.*, 81:71-78, 1992.
Brown et al., *Immunol Ser*, 53:69-82, 1990.
Brum et al. *Am. J. Physiol. Heart Circ. Physiol.*, 283:H1838-18345, 2002.
Capaldi et al., *Biochem. Biophys. Res. Comm.*, 74(2):425-433, 1977.
CIBIS-II Investigators, *Lancet*, 353:9-13, 1999.
Cohn et al., *Eur. J. Heart Fail.*, 5:659-667, 2003.
Cohn et al., *N. Engl. J. Med.*, 311:819-823, 1984.
de Arruda et al., *Expert Rev. Mol. Diagn.*, 2(5):487-496, 2002.
De Jager et al., *Semin. Nucl. Med.*, 23(2):165-179, 1993.
Dohlman et al., *Annu. Rev. Biochem.*, 60:653-688, 1991.
Domanski et al., *J. Am. Coll. Cardiol.*, 42:914-922, 2003.
Doolittle et al., *Methods Mol. Biol.*, 109:215-237, 1999.
Eichhorn et al., *Am. J. Cardiol.*, 79:794-798, 1997.
Epstein et al., *Ann. Inn. Med.*, 65:20-7, 1968.
European Appln. 201,184
European Appln. 237,362
European Appln. 258,017
European Appln. 266,032
European Appln. 320 308
European Appln. 329,822
European Appln. 50,424
European Appln. 84,796
Fowler and Bristow, *Am. J. Cardiol.*, 55(10)D120-D124, 1985.
Francis et al., *Circulation*, 87(6 Suppl):VI40-8, 1993.
French Appln. 2,650,840
Frielle et al., *Proc. Natl. Acad. Sci. USA*, 84:7920-7924, 1987.
Froehler et al., *Nucleic Acids Res.*, 14(13):5399-5407, 1986.
Frohman, In: *PCR Protocols: A Guide To Methods And Applications*, Academic Press, N.Y., 1990.

Gaffney et al., *Circ Res.,* 12:264-268, 1963.
Gilbert et al., *Amer. J. Med.,* 88:223-229, 1990.
Granger et al., *Lancet,* 362:772-776, 2003.
Great Britain Appln 2 202 328
Green et al., 1994
Gulbis and Galand, *Hum. Pathol.,* 24(12):1271-1285, 1993.
Halushka et al., *Nat. Genet.,* 22(3):239-247,1999.
Harlow and Lane, In: *Antibodies: A Laboratory Manual,* Cold Spring Harbor Laboratory, 1988
Hasselblad et al., *Drug Information J.,* 35:435-449, 2001.
Hein et al., *Nature,* 402:181-184, 1999.
Hershberger et al., *J. Cardiovasc. Pharm.,* 15:959-967, 1990.
Hjalmarson et al., *J. Am. Med. Assoc.,* 283:1295-1302, 2000.
Humphries, et al., In: *Molecular Diagnosis of Genetic Diseases,* Elles (Ed.), 321-340, 1996.
Innis et al., *Proc. Natl. Acad. Sci. USA,* 85(24):9436-9440, 1988.
Isnard et al., *Am. J. Cardiol.,* 86(4):417-421, 2000.
Johnson et al., *Clin. Pharmacol. Ther.,* 73:366-71, 2003.
Johnson et al., *Clin. Pharmacol. Ther.,* 74(1):44-52, 2003.
Jones, *Nature,* 199:280-282, 1963.
Joseph et al., *Br. J. Pharm.* 142:51-56, 2004.
Kalbfleisch et al., 1980
Kaplan et al., *J Amer. Statistical Assoc.,* 53:457-481, 1958.
Kaye et al., *J. Am. Coll. Cardiol.,* 26(5):1257-1263 1995.
Ke and Cardon *Bioinformatics,* 19(2):287-288, 2003.
Klaassen, In: *The Pharmacological Basis of Therapeutics,* Goodman and Gilman, Eds., Pergamon Press, 8th Ed., pp. 49-61, 1990.
Krum et al. *Circulation,* 92:1499-1506, 1995.
Kuppuswamy, et al., *Proc. Natl. Acad. Sci. USA,* 88:1143-1147, 1991.
Kwoh et al., *Proc. Natl. Acad. Sci. USA,* 86:1173, 1989.
Kwok and Chen, *Curr Issues Mol. Biol., April;* 5(2):43-60, 2003.
Kwok et al., *Genomics,* 23(1):138-144, 1994.
Kwok, *Annu. Rev. Genomics Hum. Genet.,* 2:235-258, 2001.
Landegren, et al., *Science* 241:1077-1080, 1988.
Landegren, et al., *Science,* 241:1077-1080, 1988.
Levin et al., *J Biol. Chem.,* 277(34):30429-30435, 2002.
Liggett et al., In: *Catecholamines,* Bouloux (Ed.), W. B. Sounders, London, 1993.
Liggett, *J. Clin. Invest.,* 107:947-948, 2001.
Liu et al., *Clin. Pharmacol. Ther.,* 74:372-9, 2003.
Lohse, *Trends Mol. Med.,* 10:55-58, 2004.
Lowes et al., *Circulation,* 102:11-628, 2000.
Lowes et al., *Circulation,* 104:11-436, 2001.
Lowes et al., *N. Engl. J. Med.,* 346:1357-1365, 2002.
Mann et al., *Circulation,* 111(21):2837-2849, 2005.
Mason et al., *J. Biol. Chem.,* 274:12670-12674, 1999.
Maxam, et al., *Proc. Natl. Acad. Sci. USA,* 74:560, 1977.
McMurray et al., *Lancet,* 362:767-771, 2003.
MERIT-HF Study Group, *Lancet,* 353:2001-2007, 1999.
Meyers, et al., *Science,* 230:1242, 1985.
Mialet et al., *Nat. Med.,* 9:1300-1305, 2003.
Modrich, *Ann. Rev. Genet.,* 25:229-253, 1991.
Mullis et al., *Cold Spring Harbor Symp. Quant. Biol.* 51:263-273, 1986.
Nakamura et al., In: *Handbook of Experimental Immunology* (4th Ed.), Weir et al., (eds). 1:27, Blackwell Scientific Publ., Oxford, 1987.
Neumister et al., *Pharmacogenet. Genomics,* 15:143-149, 2005.
Nickerson et al., *Proc. Natl. Acad. Sci. USA,* 87:8923-8927, 1990.
Nyren et al., *Anal. Biochem.* 208:171-175, 1993.
O'Shaughnessy et al., *Clin. Sci.,* 99:233-238, 2000.
Ohara et al., *Proc. Natl. Acad. Sci. USA,* 86:5673-5677, 1989.
Orita et al., *Genomics,* 5:874-879, 1989.
Packer et al., *Circulation,* 106(17):2194-2199, 2002.
Packer et al., *N. Engl. J. Med.,* 344:1651-1658, 2001.
PCT Appln. PCT/US87/00880
PCT Appln. PCT/US89/01025
PCT Appln. WO 88/10315
PCT Appln. WO 89/06700
PCT Appln. WO 93/22456
PCT Appln. WO 95/11995
PCT Appln. WO89/06700
PCT Appln. WO90/01069
PCT Appln. WO91/02087
PCT Appln. WO92/15712
Perez et al., *Nature Med.,* 9:1300-1305, 2003.
Physicians Desk Reference"
Pollock et al., *Am. J. Cardiol.,* 66:603-607, 1990.
Port et al., *Mol. Pharmacol.,* 60(4):629-631, 2001.
Prezant et al., *Hum. Mutat.,* 1:159-164, 1992.
Rathz et al., *J. Cardiovasc. Pharmacol.,* 39:155-160, 2002.
Remington's Pharmaceutical Sciences" 15th Edition, pages 1035-1038 and 1570-1580
Rockman et al., *Am. J. Cardiol.,* 64(19):1344-1348, 1989.
Ruano et al., *Nucl. Acids Res.,* 19:6877-6882, 1991.
Ruano et al., *Nucl. Acids Res.,* 17:8392, 1989.
Sallach et al., *Ann. Med.,* 35:259-266, 2003
Salomon, *Methods Enzymol.,* 195:22-28, 1991.
Sambrook et al., In: *Molecular cloning,* Cold Spring Harbor Laboratory Press, Cold Spring Harbor, N.Y., 2001.
Sanger et al., *J. Molec. Biol.,* 94:441, 1975.
SAS (r) proprietary software, release 6.12. Cary, N. C.: SAS Institute, 1996
Sederberg et al., *J. Am. Coll. Cardiol.* 35(2) 207A:147, 2000.
Sheffield, et al., *Proc. Natl. Acad. Sci. USA,* 86:232-236, 1989.
Silke et al., *J. Cardiovasc. Pharmacol.,* 30(6):817-823, 1997.
Small et al. *J. Biol. Chem.,* 275:23059-23064, 2000.
Small et al., *N. Engl. J. Med.,* 347:1135-1142, 2002.
Sofowora et al., *Clin Pharmacol Ther.,* 73:366-71, 2003.
Sokolov, *Nucl. Acids Res.* 18:3671, 1990.
Stephen, *Am. J. Cardiol.,* 18:463-472, 1966.
Stevens et al., *Biotechniques,* 34:198-203, 2003.
Strosberg, *Annu. Rev. Pharmacol. Toxicol.,* 37:421-450, 1997.
Swedberg et al., *Circulation,* 105(15):1797-803, 2002.
Swedberg et al., *Circulation,* 82(5):1730-1736, 1990.
Swedberg et al., *Eur. Heart J.,* 17(9):1306-1311, 1996.
Taillon-Miller et al., *Genome Res,* 8(7):748-754, 1998.
Taylor et al., *Cong. Heart Failure,* 10:281-288, 2004.
The Merck Index, Eleventh Edition
Trial Investigators, 2001
Turki, et al., *J. Clin. Invest.,* 95:1635-1641, 1995.
Ugozzoll et al., *GATA* 9:107-112, 1992.
van Campen et al., *J. Cardiovasc. Pharmacol.,* 32 Suppl 1:S31-S35, 1998.
Waagstein et al., *Lancet,* 342:1441-1446, 1993.
Wagoner et al., *Am. Heart J.,* 144(5):840-846, 2002.
Walker, et al., *Proc. Natl. Acad. Sci. USA,* 89:392-396, 1992.
Wartell, et al., *Nucl. Acids Res.,* 18:2699-2706, 1990.
Wedel et al., *Am. Heart J.,* 142:502-511, 2001.
White et al., *Eur. J. Heart Fail.,* 5:463-468, 2003.
Winter, et al., *Proc. Natl. Acad. Sci. USA,* 82:7575, 1985.
Xameterol Study Group, 1990
Yancy et al., *J. Am. Coll. Cardiol.,* 29:284 A, 1997.
Yancy et al., *N. Engl. J. Med.,* 344(18):1358-1365, 2001.
Yang-Feng et al., *Proc. Natl. Acad. Sci. USA,* 87:1516-1520, 1990.
Zhu et al., *Proc. Natl. Acad. Sci. USA,* 98(4):1607-12, 2001.

What is claimed is:

1. A method for treating a human patient for heart failure, cardiac arrhythmia, or hypertension with bucindolol comprising: administering bucindolol to the patient if the patient is determined to be homozygous wildtype for Del322-325 in the α2c andrenergic receptor (AR) gene based on a test of a biological sample from the patient.

2. The method of claim 1, wherein the results are obtained by receiving a report containing the information or taking a patient history that reveals the results.

3. The method of claim 1, wherein bucindolol is formulated for oral administration.

4. The method of claim 1, wherein the patient is also treated with ACE inhibitors, digoxin or a diuretic.

5. The method of claim 1, wherein bucindolol is administered every 12 hours.

6. The method of claim 1, further comprising ordering a test from a sample from the patient that determines the patient's genotype.

7. A method for treating a human patient with symptoms of or a diagnosis of heart failure, cardiac arrhythmia, or hypertension with bucindolol comprising: treating the patient with bucindolol if the patient is tested and determined not to be a Del322-325 carrier in the α2c andrenergic receptor (AR) gene based on results of a test of a biological sample from the patient.

8. The method of claim 7, wherein the results are obtained by receiving a report containing the information or taking a patient history that reveals the results.

9. The method of claim 7, wherein bucindolol is formulated for oral administration.

10. The method of claim 7, wherein the patient is also treated with ACE inhibitors, digoxin or a diuretic.

11. The method of claim 7, wherein bucindolol is administered or prescribed for administration every 12 hours.

12. The method of claim 7, further comprising ordering a test from a sample from the patient that determines the patient's genotype.

13. A method for administering bucindolol to a human patient with symptoms of or a diagnosis of heart failure, cardiac arrhythmia, or hypertension comprising:
   a) obtaining information about whether the patient's genotype is homozygous wildtype for Del322-325 in the $\alpha_{2c}$ AR gene; and
   b) then administering bucindolol to the patient if the patient's genotype is homozygous wildtype for Del322-325 in the $\alpha_{2c}$ AR gene.

14. The method of claim 13, wherein the results are obtained by receiving a report containing the information or taking a patient history that reveals the results.

15. The method of claim 13, wherein bucindolol is formulated for oral administration.

16. The method of claim 13, wherein the patient is also treated with ACE inhibitors, digoxin or a diuretic.

17. The method of claim 13, wherein bucindolol is administered every 12 hours.

18. The method of claim 13, wherein the information is obtained by ordering a test from a sample from the patient that determines the patient's genotype.

19. A method for treating a human patient for heart failure, cardiac arrhythmia, or hypertension with bucindolol comprising:
   a) obtaining results from a test that determines whether the patient's genotype is homozygous wildtype for Del322-325 in the $\alpha_{2c}$ AR gene; and,
   b) then treating the patient with bucindolol if the test indicates that the patient's genotype is homozygous wildtype for Del322-325 in the $\alpha_{2c}$ AR gene.

20. The method of claim 19, wherein the results are obtained by receiving a report containing the information or taking a patient history that reveals the results.

21. The method of claim 19, wherein bucindolol is formulated for oral administration.

22. The method of claim 19, wherein the patient is also treated with ACE inhibitors, digoxin or a diuretic.

23. The method of claim 19, further comprising ordering a test from a sample from the patient that determines the patient's genotype.

24. A method for treating heart failure or cardiac arrhythmia comprising administering bucindolol to a heart failure or cardiac arrhythmia human patient who has been determined to be homozygous wildtype for Del322-325 in the α2c andrenergic receptor (AR) gene based on a test of a biological sample from the patient.

25. The method of claim 24, wherein bucindolol is formulated for oral administration.

26. The method of claim 24, wherein the patient is also treated with ACE inhibitors, digoxin or a diuretic.

27. The method of claim 24, wherein bucindolol is administered every 12 hours.

28. The method of claim 24, further comprising ordering a test using a sample from the patient that determines the patient's genotype.

* * * * *

UNITED STATES PATENT AND TRADEMARK OFFICE
CERTIFICATE OF CORRECTION

| | | |
|---|---|---|
| PATENT NO. | : 8,080,578 B2 | Page 1 of 1 |
| APPLICATION NO. | : 11/838131 | |
| DATED | : December 20, 2011 | |
| INVENTOR(S) | : Liggett et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 300 days.

Signed and Sealed this
Seventeenth Day of April, 2012

David J. Kappos
*Director of the United States Patent and Trademark Office*

SEQUENCE LISTING

<160> NUMBER OF SEQ ID NOS: 8

<210> SEQ ID NO 1
<211> LENGTH: 1723
<212> TYPE: DNA
<213> ORGANISM: Homo sapiens
<220> FEATURE:
<221> NAME/KEY: CDS
<222> LOCATION: (87)..(1520)

<400> SEQUENCE: 1

```
tgctacccgc gcccgggctt ctggggtgtt ccccaaccac ggcccagccc tgccacaccc      60
cccgcccccg gcctccgcag ctcggc atg ggc gcg ggg gtg ctc gtc ctg ggc     113
                              Met Gly Ala Gly Val Leu Val Leu Gly
                                1               5 gcc tcc gag ccc ggt aac ctg tcg tcg gca cca ctc ccc gac ggc            161
Ala Ser Glu Pro Gly Asn Leu Ser Ser Ala Pro Leu Pro Asp Gly
 10              15                  20                  25 gcg gcc acc gcg gcg cgg ctg ctg gtg ccg gcg tcg ccg ccc gcc tcg        209
Ala Ala Thr Ala Ala Arg Leu Leu Val Pro Ala Ser Pro Pro Ala Ser
                 30                  35                  40 ttg ctg cct ccc gcc agc gaa agc ccc gag ccg ctg tct cag cag tgg        257
Leu Leu Pro Pro Ala Ser Glu Ser Pro Glu Pro Leu Ser Gln Gln Trp
             45                  50                  55 aca gcg ggc atg ggt ctg ctg atg gcg ctc atc gtg ctg ctc atc gtg        305
Thr Ala Gly Met Gly Leu Leu Met Ala Leu Ile Val Leu Leu Ile Val
         60                  65                  70 gcg ggc aat gtg ctg gtg atc gtg gcc atc gcc aag acg ccg cgg ctg        353
Ala Gly Asn Val Leu Val Ile Val Ala Ile Ala Lys Thr Pro Arg Leu
     75                  80                  85 cag acg ctc acc aac ctc ttc atc atg tcc ctg gcc agc gcc gac ctg        401
Gln Thr Leu Thr Asn Leu Phe Ile Met Ser Leu Ala Ser Ala Asp Leu
 90                  95                 100                 105 gtc atg ggg ctg ctg gtg gtg ccg ttc ggg gcc acc atc gtg gtg tgg        449
Val Met Gly Leu Leu Val Val Pro Phe Gly Ala Thr Ile Val Val Trp
                110                 115                 120 ggc cgc tgg gag tac ggc tcc ttc ttc tgc gag ctg tgg acc tca gtg        497
Gly Arg Trp Glu Tyr Gly Ser Phe Phe Cys Glu Leu Trp Thr Ser Val
            125                 130                 135 gac gtg ctg tgc gtg acg gcc agc atc gag acc ctg tgt gtc att gcc        545
Asp Val Leu Cys Val Thr Ala Ser Ile Glu Thr Leu Cys Val Ile Ala
        140                 145                 150 ctg gac cgc tac ctc gcc atc acc tcg ccc ttc cgc tac cag agc ctg        593
Leu Asp Arg Tyr Leu Ala Ile Thr Ser Pro Phe Arg Tyr Gln Ser Leu
    155                 160                 165 ctg acg cgc gcg cgg gcg cgg ggc ctc gtg tgc acc gtg tgg gcc atc        641
Leu Thr Arg Ala Arg Ala Arg Gly Leu Val Cys Thr Val Trp Ala Ile
170                 175                 180                 185 tcg gcc ctg gtg tcc ttc ctg ccc atc ctc atg cac tgg tgg cgg gcg        689
Ser Ala Leu Val Ser Phe Leu Pro Ile Leu Met His Trp Trp Arg Ala
                190                 195                 200 gag agc gac gag gcg cgc cgc tgc tac aac gac ccc aag tgc tgc gac        737
Glu Ser Asp Glu Ala Arg Arg Cys Tyr Asn Asp Pro Lys Cys Cys Asp
            205                 210                 215 ttc gtc acc aac cgg gcc tac gcc atc gcc tcg tcc gta gtc tcc ttc        785
Phe Val Thr Asn Arg Ala Tyr Ala Ile Ala Ser Ser Val Val Ser Phe
        220                 225                 230 tac gtg ccc ctg tgc atc atg gcc ttc gtg tac ctg cgg gtg ttc cgc        833
Tyr Val Pro Leu Cys Ile Met Ala Phe Val Tyr Leu Arg Val Phe Arg
    235                 240                 245
```

```
gag gcc cag aag cag gtg aag aag atc gac agc tgc gag cgc cgt ttc      881
Glu Ala Gln Lys Gln Val Lys Lys Ile Asp Ser Cys Glu Arg Arg Phe
250                 255                 260                 265 ctc ggc ggc cca gcg cgg ccg ccc tcg ccc tcg ccc tcg ccc gtc ccc      929
Leu Gly Gly Pro Ala Arg Pro Pro Ser Pro Ser Pro Ser Pro Val Pro
                270                 275                 280 gcg ccc gcg ccg ccg ccc gga ccc ccg cgc ccc gcc gcc gcc gcc          977
Ala Pro Ala Pro Pro Pro Gly Pro Pro Arg Pro Ala Ala Ala Ala
        285                 290                 295 acc gcc ccg ctg gcc aac ggg cgt gcg ggt aag cgg cgg ccc tcg cgc     1025
Thr Ala Pro Leu Ala Asn Gly Arg Ala Gly Lys Arg Arg Pro Ser Arg
300                 305                 310 ctc gtg gcc cta cgc gag cag aag gcg ctc aag acg ctg ggc atc atc     1073
Leu Val Ala Leu Arg Glu Gln Lys Ala Leu Lys Thr Leu Gly Ile Ile
315                 320                 325 atg ggc gtc ttc acg ctc tgc tgg ctg ccc ttc ttc ctg gcc aac gtg     1121
Met Gly Val Phe Thr Leu Cys Trp Leu Pro Phe Phe Leu Ala Asn Val
330                 335                 340                 345 gtg aag gcc ttc cac cgc gag ctg gtg ccc gac cgc ctc ttc gtc ttc     1169
Val Lys Ala Phe His Arg Glu Leu Val Pro Asp Arg Leu Phe Val Phe
                350                 355                 360 ttc aac tgg ctg ggc tac gcc aac tcg gcc ttc aac ccc atc atc tac     1217
Phe Asn Trp Leu Gly Tyr Ala Asn Ser Ala Phe Asn Pro Ile Ile Tyr
            365                 370                 375 tgc cgc agc ccc gac ttc cgc aag gcc ttc cag gga ctg ctc tgc tgc     1265
Cys Arg Ser Pro Asp Phe Arg Lys Ala Phe Gln Gly Leu Leu Cys Cys
        380                 385                 390 gcg cgc agg gct gcc cgc cgg cgc cac gcg acc cac gga gac cgg ccg     1313
Ala Arg Arg Ala Ala Arg Arg Arg His Ala Thr His Gly Asp Arg Pro
395                 400                 405 cgc gcc tcg ggc tgt ctg gcc cgg ccc gga ccc ccg cca tcg ccc ggg     1361
Arg Ala Ser Gly Cys Leu Ala Arg Pro Gly Pro Pro Pro Ser Pro Gly
410                 415                 420                 425 gcc gcc tcg gac gac gac gac gac gat gtc gtc ggg gcc acg ccg ccc     1409
Ala Ala Ser Asp Asp Asp Asp Asp Asp Val Val Gly Ala Thr Pro Pro
                430                 435                 440 gcg cgc ctg ctg gag ccc tgg gcc ggc tgc aac ggc ggg gcg gcg gcg     1457
Ala Arg Leu Leu Glu Pro Trp Ala Gly Cys Asn Gly Gly Ala Ala Ala
            445                 450                 455 gac agc gac tcg agc ctg gac gag ccg tgc cgc ccc ggc ttc gcc tcg     1505
Asp Ser Asp Ser Ser Leu Asp Glu Pro Cys Arg Pro Gly Phe Ala Ser
        460                 465                 470 gaa tcc aag gtg tag ggcccggcgc ggggcgcgga ctccgggcac ggcttcccag     1560
Glu Ser Lys Val
        475 gggaacgagg agatctgtgt ttacttaaga ccgatagcag gtgaactcga agcccacaat   1620 cctcgtctga atcatccgag gcaaagagaa aagccacgga ccgttgcaca aaaaggaaag   1680 tttgggaagg gatgggagag tggcttgctg atgttccttg ttg                    1723

<210> SEQ ID NO 2
<211> LENGTH: 477
<212> TYPE: PRT
<213> ORGANISM: Homo sapiens

<400> SEQUENCE: 2

Met Gly Ala Gly Val Leu Val Leu Gly Ala Ser Glu Pro Gly Asn Leu
 1               5                  10                  15

Ser Ser Ala Ala Pro Leu Pro Asp Gly Ala Ala Thr Ala Ala Arg Leu
            20                  25                  30
```

Leu Val Pro Ala Ser Pro Pro Ala Ser Leu Leu Pro Pro Ala Ser Glu
           35                  40                  45

Ser Pro Glu Pro Leu Ser Gln Gln Trp Thr Ala Gly Met Gly Leu Leu
     50                  55                  60

Met Ala Leu Ile Val Leu Ile Val Ala Gly Asn Val Leu Val Ile
 65                  70                  75                  80

Val Ala Ile Ala Lys Thr Pro Arg Leu Gln Thr Leu Thr Asn Leu Phe
                 85                  90                  95

Ile Met Ser Leu Ala Ser Ala Asp Leu Val Met Gly Leu Leu Val Val
             100                 105                 110

Pro Phe Gly Ala Thr Ile Val Val Trp Gly Arg Trp Glu Tyr Gly Ser
             115                 120                 125

Phe Phe Cys Glu Leu Trp Thr Ser Val Asp Val Leu Cys Val Thr Ala
         130                 135                 140

Ser Ile Glu Thr Leu Cys Val Ile Ala Leu Asp Arg Tyr Leu Ala Ile
145                 150                 155                 160

Thr Ser Pro Phe Arg Tyr Gln Ser Leu Leu Thr Arg Ala Arg Ala Arg
                 165                 170                 175

Gly Leu Val Cys Thr Val Trp Ala Ile Ser Ala Leu Val Ser Phe Leu
             180                 185                 190

Pro Ile Leu Met His Trp Trp Arg Ala Glu Ser Asp Glu Ala Arg Arg
             195                 200                 205

Cys Tyr Asn Asp Pro Lys Cys Cys Asp Phe Val Thr Asn Arg Ala Tyr
             210                 215                 220

Ala Ile Ala Ser Ser Val Val Ser Phe Tyr Val Pro Leu Cys Ile Met
225                 230                 235                 240

Ala Phe Val Tyr Leu Arg Val Phe Arg Glu Ala Gln Lys Gln Val Lys
                 245                 250                 255

Lys Ile Asp Ser Cys Glu Arg Arg Phe Leu Gly Gly Pro Ala Arg Pro
             260                 265                 270

Pro Ser Pro Ser Pro Ser Pro Val Pro Ala Pro Ala Pro Pro Pro Gly
             275                 280                 285

Pro Pro Arg Pro Ala Ala Ala Ala Thr Ala Pro Leu Ala Asn Gly
             290                 295                 300

Arg Ala Gly Lys Arg Arg Pro Ser Arg Leu Val Ala Leu Arg Glu Gln
305                 310                 315                 320

Lys Ala Leu Lys Thr Leu Gly Ile Ile Met Gly Val Phe Thr Leu Cys
                 325                 330                 335

Trp Leu Pro Phe Phe Leu Ala Asn Val Val Lys Ala Phe His Arg Glu
             340                 345                 350

Leu Val Pro Asp Arg Leu Phe Val Phe Phe Asn Trp Leu Gly Tyr Ala
             355                 360                 365

Asn Ser Ala Phe Asn Pro Ile Ile Tyr Cys Arg Ser Pro Asp Phe Arg
             370                 375                 380

Lys Ala Phe Gln Gly Leu Leu Cys Cys Ala Arg Arg Ala Ala Arg Arg
385                 390                 395                 400

Arg His Ala Thr His Gly Asp Arg Pro Arg Ala Ser Gly Cys Leu Ala
                 405                 410                 415

Arg Pro Gly Pro Pro Pro Ser Pro Gly Ala Ala Ser Asp Asp Asp Asp
             420                 425                 430

Asp Asp Val Val Gly Ala Thr Pro Pro Ala Arg Leu Leu Glu Pro Trp
             435                 440                 445

Ala Gly Cys Asn Gly Gly Ala Ala Ala Asp Ser Asp Ser Ser Leu Asp

```
                                  Glu Pro Cys Arg Pro Gly Phe Ala Ser Glu Ser Lys Val
                                  465                 470                 475

<210> SEQ ID NO 3
<211> LENGTH: 1434
<212> TYPE: DNA
<213> ORGANISM: Homo sapiens
<220> FEATURE:
<221> NAME/KEY: CDS
<222> LOCATION: (1)..(1434)

<400> SEQUENCE: 3 atg ggc gcg ggg gtg ctc gtc ctg ggc gcc tcc gag ccc ggt aac ctg        48
Met Gly Ala Gly Val Leu Val Leu Gly Ala Ser Glu Pro Gly Asn Leu
  1               5                  10                  15 tcg tcg gcc gca ccg ctc ccc gac ggc gcg gcc acc gcg gcg cgg ctg        96
Ser Ser Ala Ala Pro Leu Pro Asp Gly Ala Ala Thr Ala Ala Arg Leu
             20                  25                  30 ctg gtg ccc gcg tcg ccg ccc gcc tcg ttg ctg cct ccc gcc agc gaa       144
Leu Val Pro Ala Ser Pro Pro Ala Ser Leu Leu Pro Pro Ala Ser Glu
         35                  40                  45 agc ccc gag ccg ctg tct cag cag tgg aca gcg ggc atg ggt ctg ctg       192
Ser Pro Glu Pro Leu Ser Gln Gln Trp Thr Ala Gly Met Gly Leu Leu
     50                  55                  60 atg gcg ctc atc gtg ctg ctc atc gtg gcg ggc aat gtg ctg gtg atc       240
Met Ala Leu Ile Val Leu Leu Ile Val Ala Gly Asn Val Leu Val Ile
 65                  70                  75                  80 gtg gcc atc gcc aag acg ccg cgg ctg cag acg ctc acc aac ctc ttc       288
Val Ala Ile Ala Lys Thr Pro Arg Leu Gln Thr Leu Thr Asn Leu Phe
                 85                  90                  95 atc atg tcc ctg gcc agc gcc gac ctg gtc atg ggg ctg ctg gtg gtg       336
Ile Met Ser Leu Ala Ser Ala Asp Leu Val Met Gly Leu Leu Val Val
            100                 105                 110 ccg ttc ggg gcc acc atc gtg gtg tgg ggc cgc tgg gag tac ggc tcc       384
Pro Phe Gly Ala Thr Ile Val Val Trp Gly Arg Trp Glu Tyr Gly Ser
        115                 120                 125 ttc ttc tgc gag ctg tgg acc tca gtg gac gtg ctg tgc gtg acg gcc       432
Phe Phe Cys Glu Leu Trp Thr Ser Val Asp Val Leu Cys Val Thr Ala
    130                 135                 140 agc atc gag acc ctg tgt gtc att gcc ctg gac cgc tac ctc gcc atc       480
Ser Ile Glu Thr Leu Cys Val Ile Ala Leu Asp Arg Tyr Leu Ala Ile
145                 150                 155                 160 acc tcg ccc ttc cgc tac cag agc ctg ctg acg cgc gcg cgg gcg cgg       528
Thr Ser Pro Phe Arg Tyr Gln Ser Leu Leu Thr Arg Ala Arg Ala Arg
                165                 170                 175 ggc ctc gtg tgc acc gtg tgg gcc atc tcg gcc ctg gtg tcc ttc ctg       576
Gly Leu Val Cys Thr Val Trp Ala Ile Ser Ala Leu Val Ser Phe Leu
            180                 185                 190 ccc atc ctc atg cac tgg tgg cgg gcg gag agc gac gag gcg cgc cgc       624
Pro Ile Leu Met His Trp Trp Arg Ala Glu Ser Asp Glu Ala Arg Arg
        195                 200                 205 tgc tac aac gac ccc aag tgc tgc gac ttc gtc acc aac cgg gcc tac       672
Cys Tyr Asn Asp Pro Lys Cys Cys Asp Phe Val Thr Asn Arg Ala Tyr
    210                 215                 220 gcc atc gcc tcg tcc gta gtc tcc ttc tac gtg ccc ctg tgc atc atg       720
Ala Ile Ala Ser Ser Val Val Ser Phe Tyr Val Pro Leu Cys Ile Met
225                 230                 235                 240 gcc ttc gtg tac ctg cgg gtg ttc cgc gag gcc cag aag cag gtg aag       768
Ala Phe Val Tyr Leu Arg Val Phe Arg Glu Ala Gln Lys Gln Val Lys
                245                 250                 255
```

```
aag atc gac agc tgc gag cgc cgt ttc ctc ggc gga cca gcg cgg ccg    816
Lys Ile Asp Ser Cys Glu Arg Arg Phe Leu Gly Gly Pro Ala Arg Pro
            260                 265                 270 ccc tcg ccc tcg ccc tcg ccc gtc ccc gcg ccc gcg ccg ccc gga        864
Pro Ser Pro Ser Pro Ser Pro Val Pro Ala Pro Ala Pro Pro Gly
    275                 280                 285 ccc ccg cgc ccc gcc gcc gcc gcc acc gcc ccg ctg gcc aac ggg        912
Pro Pro Arg Pro Ala Ala Ala Ala Thr Ala Pro Leu Ala Asn Gly
290                 295                 300 cgt gcg ggt aag cgg cgg ccc tcg cgc ctc gtg gcc ctg cgc gag cag    960
Arg Ala Gly Lys Arg Arg Pro Ser Arg Leu Val Ala Leu Arg Glu Gln
305                 310                 315                 320 aag gcg ctc aag acg ctg ggc atc atc atg ggc gtc ttc acg ctc tgc   1008
Lys Ala Leu Lys Thr Leu Gly Ile Ile Met Gly Val Phe Thr Leu Cys
                325                 330                 335 tgg ctg ccc ttc ttc ctg gcc aac gtg gtg aag gcc ttc cac cgc gag   1056
Trp Leu Pro Phe Phe Leu Ala Asn Val Val Lys Ala Phe His Arg Glu
            340                 345                 350 ctg gtg ccc gac cgc ctc ttc gtc ttc ttc aac tgg ctg ggc tac gcc   1104
Leu Val Pro Asp Arg Leu Phe Val Phe Phe Asn Trp Leu Gly Tyr Ala
        355                 360                 365 aac tcg gcc ttc aac ccc atc atc tac tgc cgc agc ccc gac ttc cgc   1152
Asn Ser Ala Phe Asn Pro Ile Ile Tyr Cys Arg Ser Pro Asp Phe Arg
    370                 375                 380 aag gcc ttc cag cga ctg ctc tgc tgc gcg cgc agg gct gcc cgc cgg   1200
Lys Ala Phe Gln Arg Leu Leu Cys Cys Ala Arg Arg Ala Ala Arg Arg
385                 390                 395                 400 cgc cac gcg acc cac gga gac cgg ccc cgc gcc tcg ggc tgt ctg gcc   1248
Arg His Ala Thr His Gly Asp Arg Pro Arg Ala Ser Gly Cys Leu Ala
                405                 410                 415 cgg ccc gga ccc ccg cca tcg ccc ggg gcc gcc tcg gac gac gac gac   1296
Arg Pro Gly Pro Pro Pro Ser Pro Gly Ala Ala Ser Asp Asp Asp Asp
            420                 425                 430 gac gat gtc gtc ggg gcc acg ccg ccc gcg cgc ctg ctg gag ccc tgg   1344
Asp Asp Val Val Gly Ala Thr Pro Pro Ala Arg Leu Leu Glu Pro Trp
        435                 440                 445 gcc ggc tgc aac ggc ggg gcg gcg gcg gac agc gac tcg agc ctg gac   1392
Ala Gly Cys Asn Gly Gly Ala Ala Ala Asp Ser Asp Ser Ser Leu Asp
    450                 455                 460 gag ccg tgc cgc ccc ggc ttc gcc tcg gaa tcc aag gtg tag            1434
Glu Pro Cys Arg Pro Gly Phe Ala Ser Glu Ser Lys Val
465                 470                 475

<210> SEQ ID NO 4
<211> LENGTH: 477
<212> TYPE: PRT
<213> ORGANISM: Homo sapiens

<400> SEQUENCE: 4

Met Gly Ala Gly Val Leu Val Leu Gly Ala Ser Glu Pro Gly Asn Leu
  1               5                  10                  15

Ser Ser Ala Ala Pro Leu Pro Asp Gly Ala Ala Thr Ala Ala Arg Leu
                 20                  25                  30

Leu Val Pro Ala Ser Pro Pro Ala Ser Leu Leu Pro Pro Ala Ser Glu
             35                  40                  45

Ser Pro Glu Pro Leu Ser Gln Gln Trp Thr Ala Gly Met Gly Leu Leu
         50                  55                  60

Met Ala Leu Ile Val Leu Leu Ile Val Ala Gly Asn Val Leu Val Ile
 65                  70                  75                  80

Val Ala Ile Ala Lys Thr Pro Arg Leu Gln Thr Leu Thr Asn Leu Phe
```

|   |   |   |   |   | 85 |   |   |   | 90 |   |   |   |   | 95 |   |   |
|---|---|---|---|---|---|---|---|---|---|---|---|---|---|---|---|---|
| Ile | Met | Ser | Leu | Ala | Ser | Ala | Asp | Leu | Val | Met | Gly | Leu | Leu | Val |   |   |
|   |   |   | 100 |   |   |   |   | 105 |   |   |   | 110 |   |   |   |   |

Pro Phe Gly Ala Thr Ile Val Val Trp Gly Arg Trp Glu Tyr Gly Ser
        115                120               125

Phe Phe Cys Glu Leu Trp Thr Ser Val Asp Val Leu Cys Val Thr Ala
130                      135               140

Ser Ile Glu Thr Leu Cys Val Ile Ala Leu Asp Arg Tyr Leu Ala Ile
145                    150              155              160

Thr Ser Pro Phe Arg Tyr Gln Ser Leu Leu Thr Arg Ala Arg Ala Arg
        165                170              175

Gly Leu Val Cys Thr Val Trp Ala Ile Ser Ala Leu Val Ser Phe Leu
        180                185              190

Pro Ile Leu Met His Trp Trp Arg Ala Glu Ser Asp Glu Ala Arg Arg
        195                200              205

Cys Tyr Asn Asp Pro Lys Cys Cys Asp Phe Val Thr Asn Arg Ala Tyr
        210                215              220

Ala Ile Ala Ser Ser Val Val Ser Phe Tyr Val Pro Leu Cys Ile Met
225                    230              235              240

Ala Phe Val Tyr Leu Arg Val Phe Arg Glu Ala Gln Lys Gln Val Lys
        245                250              255

Lys Ile Asp Ser Cys Glu Arg Arg Phe Leu Gly Gly Pro Ala Arg Pro
        260                265              270

Pro Ser Pro Ser Pro Ser Pro Val Pro Ala Pro Ala Pro Pro Pro Gly
        275                280              285

Pro Pro Arg Pro Ala Ala Ala Ala Thr Ala Pro Leu Ala Asn Gly
        290                295              300

Arg Ala Gly Lys Arg Arg Pro Ser Arg Leu Val Ala Leu Arg Glu Gln
305                    310              315              320

Lys Ala Leu Lys Thr Leu Gly Ile Ile Met Gly Val Phe Thr Leu Cys
        325                330              335

Trp Leu Pro Phe Phe Leu Ala Asn Val Val Lys Ala Phe His Arg Glu
        340                345              350

Leu Val Pro Asp Arg Leu Phe Val Phe Phe Asn Trp Leu Gly Tyr Ala
        355                360              365

Asn Ser Ala Phe Asn Pro Ile Ile Tyr Cys Arg Ser Pro Asp Phe Arg
        370                375              380

Lys Ala Phe Gln Arg Leu Leu Cys Cys Ala Arg Arg Ala Ala Arg Arg
385                    390              395              400

Arg His Ala Thr His Gly Asp Arg Pro Arg Ala Ser Gly Cys Leu Ala
        405                410              415

Arg Pro Gly Pro Pro Ser Pro Gly Ala Ala Ser Asp Asp Asp Asp
        420                425              430

Asp Asp Val Val Gly Ala Thr Pro Pro Ala Arg Leu Leu Glu Pro Trp
        435                440              445

Ala Gly Cys Asn Gly Gly Ala Ala Ala Asp Ser Asp Ser Ser Leu Asp
450                    455              460

Glu Pro Cys Arg Pro Gly Phe Ala Ser Glu Ser Lys Val
465                    470              475

<210> SEQ ID NO 5
<211> LENGTH: 1958
<212> TYPE: DNA
<213> ORGANISM: Homo sapiens
<220> FEATURE:

```
<221> NAME/KEY: CDS
<222> LOCATION: (39)..(1427)

<400> SEQUENCE: 5
ccggctccag agggacggc gtagctcgcg ggaggacc atg gcg tcc ccg gcg ctg      56
                                         Met Ala Ser Pro Ala Leu
                                         1               5 gcg gcg gcg ctg gcg gtg gcg gca gcg gcg ggc ccc aat gcg agc ggc     104
Ala Ala Ala Leu Ala Val Ala Ala Ala Ala Gly Pro Asn Ala Ser Gly
             10                  15                  20 gcg ggc gag agg ggc agc ggg ggg gtt gcc aat gcc tcg ggg gct tcc     152
Ala Gly Glu Arg Gly Ser Gly Gly Val Ala Asn Ala Ser Gly Ala Ser
         25                  30                  35 tgg ggg ccg ccg cgc ggc cag tac tcg gcg ggc gcg gtg gca ggg ctg     200
Trp Gly Pro Pro Arg Gly Gln Tyr Ser Ala Gly Ala Val Ala Gly Leu
 40                  45                  50 gct gcc gtg gtg ggc ttc ctc atc gtc ttc acc gtg gtg ggc aac gtg     248
Ala Ala Val Val Gly Phe Leu Ile Val Phe Thr Val Val Gly Asn Val
 55                  60                  65                  70 ctg gtg gtg atc gcc gtg ctg acc agc cgg gcg ctg cgc gcg cca cag     296
Leu Val Val Ile Ala Val Leu Thr Ser Arg Ala Leu Arg Ala Pro Gln
                 75                  80                  85 aac ctc ttc ctg gtg tcg ctg gcc tcg gcc gac atc ctg gtg gcc acg     344
Asn Leu Phe Leu Val Ser Leu Ala Ser Ala Asp Ile Leu Val Ala Thr
         90                  95                 100 ctg gtc atg ccc ttc tcg ttg gcc aac gag ctc atg gcc tac tgg tac     392
Leu Val Met Pro Phe Ser Leu Ala Asn Glu Leu Met Ala Tyr Trp Tyr
    105                 110                 115 ttc ggg cag gtg tgg tgc ggc gtg tac ctg gcg ctc gat gtg ctg ttt     440
Phe Gly Gln Val Trp Cys Gly Val Tyr Leu Ala Leu Asp Val Leu Phe
120                 125                 130 tgc acc tcg tcg atc gtg cat ctg tgt gcc atc agc ctg gac cgc tac     488
Cys Thr Ser Ser Ile Val His Leu Cys Ala Ile Ser Leu Asp Arg Tyr
135                 140                 145                 150 tgg tcg gtg acg cag gcc gtc gag tac aac ctg aag cgc aca cca cgc     536
Trp Ser Val Thr Gln Ala Val Glu Tyr Asn Leu Lys Arg Thr Pro Arg
                155                 160                 165 cgc gtc aag gcc acc atc gtg gcc gtg tgg ctc atc tcg gcc gtc atc     584
Arg Val Lys Ala Thr Ile Val Ala Val Trp Leu Ile Ser Ala Val Ile
            170                 175                 180 tcc ttc ccg ccg ctg gtc tcg ctc tac cgc cag ccc gac ggc gcc gcc     632
Ser Phe Pro Pro Leu Val Ser Leu Tyr Arg Gln Pro Asp Gly Ala Ala
        185                 190                 195 tac ccg cag tgc ggc ctc aac gac gag acc tgg tac atc ctg tcc tcc     680
Tyr Pro Gln Cys Gly Leu Asn Asp Glu Thr Trp Tyr Ile Leu Ser Ser
    200                 205                 210 tgc atc ggc tcc ttc ttc gcg ccc tgc ctc atc atg ggc ctg gtc tac     728
Cys Ile Gly Ser Phe Phe Ala Pro Cys Leu Ile Met Gly Leu Val Tyr
215                 220                 225                 230 gcg cgc atc tac cga gtg gcc aag ctg cgc acg cgc acg ctc agc gag     776
Ala Arg Ile Tyr Arg Val Ala Lys Leu Arg Thr Arg Thr Leu Ser Glu
                235                 240                 245 aag cgc gcc ccc gtg ggc ccc gac ggt gcg tcc ccg act acc gaa aac     824
Lys Arg Ala Pro Val Gly Pro Asp Gly Ala Ser Pro Thr Thr Glu Asn
            250                 255                 260 ggg ctg ggc gcg gcg gca ggc gca ggc gag aac ggg cac tgc gcg ccc     872
Gly Leu Gly Ala Ala Ala Gly Ala Gly Glu Asn Gly His Cys Ala Pro
        265                 270                 275 ccg ccc gcc gac gtg gag ccg gac gag agc agc gca gcg gcc gag agg     920
Pro Pro Ala Asp Val Glu Pro Asp Glu Ser Ser Ala Ala Ala Glu Arg
    280                 285                 290
```

```
cgg cgg cgc cgg ggc gcg ttg cgg cgg ggc ggg cgg cgg cga gcg ggc      968
Arg Arg Arg Arg Gly Ala Leu Arg Arg Gly Gly Arg Arg Arg Ala Gly
295                 300                 305                 310 gcg gag ggg ggc gcg ggc ggt gcg gac ggg cag ggg gcg ggg ccg ggg     1016
Ala Glu Gly Gly Ala Gly Gly Ala Asp Gly Gln Gly Ala Gly Pro Gly
            315                 320                 325 gcg gct gag tcg ggg gcg ctg acc gcc tcc agg tcc ccg ggg ccc ggt     1064
Ala Ala Glu Ser Gly Ala Leu Thr Ala Ser Arg Ser Pro Gly Pro Gly
330                 335                 340 ggc cgc ctg tcg cgc gcc agc tcg cgc tcc gtc gag ttc ttc ctg tcg     1112
Gly Arg Leu Ser Arg Ala Ser Ser Arg Ser Val Glu Phe Phe Leu Ser
            345                 350                 355 cgc cgg cgc cgg gcg cgc agc agc gtg tgc cgc cgc aag gtg gcc cag     1160
Arg Arg Arg Arg Ala Arg Ser Ser Val Cys Arg Arg Lys Val Ala Gln
360                 365                 370 gcg cgc gag aag cgc ttc acc ttt gtg ctg gct gtg gtc atg ggc gtg     1208
Ala Arg Glu Lys Arg Phe Thr Phe Val Leu Ala Val Val Met Gly Val
375                 380                 385                 390 ttc gtg ctc tgc tgg ttc ccc ttc ttc agc tac agc ctg tac ggc         1256
Phe Val Leu Cys Trp Phe Pro Phe Phe Ser Tyr Ser Leu Tyr Gly
                395                 400                 405 atc tgc cgc gag gcc tgc cag gtg ccc ggc ccg ctc ttc aag ttc ttc     1304
Ile Cys Arg Glu Ala Cys Gln Val Pro Gly Pro Leu Phe Lys Phe Phe
            410                 415                 420 ttc tgg atc ggc tac tgc aac agc tcg ctc aac ccg gtc atc tac acg     1352
Phe Trp Ile Gly Tyr Cys Asn Ser Ser Leu Asn Pro Val Ile Tyr Thr
                425                 430                 435 gtc ttc aac cag gat ttc cgg cga tcc ttt aag cac atc ctc ttc cga     1400
Val Phe Asn Gln Asp Phe Arg Arg Ser Phe Lys His Ile Leu Phe Arg
440                 445                 450 cgg agg aga agg ggc ttc agg cag tga ctcgcacccg tctgggaatc           1447
Arg Arg Arg Arg Gly Phe Arg Gln
455                 460 ctggacagct ccgcgctcgg ggctgggcag aaggggcggc ccggacgggg gagctttccc   1507
agagacccgg ggatggattg gcctccaggg cgcaggggag ggtgcggcag ggcaggagct   1567
tggcagagag atagccgggc tccagggagt ggggaggaga gaggggagga ccccttttgcc  1627 ttccccctc agcaaggggc tgcttctggg gctccctgcc tggatccagc tctgggagcc    1687
ctgccgaggt gtggctgtga ggtcagggtt ttagagagca gtggcagagg tagccccta    1747 aatgggcaag caaggagccc cccaaagaca ctaccactcc ccatccccgt ctgaccaagg   1807
gctgacttct ccaggaccta gtcgggggt ggctgccagg gggcaaggag aaagcaccga    1867
caatctttga ttactgaaag tatttaaatg tttgccaaaa acaacagcca aaacaaccaa   1927
actattttct aaataaacct ttgtaatcta a                                  1958

<210> SEQ ID NO 6
<211> LENGTH: 462
<212> TYPE: PRT
<213> ORGANISM: Homo sapiens

<400> SEQUENCE: 6

Met Ala Ser Pro Ala Leu Ala Ala Ala Leu Ala Val Ala Ala Ala
1               5                   10                  15

Gly Pro Asn Ala Ser Gly Ala Gly Glu Arg Gly Ser Gly Gly Val Ala
                20                  25                  30

Asn Ala Ser Gly Ala Ser Trp Gly Pro Pro Arg Gly Gln Tyr Ser Ala
            35                  40                  45
```

```
Gly Ala Val Ala Gly Leu Ala Ala Val Val Gly Phe Leu Ile Val Phe
     50                  55                  60
Thr Val Val Gly Asn Val Leu Val Val Ile Ala Val Leu Thr Ser Arg
 65                  70                  75                  80
Ala Leu Arg Ala Pro Gln Asn Leu Phe Leu Val Ser Leu Ala Ser Ala
                 85                  90                  95
Asp Ile Leu Val Ala Thr Leu Val Met Pro Phe Ser Leu Ala Asn Glu
                100                 105                 110
Leu Met Ala Tyr Trp Tyr Phe Gly Gln Val Trp Cys Gly Val Tyr Leu
            115                 120                 125
Ala Leu Asp Val Leu Phe Cys Thr Ser Ser Ile Val His Leu Cys Ala
        130                 135                 140
Ile Ser Leu Asp Arg Tyr Trp Ser Val Thr Gln Ala Val Glu Tyr Asn
145                 150                 155                 160
Leu Lys Arg Thr Pro Arg Arg Val Lys Ala Thr Ile Val Ala Val Trp
                165                 170                 175
Leu Ile Ser Ala Val Ile Ser Phe Pro Pro Leu Val Ser Leu Tyr Arg
            180                 185                 190
Gln Pro Asp Gly Ala Ala Tyr Pro Gln Cys Gly Leu Asn Asp Glu Thr
        195                 200                 205
Trp Tyr Ile Leu Ser Ser Cys Ile Gly Ser Phe Phe Ala Pro Cys Leu
    210                 215                 220
Ile Met Gly Leu Val Tyr Ala Arg Ile Tyr Arg Val Ala Lys Leu Arg
225                 230                 235                 240
Thr Arg Thr Leu Ser Glu Lys Arg Ala Pro Val Gly Pro Asp Gly Ala
                245                 250                 255
Ser Pro Thr Thr Glu Asn Gly Leu Gly Ala Ala Ala Gly Ala Gly Glu
            260                 265                 270
Asn Gly His Cys Ala Pro Pro Ala Asp Val Glu Pro Asp Glu Ser Ser
        275                 280                 285
Ser Ala Ala Ala Glu Arg Arg Arg Arg Gly Ala Leu Arg Arg Gly
    290                 295                 300
Gly Arg Arg Arg Ala Gly Ala Glu Gly Ala Gly Gly Ala Asp Gly
305                 310                 315                 320
Gln Gly Ala Gly Pro Gly Ala Ala Glu Ser Gly Ala Leu Thr Ala Ser
                325                 330                 335
Arg Ser Pro Gly Pro Gly Gly Arg Leu Ser Arg Ala Ser Ser Arg Ser
            340                 345                 350
Val Glu Phe Phe Leu Ser Arg Arg Arg Ala Arg Ser Ser Val Cys
        355                 360                 365
Arg Arg Lys Val Ala Gln Ala Arg Glu Lys Arg Phe Thr Phe Val Leu
    370                 375                 380
Ala Val Val Met Gly Val Phe Val Leu Cys Trp Phe Pro Phe Phe Phe
385                 390                 395                 400
Ser Tyr Ser Leu Tyr Gly Ile Cys Arg Glu Ala Cys Gln Val Pro Gly
                405                 410                 415
Pro Leu Phe Lys Phe Phe Phe Trp Ile Gly Tyr Cys Asn Ser Ser Leu
            420                 425                 430
Asn Pro Val Ile Tyr Thr Val Phe Asn Gln Asp Phe Arg Arg Ser Phe
        435                 440                 445
Lys His Ile Leu Phe Arg Arg Arg Arg Gly Phe Arg Gln
    450                 455                 460

<210> SEQ ID NO 7
```

```
<211> LENGTH: 1377
<212> TYPE: DNA
<213> ORGANISM: Homo sapiens
<220> FEATURE:
<221> NAME/KEY: CDS
<222> LOCATION: (1)..(1377)

<400> SEQUENCE: 7 atg gcg tcc ccg gcg ctg gcg gcg gcg ctg gcg gtg gcg gca gcg gcg      48
Met Ala Ser Pro Ala Leu Ala Ala Ala Leu Ala Val Ala Ala Ala Ala
1               5                  10                  15 ggc ccc aat gcg agc ggc gcg ggc gag agg ggc agc ggc ggg gtt gcc      96
Gly Pro Asn Ala Ser Gly Ala Gly Glu Arg Gly Ser Gly Gly Val Ala
            20                  25                  30 aat gcc tcg ggg gct tcc tgg ggg ccg ccg cgc ggc cag tac tcg gcg     144
Asn Ala Ser Gly Ala Ser Trp Gly Pro Pro Arg Gly Gln Tyr Ser Ala
        35                  40                  45 ggc gcg gtg gca ggg ctg gct gcc gtg gtg ggc ttc ctc atc gtc ttc     192
Gly Ala Val Ala Gly Leu Ala Ala Val Val Gly Phe Leu Ile Val Phe
    50                  55                  60 acc gtg gtg ggc aac gtg ctg gtg gtg atc gcc gtg ctg acc agc cgg     240
Thr Val Val Gly Asn Val Leu Val Val Ile Ala Val Leu Thr Ser Arg
65                  70                  75                  80 gcg ctg cgc gcg cca cag aac ctc ttc ctg gtg tcg ctg gcc tcg gcc     288
Ala Leu Arg Ala Pro Gln Asn Leu Phe Leu Val Ser Leu Ala Ser Ala
                85                  90                  95 gac atc ctg gtg gcc acg ctg gtc atg ccc ttc tcg ttg gcc aac gag     336
Asp Ile Leu Val Ala Thr Leu Val Met Pro Phe Ser Leu Ala Asn Glu
            100                 105                 110 ctc atg gcc tac tgg tac ttc ggg cag gtg tgg tgc ggc gtg tac ctg     384
Leu Met Ala Tyr Trp Tyr Phe Gly Gln Val Trp Cys Gly Val Tyr Leu
        115                 120                 125 gcg ctc gat gtg ctg ttt tgc acc tcg tcg atc gtg cat ctg tgt gcc     432
Ala Leu Asp Val Leu Phe Cys Thr Ser Ser Ile Val His Leu Cys Ala
    130                 135                 140 atc agc ctg gac cgc tac tgg tcg gtg acg cag gcc gtc gag tac aac     480
Ile Ser Leu Asp Arg Tyr Trp Ser Val Thr Gln Ala Val Glu Tyr Asn
145                 150                 155                 160 ctg aag cgc aca cca cgc cgc gtc aag gcc acc atc gtc gcc gtg tgg     528
Leu Lys Arg Thr Pro Arg Arg Val Lys Ala Thr Ile Val Ala Val Trp
                165                 170                 175 ctc atc tcg gcc gtc atc tcc ttc ccg ccg ctg gtc tcg ctc tac cgc     576
Leu Ile Ser Ala Val Ile Ser Phe Pro Pro Leu Val Ser Leu Tyr Arg
            180                 185                 190 cag ccc gac ggc gcc gcc tac ccg cag tgc ggc ctc aac gac gag acc     624
Gln Pro Asp Gly Ala Ala Tyr Pro Gln Cys Gly Leu Asn Asp Glu Thr
        195                 200                 205 tgg tac atc ctg tcc tcc tgc atc ggc tcc ttc ttc gcg ccc tgc ctc     672
Trp Tyr Ile Leu Ser Ser Cys Ile Gly Ser Phe Phe Ala Pro Cys Leu
    210                 215                 220 atc atg ggc ctg gtc tac gcg cgc atc tac cga gtg gcc aag ctg cgc     720
Ile Met Gly Leu Val Tyr Ala Arg Ile Tyr Arg Val Ala Lys Leu Arg
225                 230                 235                 240 acg cgc acg ctc agc gag aag cgc gcc ccc gtg ggc ccc gac ggt gcg     768
Thr Arg Thr Leu Ser Glu Lys Arg Ala Pro Val Gly Pro Asp Gly Ala
                245                 250                 255 tcc ccg act acc gaa aac ggg ctg ggc gcg gcg gca ggc gca ggc gag     816
Ser Pro Thr Thr Glu Asn Gly Leu Gly Ala Ala Ala Gly Ala Gly Glu
            260                 265                 270 aac ggg cac tgc gcg ccc ccg ccc gcc gac gtg gag ccg gac gag agc     864
Asn Gly His Cys Ala Pro Pro Pro Ala Asp Val Glu Pro Asp Glu Ser
        275                 280                 285
```

| | | | | | | | | | | | | | | | | |
|---|---|---|---|---|---|---|---|---|---|---|---|---|---|---|---|---|
| agc | gca | gcg | gcc | gag | agg | cgg | cgg | cgc | cgg | ggc | gcg | ttg | cgg | cgg | ggc | 912 |
| Ser | Ala | Ala | Ala | Glu | Arg | Arg | Arg | Arg | Arg | Gly | Ala | Leu | Arg | Arg | Gly | |
| | 290 | | | | 295 | | | | 300 | | | | | | | |

| | | | | | | | | | | | | | | | | |
|---|---|---|---|---|---|---|---|---|---|---|---|---|---|---|---|---|
| ggg | cgg | cgg | cga | gcg | ggc | gcg | gag | ggg | ggc | gcg | ggc | ggt | gcg | gac | ggg | 960 |
| Gly | Arg | Arg | Arg | Ala | Gly | Ala | Glu | Gly | Gly | Ala | Gly | Gly | Ala | Asp | Gly | |
| 305 | | | | | 310 | | | | | 315 | | | | | 320 | |

| | | | | | | | | | | | | | | | | |
|---|---|---|---|---|---|---|---|---|---|---|---|---|---|---|---|---|
| cag | ggg | gcg | gct | gag | tcg | ggg | gcg | ctg | acc | gcc | tcc | agg | tcc | ccg | ggg | 1008 |
| Gln | Gly | Ala | Ala | Glu | Ser | Gly | Ala | Leu | Thr | Ala | Ser | Arg | Ser | Pro | Gly | |
| | | | | 325 | | | | | 330 | | | | | 335 | | |

| | | | | | | | | | | | | | | | | |
|---|---|---|---|---|---|---|---|---|---|---|---|---|---|---|---|---|
| ccc | ggt | ggc | cgc | ctc | tcg | cgc | gcc | agc | tcg | cgc | tcc | gtc | gag | ttc | ttc | 1056 |
| Pro | Gly | Gly | Arg | Leu | Ser | Arg | Ala | Ser | Ser | Arg | Ser | Val | Glu | Phe | Phe | |
| | | 340 | | | | | 345 | | | | | 350 | | | | |

| | | | | | | | | | | | | | | | | |
|---|---|---|---|---|---|---|---|---|---|---|---|---|---|---|---|---|
| ctg | tcg | cgc | cgg | cgc | cgg | gcg | cgc | agc | agc | gtg | tgc | cgc | cgc | aag | gtg | 1104 |
| Leu | Ser | Arg | Arg | Arg | Arg | Ala | Arg | Ser | Ser | Val | Cys | Arg | Arg | Lys | Val | |
| | 355 | | | | | 360 | | | | | 365 | | | | | |

| | | | | | | | | | | | | | | | | |
|---|---|---|---|---|---|---|---|---|---|---|---|---|---|---|---|---|
| gcc | cag | gcg | cgc | gag | aag | cgc | ttc | acc | ttt | gtg | ctg | gct | gtg | gtc | atg | 1152 |
| Ala | Gln | Ala | Arg | Glu | Lys | Arg | Phe | Thr | Phe | Val | Leu | Ala | Val | Val | Met | |
| 370 | | | | | 375 | | | | | 380 | | | | | | |

| | | | | | | | | | | | | | | | | |
|---|---|---|---|---|---|---|---|---|---|---|---|---|---|---|---|---|
| ggc | gtg | ttc | gtg | ctc | tgc | tgg | ttc | ccc | ttc | ttc | agc | tac | agc | ctg | | 1200 |
| Gly | Val | Phe | Val | Leu | Cys | Trp | Phe | Pro | Phe | Phe | Ser | Tyr | Ser | Leu | | |
| 385 | | | | 390 | | | | | 395 | | | | | 400 | | |

| | | | | | | | | | | | | | | | | |
|---|---|---|---|---|---|---|---|---|---|---|---|---|---|---|---|---|
| tac | ggc | atc | tgc | cgc | gag | gcc | tgc | cag | gtg | ccc | ggc | ccg | ctc | ttc | aag | 1248 |
| Tyr | Gly | Ile | Cys | Arg | Glu | Ala | Cys | Gln | Val | Pro | Gly | Pro | Leu | Phe | Lys | |
| | | | 405 | | | | | 410 | | | | | 415 | | | |

| | | | | | | | | | | | | | | | | |
|---|---|---|---|---|---|---|---|---|---|---|---|---|---|---|---|---|
| ttc | ttc | ttc | tgg | atc | ggc | tac | tgc | aac | agc | tcg | ctc | aac | ccg | gtc | atc | 1296 |
| Phe | Phe | Phe | Trp | Ile | Gly | Tyr | Cys | Asn | Ser | Ser | Leu | Asn | Pro | Val | Ile | |
| | | 420 | | | | | 425 | | | | | 430 | | | | |

| | | | | | | | | | | | | | | | | |
|---|---|---|---|---|---|---|---|---|---|---|---|---|---|---|---|---|
| tac | acg | gtc | ttc | aac | cag | gat | ttc | cgg | cga | tcc | ttt | aag | cac | atc | ctc | 1344 |
| Tyr | Thr | Val | Phe | Asn | Gln | Asp | Phe | Arg | Arg | Ser | Phe | Lys | His | Ile | Leu | |
| | | 435 | | | | | 440 | | | | | 445 | | | | |

| | | | | | | | | | |
|---|---|---|---|---|---|---|---|---|---|
| ttc | cga | cgg | agg | aga | agg | ggc | ttc | agg | cag | tga | 1377 |
| Phe | Arg | Arg | Arg | Arg | Arg | Gly | Phe | Arg | Gln | | |
| | 450 | | | | | 455 | | | | | |

<210> SEQ ID NO 8
<211> LENGTH: 458
<212> TYPE: PRT
<213> ORGANISM: Homo sapiens

<400> SEQUENCE: 8

Met Ala Ser Pro Ala Leu Ala Ala Ala Leu Ala Val Ala Ala Ala
1               5                   10                  15

Gly Pro Asn Ala Ser Gly Ala Gly Glu Arg Gly Ser Gly Gly Val Ala
            20                  25                  30

Asn Ala Ser Gly Ala Ser Trp Gly Pro Pro Arg Gly Gln Tyr Ser Ala
        35                  40                  45

Gly Ala Val Ala Gly Leu Ala Ala Val Val Gly Phe Leu Ile Val Phe
    50                  55                  60

Thr Val Val Gly Asn Val Leu Val Ile Ala Val Leu Thr Ser Arg
65                  70                  75                  80

Ala Leu Arg Ala Pro Gln Asn Leu Phe Leu Val Ser Leu Ala Ser Ala
                85                  90                  95

Asp Ile Leu Val Ala Thr Leu Val Met Pro Phe Ser Leu Ala Asn Glu
            100                 105                 110

Leu Met Ala Tyr Trp Tyr Phe Gly Gln Val Trp Cys Gly Val Tyr Leu
        115                 120                 125

Ala Leu Asp Val Leu Phe Cys Thr Ser Ser Ile Val His Leu Cys Ala
    130                 135                 140

-continued

```
Ile Ser Leu Asp Arg Tyr Trp Ser Val Thr Gln Ala Val Glu Tyr Asn
145                 150                 155                 160
Leu Lys Arg Thr Pro Arg Arg Val Lys Ala Thr Ile Val Ala Val Trp
                165                 170                 175
Leu Ile Ser Ala Val Ile Ser Phe Pro Pro Leu Val Ser Leu Tyr Arg
            180                 185                 190
Gln Pro Asp Gly Ala Ala Tyr Pro Gln Cys Gly Leu Asn Asp Glu Thr
        195                 200                 205
Trp Tyr Ile Leu Ser Ser Cys Ile Gly Ser Phe Phe Ala Pro Cys Leu
    210                 215                 220
Ile Met Gly Leu Val Tyr Ala Arg Ile Tyr Arg Val Ala Lys Leu Arg
225                 230                 235                 240
Thr Arg Thr Leu Ser Glu Lys Arg Ala Pro Val Gly Pro Asp Gly Ala
                245                 250                 255
Ser Pro Thr Thr Glu Asn Gly Leu Gly Ala Ala Ala Gly Ala Gly Glu
            260                 265                 270
Asn Gly His Cys Ala Pro Pro Pro Ala Asp Val Glu Pro Asp Glu Ser
        275                 280                 285
Ser Ala Ala Ala Glu Arg Arg Arg Arg Gly Ala Leu Arg Arg Gly
    290                 295                 300
Gly Arg Arg Arg Ala Gly Ala Glu Gly Gly Ala Gly Gly Ala Asp Gly
305                 310                 315                 320
Gln Gly Ala Ala Glu Ser Gly Ala Leu Thr Ala Ser Arg Ser Pro Gly
                325                 330                 335
Pro Gly Gly Arg Leu Ser Arg Ala Ser Ser Arg Ser Val Glu Phe Phe
            340                 345                 350
Leu Ser Arg Arg Arg Arg Ala Arg Ser Ser Val Cys Arg Arg Lys Val
    355                 360                 365
Ala Gln Ala Arg Glu Lys Arg Phe Thr Phe Val Leu Ala Val Val Met
    370                 375                 380
Gly Val Phe Val Leu Cys Trp Phe Pro Phe Phe Phe Ser Tyr Ser Leu
385                 390                 395                 400
Tyr Gly Ile Cys Arg Glu Ala Cys Gln Val Pro Gly Pro Leu Phe Lys
                405                 410                 415
Phe Phe Phe Trp Ile Gly Tyr Cys Asn Ser Ser Leu Asn Pro Val Ile
            420                 425                 430
Tyr Thr Val Phe Asn Gln Asp Phe Arg Arg Ser Phe Lys His Ile Leu
        435                 440                 445
Phe Arg Arg Arg Arg Arg Gly Phe Arg Gln
450                 455
```